(12) United States Patent
Sprecher et al.

(10) Patent No.: US 7,763,713 B2
(45) Date of Patent: *Jul. 27, 2010

(54) ZALPHA11 CYTOKINE RECEPTORS

(75) Inventors: Cindy A. Sprecher, Seattle, WA (US); Julia E. Novak, Bainbridge Island, WA (US); James W. West, Seattle, WA (US); Scott R. Presnell, Tacoma, WA (US); Richard D. Holly, Seattle, WA (US); Andrew J. Nelson, Shoreline, WA (US)

(73) Assignee: ZymoGenetics, Inc., Seattle, WA (US)

( * ) Notice: Subject to any disclaimer, the term of this patent is extended or adjusted under 35 U.S.C. 154(b) by 952 days.

This patent is subject to a terminal disclaimer.

(21) Appl. No.: 11/538,359

(22) Filed: Oct. 3, 2006

(65) Prior Publication Data

US 2009/0221802 A1 Sep. 3, 2009

Related U.S. Application Data

(63) Continuation of application No. 10/872,087, filed on Jun. 18, 2004, now Pat. No. 7,189,695.

(51) Int. Cl.
*C07K 14/435* (2006.01)
*C07K 14/52* (2006.01)
(52) U.S. Cl. ...................................... 530/350; 530/351
(58) Field of Classification Search ........................ None
See application file for complete search history.

(56) References Cited

U.S. PATENT DOCUMENTS

| | | | |
|---|---|---|---|
| 6,057,128 A | 5/2000 | Donaldson et al. | 435/69.1 |
| 6,307,024 B1 | 10/2001 | Novak et al. | 530/351 |
| 6,576,744 B1 | 6/2003 | Presnell et al. | 530/351 |
| 6,777,539 B2 * | 8/2004 | Sprecher et al. | 530/350 |
| 7,189,695 B2 * | 3/2007 | Sprecher et al. | 514/12 |

FOREIGN PATENT DOCUMENTS

| | | |
|---|---|---|
| EP | 1088831 A | 4/2001 |
| WO | WO 95/33059 | 12/1995 |
| WO | WO 98/31811 | 7/1998 |
| WO | WO 99/47675 | 9/1999 |
| WO | WO 99/67290 | 12/1999 |
| WO | WO 00/08152 | 2/2000 |
| WO | WO 00/17235 | 3/2000 |
| WO | WO 00/69880 | 11/2000 |

OTHER PUBLICATIONS

Parrish, J et al., *Am. J. Hum. Genetics.* 65:A378, 1999.
Parrish-Novak, J et al., *Nature* 408:57-63, 2000.
Ozaki, K et al., *Proc. Nat. Acad. Sci. USA* 97:11439-11444, 2000.
Asoa, H. et al., *J. Immunology* 167:1-5, 2001.
Bazan, JF *J. Biol. Chem.* 87:6934-6938, 1990.
U.S. Appl. No. 11/563,928, filed Nov. 28, 2006, Sivakumar et al.
U.S. Appl. No. 11/564,001, filed Nov. 28, 2006, Sivakumar et al.
U.S. Appl. No. 12/560,637, filed Sep. 16, 2009 in the name of Sprecher.

* cited by examiner

*Primary Examiner*—Ruixiang Li
(74) *Attorney, Agent, or Firm*—Nicholas V. Sherbina; Deborah A. Sawislak; Jennifer K. Johnson

(57) ABSTRACT

Novel polypeptide combinations, polynucleotides encoding the polypeptides, and related compositions and methods are disclosed for soluble zalpha11 receptors that may be used as novel cytokine antagonists, and within methods for detecting ligands that stimulate the proliferation and/or development of hematopoietic, lymphoid and myeloid cells in vitro and in vivo. Ligand-binding receptor polypeptides can also be used to block zalpha11 Ligand activity in vitro and in vivo, and may be used in conjunction with zalpha11 Ligand and other cytokines to selectively stimulate the immune system. The present invention also includes methods for producing the protein, uses therefor and antibodies thereto.

11 Claims, No Drawings

US 7,763,713 B2

ZALPHA11 CYTOKINE RECEPTORS

REFERENCE TO RELATED APPLICATIONS

This application is a continuation of U.S. patent application Ser. No. 10/872,087, filed Jun. 18, 2004, issued as U.S. Pat. No. 7,189,695, which claims benefit of U.S. Provisional Application 60/194,731, filed on Apr. 5, 2000, and U.S. Provisional Application 60/222,121, filed on Jul. 28, 2000, all of which are incorporated by reference. Under 35 U.S.C. §119 (e)(1), this application claims benefit of said Provisional Applications. Additionally, this application claims benefit of application Ser. No. 09/825,561 filed on Apr. 3, 2001, issued as U.S. Pat. No. 6,777,539, under 35 U.S.C. 35 §120.

BACKGROUND OF THE INVENTION

Hormones and polypeptide growth factors control proliferation and differentiation of cells of multicellular organisms. These diffusible molecules allow cells to communicate with each other and act in concert to form cells and organs, and to repair damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to receptors. Receptors may be integral membrane proteins that are linked to signaling pathways within the cell, such as second messenger systems. Other classes of receptors are soluble molecules, such as the transcription factors. Of particular interest are receptors for cytokines, molecules that promote the proliferation and/or differentiation of cells. Examples of cytokines include erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia, thrombocytopenia, and neutropenia or receiving chemotherapy for cancer.

The demonstrated in vivo activities of these cytokines illustrate the enormous clinical potential of, and need for, other cytokines, cytokine agonists, and cytokine antagonists or binding partners. The present invention addresses these needs by providing a new cytokine antagonist or binding partner, a soluble hematopoietic cytokine receptor, as well as related compositions and methods.

The present invention provides such polypeptides for these and other uses that should be apparent to those skilled in the art from the teachings herein.

DESCRIPTION OF THE INVENTION

Within one aspect, the present invention provides an isolated polynucleotide that encodes a soluble receptor polypeptide comprising a sequence of amino acid residues that is at least 90% identical to the amino acid sequence as shown in SEQ ID NO:6, and wherein the soluble receptor polypeptide encoded by the polynucleotide sequence binds a ligand comprising a polypeptide of SEQ ID NO:10 or SEQ ID NO:47, or antagonizes the ligand activity. In one embodiment, the isolated polynucleotide is as disclosed above, wherein the soluble receptor polypeptide encoded by the polynucleotide forms a homodimeric receptor complex.

Within another aspect, the present invention provides an isolated polynucleotide that encodes a soluble receptor polypeptide comprising a sequence of amino acid residues that is at least 90% identical to the amino acid sequence as shown in SEQ ID NO:6, wherein the soluble receptor polypeptide encoded by the polynucleotide forms a heterodimeric or multimeric receptor complex. In one embodiment, the isolated polynucleotide is as disclosed above, wherein the soluble receptor polypeptide encoded by the polynucleotide forms a heterodimeric or multimeric receptor complex further comprising a soluble Class I cytokine receptor.

In one embodiment, the isolated polynucleotide is as disclosed above, wherein the soluble receptor polypeptide encoded by the polynucleotide forms a heterodimeric or multimeric receptor complex further comprising a soluble IL-2Rγ receptor polypeptide (SEQ ID NO:4) or a soluble IL-13α' receptor polypeptide (SEQ ID NO:82). In another embodiment, the isolated polynucleotide is as disclosed above, wherein the polypeptide further comprises a WSXWS motif as shown in SEQ ID NO:13.

Within another aspect, the present invention provides an isolated polynucleotide that encodes a soluble receptor polypeptide comprising a sequence of amino acid residues as shown in SEQ ID NO:6, wherein the soluble receptor polypeptide encoded by the polynucleotide forms a heterodimeric or multimeric receptor complex. In one embodiment, the isolated polynucleotide is as disclosed above, wherein the soluble receptor polypeptide encoded by the polynucleotide further comprises a soluble Class I cytokine receptor. In another embodiment, the isolated polynucleotide is as disclosed above, wherein the soluble receptor polypeptide encoded by the polynucleotide forms a heterodimeric or multimeric receptor complex further comprising a soluble IL-2Rγ receptor polypeptide (SEQ ID NO:4) or a soluble IL-13α' receptor polypeptide (SEQ ID NO:82). In another embodiment, the isolated polynucleotide is as disclosed above, wherein the soluble receptor polypeptide is encoded by the polynucleotide as shown in SEQ ID NO:7. In another embodiment, the isolated polynucleotide is as disclosed above, wherein the soluble receptor polypeptide further comprises an affinity tag.

Within a second aspect, the present invention provides an expression vector comprising the following operably linked elements: (a) a transcription promoter; a first DNA segment encoding a soluble receptor polypeptide having an amino acid sequence as shown in SEQ ID NO:6; and a transcription terminator; and (b) a second transcription promoter; a second DNA segment encoding a soluble Class I cytokine receptor polypeptide; and a transcription terminator; and wherein the first and second DNA segments are contained within a single expression vector or are contained within independent expression vectors. In one embodiment, the expression vector disclosed above further comprises a secretory signal sequence operably linked to the first and second DNA segments. In another embodiment, the expression vector is as disclosed above, wherein the second DNA segment encodes a soluble IL-2Rγ receptor polypeptide (SEQ ID NO:4) or a soluble IL-13α' receptor polypeptide (SEQ ID NO:82).

Within a third aspect, the present invention provides a cultured cell comprising an expression vector as disclosed above, wherein the cell expresses the polypeptides encoded by the DNA segments. In one embodiment, the cultured cell comprising an expression vector is as disclosed above, wherein the first and second DNA segments are located on independent expression vectors and are co-transfected into the cell, and cell expresses the polypeptides encoded by the DNA segments. In another embodiment, the cultured cell comprising an expression vector is as disclosed above, wherein the cell expresses a heterodimeric or multimeric soluble receptor polypeptide encoded by the DNA segments. In another embodiment, the cultured cell comprising an expression vector is as disclosed above, wherein the cell secretes a soluble receptor polypeptide heterodimer or multimeric complex. In another embodiment, the cultured cell comprising an expression vector is as disclosed above, wherein the cell secretes a soluble receptor polypeptide heterodimer or multimeric complex that binds a ligand comprising a polypeptide of SEQ ID NO:10 or SEQ ID NO:47, or antagonizes the ligand activity.

Within another aspect, the present invention provides a DNA construct encoding a fusion protein comprising: a first DNA segment encoding a polypeptide having a sequence of amino acid residues as shown in SEQ ID NO:6; and at least one other DNA segment encoding a soluble Class I cytokine receptor polypeptide, wherein the first and other DNA segments are connected in-frame; and wherein the first and other DNA segments encode the fusion protein. In one embodiment, the DNA construct encodes a fusion protein as disclosed above, wherein at least one other DNA segment encodes a soluble IL-2Rγ receptor polypeptide (SEQ ID NO:4) or a soluble IL-13α' receptor polypeptide (SEQ ID NO:82).

Within another aspect, the present invention provides an expression vector comprising the following operably linked elements: a transcription promoter; a DNA construct encoding a fusion protein as disclosed above; and a transcription terminator, wherein the promoter is operably linked to the DNA construct, and the DNA construct is operably linked to the transcription terminator.

Within another aspect, the present invention provides a cultured cell comprising an expression vector as disclosed above, wherein the cell expresses a polypeptide encoded by the DNA construct.

Within another aspect, the present invention provides a method of producing a fusion protein comprising: culturing a cell as disclosed above; and isolating the polypeptide produced by the cell.

Within another aspect, the present invention provides an isolated soluble receptor polypeptide comprising a sequence of amino acid residues that is at least 90% identical to an amino acid sequence as shown in SEQ ID NO:6, and wherein the soluble receptor polypeptide binds a ligand comprising a polypeptide of SEQ ID NO:10 or SEQ ID NO:47, or antagonizes the ligand activity. In one embodiment, the isolated polypeptide is as disclosed above, wherein the soluble receptor polypeptide forms a homodimeric receptor complex.

Within another aspect, the present invention provides an isolated polypeptide comprising a sequence of amino acid residues that is at least 90% identical to an amino acid sequence as shown in SEQ ID NO:6, wherein the soluble receptor polypeptide forms a heterodimeric or multimeric receptor complex. In one embodiment, the isolated polypeptide is as disclosed above, wherein the soluble receptor polypeptide forms a heterodimeric or multimeric receptor complex further comprising a soluble Class I cytokine receptor. In another embodiment, the isolated polypeptide is as disclosed above, wherein the soluble receptor polypeptide forms a heterodimeric or multimeric receptor complex further comprising a soluble IL-2Rγ receptor polypeptide (SEQ ID NO:4) or a soluble IL-13α' receptor polypeptide (SEQ ID NO:82). In another embodiment, the isolated polypeptide is as disclosed above, wherein the polypeptide further comprises a WSXWS motif as shown in SEQ ID NO:13.

Within another aspect, the present invention provides an isolated soluble receptor polypeptide comprising a sequence of amino acid residues as shown in SEQ ID NO:6, wherein the soluble receptor polypeptide forms a heterodimeric or multimeric receptor complex. In one embodiment, the isolated polypeptide is as disclosed above, wherein the soluble receptor polypeptide forms a heterodimeric or multimeric receptor complex further comprising a soluble Class I cytokine receptor. In another embodiment, the isolated polypeptide is as disclosed above, wherein the soluble receptor polypeptide forms a heterodimeric or multimeric receptor complex comprising a soluble IL-2Rγ receptor polypeptide (SEQ ID NO:4) or a soluble IL-13α' receptor polypeptide (SEQ ID NO:82). In another embodiment, the isolated polypeptide is as disclosed above, wherein the soluble receptor polypeptide further comprises an affinity tag, chemical moiety, toxin, or label.

Within another aspect, the present invention provides an isolated heterodimeric or multimetric soluble receptor complex comprising soluble receptor subunits, wherein at least one of soluble receptor subunits comprises a soluble receptor polypeptide comprising a sequence of amino acid residues as shown in SEQ ID NO:6. In one embodiment, the isolated heterodimeric or multimetric soluble receptor complex disclosed above further comprises a soluble Class I cytokine receptor polypeptide. In another embodiment, the isolated heterodimeric or multimetric soluble receptor complex disclosed above further comprises a soluble IL-2Rγ receptor polypeptide (SEQ ID NO:4) or a soluble IL-13α' receptor polypeptide (SEQ ID NO:82).

Within another aspect, the present invention provides a method of producing a soluble receptor polypeptide that form a heterodimeric or multimeric complex comprising: culturing a cell as disclosed above; and isolating the soluble receptor polypeptides produced by the cell.

Within another aspect, the present invention provides a method of producing an antibody to a soluble receptor polypeptide comprising: inoculating an animal with a soluble receptor polypeptide complex selected from the group consisting of: (a) a polypeptide comprising a homodimeric soluble receptor complex comprising SEQ ID NO:6; (b) a polypeptide comprising a soluble receptor heterodimeric or multimeric receptor complex comprising SEQ ID NO:6; (b) a polypeptide comprising a soluble receptor heterodimeric or multimeric receptor complex comprising SEQ ID NO:6, and further comprising a soluble Class I cytokine receptor polypeptide; (c) a polypeptide comprising a soluble receptor heterodimeric or multimeric receptor complex comprising SEQ ID NO:6, and further comprising a soluble IL-2Rγ receptor polypeptide (SEQ ID NO:4); (d) a polypeptide comprising a soluble receptor heterodimeric or multimeric receptor complex comprising SEQ ID NO:6, and further comprising a soluble IL-13α' receptor polypeptide (SEQ ID NO:82); and wherein the polypeptide complex elicits an immune response in the animal to produce the antibody; and isolating the antibody from the animal.

Within another aspect, the present invention provides an antibody produced by the method as disclosed above, which specifically binds to a homodimeric, heterodimeric or multimeric receptor complex comprising a soluble receptor polypeptide comprising SEQ ID NO:6. In one embodiment the antibody disclosed above is a monoclonal antibody.

Within another aspect, the present invention provides an antibody which specifically binds to a homodimeric, heterodimeric or multimeric receptor complex as disclosed above.

Within another aspect, the present invention provides a method for inhibiting a ligand comprising a polypeptide of SEQ ID NO:10 or SEQ ID NO:47, or antagonizing the ligand activity-induced proliferation of hematopoietic cells and hematopoietic cell progenitors comprising culturing bone marrow or peripheral blood cells with a composition comprising an amount of soluble receptor comprising SEQ ID NO:6 sufficient to reduce proliferation of the hematopoietic cells in the bone marrow or peripheral blood cells as compared to bone marrow or peripheral blood cells cultured in the absence of soluble receptor. In one embodiment the method is as disclosed above, wherein the hematopoietic cells and hematopoietic progenitor cells are lymphoid cells. In another embodiment the method is as disclosed above, wherein the lymphoid cells are NK cells or cytotoxic T cells.

Within another aspect, the present invention provides a method of reducing proliferation of neoplastic B or T cells comprising administering to a mammal with a B or T cell neoplasm an amount of a composition of soluble receptor comprising SEQ ID NO:6 sufficient to reduce proliferation of the neoplastic B or T cells.

Within another aspect, the present invention provides a method of suppressing an immune response in a mammal exposed to an antigen or pathogen comprising: (1) determining a level of an antigen- or pathogen-specific antibody; (2) administering a composition of soluble receptor polypeptide comprising SEQ ID NO:6 in an acceptable pharmaceutical vehicle; (3) determining a post administration level of antigen- or pathogen-specific antibody; (4) comparing the level of antibody in step (1) to the level of antibody in step (3), wherein a lack of increase or a decrease in antibody level is indicative of suppressing an immune response.

These and other aspects of the invention will become evident upon reference to the following detailed description of the invention.

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzmol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species.

Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14-17 nucleotides) can be used. PCR primers are at least 5 nucleotides in length, preferably 15 or more nt, more preferably 20-30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" is used herein to denote a cell-associated protein, or a polypeptide subunit of such a protein, that binds to a bioactive molecule (the "ligand") and mediates the effect of the ligand on the cell. Binding of ligand to receptor results in a conformational change in the receptor (and, in some cases, receptor multimerization, i.e., association of identical or different receptor subunits) that causes interactions between the effector domain(s) and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. Cell-surface cytokine receptors are characterized by a multi-domain structure as discussed in more detail below. These receptors are anchored in the cell membrane by a transmembrane domain characterized by a sequence of hydrophobic amino acid residues (typically about 21-25 residues), which is commonly flanked by positively charged residues (Lys or Arg). In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). The term "receptor polypeptide" is used to denote complete receptor polypeptide chains and portions thereof, including isolated functional domains (e.g., ligand-binding domains).

A "secretory signal sequence" is a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis. Soluble receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel heterodimeric soluble receptor protein having the structure of a class I cytokine receptor. The heterodimeric soluble receptor includes at least one zalpha11 soluble receptor subunit, disclosed in the commonly owned U.S. patent application Ser. No. 09/404,641. A second soluble receptor polypeptide included in the heterodimeric soluble receptor belongs to the receptor subfamily that includes the IL-2 γ-common receptor (IL-2Rγ, or γ$_C$), IL-2 receptor β-subunit, and the β-common receptor (i.e., IL3, IL-5, IL-13, IL-15 and GM-CSF receptor β-subunits), IL-13α, IL-13α', IL-15 receptor subunits, and the like. The soluble human and mouse zalpha11 receptor (IL-21R) monomer and homodimer was shown to antagonize of the activity of the natural ligand for the zalpha11 receptor, zalpha11 Ligand (IL-21) (Parrish-Novak, J. et al., Nature 408:57-63, 2000). The zalpha11 Ligand is disclosed in the commonly owned U.S. patent application Ser. No. 09/522,217. According to the present invention, a heterodimeric soluble zalpha11 receptor, as exemplified by a preferred embodiment of a soluble zalpha11 receptor+ soluble IL-2Rγ receptor heterodimer (zalpha11/IL-2Rγ), was shown to act as a potent antagonist of the zalpha11 Ligand. As disclosed in the examples herein, the preferred zalpha11/IL-2Rγ heterodimer was a more effective antagonist zalpha11 Ligand activity, and hence more superior antagonist, than a zalpha11 homodimer or monomer.

Moreover, also contemplated by the present invention are homodimeric and monomeric zalpha11-comprising soluble receptors; as well as homodimeric, heterodimeric, and multimeric zalpha11-comprising receptors that are capable of intracellular signaling. Such receptors can comprise at least one an extracellular domain of a zalpha11 receptor, and an intracellular domain from zalpha11 or another class I cytokine receptor. The additional heterodimeric or multimeric subunit can comprise the extracellular domain from IL-2Rγreceptor (e.g., SEQ ID NO:4), IL-13α (also known as IL-13RA2; SEQ ID NO:84), IL-13α' (also known as IL-13RA1; SEQ ID NO:82, IL-15 (SEQ ID NO:86) receptor, or other class I receptor, and an intracellular domain from zalpha11 or another class I cytokine receptor.

The nucleotide sequence of a representative zalpha11-encoding DNA is described in SEQ ID NO:1 (from nucleotide 1 to 1614), and its deduced 538 amino acid sequence is described in SEQ ID NO:2. In its entirety, the zalpha11 polypeptide (SEQ ID NO:2) represents a full-length polypeptide segment (residue 1 (Met) to residue 538 (Ser) of SEQ ID NO:2). The domains and structural features of the zalpha11 polypeptide are further described below.

Analysis of the zalpha11 polypeptide encoded by the DNA sequence of SEQ ID NO: 1 revealed an open reading frame encoding 538 amino acids (SEQ ID NO:2) comprising a predicted secretory signal peptide of 19 amino acid residues (residue 1 (Met) to residue 19 (Gly) of SEQ ID NO:2), and a mature polypeptide of 519 amino acids (residue 20 (Cys) to residue 538 (Ser) of SEQ ID NO:2). In addition to the WSXWS motif (SEQ ID NO:13) corresponding to residues 214 to 218 of SEQ ID NO:2, the receptor comprises a cytokine-binding domain of approximately 200 amino acid residues (residues 20 (Cys) to 237 (His) of SEQ ID NO:2); a domain linker (residues 120 (Pro) to 123 (Pro) of SEQ ID NO:2); a penultimate strand region (residues 192 (Lys) to 202 (Ala) of SEQ ID NO:2); a transmembrane domain (residues 238 (Leu) to 255 (Leu) of SEQ ID NO:2); complete intracellular signaling domain (residues 256 (Lys) to 538 (Ser) of SEQ ID NO:2) which contains a "Box I" signaling site (residues 267 (Ile) to 273 (Pro) of SEQ ID NO:2), and a "Box II" signaling site (residues 301 (Leu) to 304 (Gly) of SEQ ID NO:2). Moreover, there is a STAT3 binding site (YXXQ) located near the C-terminus from residues 519 (Tyr) to 522 (Gln) of SEQ ID NO:2. Those skilled in the art will recognize that these domain boundaries are approximate, and are based on alignments with known proteins and predictions of protein folding. In addition to these domains, conserved receptor features in the encoded receptor include (as shown in SEQ ID NO:2) a conserved Trp residue at position 138, and a conserved Arg residue at position 201. Moreover the zalpha11 contains conserved Cys residues typical of class I cytokine receptors, shown in residues 25, 35, 65, and 81 of SEQ ID NO:2, and corresponding regions of SEQ ID NO:6 and SEQ ID NO:69 described below. The corresponding polynucleotides encoding the zalpha11 polypeptide regions, domains, motifs, residues and sequences described above are as shown in SEQ ID NO:1. The human zalpha11 soluble receptor polypeptide, comprising residues 20 (Cys) to 237 (His) of SEQ ID NO:2, is shown in SEQ ID NO:6, and the corresponding polynucleotide sequence for the human zalpha11 soluble receptor polypeptide is shown in SEQ ID NO:5.

SEQ ID NO:3 is a polynucleotide sequence comprising a fragment of the human IL-2Rγ receptor that encodes a soluble 232 amino acid soluble IL-2Rγ receptor polypeptide (SEQ ID NO:4). Those skilled in the art will recognize that these domain boundaries for the IL-2Rγ receptor extracellular domain are approximate, and other soluble IL-2Rγ receptor polypeptides, such as those including an IL-2Rγ receptor polypeptide secretory signal sequence or additional IL-2Rγ receptor polypeptide amino acids in the extracellular domain, are encompassed within the scope of the present invention.

A variant form of the human zalpha11 polypeptide was identified (WIPO publication No. WO 00/27822 shown as SEQ ID NO:3 and SEQ ID NO:4 therein) and is shown in the DNA sequence of SEQ ID NO:64; and corresponding polypeptide sequence shown in (SEQ ID NO:65). This particular alternative zalpha11 receptor polypeptide contains 568 amino acids, and comprises a predicted secretory signal peptide of 20 amino acid residues (residue 1 (Met) to residue 20 (Gly) of SEQ ID NO:65), and a mature polypeptide of 548 amino acids (residue 21 (Met) to residue 568 (Ser) of SEQ ID NO:65). In addition to the WSXWS motif (SEQ ID NO:13) corresponding to residues 244 to 248 of SEQ ID NO:65, the receptor comprises a cytokine-binding domain of approximately 200 amino acid residues (residues 21 (Met) to 267 (His) of SEQ ID NO:65); no domain linker; a penultimate strand region (residues 222 (Lys) to 232 (Ala) of SEQ ID NO:65); a transmembrane domain (residues 268 (Leu) to 285 (Leu) of SEQ ID NO:65); complete intracellular signaling domain (residues 286 (Lys) to 568 (Ser) of SEQ ID NO:65) which contains a "Box I" signaling site (residues 297 (Ile) to 303 (Pro) of SEQ ID NO:65), and a "Box II" signaling site (residues 331 (Leu) to 334 (Gly) of SEQ ID NO:65). Moreover, there is a STAT3 binding site (YXXQ) located near the C-terminus from residues 549 (Tyr) to 552 (Gln) of SEQ ID NO:65. Those skilled in the art will recognize that these domain boundaries are approximate, and are based on alignments with known proteins and predictions of protein folding. In addition to these domains, conserved receptor features in the encoded receptor include (as shown in SEQ ID NO:65) a conserved Trp residue at position 168, and a conserved Arg residue at position 231. The corresponding polynucleotides encoding the zalpha11 polypeptide regions, domains, motifs, residues and sequences described above are as shown in SEQ ID NO:64. This particular human zalpha11 soluble receptor variant polypeptide, comprising residues 21 (Met) to 267 (His) of SEQ ID NO:65 (SEQ ID NO:69) and the corresponding polynucleotide sequence for this particular human zalpha11 soluble receptor polypeptide is shown in SEQ ID NO:68. This variant form of the human zalpha11 receptor is included in the heterodimeric and multimeric zalpha11 receptor complexes of the present invention, disclosed herein.

In addition, other variant forms of zalpha11 receptor are contemplated by the present invention, wherein the extracellular domain of the variant form disclosed above (e.g., 21 (Met) to 267 (His) of SEQ ID NO:65, or SEQ ID NO:69) comprises a domain linker comprising the amino acids PAPP (SEQ ID NO:70) inserted between amino acid 161 (Ser) and 162 (Arg) of SEQ ID NO:65, or the corresponding region of SEQ ID NO:69. A preferred domain linker comprises a sequence of amino acids from preferably 4 to 14 amino acids long, most preferably 14 amino acids long, wherein aside from the PAPP (SEQ ID NO:70) motif sequence any amino acid may be present. For example, a representative linker-containing variant zalpha11 soluble receptor is shown in SEQ ID NO:71. Moreover, other variant zalpha11 sequences can include, in reference to SEQ ID NO:65 a Gly at position 162 rather than an Arg, or the same Arg to Gly substitution in the corresponding region of SEQ ID NO:69 or SEQ ID NO:71, or other variant of SEQ ID NO:65 or SEQ ID NO:69 containing a domain linker as described above. Corresponding DNA sequences that encode such variants can be readily determined by one of skill in the art upon using the information present in Table 1 and Table 2.

The zalpha11 Ligand is a "short-helix" form secreted four-helical bundle cytokine. The zalpha11 Ligand polynucleotide sequence is shown in SEQ ID NO:9 and corresponding amino acid sequence shown in SEQ ID NO:10. The secretory signal sequence comprises amino acid residues 1 (Met) to 31 (Gly), and the mature polypeptide comprises amino acid residues 32 (Gln) to 162 (Ser) (as shown in SEQ ID NO:10). In general, cytokines are predicted to have a four-alpha helix structure, with helices A, C and D being most important in ligand-receptor interactions, and are more highly conserved among members of the family. Referring to the human zalpha11 Ligand amino acid sequence shown in SEQ ID NO:10, alignment of human zalpha11 Ligand, human IL-115, human IL-4, and human GM-CSF amino acid sequences it is predicted that zalpha11 Ligand helix A is defined by amino acid residues 41-56; helix B by amino acid residues 69-84; helix C by amino acid residues 92-105; and helix D by amino acid residues 135-148; as shown in SEQ ID NO:10. Structural analysis suggests that the A/B loop is long, the B/C loop is short and the C/D loop is parallel long. Conserved cysteine residues within zalpha11 Ligand correspond to amino acid residues 71, 78, 122 and 125 of SEQ ID NO:10. Consistent cysteine placement is further confirmation of the four-helical-bundle structure. Also highly conserved in the family comprising IL-15, IL-2, IL-4, GM-CSF and zalpha11 Ligand is the Glu-Phe-Leu sequence as shown in SEQ ID NO:10 at residues 136-138.

Further analysis of zalpha11 Ligand based on multiple alignments of known cytokines predicts that amino acid residues 44, 47 and 135 (as shown in SEQ ID NO:10) play an important role in zalpha11 Ligand binding to its cognate receptor. Based on comparison between sequences of human and murine zalpha11 Ligand well-conserved residues were found in the regions predicted to encode alpha helices A and D. The corresponding polynucleotides encoding the zalpha11 Ligand polypeptide regions, domains, motifs, residues and sequences described herein are as shown in SEQ ID NO:9. The murine zalpha11 Ligand is shown in SEQ ID NO:46, and corresponding polypeptide sequence shown in SEQ ID NO:47.

The activity of molecules of the present invention can be measured using a variety of assays that measure proliferation of and/or binding to cells expressing the zalpha11 receptor. Of particular interest are changes in zalpha11 Ligand-dependent cells. A suitable cell line was engineered to be zalpha11 Ligand-dependent that comprises an IL-3-dependent BaF3 cell line (Palacios and Steinmetz, *Cell* 41: 727-734, 1985; Mathey-Prevot et al., *Mol. Cell. Biol.* 6: 4133-4135, 1986). Moreover, other suitable cell lines to be engineered to be zalpha11 Ligand-dependent include FDC-P1 (Hapel et al., *Blood* 64: 786-790, 1984); and MO7e (Kiss et al., *Leukemia* 7: 235-240, 1993). Growth factor-dependent cell lines can be established according to published methods (e.g. Greenberger et al., *Leukemia Res.* 8: 363-375, 1984; Dexter et al., in Baum et al. Eds., *Experimental Hematology Today,* 8th Ann. Mtg. Int. Soc. Exp. Hematol. 1979, 145-156, 1980).

Zalpha11 Ligand stimulates proliferation, activation, differentiation and/or induction or inhibition of specialized cell function of cells involved homeostasis of hematopoiesis and immune function. In particular, zalpha11 Ligand polypeptides stimulate proliferation, activation, differentiation, induction or inhibition of specialized cell functions of cells of the hematopoietic lineages, including, but not limited to, T cells, B cells, NK cells, dendritic cells, monocytes, and macrophages, as well as epithelial cells. Proliferation and/or differentiation of hematopoietic cells can be measured in vitro using cultured cells or in vivo by administering zalpha11 Ligand to the appropriate animal model. Assays measuring cell proliferation or differentiation are well known in the art and described herein. For example, assays measuring proliferation include such assays as chemosensitivity to neutral red dye (Cavanaugh et al., *Investigational New Drugs* 8:347-354, 1990, incorporated herein by reference), incorporation of radiolabeled nucleotides (Cook et al., *Analytical Biochem.* 179:1-7, 1989, incorporated herein by reference), incorporation of 5-bromo-2'-deoxyuridine (BrdU) in the DNA of proliferating cells (Porstmann et al., *J. Immunol. Methods* 82:169-179, 1985, incorporated herein by reference), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988; all incorporated herein by reference). Assays measuring differentiation include, for example, measuring cell-surface markers associated with stage-specific expression of a tissue, enzymatic activity, functional activity or morphological changes (Watt, *FASEB,* 5:281-284, 1991; Francis, *Differentiation* 57:63-75, 1994; Raes, *Adv. Anim. Cell Biol. Technol. Bioprocesses,* 161-171, 1989; all incorporated herein by reference). Conversely, these assays can be used in a competition to assess the antagonist or zalpha11 Ligand binding activity of the soluble zalpha11 receptor or soluble zalpha11 heterodimeric polypeptide, such as soluble zalpha11/IL-2Rγ receptors of the present invention. Moreover, the soluble zalpha11 receptor or soluble zalpha11 heterodimeric polypeptide, such as soluble zalpha11/IL-2Rγ receptors of the present invention can be used as an antagonist or Ligand binding agent to modulate the immune system and hematopoietic activities of the zalpha11 Ligand.

Zalpha11 Ligand was isolated from tissue known to have important immunological function and which contain cells that play a role in the immune system. Zalpha11 Ligand is expressed in CD3+ selected, activated peripheral blood cells, and it has been shown that zalpha11 Ligand expression increases after T cell activation. Moreover, results of experiments described in commonly owned U.S. patent application Ser. No. 09/522,217, and the Examples section herein, demonstrate that zalpha11 Ligand has an effect on the growth/expansion and/or differentiated state of NK cells or NK progenitors. Additional evidence demonstrates that zalpha11 Ligand affects proliferation and/or differentiation of T cells and B cells in vivo. Factors that both stimulate proliferation of hematopoietic progenitors and activate mature cells are generally known. NK cells are responsive to IL-2 alone, but proliferation and activation generally require additional growth factors. For example, it has been shown that IL-7 and Steel Factor (c-kit ligand) were required for colony formation of NK progenitors. IL-15+IL-2 in combination with IL-7 and Steel Factor was more effective (Mró zek et al., *Blood* 87:2632-2640, 1996). However, unidentified cytokines may be necessary for proliferation of specific subsets of NK cells and/or NK progenitors (Robertson et. al., *Blood* 76:2451-2438, 1990). A composition comprising zalpha11 Ligand and IL-15 stimulates NK progenitors and NK cells, with evidence that this composition is more potent than previously described factors and combinations of factors. Such compositions can further comprise kit ligand or stem cell factor. Thus, the soluble zalpha11 receptor or soluble zalpha11 heterodimeric polypeptide, such as soluble zalpha11/IL-2Rγ receptors of the present invention can be used as an antagonist or Ligand binding agent to decrease the activity of the zalpha11 Ligand on NK cells.

Moreover, the tissue distribution of a receptor for a given cytokine offers a strong indication of the potential sites of action of that cytokine. Northern analysis of zalpha11 receptor revealed transcripts in human spleen, thymus, lymph node, bone marrow, and peripheral blood leukocytes. Specific cell types were identified as expressing zalpha11 receptors, and strong signals were seen in a mixed lymphocyte reaction (MLR) and in the Burkitt's lymphoma Raji. The two monocytic cell lines, THP-1 (Tsuchiya et al., *Int. J. Cancer* 26:171-176, 1980) and U937 (Sundstrom et al., *Int. J. Cancer* 17:565-577, 1976), were negative. Zalpha11 receptor is expressed at relatively high levels in the MLR, in which peripheral blood mononuclear cells (PBMNC) from two individuals are mixed, resulting in mutual activation. Detection of high levels of transcript in the MLR but not in resting T or B cell populations suggests that zalpha11 receptor expression may be induced in one or more cell types during activation. Activation of isolated populations of T and B cells can be artificially achieved by stimulating cells with PMA and Ionomycin. When sorted cells were subjected to these activation conditions, levels of zalpha11 receptor transcript increased in both cell types, supporting a role for this receptor and zalpha11 Ligand in immune responses, especially in autocrine and paracrine T and B cell expansions during activation. Zalpha11 Ligand may also play a role in the expansion of more primitive progenitors involved in lymphopoiesis. Thus, the soluble zalpha11 receptor or soluble zalpha11 heterodimeric polypeptide, such as soluble zalpha11/IL-2Rγ receptors of the present invention can be used as an antagonist or Ligand binding agent to modulate the lymphopoietic activities of the zalpha11 Ligand.

Zalpha11 receptor was found to be present at low levels in resting T and B cells, and was upregulated during activation in both cell types. Interestingly, the B cells also down-regulate the message more quickly than do T cells, suggesting that amplitude of signal and timing of quenching of signal are important for the appropriate regulation of B cell responses.

In addition, a large proportion of intestinal lamina propria cells show positive hybridization signals with zalpha11 receptor. This tissue consists of a mixed population of lymphoid cells, including activated CD4+ T cells and activated B cells. Immune dysfunction, in particular chronic activation of the mucosal immune response, plays an important role in the etiology of Crohn's disease and inflammatory bowel disease (IBD); abnormal response to and/or production of proinflammatory cytokines is also a suspected factor (Braegger et al., *Annals Allergy* 72:135-141, 1994; Sartor R B *Am. J. Gastroenterol.* 92:5 S-11S, 1997). The zalpha11 Ligand in concert with IL-15 expands NK cells from bone marrow progenitors and augments NK cell effector function. Zalpha11 Ligand also co-stimulates mature B cells stimulated with anti-CD40 antibodies, but inhibits B cell proliferation to signals through IgM. Zalpha11 Ligand enhances T cell proliferation in concert with a signal through the T cell receptor, and over expression in transgenic mice leads to lymphopenia and an expansion of monocytes and granulocytes. These pleiotropic effects of zalpha11 Ligand suggest that molecules that antagonize or bind zalpha11 Ligand, such as the molecules of the present invention, can provide therapeutic utility for a wide range of diseases arising from defects in the immune system, including (but not limited to) systemic lupus erythematosus (SLE), rheumatoid arthritis (RA), multiple sclerosis (MS), myasthenia gravis, Crohn's Disease, IBD, and diabetes. It is important to note that these diseases are the result of a complex network of immune dysfunction (SLE, for example, is the manifestation of defects in both T and B cells), and that immune cells are dependent upon interaction with one another to elicit a potent immune response. Therefore, zalpha11 Ligand (or an antagonist of the Ligand, such a molecule of the present invention) that can be used to manipulate more than one type of immune cell is an attractive therapeutic candidate for intervention at multiple stages of disease.

Similarly, the tissue distribution of the mRNA corresponding to IL-2Rγ receptor cDNA shows expression in hematopoietic and lymphoid cells including CD4+ T-cells, CD8+ T-cells, CD20+ B-cells, CD56+ NK cells, CD14+ monocytes, as well as granulocytes. IL-2Rγ receptor cDNA is generally not found in other cell types, including epithelial cells and fibroblast cells. The expression pattern of this receptor correlates with the activities of the zalpha11 Ligand and the localization of the zalpha11 receptor. Moreover, antibodies to the IL-2Rγ receptor decrease or ablate the effect of zalpha11 Ligand in B-cells and BaF3/zalpha11 receptor cells, demonstrating that the zalpha11 receptor and IL-2Rγ receptor can heterodimerize in vivo and in vitro.

The zalpha11 Ligand both promotes expansion of NK cell populations from bone marrow and regulates the proliferation of mature T and B cells in response to activating stimuli. The zalpha11 Ligand acts through a receptor complex that includes at least one zalpha11 receptor subunit and the $\gamma_C$ subunit of IL2R, even though the cytoplasmic domain of zalpha11 receptor is capable of transducing signal in a homodimeric configuration (commonly owned U.S. patent application Ser. No. 09/522,217). IL4Rα is also capable of signaling as a homodimer (Kammer, W. et al., J. Biol. Chem. 271:23634-23637, 1996), although the true functional IL4 receptor complex is a IL4Rα/$\gamma_C$ heterodimer. Signaling in BaF3/zalpha11 receptor could have resulted from interactions of the human zalpha11 receptor with endogenous murine $\gamma_C$, and Examples herein show that antibodies to the $\gamma_C$ subunit decrease zalpha11 Ligand signaling in these cells.

Moreover, the IL2 receptor has been studied in detail and is composed of an α-β-$\gamma_C$ heterotrimer. The β and $\gamma_C$ subunits are both essential for signal transduction and are members of the hematopoietin receptor superfamily (Cosman, D., *Cytokine* 5:95-106, 1993), whereas the α subunit appears to primarily be involved in high-affinity binding conversion and is structurally distinct from the hematopoietin receptor family. The $\gamma_C$ subunit has been shown to participate in forming the receptors for IL4, IL7, IL9, and IL15, in addition to IL2 (for review, see Sugamura, K., et al., *Annu. Rev. Immunol.* 14:179-205, 1996), and null mutations in the $\gamma_C$ gene have been shown to cause X-linked severe combined immunodeficiency (X—SCID) (Noguchi, M. et al., *Cell* 73:147-157, 1993).

Zalpha11 Ligand antagonism of anti-IgM and IL4-induced B cell proliferation (commonly owned U.S. patent application Ser. No. 09/522,217, and examples herein) could be due to competition for γ$_C$; however, it is clear that IL4 can signal through a γ$_C$-independent receptor (IL4Rα+IL13Rα') (Murata, T. et al., *Blood* 91:3884-3891, 1998). B cells from human SCID patients proliferate normally in response to anti-IgM and IL4 (Matthews, D. J. et al., Blood 85:38-42, 1995), and IL4 responsiveness in normal human B cells is associated with both IL13 responsiveness and levels of IL13R (Ford, D. et al., *J. Immunol.* 163:3185-3193, 1999). Similarly, Zalpha11 Ligand may signal through a heterodimeric, heterotrimeric or multimeric complex that includes zalpha11 receptor and a non-γ$_C$-subunit. As such, the present invention contemplates soluble zalpha11 receptor heterodimeric antagonists and binding agents to the zalpha11 Ligand that do not include the γ$_C$ subunit, but include an additional Class I cytokine subunit, for example, IL13Rα' and the like.

The soluble receptors of the present invention are useful as antagonists of the zalpha11 Ligand cytokine. Such antagonistic effects can be achieved by direct neutralization or binding of the zalpha11 Ligand. In addition to antagonistic uses, the soluble receptors of the present invention can bind zalpha11 Ligand and act as carrier proteins for the zalpha11 Ligand cytokine, in order to transport the Ligand to different tissues, organs, and cells within the body. As such, the soluble receptors of the present invention can be fused or coupled to molecules, polypeptides or chemical moieties that direct the soluble-receptor-Ligand complex to a specific site, such as a tissue, specific immune cell, or tumor. Thus, the soluble receptors of the present invention can be used to specifically direct the action of the zalpha11 Ligand. See, Cosman, D. *Cytokine* 5: 95-106, 1993; and Fernandez-Botran, R. *Exp. Opin. Invest. Drugs* 9:497-513, 2000.

Moreover, the soluble receptors of the present invention can be used to stabilize the zalpha11 Ligand, to increase the bio-availability, therapeutic longevity, and/or efficacy of the Ligand by stabilizing the Ligand from degradation or clearance, or by targeting the ligand to a site of action within the body. For example the naturally occurring IL-6/soluble IL-6R complex stabilizes IL-6 and can signal through the gp130 receptor. See, Cosman, D. supra., and Fernandez-Botran, R. supra.

For example, the Zalpha11 Ligand will be useful in treating tumorgenesis, and therefore would be useful in the treatment of cancer. Zalpha11 Ligand inhibits IL-4 stimulated proliferation of anti-IgM stimulated normal B-cells and a similar effect is observed in B-cell tumor lines suggesting that there may be therapeutic benefit in treating patients with the zalpha11 Ligand in order to induce the B cell tumor cells into a less proliferative state. The ligand could be administered in combination with other agents already in use including both conventional chemotherapeutic agents as well as immune modulators such as interferon alpha. Alpha/beta interferons have been shown to be effective in treating some leukemias and animal disease models, and the growth inhibitory effects of interferon-alpha and zalpha11 Ligand are additive for at least one B-cell tumor-derived cell line. Moreover, stabilization of the zalpha11 Ligand or ability to target the Ligand to specific sites of action with the soluble receptors of the present invention would be desirable in this therapeutic endeavor.

The present invention provides a method of reducing proliferation of neoplastic B or T cells comprising administering to a mammal with a B or T cell neoplasm an amount of a composition of zalpha11 Ligand antagonist, such as the soluble receptors of the present invention, sufficient to reduce proliferation of the neoplastic B or T cells. In other embodiments, the composition can comprise at least one other cytokine selected from the group consisting of IL-2, IL-15, IL-4, GM-CSF, Flt3 ligand or stem cell factor. Furthermore, the zalpha11 Ligand antagonist can be a toxic fusion. Similarly, soluble receptor-toxic fusions and soluble receptors of the present invention can be used to reduce proliferation of lymphoid and hematopoietic neoplasms that over-express or grow in response to zalpha11 Ligand. Moreover, indirect effects of the soluble receptors of the present invention can modulate NK cell function induced by zalpha11 Ligand, and hence indirectly enhance tumor cell killing.

The present invention provides polynucleotide molecules, including DNA and RNA molecules that encode the heterodimeric zalpha11 receptor polypeptides disclosed herein. Those skilled in the art will recognize that, in view of the degeneracy of the genetic code, considerable sequence variation is possible among these polynucleotide molecules. SEQ ID NO:7 is a degenerate DNA sequence that encompasses all DNAs that encode the soluble zalpha11 receptor polypeptide of SEQ ID NO:6. SEQ ID NO:66 is a degenerate DNA sequence that encompasses all DNAs that encode the soluble zalpha11 receptor polypeptide of SEQ ID NO:69. SEQ ID NO:8 is a degenerate DNA sequence that encompasses all DNAs that encode the soluble human IL-2Rγ polypeptide of SEQ ID NO:4. Those skilled in the art will recognize that the degenerate sequence of SEQ ID NO:7, SEQ ID NO:66 and SEQ ID NO:8 also provide all RNA sequences encoding SEQ ID NO:6, SEQ ID NO:69 and SEQ ID NO:4 respectively by substituting U for T. Thus, zalpha11 polypeptide-encoding polynucleotides comprising nucleotide 1 to nucleotide 654 of SEQ ID NO:7 or comprising nucleotide 1 to nucleotide 741 of SEQ ID NO:66, soluble human IL-2Rγ polypeptide-encoding polynucleotides comprising nucleotide 1 to nucleotide 696 of SEQ ID NO:8, and their RNA equivalents are contemplated by the present invention. Table 1 sets forth the one-letter codes used within SEQ ID NO:7, SEQ ID NO:66 and SEQ ID NO:8 to denote degenerate nucleotide positions. "Resolutions" are the nucleotides denoted by a code letter. "Complement" indicates the code for the complementary nucleotide (s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:7, SEQ ID NO:66 and SEQ ID NO:8 encompass all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:6, SEQ ID NO:69 or SEQ ID NO:4. Variant sequences can be readily tested for functionality as described herein.

One of ordinary skill in the art will also appreciate that different species can exhibit "preferential codon usage." In general, see, Grantham, et al., *Nuc. Acids Res.* 8:1893-912, 1980; Haas, et al. *Curr. Biol.* 6:315-24, 1996; Wain-Hobson, et al., *Gene* 13:355-64, 1981; Grosjean and Fiers, *Gene* 18:199-209, 1982; Holm, *Nuc. Acids Res.* 14:3075-87, 1986; Ikemura, *J. Mol. Biol.* 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:7, SEQ ID NO:66 and SEQ ID NO:8 serves as a template for optimizing expression of polynucleotides and polypeptides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:5, SEQ ID NO:68 or SEQ ID NO:3, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Numerous equations for calculating $T_m$ are known in the art, and are specific for DNA, RNA and DNA-RNA hybrids and polynucleotide probe sequences of varying length (see, for example, Sambrook et al, *Molecular Cloning: A Laboratory Manual*, Second Edition (Cold Spring Harbor Press 1989); Ausubel et at., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating $T_m$ based on user-defined criteria. Such programs can also analyze a given sequence under defined conditions and identify suitable probe sequences. Typically, hybridization of longer polynucleotide sequences (e.g., >50 base pairs) is performed at temperatures of about 20-25° C. below the calculated $T_m$. For smaller probes (e.g., <50 base pairs) hybridization is typically carried out at the $T_m$ or 5-10° C. below. This allows for the maximum rate of hybridization for DNA-DNA and DNA-RNA hybrids. Higher degrees of stringency at lower temperatures can be achieved with the addition of formamide which reduces the $T_m$ of the hybrid about 1° C. for each 1% formamide in the buffer solution. Suitable stringent hybridization conditions are equivalent to about a 5 h to overnight incubation at about 42° C. in a solution comprising: about 40-50% formamide, up to about 6×SSC, about 5×Denhardt's solution, zero up to about 10% dextran sulfate, and about 10-20 µg/ml denatured commercially-available carrier DNA. Generally, such stringent conditions include temperatures of 20-70° C. and a hybridization buffer containing up to 6×SSC and 0-50% formamide; hybridization is then followed by washing filters in up to about 2×SSC. For example, a suitable wash stringency is equivalent to 0.1×SSC to 2×SSC, 0.1% SDS, at 55°

C. to 65° C. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes. Stringent hybridization and wash conditions depend on the length of the probe, reflected in the Tm, hybridization and wash solutions used, and are routinely determined empirically by one of skill in the art.

As previously noted, the isolated polynucleotides of the present invention include DNA and RNA. Methods for preparing DNA and RNA are well known in the art. In general, RNA is isolated from a tissue or cell that produces large amounts of zalpha11 receptor RNA or the RNA for the heterodimeric component of the receptor, such as IL-2Rγ, or other class I cytokine receptor. Such tissues and cells are identified by Northern blotting (Thomas, *Proc. Natl. Acad. Sci. USA* 77:5201, 1980), and include PBLs, spleen, thymus, and lymph tissues, Raji cells, human erythroleukemia cell lines (e.g., TF-1), acute monocytic leukemia cell lines, other lymphoid and hematopoietic cell lines, and the like, for the zalpha11 receptor. RNA for a heterodimeric component of the receptor, such as IL-2Rγ, or other class I cytokine receptor can be isolated from lymphoid cells, such as those described above, and other cells and tissues as is known in the art for these receptors. Total RNA can be prepared using guanidinium isothiocyanate extraction followed by isolation by centrifugation in a CsCl gradient (Chirgwin et al., *Biochemistry* 18:52-94, 1979). Poly (A)+ RNA is prepared from total RNA using the method of Aviv and Leder (*Proc. Natl. Acad. Sci. USA* 69:1408-12, 1972). Complementary DNA (cDNA) is prepared from poly(A)+ RNA using known methods. In the alternative, genomic DNA can be isolated. Polynucleotides encoding zalpha11 polypeptides are then identified and isolated by, for example, hybridization or polymerase chain reaction (PCR) (Mullis, U.S. Pat. No. 4,683,202).

The polynucleotides of the present invention can also be synthesized using DNA synthesis machines. Currently the method of choice is the phosphoramidite method. If chemically synthesized double stranded DNA is required for an application such as the synthesis of a gene or a gene fragment, then each complementary strand is made separately. The production of short polynucleotides (60 to 80 bp) is technically straightforward and can be accomplished by synthesizing the complementary strands and then annealing them. However, for producing longer polynucleotides (>300 bp), special strategies are usually employed, because the coupling efficiency of each cycle during chemical DNA synthesis is seldom 100%. To overcome this problem, synthetic genes (double-stranded) are assembled in modular form from single-stranded fragments that are from 20 to 100 nucleotides in length.

An alternative way to prepare a full-length gene is to synthesize a specified set of overlapping oligonucleotides (40 to 100 nucleotides). After the 3' and 5' short overlapping complementary regions (6 to 10 nucleotides) are annealed, large gaps still remain, but the short base-paired regions are both long enough and stable enough to hold the structure together. The gaps are filled and the DNA duplex is completed via enzymatic DNA synthesis by *E. coli* DNA polymerase I. After the enzymatic synthesis is completed, the nicks are sealed with T4 DNA ligase. Double-stranded constructs are sequentially linked to one another to form the entire gene sequence which is verified by DNA sequence analysis. See Glick and Pasternak, *Molecular Biotechnology, Principles & Applications of Recombinant DNA*, (ASM Press, Washington, D.C. 1994); Itakura et al., *Annu. Rev. Biochem.* 53: 323-56, 1984 and Climie et al., *Proc. Natl. Acad. Sci. USA* 87:633-7, 1990. Moreover, other sequences are generally added that contain signals for proper initiation and termination of transcription and translation.

The present invention further provides counterpart polypeptides and polynucleotides from other species (orthologs). These species include, but are not limited to mammalian, avian, amphibian, reptile, fish, insect and other vertebrate and invertebrate species. Of particular interest are heterodimeric soluble receptor complexes combining soluble zalpha11 receptor and soluble human IL-2Rγ or other soluble Class I cytokine receptor polypeptides from other mammalian species, including murine, porcine, ovine, bovine, canine, feline, equine, and other primate polypeptides. Known and unknown orthologs of human soluble zalpha11 receptor and soluble human IL-2Rγ or other soluble Class I cytokine receptors can be cloned using information and compositions provided by the present invention in combination with conventional cloning techniques. For example, a cDNA can be cloned using mRNA obtained from a tissue or cell type, such as lymphoid cells, that expresses zalpha11receptor, human IL-2Rγ or other Class I cytokine receptors. Moreover, suitable sources of mRNA can be identified by probing Northern blots with probes designed from the sequences disclosed herein. A library is then prepared from mRNA of a positive tissue or cell line. A zalpha11-encoding cDNA can then be isolated by a variety of methods, such as by probing with a complete or partial human cDNA or with one or more sets of degenerate probes based on the disclosed sequences. A cDNA can also be cloned using PCR (Mullis, supra.), using primers designed from the representative human zalpha11 sequence, or soluble human IL-2Rγ sequence, disclosed herein. Within an additional method, cDNA library can be used to transform or transfect host cells, and expression of the cDNA of interest can be detected with an antibody to zalpha11 polypeptide. Similar techniques can also be applied to the isolation of genomic clones.

Cytokine receptor subunits are characterized by a multi-domain structure comprising an extracellular domain, a transmembrane domain that anchors the polypeptide in the cell membrane, and an intracellular domain. The extracellular domain of the zalpha11 receptor is a ligand-binding domain, that binds zalpha11 Ligand, and the intracellular domain is an effector domain involved in signal transduction, although ligand-binding and effector functions can reside on separate subunits of a multimeric receptor. The ligand-binding domain may itself be a multi-domain structure. Multimeric receptors include homodimers (e.g., PDGF receptor αα and ββ isoforms, erythropoietin receptor, MPL, and G-CSF receptor), heterodimers whose subunits each have ligand-binding and effector domains (e.g., PDGF receptor αβ isoform), and multimers having component subunits with disparate functions (e.g., IL-2, IL-3, IL-4, IL-5, IL-6, IL-7, IL-13, IL-15 and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of their structure and function. Hematopoietic receptors, for example, are characterized by the presence of a domain containing conserved cysteine residues and the WSXWS motif (SEQ ID NO:13). Cytokine receptor structure has been reviewed by Urdal, *Ann. Reports Med. Chem.* 26:221-228, 1991; and Cosman, *Cytokine* 5:95-106, 1993. Under selective pressure for organisms to acquire new biological functions, new receptor family members likely arise from duplication of existing receptor genes leading to the existence of multi-gene families. Family members thus contain vestiges of the ancestral gene, and these characteristic features can be exploited in the isolation and identification of additional family members. Thus, the cytokine receptor superfamily is subdivided into several families, for example, the immunoglobulin family (including CSF-1, MGF, IL-1, and PDGF receptors); the hematopoietin family (including IL-2 receptor β-subunit, GM-CSF receptor α-subunit, GM-CSF receptor β-subunit; and G-CSF, EPO, IL-3, IL-4, IL-5, IL-6, IL-7, IL-9, IL-13 and IL-15 receptors); TNF receptor family (including TNF (p80) TNF (p60) receptors, CD27, CD30, CD40, Fas, and NGF receptor).

Analysis of the zalpha11 receptor sequence suggests that it is a member of the same receptor subfamily as the IL-2 receptor β-subunit, IL-4, and IL-9, receptors. Certain receptors in this subfamily (e.g., EPO-R or MPL) associate to form homodimers that transduce a signal. Other members of the subfamily (e.g., IL-6, IL-11, and LIF receptors) combine with a second subunit (termed a β-subunit) to bind ligand and transduce a signal. Specific β-subunits associate with a plurality of specific cytokine receptor subunits. For example, the β-subunit gp130 (Hibi et al., *Cell* 63:1149-1157, 1990) associates with receptor subunits specific for IL-6, IL-11, and LIF (Gearing et al., *EMBO J.* 10:2839-2848, 1991; Gearing et al., U.S. Pat. No. 5,284,755). Oncostatin M binds to a heterodimer of LIF receptor and gp130. CNTF binds to trimeric receptors comprising CNTF receptor, LIF receptor, and gp130 subunits. Moreover, IL-4 and IL-13 elicit responses through the IL-4 and IL-13 receptors by acting upon various functional heterodimeric receptor complexes, e.g. with and without the $\gamma_C$ subunit, and such heterodimeric receptor complexes may affect whether the cytokines act upon hematopoietic or non-hematopoietic cells (Andersson, A. et al., *Eur. J. Immunol.* 27:1762-1768, 1997; Murata, T. et al., *Blood* 10:3884-3891, 1998). Moreover, binding affinity of IL-4 on its receptor is increased when the $\gamma_C$ subunit of the IL4R complex is replaced by an IL-13Rα' subunit (Murata, T. et al., supra.). Thus, the soluble receptors of the present invention include zalpha11 receptor homodimers; and heterodimers that have a zalpha11 receptor component, such as soluble zalpha11/IL-2Rγ or soluble zalpha11 receptor heterodimerized with another soluble Class I cytokine receptor, such as IL-13Rα (SEQ ID NO:84), IL-13Rα' (SEQ ID NO:82) or an IL-15 (SEQ ID NO:86) receptor subunit.

For example, suitable Class I cytokine soluble receptors that can heterodimerize with a soluble zalpha11 receptor component (e.g., SEQ ID NO:6), include a soluble receptor for IL-13Rα as shown in SEQ ID NO:84, IL-13Rα as shown in SEQ ID NO:82, or IL-15 as shown in SEQ ID NO:86. Moreover, functional sub-fragments, such as minimal cytokine binding fragments, of these Class I cytokine soluble receptors can be used. Such functional fragments include 1 to 322, 7 to 322, and 105 to 322 of SEQ ID NO:82; 1 to 317, 10 to 317, and 105 to 317 of SEQ ID NO:84; and 1 to 173 of SEQ ID NO:86. The corresponding polynucleotide sequences are as shown in SEQ ID NO:81, SEQ ID NO:83 and SEQ ID NO:85 respectively. It is well within the level of one of skill in the art to delineate what sequences of a known class I cytokine sequence comprise the extracellular cytokine binding domain free of a transmembrane domain and intracellular domain.

A polynucleotide sequence for the mouse ortholog of human zalpha11 receptor has been identified and is shown in SEQ ID NO:11 and the corresponding amino acid sequence shown in SEQ ID NO:12. Analysis of the mouse zalpha11 polypeptide encoded by the DNA sequence of SEQ ID NO:11 revealed an open reading frame encoding 529 amino acids (SEQ ID NO:12) comprising a predicted secretory signal peptide of 19 amino acid residues (residue 1 (Met) to residue 19 (Ser) of SEQ ID NO:12), and a mature polypeptide of 510 amino acids (residue 20 (Cys) to residue 529 (Ser) of SEQ ID NO:2). In addition to the WSXWS motif (SEQ ID NO:13) corresponding to residues 214 to 218 of SEQ ID NO:12, the receptor comprises a cytokine-binding domain of approximately 200 amino acid residues (residues 20 (Cys) to 237 (His) of SEQ ID NO:12); a domain linker (residues 120 (Pro) to 123 (Pro) of SEQ ID NO:12); a penultimate strand region (residues 192 (Lys) to 202 (Ala) of SEQ ID NO:12); a transmembrane domain (residues 238 (Met) to 254 (Leu) of SEQ ID NO:12); complete intracellular signaling domain (residues 255 (Lys) to 529 (Ser) of SEQ ID NO:12) which contains a "Box I" signaling site (residues 266 (Ile) to 273 (Pro) of SEQ ID NO:12), and a "Box II" signaling site (residues 301 (Ile) to 304 (Val) of SEQ ID NO:2). A comparison of the human and mouse amino acid sequences reveals that both the human and orthologous polypeptides contain corresponding structural features described above. The mature sequence for the mouse zalpha11 begins at $Cys_{20}$ (as shown in SEQ ID NO:12), which corresponds to $Cys_{20}$ (as shown in SEQ ID NO:2) in the human sequence. There is about 69% identity a between the mouse and human zalpha11 sequences over the extracellular cytokine binding domain corresponding to residues 20 (Cys) to 237 (His) of SEQ ID NO:2 (SEQ ID NO:6) and residues 20 (Cys) to 237 (His) of SEQ ID NO:12. The above percent identities were determined using a FASTA program with ktup=1, gap opening penalty=12, gap extension penalty=2, and substitution matrix=BLOSUM62, with other FASTA program parameters set as default. The corresponding polynucleotides encoding the mouse zalpha11 polypeptide regions, domains, motifs, residues and sequences described above are as shown in SEQ ID NO:11.

The present invention also provides for a heterodimeric soluble receptor, wherein the isolated soluble zalpha11 receptor polypeptide therein is substantially similar to the polypeptides of SEQ ID NO:6 and their orthologs. Moreover, in a preferred embodiment, the present invention also provides for a heterodimeric soluble receptor, wherein an isolated soluble IL-2Rγ receptor polypeptide therein is substantially similar to the polypeptides of SEQ ID NO:4 and their orthologs. The term "substantially similar" is used herein to denote polypeptides having at least 70%, more preferably at least 80%, sequence identity to the sequences shown in SEQ ID NO:6 or their orthologs. Such polypeptides will more preferably be at least 90% identical, and most preferably 95% or more identical to SEQ ID NO:6 or SEQ ID NO:4 their orthologs.) Percent sequence identity is determined by conventional methods. See, for example, Altschul et al., *Bull. Math. Bio.* 48: 603-616, 1986 and Henikoff and Henikoff, *Proc. Natl. Acad. Sci. USA* 89:10915-10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{\left[\begin{array}{c}\text{length of the longer sequence plus}\\ \text{the number of gaps introduced into}\\ \text{the longer sequence in order to align}\\ \text{the two sequences}\end{array}\right]} \times 100$$

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zsig57. The FASTA algorithm is described by Pearson and Lipman, Proc. Nat'l Acad. Sci. USA 85:2444 (1988), and by Pearson, Meth. Enzmol. 183:63 (1990).

Briefly, FASTA first characterizes sequence similarity by identifying regions shared by the query sequence (e.g., SEQ ID NO:6) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Preferred program parameters for FASTA analysis are: ktup=1, gap opening penalty=10, gap extension penalty=1, and substitution matrix=BLOSUM62, with other parameters set as default. These FASTA program parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other program parameters set as default.

The BLOSUM62 table (Table 3) is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed below), the language "conservative amino acid substitution" preferably refers to a substitution represented by a BLOSUM62 value of greater than -1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Variant zalpha11 polypeptides or substantially homologous zalpha11 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag. The present invention thus includes zalpha11 soluble receptor polypeptides of from about 190 to about 245 amino acid residues that comprise a sequence that is at least 80%, preferably at least 90%, and more preferably 95% or more identical to the corresponding region of SEQ ID NO:6. Polypeptides comprising affinity tags can further comprise a proteolytic cleavage site between the zalpha11 polypeptide and the affinity tag. Suitable sites include thrombin cleavage sites and factor Xa cleavage sites.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions and related multimeric proteins comprising one or more polypeptide fusions. For example, a soluble zalpha11 receptor or soluble zalpha11 heterodimeric polypeptide, such as soluble zalpha11/IL-2Rγ can be prepared as a fusion to a dimerizing protein as disclosed in U.S. Pat. Nos. 5,155,027 and 5,567,584. Preferred dimerizing proteins in this regard include immunoglobulin constant region domains, e.g., IgGγ1, and the human κ light chain. Immunoglobulin-soluble zalpha11 receptor or immunoglobulin-soluble zalpha11 heterodimeric polypeptide, such as immunoglobulin-soluble zalpha11/IL-2Rγ fusions can be expressed in genetically engineered cells to produce a variety of multimeric zalpha11 receptor analogs. Auxiliary domains can be fused to soluble zalpha11 receptor or soluble zalpha11 heterodimeric polypeptide, such as soluble zalpha11/IL-2Rγ to target them to specific cells, tissues, or macromolecules (e.g., collagen, or cells expressing the zalpha11 Ligand). A zalpha11 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* oocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for zalpha11 amino acid residues.

Essential amino acids in the polypeptides of the present invention can be identified according to procedures known in the art, such as site-directed mutagenesis or alanine-scanning mutagenesis (Cunningham and Wells, *Science* 244: 1081-5, 1989; Bass et al., *Proc. Natl. Acad. Sci. USA* 88:4498-502, 1991). In the latter technique, single alanine mutations are introduced at every residue in the molecule, and the resultant mutant molecules are tested for biological activity (e.g. ligand binding and signal transduction) as disclosed below to identify amino acid residues that are critical to the activity of the molecule. See also, Hilton et al., *J. Biol. Chem.* 271:4699-4708, 1996. Sites of ligand-receptor, protein-protein or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-312, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related receptors.

Determination of amino acid residues that are within regions or domains that are critical to maintaining structural integrity can be determined. Within these regions one can determine specific residues that will be more or less tolerant of change and maintain the overall tertiary structure of the molecule. Methods for analyzing sequence structure include, but are not limited to, alignment of multiple sequences with high amino acid or nucleotide identity and computer analysis using available software (e.g., the Insight II® viewer and homology modeling tools; MSI, San Diego, Calif.), secondary structure propensities, binary patterns, complementary packing and buried polar interactions (Barton, *Current Opin. Struct. Biol.* 5:372-376, 1995; and, Cordes et al., *Current Opin. Struct. Biol.* 6:3-10, 1996). In general, when designing modifications to molecules or identifying specific fragments determination of structure will be accompanied by evaluating activity of modified molecules.

Amino acid sequence changes are made in soluble zalpha11 receptor or soluble zalpha11 heterodimeric polypeptide, such as soluble zalpha11/IL-2Rγ, so as to minimize disruption of higher order structure essential to biological activity. For example, where the soluble zalpha11 receptor or soluble zalpha11 heterodimeric polypeptide, such as soluble zalpha11/IL-2Rγ comprises one or more helices, changes in amino acid residues will be made so as not to disrupt the helix geometry and other components of the molecule where changes in conformation abate some critical function, for example, binding of the molecule to the zalpha11 Ligand, or antagonizing zalpha11 Ligand activity. The effects of amino acid sequence changes can be predicted by, for example, computer modeling as disclosed above or determined by analysis of crystal structure (see, e.g., Lapthorn et al., *Nat. Struct. Biol.* 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same disulfide bonding pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance MR), digestive peptide mapping and epitope mapping are also known methods for analyzing folding and structural similarities between proteins and polypeptides (Schaanan et al., *Science* 257:961-964, 1992).

A Hopp/Woods hydrophilicity profile of the zalpha11 protein sequence as shown in SEQ ID NO:6 can be generated (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. For example, in the soluble zalpha11 receptor, hydrophilic regions include amino acid residues 55 through 60 of SEQ ID NO:2, amino acid residues 56 through 61 of SEQ ID NO:2, amino acid residues 139 through 144 of SEQ ID NO: 2, and amino acid residues 227 through 232 of SEQ ID NO:2. The corresponding hydrophilic regions in reference to SEQ ID NO:6 can be made with cross-reference to the above amino acid residues of SEQ ID NO:2.

Those skilled in the art will recognize that hydrophilicity or hydrophobicity will be taken into account when designing modifications in the amino acid sequence of a soluble zalpha11 receptor or soluble zalpha11 heterodimeric polypeptide, such as soluble zalpha11/IL-2Rγ, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include such residues as shown in SEQ ID NO:6, SEQ ID NO:69 and SEQ ID NO:4. However, Cysteine residues could be relatively intolerant of substitution.

The identities of essential amino acids can also be inferred from analysis of sequence similarity between Class I cytokine receptor family members with soluble zalpha11 receptor or soluble IL-2Rγ receptor. Using methods such as "FASTA" analysis described previously, regions of high similarity are identified within a family of proteins and used to analyze amino acid sequence for conserved regions. An alternative approach to identifying a variant extracellular domain zalpha11 polynucleotide on the basis of structure is to determine whether a nucleic acid molecule encoding a potential variant zalpha11 polynucleotide can hybridize to a nucleic acid molecule having the nucleotide sequence of SEQ ID NO:5, or SEQ ID NO:68 as discussed above. Likewise, variants of soluble class I cytokine receptor contained within a zalpha11 heterodimeric polypeptide, such as the soluble IL-2Rγ receptor component in soluble zalpha11/IL-2Rγ, can be identified as described above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al, *J. Biol. Chem.* 271:4699 (1996).

The present invention also includes functional fragments of soluble zalpha11 receptor polypeptides or soluble zalpha11 heterodimeric polypeptide, such as soluble zalpha11/IL-2Rγ polypeptides and nucleic acid molecules encoding such functional fragments. A "functional" soluble zalpha11 receptor polypeptide or soluble zalpha11 heterodimeric polypeptide, such as soluble zalpha11/IL-2Rγ polypeptide, or fragment thereof defined herein is characterized by its by its ability to bind to an anti-zalpha11 antibody, or to zalpha11 Ligand (either soluble or immobilized), or to antagonize zalpha11 Ligand activity in, for example, a biological or binding assay. As previously described herein, zalpha11 receptor is characterized by a class I cytokine receptor structure. Thus, the present invention further provides fusion proteins encompassing: (a) homodimeric or multimeric polypeptide molecules comprising an extracellular domain described herein; and (b) functional fragments comprising one or more of these domains. The other polypeptide portion of the fusion protein may be contributed by another class I cytokine receptor, for example, IL-2Rγ, IL-2 receptor β-subunit and the β-common receptor (i.e., IL3, IL-5, and GM-CSF receptor β-subunits), IL-13α, IL-13α', or IL-15 receptor subunits, or by a non-native and/or an unrelated secretory signal peptide that facilitates secretion of the soluble fusion protein.

Routine deletion analyses of nucleic acid molecules can be performed to obtain functional fragments of a nucleic acid molecule that encode a soluble zalpha11 receptor or soluble zalpha11 heterodimeric polypeptide, such as soluble zalpha11/IL-2Rγ. As an illustration, DNA molecules having the nucleotide sequence of SEQ ID NO:1 or fragments thereof, can be digested with Bal31 nuclease to obtain a series of nested deletions. These DNA fragments are then inserted into expression vectors in proper reading frame, and the expressed polypeptides are isolated and tested for antagonizing zalpha11 Ligand biological or zalpha11 Ligand binding activity; or for the ability to bind anti-soluble zalpha11 receptor or anti-soluble zalpha11 heterodimeric polypeptide antibodies; or for the ability to bind zalpha11 Ligand. One alternative to exonuclease digestion is to use oligonucleotide-directed mutagenesis to introduce deletions or stop codons to specify production of a desired polypeptide fragment. Alternatively, particular fragments of a soluble zalpha11 receptor or soluble zalpha11 heterodimeric polypeptide polynucleotide can be synthesized using the polymerase chain reaction.

Standard methods for identifying functional domains, such as Ligand binding domains, are routine for those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993); Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987); Herschman, "The EGF Receptor," in *Control of Animal Cell Proliferation* 1, Boynton et al., (eds.) pages 169-199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

Multiple amino acid substitutions can be made and tested using known methods of mutagenesis and screening, such as those disclosed by Reidhaar-Olson and Sauer (*Science* 241:53-57, 1988) or Bowie and Sauer (*Proc. Natl. Acad. Sci. USA* 86:2152-2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-10837, 1991; Ladner et al., U.S. Pat. No. 5,223,409; Huse, WIPO Publication WO 92/062045) and region-directed mutagenesis (Derbyshire et al., *Gene* 46:145, 1986; Ner et al., *DNA* 7:127, 1988).

Variants of the disclosed soluble zalpha11 receptor or soluble zalpha11 heterodimeric polypeptide DNA and polypeptide sequences can be generated through DNA shuffling as disclosed by Stemmer, *Nature* 370:389-91, 1994, Stemmer, *Proc. Natl. Acad. Sci. USA* 91:10747-51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect zalpha11 Ligand antagonist or binding activity in host cells of cloned, mutagenized soluble zalpha11 receptor or soluble zalpha11 heterodimeric receptor polypeptides. Preferred assays in this regard include cell proliferation assays and biosensor-based ligand-binding assays, which are described below and in the Examples. Mutagenized DNA molecules that encode active receptors or portions thereof (e.g., ligand-binding fragments, and the like) can be recovered from the host cells and rapidly sequenced using modern equipment. These methods allow the rapid determination of the importance of individual amino acid residues in a polypeptide of interest, and can be applied to polypeptides of unknown structure.

The present invention thus provides a series of novel, hybrid molecules in which a segment comprising one or more of the domains of soluble zalpha11 receptor is fused to another soluble receptor polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides.

Using the methods discussed herein, one of ordinary skill in the art can identify and/or prepare a variety of polypeptide fragments or variants of SEQ ID NO:6 that retain zalpha11 Ligand binding or antagonist activity. For example, one can make a zalpha11 soluble receptor by preparing a variety of polypeptides that are substantially homologous to the cytokine-binding domain (residues 20 (Cys) to 237 (His) of SEQ ID NO:2 (SEQ ID NO:6), or a subsequence therein that binds zalpha11 Ligand, or allelic variants or species orthologs thereof) and retain ligand-binding activity of the wild-type zalpha11 protein. Such polypeptides may include additional amino acids from, for example, part or all of the signal peptide sequence, transmembrane and intracellular domains. Such polypeptides may also include additional polypeptide segments as generally disclosed herein such as labels, affinity tags, and the like. Similarly, one of ordinary skill in the art can identify and/or prepare a variety of polypeptide fragments or variants of SEQ ID NO:4, or other soluble class I cytokine receptors that form heterodimers with zalpha11 receptor.

For any soluble zalpha11 receptor polypeptide, including variants, and fusion polypeptides or proteins, one of ordinary skill in the art can readily generate a fully degenerate polynucleotide sequence encoding that variant using the information set forth in Tables 1 and 2 above.

The soluble zalpha11 receptor or soluble zalpha11 heterodimeric receptor polypeptides of the present invention, including full-length soluble receptor polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual,* 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zalpha11 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a soluble zalpha11 receptor or soluble zalpha11 heterodimeric polypeptide, such as soluble zalpha11/IL-2Rγ into the secretory pathway of a host cell, a secretory signal sequence (also known as a leader sequence, prepro sequence or pre sequence) is provided in the expression vector. The secretory signal sequence may be that of zalpha11 receptor disclosed herein, the IL-2Rγ (amino acid 1 (Met) to 22 (Gly) of SEQ ID NO:18), or may be derived from another secreted protein (e.g., t-PA) or synthesized de novo. The secretory signal sequence is operably linked to the zalpha11 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980-90, 1989; Wang and Finer, *Nature Med.* 2:714-716, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus (CMV). See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting, flow cytometry, or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant zalpha11 baculovirus utilizes a transposon-based system described by Luckow (Luckow, V. A, et al., *J Virol* 67:4566-79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zalpha11 polypeptide into a baculovirus genome maintained in *E. coli* as a large plasmid called a "bacmid." See, Hill-Perkins, M. S, and Possee, R. D., *J Gen Virol* 71:971-6, 1990; Bonning, B. C. et al., *J Gen Virol* 75:1551-6, 1994; and, Chazenbalk, G. D., and Rapoport, B., *J Biol Chem* 270:1543-9, 1995. In addition, transfer vectors can include an in-frame fusion with DNA encoding an epitope tag at the C- or N-terminus of the expressed zalpha11 polypeptide, for example, a Glu-Glu epitope tag (Grussenmeyer, T. et al., *Proc. Natl. Acad. Sci.* 82:7952-4, 1985). Using a technique known in the art, a transfer vector containing zalpha11 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zalpha11 is subsequently produced. Recombinant viral stocks are made by methods commonly used in the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. Procedures used are generally described in available laboratory manuals (King, L. A. and Possee, R. D., ibid.; O'Reilly, D. R. et al., ibid.; Richardson, C. D., ibid.). Subsequent purification of the zalpha11 polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459-3465, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli*, *Bacillus* and other genera are also useful host cells within the present invention. Techniques for transforming these hosts and expressing foreign DNA sequences cloned therein are well known in the art (see, e.g., Sambrook et al., ibid.). When expressing a zalpha11 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Mammalian cells suitable for use in assaying antagonist activity of the novel soluble receptors of the present invention express a zalpha11 receptor or receptor fusion capable of signaling and transducing a receptor-mediated signal of the zalpha11 Ligand. Such cells include cells that express a β-subunit, such as gp130, IL-2Rγ and cells that co-express receptors (Gearing et al., *EMBO J.* 10:2839-2848, 1991; Gearing et al., U.S. Pat. No. 5,284,755). In this regard it is generally preferred to employ a cell that is responsive to other cytokines that bind to receptors in the same subfamily, such as IL-6 or LIF, because such cells will contain the requisite signal transduction pathway(s). Preferred cells of this type include the human TF-1 cell line (ATCC number CRL-2003) and the DA-1 cell line (Branch et al., *Blood* 69:1782, 1987; Broudy et al., *Blood* 75:1622-1626, 1990). In the alternative, suitable host cells can be engineered to produce a β-subunit or other cellular component needed for the desired cellular response. For example, the murine cell line BaF3 (Palacios and Steinmetz, *Cell* 41:727-734, 1985; Mathey-Prevot et al., *Mol. Cell. Biol.* 6: 4133-4135, 1986) has been used to produce a cell line responsive to the zalpha11 Ligand (see Examples).

Other such lines include a baby hamster kidney (BHK) cell line, or the CTLL-2 cell line (ATCC TIB-214) can be transfected to express an IL-2Rγ subunit in addition to zalpha11 receptor. It is generally preferred to use a host cell and receptor(s) from the same species, however this approach allows cell lines to be engineered to express multiple receptor subunits from any species, thereby overcoming potential limitations arising from species specificity. In the alternative, species homologs of the human receptor cDNA can be cloned and used within cell lines from the same species, such as a mouse cDNA in the BaF3 cell line. Cell lines that are dependent upon one hematopoietic growth factor, such as IL-3, can thus be engineered to become dependent upon a zalpha11 ligand. Such cells can be used as described herein in the presence of zalpha11 Ligand to assess the antagonist activity of soluble zalpha11 receptor or soluble zalpha11 heterodimeric polypeptide, such as soluble zalpha11/IL-2Rγ on zalpha11 Ligand signaling and proliferative activity.

Cells expressing functional soluble zalpha11 receptor or soluble zalpha11 heterodimeric polypeptide, such as soluble zalpha11/IL-2Rγ are used within screening assays. A variety of suitable assays are known in the art. These assays are based on the detection of a biological response in the target cell to the zalpha11 Ligand in the presence or absence of the soluble receptors of the present invention. One such assay is a cell proliferation assay. Cells are cultured in the presence or absence of zalpha11 Ligand with or without the addition other cytokines or proliferative agents, and cell proliferation is detected by, for example, measuring incorporation of tritiated thymidine or by colorimetric assay based on the metabolic breakdown of Alamar Blue™ (AccuMed, Chicago, Ill.) or 3-(4,5-dimethylthiazol-2-yl)-2,5-diphenyl tetrazolium bromide (MTT) (Mosman, *J. Immunol. Meth.* 65: 55-63, 1983). An alternative assay format uses cells that are further engineered to express a reporter gene. The reporter gene is linked to a promoter element that is responsive to the receptor-linked pathway, and the assay detects activation of transcription of the reporter gene. DNA response elements can include, but are not limited to, cyclic AMP response elements (CRE), hormone response elements (HRE) insulin response element (IRE) (Nasrin et al., *Proc. Natl. Acad. Sci. USA* 87:5273-7, 1990) and serum response elements (SRE) (Shaw et al. *Cell* 56: 563-72, 1989). Cyclic AMP response elements are reviewed in Roestler et al., *J. Biol. Chem.* 263 (19):9063-6; 1988 and Habener, *Molec. Endocrinol.* 4 (8):1087-94; 1990. Hormone response elements are reviewed in Beato, *Cell* 56:335-44; 1989. A preferred promoter element in this regard is a serum response element, or SRE (see, for example, Shaw et al., *Cell* 56:563-572, 1989). A preferred such reporter gene is a luciferase gene (de Wet et al., *Mol. Cell. Biol.* 7:725, 1987). Expression of the luciferase gene is detected by luminescence using methods known in the art (e.g., Baumgartner et al., *J. Biol. Chem.* 269:19094-29101, 1994; Schenborn and Goiffin, *Promega Notes* 41:11, 1993). Luciferase assay kits are commercially available from, for example, Promega Corp., Madison, Wis. Target cell lines of this type can be used to screen libraries of chemicals, cell-conditioned culture media, fungal broths, soil samples, water samples, and the like for antagonist activity. Such cells can be used as described herein in the presence of zalpha11 Ligand in a competitive inhibition type assay to assess the antagonist activity of soluble zalpha11 receptor or soluble zalpha11 heterodimeric polypeptide, such as soluble zalpha11/IL-2Rγ on zalpha11 Ligand signaling and proliferative activity.

T- and B-cell proliferation assay methods can also be used to assess the antagonist activity of soluble zalpha11 receptor or soluble zalpha11 heterodimeric polypeptide, such as soluble zalpha11/IL-2Rγ on zalpha11 Ligand signaling and proliferative activity in the presence of other cytokines, for example, IL-15, Flt3 and the like. Such assays are described in the examples herein, and are know in the art. Briefly, using flow cytometry, mature or immature subsets of T-cells or B-cells are isolated based on the presence or absence of various cell surface molecules (e.g., CD4, CD8, CD19, CD3, CD40, CD28, etc.). Cells can be selected prior to or after exposure to zalpha11 Ligand, depending on the cell type being studied, and the effect of zalpha11 Ligand thereon. The soluble receptors or antibodies of the present invention can be added at a range of concentrations to assess the antagonistic or binding activity on the Ligand in the T-cell or B-cell proliferation assay. Such assays are well known in the art, and described herein.

Moreover, a secretion trap method employing soluble zalpha11 receptor or soluble zalpha11 heterodimeric receptor polypeptides can be used to isolate transfected cells that express zalpha11 Ligand. For the method, see, Aldrich, et al, *Cell* 87: 1161-1169, 1996. A cDNA expression library prepared from a known or suspected ligand source is transfected into COS-7 cells. The cDNA library vector generally has an SV40 origin for amplification in COS-7 cells, and a CMV promoter for high expression. The transfected COS-7 cells are grown in a monolayer and then fixed and permeabilized. Tagged or biotin-labeled soluble zalpha11 receptor or soluble zalpha11 heterodimeric receptor polypeptides, described herein, is then placed in contact with the cell layer and allowed to bind cells in the monolayer that express an anti-complementary molecule, i.e., a zalpha11 Ligand. A cell expressing a ligand will thus be bound with receptor molecules. An anti-tag antibody (anti-Ig for Ig fusions, M2 or anti-FLAG for FLAG-tagged fusions, streptavidin, and the like) which is conjugated with horseradish peroxidase (HRP) is used to visualize these cells to which the tagged or biotin-labeled soluble zalpha11 receptor or soluble zalpha11 heterodimeric receptor polypeptides has bound. The HRP catalyzes deposition of a tyramide reagent, for example, tyramide-FITC. A commercially-available kit can be used for this detection (for example, Renaissance TSA-Direct™ Kit; NEN Life Science Products, Boston, Mass.). Cells which express zalpha11 receptor Ligand will be identified under fluorescence microscopy as green cells and picked for subsequent cloning of the ligand using procedures for plasmid rescue as outlined in Aldrich, et al, supra., followed by subsequent rounds of secretion trap assay until single clones are identified.

Moreover, histologic and immunohistochemical methods employing soluble zalpha11 receptor or soluble zalpha11 heterodimeric receptor polypeptides can be used to identify cells and tissues cells that express zalpha11 Ligand. Such methods are known in the art and described herein.

Additional assays to detect the antagonist or binding activity of soluble zalpha11 receptor or soluble zalpha11 heterodimeric receptor polypeptides provided by the present invention include the use of hybrid receptor polypeptides. These hybrid polypeptides fall into two general classes. Within the first class, the intracellular domain of zalpha11, comprising approximately residues 256 (Lys) to 528 (Ser) of SEQ ID NO:2, is joined to the ligand-binding domain of a second receptor. It is preferred that the second receptor be a hematopoietic cytokine receptor, such as mpl receptor (Souyri et al., *Cell* 63:1137-1147, 1990). The hybrid receptor will further comprise a transmembrane domain, which may be derived from either receptor. A DNA construct encoding the hybrid receptor is then inserted into a host cell. Cells expressing the hybrid receptor are cultured in the presence of a ligand for the binding domain and assayed for a response. This system provides a means for analyzing signal transduction mediated by zalpha11 while using readily available ligands. This system can also be used to determine if particular cell lines are capable of responding to signals transduced by zalpha11. A second class of hybrid receptor polypeptides comprise the extracellular (ligand-binding) domain of zalpha11 (approximately residues 20 (Cys) to 237 (His) of SEQ ID NO:2) (SEQ ID NO:6) with a cytoplasmic domain of a second receptor, preferably a cytokine receptor, and a transmembrane domain. The transmembrane domain may be derived from either receptor. Such hybrid receptors are expressed in cells known to be capable of responding to signals transduced by the receptor comprising the extracellular domain, such as in the presence of the zalpha11 Ligand. Addition of the soluble zalpha11 receptor or soluble zalpha11 heterodimeric receptor polypeptides, in the presence of the zalpha11 Ligand, is used to assess the zalpha11 Ligand antagonist or binding activity of the soluble zalpha11 receptor or soluble zalpha11 heterodimeric receptor polypeptides to the zalpha11 Ligand.

The tissue specificity and biological activities of zalpha11 Ligand expression suggest a role in early NK cell and thymocyte development, mature B-cell expansion, general immune response stimulation, and immune response regulation. These processes involve stimulation of cell proliferation and differentiation in response to the binding of the zalpha11 Ligand to its cognate receptor, comprising at least one zalpha11 receptor subunit. In view of the biological activity observed for this Ligand, antagonists have enormous potential in both in vitro and in vivo applications. As antagonists of the zalpha11 Ligand, soluble zalpha11 receptor or soluble zalpha11 heterodimeric receptor polypeptides can find utility in the suppression of the immune system, such as in the treatment of autoimmune diseases, including rheumatoid arthritis, multiple sclerosis, diabetes mellitus, inflammatory bowel disease, Crohn's disease, and the like. Immune suppression can also be used to reduce rejection of tissue or organ transplants and grafts and to treat B-cell malignancies, T-cell specific leukemias or lymphomas by inhibiting proliferation of the affected cell type.

Soluble zalpha11 receptor or soluble zalpha11 heterodimeric receptor polypeptides may also be used within diagnostic systems for the detection of circulating levels of zalpha11 Ligand. Within a related embodiment, antibodies or other agents that specifically bind to soluble zalpha11 receptor or soluble zalpha11 heterodimeric receptor polypeptides can be used to detect circulating receptor polypeptides. Elevated or depressed levels of Ligand or receptor polypeptides may be indicative of pathological conditions, including cancer. Soluble receptor polypeptides may contribute to pathologic processes and can be an indirect marker of an underlying disease. For example, elevated levels of soluble IL-2 receptor in human serum have been associated with a wide variety of inflammatory and neoplastic conditions, such as myocardial infarction, asthma, myasthenia gravis, rheumatoid arthritis, acute T-cell leukemia, B-cell lymphomas, chronic lymphocytic leukemia, colon cancer, breast cancer, and ovarian cancer (Heaney et al., *Blood* 87:847-857, 1996).

A ligand-binding polypeptide of a zalpha11 receptor, such as soluble zalpha11 receptor or soluble zalpha11 heterodimeric polypeptide, such as soluble zalpha11/IL-2Rγ can be prepared by expressing a truncated DNA encoding the zalpha11 cytokine binding domain (approximately residue 20 (Cys) through residue 237 (His) of the human receptor (SEQ ID NO:2) (SEQ ID NO:6)) or the corresponding region of a non-human receptor (e.g., SEQ ID NO:12). A soluble zalpha11 heterodimeric polypeptide, such as soluble zalpha11/IL-2Rγ can be prepared by co-expressing a truncated DNA encoding the zalpha11 cytokine binding domain (SEQ ID NO:6) and the truncated DNA encoding the extracellular domain of another class I cytokine receptor, such as IL-2Rγ (SEQ ID NO:4). It is preferred that the extracellular domains of the soluble zalpha11 homodimer or heterodimer be prepared in a form substantially free of transmembrane and intracellular polypeptide segments. Moreover, ligand-binding polypeptide fragments within the soluble zalpha11 receptor or soluble zalpha11 heterodimeric polypeptide (e.g., soluble zalpha11/IL-2Rγ), or cytokine-binding domain, described above, can also serve as zalpha11 soluble receptors for uses described herein. To direct the export of a receptor polypeptide from the host cell, the receptor DNA is linked to a second DNA segment encoding a secretory peptide, such as a t-PA secretory peptide, secretory peptide from another cytokine receptor, other secreted molecule, or a zalpha11 receptor secretory peptide. To facilitate purification of the secreted receptor polypeptide, a C-terminal extension, such as a poly-histidine tag, substance P, Flag™ peptide (Hopp et al., *Bio/Technology* 6:1204-1210, 1988; available from Eastman Kodak Co., New Haven, Conn.), Glu-glu tag (SEQ ID NO:14) or another polypeptide or protein for which an antibody or other specific binding agent is available, can be fused to the soluble receptor polypeptide.

In an alternative approach, a receptor extracellular domain can be expressed as a fusion with immunoglobulin heavy chain constant regions, typically an $F_C$ fragment, which contains two constant region domains and lacks the variable region. Such fusions are typically secreted as multimeric molecules wherein the Fc portions are disulfide bonded to each other and two receptor polypeptides are arrayed in close proximity to each other. Fusions of this type can be used to affinity purify the cognate ligand from solution, as an in vitro assay tool, to block signals in vitro by specifically titrating out Ligand, and as antagonists in vivo by administering them parenterally to bind circulating ligand and clear it from the circulation. To purify ligand, a zalpha11-Ig chimera (e.g., Zalpha11-Fc4 described herein), is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. Collected fractions can be re-fractionated until the desired level of purity is reached.

Moreover, soluble zalpha11 receptor or soluble zalpha11 heterodimeric receptor polypeptides, such as soluble zalpha11/IL-2Rγ, can be used as a "ligand sink," i.e., antagonist, to bind ligand in vivo or in vitro in therapeutic or other applications where the presence of the ligand is not desired. For example, in cancers that are expressing large amounts of bioactive zalpha11 Ligand, soluble zalpha11 receptor or soluble zalpha11 heterodimeric receptor polypeptides, such as soluble zalpha11/IL-2Rγ can be used as a direct antagonist of the ligand in vivo, and may aid in reducing progression and symptoms associated with the disease, and can be used in conjunction with other therapies (e.g., chemotherapy) to enhance the effect of the therapy in reducing progression and symptoms, and preventing relapse. Moreover, soluble zalpha11 receptor or soluble zalpha11 heterodimeric receptor polypeptides, such as soluble zalpha11/IL-2Rγ can be used to slow the progression of cancers that over-express zalpha11 receptors, by binding ligand in vivo that would otherwise enhance proliferation of those cancers.

Moreover, soluble zalpha11 receptor or soluble zalpha11 heterodimeric receptor polypeptides, such as soluble zalpha11/IL-2Rγ can be used in vivo or in diagnostic applications to detect zalpha11 Ligand-expressing cancers in vivo or in tissue samples. For example, the soluble zalpha11 receptor or soluble zalpha11 heterodimeric receptor polypeptides, such as soluble zalpha11/IL-2Rγ can be conjugated to a radiolabel or fluorescent label as described herein, and used to detect the presence of the zalpha11 Ligand in a tissue sample using an in vitro ligand-receptor type binding assay, or fluorescent imaging assay. Moreover, a radiolabeled soluble zalpha11 receptor or soluble zalpha11 heterodimeric receptor polypeptides, such as soluble zalpha11/IL-2Rγ could be administered in vivo to detect Ligand-expressing solid tumors through a radio-imaging method known in the art.

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant soluble zalpha11 receptor or soluble zalpha11 heterodimeric receptor polypeptides, such as soluble zalpha11/IL-2Rγ (or zalpha11 chimeric or fusion polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their biochemical, structural, and biological properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1-7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp. 529-39). Within additional embodiments of the invention, a fusion of the polypeptide of interest and an affinity tag (e.g., maltose-binding protein, an immunoglobulin domain) may be constructed to facilitate purification. Moreover zalpha11 Ligand affinity columns can be used to purify soluble zalpha11 receptor or soluble zalpha11 heterodimeric receptor polypeptides, such as soluble zalpha11/IL-2Rγ. Such affinity chromatography methods are well known in the art.

Moreover, using methods described in the art, polypeptide fusions, or hybrid zalpha11 proteins, are constructed using regions or domains of the inventive zalpha11 in combination with those of other human cytokine receptor family proteins, or heterologous proteins (Sambrook et al., ibid., Altschul et al., ibid., Picard, *Cur. Opin. Biology,* 5:511-5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Soluble receptor fusion polypeptides or proteins can be prepared by methods known to those skilled in the art by preparing each component of the fusion protein and chemically conjugating them. Alternatively, a polynucleotide encoding one or more components of the fusion protein in the proper reading frame can be generated using known techniques and expressed by the methods described herein. For example, part or all of a domain(s) conferring a biological function may be swapped between zalpha11 of the present invention with the functionally equivalent domain(s) from another cytokine family member.

Such domains include, but are not limited to, the extracellular cytokine binding domain, ligand binding domain and residues, transmembrane domain, as disclosed herein. Such fusion proteins would be expected to have a biological functional profile that is the same or similar to polypeptides of the present invention or other known family proteins, depending on the fusion constructed. Moreover, such fusion proteins may exhibit other properties as disclosed herein.

Standard molecular biological and cloning techniques can be used to swap the equivalent domains between the zalpha11 polypeptide and those polypeptides to which they are fused. Generally, a DNA segment that encodes a domain of interest, e.g., a zalpha11 domain described herein, is operably linked in frame to at least one other DNA segment encoding an additional polypeptide (for instance a domain or region from another cytokine receptor, such as the IL-2Rγ receptor), and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a cytokine-binding domain. Such fusion proteins can be expressed, isolated, and assayed for activity as described herein.

Soluble zalpha11 receptor or soluble zalpha11 heterodimeric receptor polypeptides, such as soluble zalpha11/IL-2Rγ polypeptides, or fragments thereof may also be prepared through chemical synthesis. Such polypeptides may be monomers or multimers; glycosylated or non-glycosylated; pegylated or non-pegylated; and may or may not include an initial methionine amino acid residue.

Polypeptides of the present invention can also be synthesized by exclusive solid phase synthesis, partial solid phase methods, fragment condensation or classical solution synthesis. Methods for synthesizing polypeptides are well known in the art. See, for example, Merrifield, *J. Am. Chem. Soc.* 85:2149, 1963; and Kaiser et al., *Anal. Biochem.* 34:595, 1970. After the entire synthesis of the desired peptide on a solid support, the peptide-resin is with a reagent that cleaves the polypeptide from the resin and removes most of the side-chain protecting groups. Such methods are well established in the art.

The activity of molecules of the present invention can be measured using a variety of assays that measure cell differentiation and proliferation. Such assays are well known in the art and described herein.

Proteins of the present invention are useful for example, in treating lymphoid, immune, hematopoietic, inflammatory disorders and the like, and can be measured in vitro using cultured cells or in vivo by administering molecules of the claimed invention to the appropriate animal model. For instance, host cells expressing a soluble zalpha11 receptor or soluble zalpha11 heterodimeric receptor polypeptides, such as soluble zalpha11/IL-2Rγ can be embedded in an alginate environment and injected (implanted) into recipient animals. Alginate-poly-L-lysine microencapsulation, permselective membrane encapsulation and diffusion chambers are a means to entrap transfected mammalian cells or primary mammalian cells. These types of non-immunogenic "encapsulations" permit the diffusion of proteins and other macromolecules secreted or released by the captured cells to the recipient animal. Most importantly, the capsules mask and shield the foreign, embedded cells from the recipient animal's immune response. Such encapsulations can extend the life of the injected cells from a few hours or days (naked cells) to several weeks (embedded cells). Alginate threads provide a simple and quick means for generating embedded cells.

The materials needed to generate the alginate threads are known in the art. In an exemplary procedure, 3% alginate is prepared in sterile $H_2O$, and sterile filtered. Just prior to preparation of alginate threads, the alginate solution is again filtered. An approximately 50% cell suspension (containing about $5\times10^5$ to about $5\times10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle). A large bore needle is then attached to the syringe, and the thread is intraperitoneally injected into a recipient in a minimal volume of the Lactated Ringer's Solution.

Adenoviral and other viral systems, such as vaccinia virus can be used to express and produce the proteins of the present invention. For example, using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). If the adenoviral delivery system has an E1 gene deletion, the virus cannot replicate in human cells, but will express and process (and, if a secretory signal sequence is present, secrete) the heterologous protein. Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615-623, 1997.

The adenovirus system can be used for protein production in vitro. By culturing adenovirus-infected non-293 cells under conditions where the cells are not rapidly dividing, the cells can produce proteins for extended periods of time. For instance, BHK cells are grown to confluence in cell factories, are exposed to the adenoviral vector encoding the secreted protein of interest. The cells are then grown under serum-free conditions, which allows infected cells to survive for several weeks without significant cell division.

Alternatively, adenovirus vector infected 293 cells can be grown as adherent cells or in suspension culture at relatively high cell density to produce significant amounts of protein (See Garnier et al., *Cytotechnol.* 15:145-55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

Soluble zalpha11 receptor or soluble zalpha11 heterodimeric receptor polypeptides, such as soluble zalpha11/IL-2Rγ receptor antagonists can be used in vitro in an assay to measure a decrease in stimulation of colony formation by zalpha11 Ligand from isolated primary bone marrow cultures. Such assays are disclosed herein and are well known in the art.

Zalpha11 Ligand antagonists and binding agents are also useful as research reagents for characterizing sites of ligand-receptor interaction. Inhibitors of zalpha11 Ligand activity (zalpha11 Ligand antagonists) include anti-soluble zalpha11 receptor or anti-soluble zalpha11 heterodimeric receptor polypeptide antibodies, such as anti-soluble zalpha11/IL-2Rγ antibodies and soluble zalpha11 receptor or soluble zalpha11 heterodimeric receptor polypeptides, such as soluble zalpha11/IL-2Rγ receptors, as well as other peptidic and non-peptidic agents (including ribozymes).

A soluble zalpha11 receptor or soluble zalpha11 heterodimeric receptor polypeptides, such as soluble zalpha11/IL-2Rγ ligand-binding polypeptide of the present invention, can also be used for purification of zalpha11 Ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument may be advantageously employed (e.g., BIAcore™, Pharmacia Biosensor, Piscataway, N.J.; or SELDI™ technology, Ciphergen, Inc., Palo Alto, Calif.). Such receptor, antibody, member of a complement/anti-complement pair or fragment is immobilized onto the surface of a receptor chip. Use of this instrument is disclosed by Karlsson, *J. Immunol. Methods* 145:229-240, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides, such as those of the present invention, can also be used within other assay systems known in the art. Such systems include Scatchard analysis for determination of binding affinity (see Scatchard, *Ann. NY Acad. Sci.* 51: 660-672, 1949) and calorimetric assays (Cunningham et al., *Science* 253:545-48, 1991; Cunningham et al., *Science* 245:821-25, 1991).

Soluble zalpha11 receptor or soluble zalpha11 heterodimeric polypeptide, such as soluble zalpha11/IL-2Rγ polypeptides can also be used to prepare antibodies that bind to epitopes, peptides, or polypeptides contained within the antigen. The zalpha11 receptor or soluble zalpha11 heterodimeric polypeptide, such as soluble zalpha11/IL-2Rγ polypeptides or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a zalpha11 receptor or soluble zalpha11 heterodimeric polypeptide, such as soluble zalpha11/IL-2Rγ polypeptides (e.g., SEQ ID NO:2, SEQ ID NO:6, SEQ ID NO:4). Polypeptides comprising a larger portion of a zalpha11 receptor or soluble zalpha11 heterodimeric polypeptide, such as soluble zalpha11/IL-2Rγ polypeptides i.e., from 30 to 100 residues up to the entire length of the amino acid sequence are included. Antigens or immunogenic epitopes can also include attached tags, adjuvants and carriers, as described herein. Suitable antigens include the zalpha11 polypeptide encoded by SEQ ID NO:2 from amino acid number 20 (Cys) to amino acid number 237 (His) (SEQ ID NO:6), or a contiguous 9 to 218 AA amino acid fragment thereof. Preferred peptides to use as antigens are the cytokine binding domain, disclosed herein, and zalpha11 hydrophilic peptides such as those predicted by one of skill in the art from a hydrophobicity plot, determined for example, from a Hopp/Woods hydrophilicity profile based on a sliding six-residue window, with buried G, S, and T residues and exposed H, Y, and W residues ignored. For example, zalpha11 hydrophilic peptides include peptides comprising amino acid sequences selected from the group consisting of: (1) amino acid number 51 (Trp) to amino acid number 61 (Glu) of SEQ ID NO:2; (2) amino acid number 136 (Ile) to amino acid number 143 (Glu) of SEQ ID NO:2; (3) amino acid number 187 (Pro) to amino acid number 195 (Ser) of SEQ ID NO:2; and (4) amino acid number 223 (Phe) to amino acid number 232 (Glu) of SEQ ID NO:2. The corresponding hydrophilic regions in reference to SEQ ID NO:6 can be made with cross-reference to the above amino acid residues of SEQ ID NO:2. Moreover, antigenic epitope-bearing polypeptides as predicted by a Jameson-Wolf plot, e.g., using DNASTAR Protean program (DNASTAR, Inc., Madison, Wis.) are suitable antigens. In addition, conserved motifs, and variable regions between conserved motifs of zalpha11 soluble receptor are suitable antigens. Suitable antigens also include the zalpha11 polypeptides disclosed above in combination with another class I cytokine extracellular domain, such as those that form soluble zalpha11 heterodimeric polypeptides, such as soluble zalpha11/IL-2Rγ. Moreover, corresponding regions of the mouse soluble zalpha11 receptor polypeptide (residues 20 (Cys) to 237 (His) SEQ ID NO:12) can be used to generate antibodies against the soluble mouse zalpha11 receptor. In addition Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a soluble zalpha11 receptor or soluble zalpha11 heterodimeric polypeptide, such as soluble zalpha11/IL-2Rγ polypeptide or a fragment thereof. The immunogenicity of a zalpha11 polypeptide may be increased through the use of an adjuvant, such as alum (aluminum hydroxide) or Freund's complete or incomplete adjuvant. Polypeptides useful for immunization also include fusion polypeptides, such as fusions of zalpha11 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Antibodies are considered to be specifically binding if: 1) they exhibit a threshold level of binding activity, and 2) they do not significantly cross-react with related polypeptide molecules. A threshold level of binding is determined if anti-soluble zalpha11 receptor or anti-soluble zalpha11 heterodimeric polypeptide, such as anti-soluble zalpha11/IL-2Rγ antibodies herein bind to a soluble zalpha11 receptor or soluble zalpha11 heterodimeric polypeptide, such as soluble zalpha11/IL-2Rγ polypeptide, peptide or epitope with an affinity at least 10-fold greater than the binding affinity to control (non-soluble zalpha11 receptor or soluble zalpha11 heterodimeric polypeptide, such as soluble zalpha11/IL-2Rγ) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660-672, 1949).

Whether anti-soluble zalpha11 receptor or anti-soluble zalpha11 heterodimeric polypeptide, such as anti-soluble zalpha11/IL-2Rγ antibodies do not significantly cross-react with related polypeptide molecules is shown, for example, by the antibody detecting soluble zalpha11 receptor or soluble zalpha11 heterodimeric polypeptide, such as soluble zalpha11/IL-2Rγ polypeptide but not known related polypeptides using a standard Western blot analysis (Ausubel et al., ibid.). Examples of known related polypeptides are those disclosed in the prior art, such as known orthologs, and paralogs, and similar known members of a protein family. Screening can also be done using non-human soluble zalpha11 receptor or soluble zalpha11 heterodimeric polypeptide, such as soluble zalpha11/IL-2Rγ, and soluble zalpha11 receptor or soluble zalpha11 heterodimeric polypeptide, such as soluble zalpha11/IL-2Rγ mutant polypeptides. Moreover, antibodies can be "screened against" known related polypeptides, to isolate a population that specifically binds to the soluble zalpha11 receptor or soluble zalpha11 heterodimeric polypeptide, such as soluble zalpha11/IL-2Rγ polypeptides. For example, antibodies raised to soluble zalpha11 receptor or soluble zalpha11 heterodimeric polypeptide, such as soluble zalpha11/IL-2Rγ are adsorbed to related polypeptides adhered to insoluble matrix; antibodies specific to soluble zalpha11 receptor or soluble zalpha11 heterodimeric polypeptide, such as soluble zalpha11/IL-2Rγ will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1-98, 1988; *Monoclonal Antibodies: Principles and Practice*, Goding, J. W. (eds.), *Academic Press Ltd.,* 1996; Benjamin et al., *Ann. Rev. Immunol.* 2: 67-101, 1984. Specifically binding anti-soluble zalpha11 receptor or anti-soluble zalpha11 heterodimeric polypeptide, such as anti-soluble zalpha11/IL-2Rγ antibodies can be detected by a number of methods in the art, and disclosed below.

A variety of assays known to those skilled in the art can be utilized to detect antibodies that bind to soluble zalpha11 receptor or soluble zalpha11 heterodimeric polypeptide, such as soluble zalpha11/IL-2Rγ proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant soluble zalpha11 receptor or soluble zalpha11 heterodimeric polypeptide, such as soluble zalpha11/IL-2Rγ protein or polypeptide.

Alternative techniques for generating or selecting antibodies useful herein include in vitro exposure of lymphocytes to soluble zalpha11 receptor or soluble zalpha11 heterodimeric polypeptide, such as soluble zalpha11/IL-2Rγ protein or peptide, and selection of antibody display libraries in phage or similar vectors (for instance, through use of immobilized or labeled soluble zalpha11 receptor or soluble zalpha11 heterodimeric polypeptide, such as soluble zalpha11/IL-2Rγ protein or peptide). Genes encoding polypeptides having potential binding domains for soluble zalpha11 receptor or soluble zalpha11 heterodimeric polypeptide, such as soluble zalpha11/IL-2Rγ polypeptide, can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the soluble zalpha11 receptor or soluble zalpha11 heterodimeric polypeptide, such as soluble zalpha11/IL-2Rγ sequences disclosed herein to identify proteins which bind to soluble zalpha11 receptor or soluble zalpha11 heterodimeric polypeptide, such as soluble zalpha11/IL-2Rγ. These "binding polypeptides" which interact with soluble zalpha11 receptor or soluble zalpha11 heterodimeric polypeptide, such as soluble zalpha11/IL-2Rγ polypeptides can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between ligand and receptor, or viral binding to a receptor. The binding polypeptides can also be used for diagnostic assays for determining circulating levels of soluble zalpha11 receptor or soluble zalpha11 heterodimeric polypeptide, such as soluble zalpha11/IL-2Rγ polypeptides; for detecting or quantitating soluble zalpha11 receptor or soluble zalpha11 heterodimeric polypeptide, such as soluble zalpha11/IL-2Rγ polypeptides as marker of underlying pathology or disease. These binding polypeptides can also act as zalpha11 receptor or zalpha11 heterodimeric polypeptide, such as zalpha11/IL- 2Rγ "antagonists" to block zalpha11 receptor or zalpha11 heterodimeric polypeptide, such as zalpha11/IL-2Rγ binding and signal transduction in vitro and in vivo. Again, these anti-soluble zalpha11 receptor or anti-soluble zalpha11 heterodimeric polypeptide, such as anti-soluble zalpha11/IL-2Rγ binding polypeptides would be useful for inhibiting zalpha11 Ligand activity, as well as receptor activity or protein-binding. Antibodies raised to the heterodimer or multimeric combinations of the present invention are preferred embodiments, as they may act more specifically against the zalpha11 Ligand, or more potently than antibodies raised to only one subunit. Moreover, the antagonistic and binding activity of the antibodies of the present invention can be assayed in the zalpha11 Ligand proliferation and other biological assays described herein.

Antibodies to soluble zalpha11 receptor or soluble zalpha11 heterodimeric polypeptide, such as soluble zalpha11/IL-2Rγ may be used for tagging cells that express zalpha11 receptor or zalpha11 heterodimeric polypeptides, such as zalpha11/IL-2Rγ; for isolating soluble zalpha11 receptor or soluble zalpha11 heterodimeric polypeptide, such as soluble zalpha11/IL-2Rγ polypeptide by affinity purification; for diagnostic assays for determining circulating levels of soluble zalpha11 receptor or soluble zalpha11 heterodimeric polypeptide, such as soluble zalpha11/IL-2Rγ polypeptides; for detecting or quantitating soluble zalpha11 receptor or soluble zalpha11 heterodimeric polypeptide, such as soluble zalpha11/IL-2Rγ as marker of underlying pathology or disease; in analytical methods employing FACS; for screening expression libraries; for generating anti-idiotypic antibodies; and as neutralizing antibodies or as antagonists to block zalpha11 receptor or zalpha11 heterodimeric polypeptide, such as zalpha11/IL-2Rγ, or zalpha11 Ligand activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to soluble zalpha11 receptor or soluble zalpha11 heterodimeric polypeptide, such as soluble zalpha11/IL-2Rγ or fragments thereof may be used in vitro to detect denatured or non-denatured soluble zalpha11 receptor or soluble zalpha11 heterodimeric polypeptide, such as soluble zalpha11/IL-2Rγ or fragments thereof in assays, for example, Western Blots or other assays known in the art.

Antibodies to soluble zalpha11 receptor or soluble zalpha11 heterodimeric polypeptide, such as soluble zalpha11/IL-2Rγ are useful for tagging cells that express the corresponding receptors and assaying their expression levels, for affinity purification, within diagnostic assays for determining circulating levels of soluble receptor polypeptides, analytical methods employing fluorescence-activated cell sorting. Moreover, divalent antibodies, and anti-idiotypic antibodies may be used as agonists to mimic the effect of the zalpha11 Ligand.

Antibodies herein can also be directly or indirectly conjugated to drugs, toxins, radionuclides and the like, and these conjugates used for in vivo diagnostic or therapeutic applications. For instance, antibodies or binding polypeptides which recognize soluble zalpha11 receptor or soluble zalpha11 heterodimeric polypeptide, such as soluble zalpha11/IL-2Rγ polypeptides of the present invention can be used to identify or treat tissues or organs that express a corresponding anti-complementary molecule (i.e., a zalpha11 receptor, or zalpha11 heterodimeric receptor, such as zalpha11/IL-2Rγ). More specifically, anti-soluble zalpha11 receptor or anti-soluble zalpha11 heterodimeric polypeptide, such as anti-soluble zalpha11/IL-2Rγ antibodies, or bioactive fragments or portions thereof, can be coupled to detectable or cytotoxic molecules and delivered to a mammal having cells, tissues or organs that express the zalpha11 receptor or a zalpha11 heterodimeric receptor, such as zalpha11/IL-2Rγ receptor molecules.

Suitable detectable molecules may be directly or indirectly attached to polypeptides that bind soluble zalpha11 receptor or soluble zalpha11 heterodimeric polypeptide, such as soluble zalpha11/IL-2Rγ ("binding polypeptides," including binding peptides disclosed above), antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

In another embodiment, binding polypeptide-toxin fusion proteins or antibody-toxin fusion proteins can be used for targeted cell or tissue inhibition or ablation (for instance, to treat cancer cells or tissues). Alternatively, if the binding polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, soluble zalpha11 receptor or soluble zalpha11 heterodimeric polypeptide, such as soluble zalpha11/IL-2Rγ binding polypeptide-cytokine or antibody-cytokine fusion proteins can be used for enhancing in vivo killing of target tissues (for example, blood, lymphoid, colon, and bone marrow cancers), if the binding polypeptide-cytokine or anti-soluble zalpha11 receptor or anti-soluble zalpha11 heterodimeric polypeptide, such as anti-soluble zalpha11/IL-2Rγ antibody targets the hyperproliferative cell (See, generally, Hornick et al., *Blood* 89:4437-47, 1997). The described fusion proteins enable targeting of a cytokine to a desired site of action, thereby providing an elevated local concentration of cytokine. Suitable anti-zalpha11 homodimer and heterodimer antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

Alternatively, soluble zalpha11 receptor or soluble zalpha11 heterodimeric polypeptide, such as soluble zalpha11/IL-2Rγ binding polypeptide or antibody fusion proteins described herein can be used for enhancing in vivo killing of target tissues by directly stimulating a zalpha11 receptor-modulated apoptotic pathway, resulting in cell death of hyperproliferative cells expressing zalpha11 receptor or a zalpha11 heterodimeric receptor, such as soluble zalpha11/IL-2Rγ receptor.

Four-helix bundle cytokines that bind to cytokine receptors as well as other proteins produced by activated lymphocytes play an important biological role in cell differentiation, activation, recruitment and homeostasis of cells throughout the body. Therapeutic utility includes treatment of diseases that require immune regulation including autoimmune diseases, such as, rheumatoid arthritis, multiple sclerosis, myasthenia gravis, systemic lupus erythomatosis and diabetes. Zalpha11 Ligand antagonists, including soluble zalpha11 receptor or soluble zalpha11 heterodimeric polypeptide, such as soluble zalpha11/IL-2Rγ, may be important in the regulation of inflammation, and therefore would be useful in treating rheumatoid arthritis, asthma, ulcerative colitis, inflammatory bowel disease, Crohn's disease, and sepsis. There may be a role of zalpha11 Ligand antagonists, including soluble zalpha11 receptor or soluble zalpha11 heterodimeric polypeptide, such as soluble zalpha11/IL-2Rγ, in mediating tumorgenesis, and therefore would be useful in the treatment of cancer. Zalpha11 Ligand antagonists, including soluble zalpha11 receptor or soluble zalpha11 heterodimeric polypeptide, such as soluble zalpha11/IL-2Rγ, may be a potential therapeutic in suppressing the immune system that would be important for reducing graft rejection. Soluble zalpha11 receptor or soluble zalpha11 heterodimeric polypeptide, such as soluble zalpha11/IL-2Rγ may have usefulness in prevention of graft vs. host disease.

Alternatively, zalpha11 Ligand antagonists, including soluble zalpha11 receptor or soluble zalpha11 heterodimeric polypeptide, such as soluble zalpha11/IL-2Rγ receptors in conjunction with other cytokines may enable selective activation, enhancement, or selective suppression, of the immune system in conjunction with zalpha11 Ligand on other cytokines which would be important in boosting immunity to infectious diseases, treating immunocompromised patients, such as HIV+ patient, or in improving vaccines. In particular, zalpha11 antagonists, including soluble zalpha11 receptor or soluble zalpha11 heterodimeric polypeptide, such as soluble zalpha11/IL-2Rγ, could prevent the expansion of a subset of the immune system involving zalpha11 Ligand (e.g., NK cells and mature B-cells), while enabling expansion of progenitors induced by other cytokines (e.g., T-cells), and would provide therapeutic value in treatment of viral infection and other infection. For example, with Dengue virus infection, which causes dengue hemorrhagic fever/Dengue Shock syndrome (DHF/DSS) it is believed that severe DHF/DSS occurs as a result of "immune enhancement" i.e., enhanced replication of the virus in the presence of preexisting antibodies against another serotype. In the second infection by a different Dengue virus serotype, the immune system raises antibodies against the first virus that cross-react but do not neutralize the virus, and that potentially aid its entry into macrophages. Thus, suppression of the antibody immune response, or B cell response, during a second or third Dengue infection may help the immune system react appropriately in the second infection to neutralize the virus by suppressing the "enhancing" antibodies from the first serotpye infection, and consequently avoiding severe DHF/DSS. For review, see White, D. O. and Fenner F. J. (Eds.) *Medical Virology,* 3$^{rd}$ ed., Academic Press, Orlando Fl, 1986, pages 479-508). Similarly, suppression of maternal antibody responses against fetal antigens by soluble receptors of the present invention can aid in preventing birth defects and spontaneous abortion. Moreover, in such applications the soluble receptors of the present invention can be used in conjunction with other cytokines to suppress some immune system activities (e.g., B-cell proliferation, using the soluble receptors) but allowing others to increase, e.g., in the presence of other cytokines described herein and known in the art.

The bioactive binding polypeptide or antibody conjugates described herein can be delivered orally, intravenously, intraarterially or intraductally, or may be introduced locally at the intended site of action. For pharmaceutical use, the soluble zalpha11 receptor or soluble zalpha11 heterodimeric polypeptide, such as soluble zalpha11/IL-2Rγ receptor polypeptides of the present invention are formulated for parenteral, particularly intravenous or subcutaneous, delivery according to conventional methods. Intravenous administration will be by bolus injection or infusion over a typical period of one to several hours. In general, pharmaceutical formulations will include a zalpha11 soluble receptor polypeptide in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 μg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of zalpha11 soluble receptor polypeptide is an amount sufficient to produce a clinically significant effect.

The invention is further illustrated by the following non-limiting examples.

EXAMPLES

Example 1

Construction of Expression Vector Expressing Full-length zalpha11

The entire zalpha11 receptor was isolated from a plasmid containing zalpha11 receptor cDNA (SEQ ID NO:1) using PCR with primers ZC19,905 (SEQ ID NO:19) and ZC19,906 (SEQ ID NO:20). The reaction conditions were as follows: 95° C. for 1 min; 35 cycles at 95° C. for 1 min, 55° C. for 1 min, 72° C. for 2 min; followed by 72° C. at 10 min; then a 10° C. soak. The PCR product was run on a 1% low melting point agarose (Boerhinger Mannheim) gel and the approximately 1.5 kb zalpha11 cDNA isolated using Qiaquick™ gel extraction kit (Qiagen) as per manufacturer's instructions.

The purified zalpha11 cDNA was digested with BamHI (Boerhinger Mannheim) and EcoRI (BRL) as per manufacturer's instructions. The entire digest was run on a 1% low melting point agarose (Boerhinger Mannheim) gel and the cleaved zalpha11 fragment was purified the using Qiaquick™ gel extraction kit as per manufacturer's instructions. The resultant cleaved zalpha11 fragment was inserted into an expression vector as described below.

Recipient expression vector pZP-5N was digested with BamHI (Boerhinger Mannheim) and EcoRI (BRL) as per manufacturer's instructions, and gel purified as described above. This vector fragment was combined with the BamHI and EcoRI cleaved zalpha11 fragment isolated above in a ligation reaction using T4 Ligase (BRL). The ligation was incubated at 15° C. overnight. A sample of the ligation was electroporated in to DH10B electroMAX™ electrocompetent E. coli cells (25 µF, 200Ω, 2.3V). Transformants were plated on LB+Ampicillin plates and single colonies screened by PCR to check for the zalpha11 sequence using ZC19,905 (SEQ ID NO:19) and ZC19,906 (SEQ ID NO:20) using the PCR conditions as described above. Confirmation of the zalpha11 sequence was made by sequence analysis. The insert was approximately 1.6 kb, and was full-length.

Example 2

Zalpha11 Based Proliferation in BAF3 Assay Using Alamar Blue

BaF3 cells expressing the full-length zalpha11 receptor were constructed, using the zalpha11 expression vector, described in Example 1. The BaF3 cells expressing the zalpha11 receptor mRNA were designated BaF3/zalpha11. These cells provide an assay system for detecting zalpha11 Ligand activity as described in numerous Examples below. Conversely, these cells provide also an assay system for detecting zalpha11 Ligand antagonist or inhibitory activity by the soluble receptors and antibodies of the present invention.

A. Construction of BaF3 Cells Expressing Human Zalpha11 Receptor

BaF3, an interleukin-3 (IL-3) dependent pre-lymphoid cell line derived from murine bone marrow (Palacios and Steinmetz, Cell 41: 727-734, 1985; Mathey-Prevot et al., Mol. Cell. Biol. 6: 4133-4135, 1986), was maintained in complete media (RPMI medium (JRH Bioscience Inc., Lenexa, Kans.) supplemented with 10% heat-inactivated fetal calf serum, 2 ng/ml murine IL-3 (m/L-3) (R & D, Minneapolis, Minn.), 2 mM L-glutaMax-1™ (Gibco BRL), 1 mM Sodium Pyruvate (Gibco BRL), and PSN antibiotics (GIBCO BRL)). Prior to electroporation, pZP-5N/zalpha11 plasmid DNA (Example 1) was prepared and purified using a Qiagen Maxi Prep kit (Qiagen) as per manufacturer's instructions. BaF3 cells for electroporation were washed once in RPMI media and then resuspended in RPMI media at a cell density of $10^7$ cells/ml. One ml of resuspended BaF3 cells was mixed with 30 µg of the pZP-5N/zalpha11 plasmid DNA and transferred to separate disposable electroporation chambers (GIBCO BRL). Following a 15 minute incubation at room temperature the cells were given two serial shocks (800 lFad/300 V.; 1180 lFad/300 V.) delivered by an electroporation apparatus (CELL-PORATOR™; GIBCO BRL). After a 5 minute recovery time, the electroporated cells were transferred to 50 ml of complete media and placed in an incubator for 15-24 hours (37° C., 5% $CO_2$). The cells were then spun down and resuspended in 50 ml of complete media containing Geneticin™ (Gibco) selection (500 µg/ml G418) in a T-162 flask to isolate the G418-resistant pool. Pools of the transfected BaF3 cells, hereinafter called BaF3/zalpha11 cells, were assayed for signaling capability as described below.

B. Testing the Signaling Capability of the BaF3/Zalpha11 Cells Using an Alamar Blue Proliferation Assay BaF3/zalpha11 cells were spun down and washed in the complete media, described above, but without mIL-3 (hereinafter referred to as "mIL-3 free media"). The cells were spun and washed 3 times to ensure the removal of the mIL-3. Cells were then counted in a hemacytometer. Cells were plated in a 96-well format at 5000 cells per well in a volume of 100 µl per well using the mIL-3 free media.

Proliferation of the BaF3/zalpha11 cells was assessed using conditioned media from zalpha11 Ligand-expressing cells diluted with mIL-3 free media to 50%, 25%, 12.5%, 6.25%, 3.125%, 1.5%, 0.75% and 0.375% concentrations; or purified zalpha11 Ligand (commonly owned U.S. patent application Ser. No. 09/522,217) diluted with mIL-3 free media to 500 ng/ml, 250 ng/ml, 125 ng/ml, 62 ng/ml, 30 ng/ml, 15 ng/ml, 7.5 ng/ml, 3.75 ng/ml, 1.8 ng/ml, 0.9 ng/ml, 0.5 ng/ml and 0.25 ng/ml concentrations. 100 µl of the diluted mTPO was added to the BaF3/zalpha11 cells. The total assay volume is 200 µl. Negative controls were run in parallel using mIL-3 free media only. The assay plates were incubated at 37° C., 5% $CO_2$ for 3 days at which time Alamar Blue (Accumed, Chicago, Ill.) was added at 20 µl/well. Alamar Blue gives a fluourometric readout based on the metabolic activity of cells, and is thus a direct measurement of cell proliferation in comparison to a negative control. Plates were again incubated at 37° C., 5% $CO_2$ for 24 hours. Plates were read on the Fmax™ plate reader (Molecular Devices Sunnyvale, Calif.) using the SoftMax™ Pro program, at wavelengths 544 (Excitation) and 590 (Emmission). Results confirmed the signaling capability of the zalpha11 receptor, as the zalpha11 Ligand significantly induced proliferation over background levels.

Example 3

Screening for Zalpha11 Ligand Using BaF3/Zalpha11 Cells Using an Alamar Blue Proliferation Assay A. Activation of Primary Monkey Splenocytes to Test for Presence of Zalpha11 Ligand Monkey splenocytes were stimulated in vitro to produce conditioned media to test for the presence of zalpha11 Ligand activity as described below. Monkey spleens were obtained from 8 year old female M. nesestrian monkeys. The spleens were teased part to produce a single cell suspension. The mononuclear cells were isolated by Ficoll-Paque® PLUS (Pharmacia Biotech, Uppsala, Sweden) density gradient. The mononuclear cells were seeded at $2\times10^6$ cells/ml in RPMI-1640 media supplemented with 10% FBS and activated with 5 ng/ml Phorbol-12-myristate-13-acetate (PMA) (Calbiochem, San Diego, Calif.), and 0.5 mg/ml Ionomycin™ (Calbiochem) for 48 h. The supernatant from the stimulated monkey spleen cells was used to assay proliferation of the BaF3/zalpha11 cells as described below.

B. Screening for Zalpha11 Ligand Using BaF3/Zalpha11 Cells Using an Alamar Blue Proliferation Assay BaF3/Zalpha11 cells were spun down and washed in mIL-3 free media. The cells were spun and washed 3 times to ensure the removal of the mIL-3. Cells were then counted in a hemacytometer. Cells were plated in a 96-well format at 5000 cells per well in a volume of 100 µl per well using the mIL-3 free media.

Proliferation of the BaF3/Zalpha11 cells was assessed using conditioned media from activated monkey spleen (see Example 3A). Conditioned media was diluted with mIL-3 free media to 50%, 25%, 12.5%, 6.25%, 3.125%, 1.5%, 0.75% and 0.375% concentrations. 100 µl of the diluted conditioned media was added to the BaF3/Zalpha11 cells. The total assay volume is 200 µl. The assay plates were incubated at 37° C., 5% $CO_2$ for 3 days at which time Alamar Blue (Accumed, Chicago, Ill.) was added at 20 µl well. Plates were again incubated at 37° C., 5% $CO_2$ for 24 hours. Plates were read on the Fmax™ plate reader (Molecular devices) as described above (Example 2).

Results confirmed the proliferative response of the BaF3/Zalpha11 cells to a factor present in the activated monkey spleen conditioned media. The response, as measured, was approximately 4-fold over background at the 50% concentration. The untransfected BaF3 cells did not proliferate in response to this factor, showing that this factor is specific for the Zalpha11 receptor.

C. Human Primary Source Used to Isolate Zalpha11 Ligand 100 ml blood draws were taken from each of six donors. The blood was drawn using 10×10 ml vacutainer tubes containing heparin. Blood was pooled from six donors (600 ml), diluted 1:1 in PBS, and separated using a Ficoll-Paque® PLUS (Pharmacia Biotech). The isolated primary human cell yield after separation on the ficoll gradient was $1.2 \times 10^9$ cells.

Cells were suspended in 9.6 ml MACS buffer (PBS, 0.5% EDTA, 2 mM EDTA). 1.6 ml of cell suspension was removed and 0.4 ml CD3 microbeads (Miltenyi Biotec, Auburn, Calif.) added. The mixture was incubated for 15 min. at 4° C. These cells labeled with CD3 beads were washed with 30 ml MACS buffer, and then resuspended in 2 ml MACS buffer.

A VS+ column (Miltenyi) was prepared according to the manufacturer's instructions. The VS+ column was then placed in a VarioMACS™ magnetic field (Miltenyi). The column was equilibrated with 5 ml MACS buffer. The isolated primary human cells were then applied to the column. The CD3 negative cells were allowed to pass through. The column was rinsed with 9 ml (3×3 ml) MACS buffer. The column was then removed from the magnet and placed over a 15 ml falcon tube. CD3+ cells were eluted by adding 5 ml MACS buffer to the column and bound cells flushed out using the plunger provided by the manufacturer. The incubation of the cells with the CD3 magnetic beads, washes, and VS+ column steps (incubation through elution) above were repeated five more times. The resulting CD3+ fractions from the six column separations were pooled. The yield of CD3+ selected human cells were $3 \times 10^8$ total cells.

A sample of the pooled CD3+ selected human cells was removed for staining and sorting on a fluorescent antibody cell sorter (FACS) to assess their purity. The human CD3+ selected cells were 91% CD3+ cells.

The human CD3+ selected cells were activated by incubating in RPMI+5% FBS+PMA 10 ng/ml and Ionomycin 0.5 µg/ml (Calbiochem) for 13 hours 37° C. The supernatant from these activated human CD3+ selected human cells was tested for zalpha11 Ligand activity as described below. Moreover, the activated CD3+ selected human cells were used to prepare a cDNA library, as described in commonly owned U.S. patent application Ser. No. 09/522,217.

D. Testing Supernatant from Activated CD3+ Selected Human Cells for Zalpha11 Ligand Using BaF3/Zalpha11 Cells and an Alamar Blue Proliferation Assay BaF3/Zalpha11 cells were spun down and washed in mIL-3 free media. The cells were spun and washed 3 times to ensure the removal of the mIL-3. Cells were then counted in a hemacytometer. Cells were plated in a 96-well format at 5000 cells per well in a volume of 100 µl per well using the mIL-3 free media.

Proliferation of the BaF3/Zalpha11 cells was assessed using conditioned media from activated CD3+ selected human cells (see Example 5C) diluted with mIL-3 free media to 50%, 25%, 12.5%, 6.25%, 3.125%, 1.5%, 0.75% and 0.375% concentrations. 100 µl of the diluted conditioned media was added to the BaF3/Zalpha11 cells. The total assay volume is 200 µl. The assay plates were incubated and assayed as described in Example 5B.

Results confirmed the proliferative response of the BaF3/Zalpha11 cells to a factor present in the activated CD3+ selected human cell conditioned media. The response, as measured, was approximately 10-fold over background at the 50% concentration. The untransfected BaF3 cells did not proliferate in response to this factor, showing that this factor is specific for the Zalpha11 receptor. Moreover soluble zalpha11 receptor blocked this proliferative activity in the BaF3/Zalpha11 cells (see, Example 16).

Example 4

Construction of Mammalian Expression Vectors that Express Zalpha11 Soluble Receptors: Zalpha11CEE, Zalpha11CFLG, Zalpha11CHIS and Zalpha11-Fc4

A. Construction of Zalpha11 Mammalian Expression Vector Containing Zalpha11 CEE, Zalpha11CFLG and Zalpha11CHIS An expression vector was prepared for the expression of the soluble, extracellular domain of the zalpha11 polypeptide, pC4zalpha11CEE, wherein the construct is designed to express a zalpha11 polypeptide comprised of the predicted initiating methionine and truncated adjacent to the predicted transmembrane domain, and with a C-terminal Glu-Glu tag (SEQ ID NO:14).

A 700 bp PCR generated zalpha11 DNA fragment was created using ZC19,931 (SEQ ID NO:21) and ZC19,932 (SEQ ID NO:22) as PCR primers to add Asp718 and BamHI restriction sites. A plasmid containing the zalpha11 receptor cDNA (SEQ ID NO:1) was used as a template. PCR amplification of the zalpha11 fragment was performed as follows: Twenty five cycles at 94° C. for 0.5 minutes; five cycles at 94° C. for 10 seconds, 50° C. for 30 seconds, 68° C. for 45 seconds, followed by a 4° C. hold. The reaction was purified by chloroform/phenol extraction and isopropanol precipitation, and digested with Asp718 and BamHI (Gibco BRL) following manufacturer's protocol. A band of the predicted size, 700 bp, was visualized by 1% agarose gel electrophoresis, excised and the DNA was purified using a QiaexII™ purification system (Qiagen) according the manufacturer's instructions.

The excised DNA was subcloned into plasmid pC4EE which had been cut with BamHI and Asp718. The pC4zalpha11CEE expression vector uses the native zalpha11 signal peptide and attaches the Glu-Glu tag (SEQ ID NO:14) to the C-terminus of the zalpha11 polypeptide-encoding polynucleotide sequence. Plasmid pC4EE, is a mammalian expression vector containing an expression cassette having the mouse metallothionein-1 promoter, multiple restriction sites for insertion of coding sequences, a stop codon and a human growth hormone terminator. The plasmid also has an E. coli origin of replication, a mammalian selectable marker expression unit having an SV40 promoter, enhancer and origin of replication, a DHFR gene and the SV40 terminator.

About 30 ng of the restriction digested zalpha11 insert and about 12 ng of the digested vector were ligated overnight at 16° C. One microliter of each ligation reaction was independently electroporated into DH10B competent cells (GIBCO BRL, Gaithersburg, Md.) according to manufacturer's direction and plated onto LB plates containing 50 mg/ml ampicillin, and incubated overnight. Colonies were screened by restriction analysis of DNA prepared from 2 ml liquid cultures of individual colonies. The insert sequence of positive clones was verified by sequence analysis. A large scale plasmid preparation was done using a QIAGEN® Maxi prep kit (Qiagen) according to manufacturer's instructions.

The same process was used to prepare the zalpha11 soluble receptors with a C-terminal his tag, composed of 6 His residues in a row; and a C-terminal flag (SEQ ID NO:23) tag, zalpha11 CFLAG. To construct these constructs, the aforementioned vector has either the HIS or the FLAG® tag in place of the glu-glu tag (SEQ ID NO:14).

B. Mammalian Expression Construction of Soluble Zalpha11 Receptor Zalpha11-Fc4

An expression plasmid containing all or part of a polynucleotide encoding zalpha11 was constructed via homologous recombination. A fragment of zalpha11 cDNA was isolated using PCR that includes the polynucleotide sequence from extracellular domain of the zalpha11 receptor. The two primers used in the production of the zalpha11 fragment were: (1) The primers for PCR each include from 5' to 3' end: 40 bp of the vector flanking sequence (5' of the insert) and 17 bp corresponding to the 5' end of the zalpha11 extracellular domain (SEQ ID NO:24); and (2) 40 bp of the 5' end of the Fc4 polynucleotide sequence (SEQ ID NO:25) and 17 bp corresponding to the 3' end of the zalpha11 extracellular domain (SEQ ID NO:26). The fragment of Fc4 for fusion with the zalpha11 was generated by PCR in a similar fashion. The two primers used in the production of the Fc4 fragment were: (1) a 5' primer consisting of 40 bp of sequence from the 3' end of zalpha11 extracellular domain and 17 bp of the 5' end of Fc4 (SEQ ID NO:27); and (2) a 3' primer consisting of 40 bp of vector sequence (3' of the insert) and 17 bp of the 3' end of Fc4 (SEQ ID NO:28).

PCR amplification of the each of the reactions described above was performed as follows: one cycle at 94° C. for 2 minutes; twenty-five cycles at 94° C. for 30 seconds, 60° C. for 30 seconds, 72° C. for 1 minute; one cycle at 72° C. for 5 minutes; followed by a 4° C. hold. Ten µl of the 100 µl PCR reaction was run on a 0.8% LMP agarose gel (Seaplaque GTG) with 1×TBE buffer for analysis. The remaining 90 µl of PCR reaction is precipitated with the addition of 5 µl 1 M NaCl and 250 µl of absolute ethanol. The expression vector used was derived from the plasmid pCZR199 (deposited at the American Type Culture Collection, 10801 University Boulevard, Manassas, Va. 20110-2209, designated No. 98668), and was cut with SmaI (BRL). The expression vector was derived from the plasmid pCZR199, and is a mammalian expression vector containing an expression cassette having the CMV immediate early promoter, a consensus intron from the variable region of mouse immunoglobulin heavy chain locus, multiple restriction sites for insertion of coding sequences, a stop codon and a human growth hormone terminator. The expression vector also has an *E. coli* origin of replication, a mammalian selectable marker expression unit having an SV40 promoter, enhancer and origin of replication, a DHFR gene and the SV40 terminator. The expression vector used was constructed from pCZR199 by the replacement of the metallothionein promoter with the CMV immediate early promoter.

One hundred microliters of competent yeast cells (*S. cerevisiae*) were combined with 10 µl containing approximately 1 µg each of the zalpha11 and Fc4 inserts, and 100 ng of SmaI (BRL) digested expression vector and transferred to a 0.2 cm electroporation cuvette. The yeast/DNA mixtures were electropulsed at 0.75 kV (5 kV/cm), "infinite" ohms, 25 µF. To each cuvette is added 600 µl of 1.2 M sorbitol and the yeast was plated in two 300 µl aliquots onto two URA-D plates and incubated at 30° C.

After about 48 hours, the Ura+ yeast transformants from a single plate were resuspended in 1 ml $H_2O$ and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 µl acid washed glass beads and 200 µl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 µl ethanol (EtOH), followed by centrifugation for 10 minutes at 4° C. The DNA pellet was resuspended in 100 µl $H_2O$.

Transformation of electrocompetent *E. coli* cells (DH10B, GibcoBRL) is done with 0.5-2 ml yeast DNA prep and 40 ul of DH10B cells. The cells were electropulsed at 2.0 kV, 25 mF and 400 ohms. Following electroporation, 1 ml SOC (2% Bacto® Tryptone (Difco, Detroit, Mich.), 0.5% yeast extract (Difco), 10 mM NaCl, 2.5 mM KCl, 10 mM MgCl2, 10 mM $MgSO_4$, 20 mM glucose) was plated in 250 µl aliquots on four LB AMP plates (LB broth (Lennox), 1.8% Bacto Agar (Difco), 100 mg/L Ampicillin).

Individual clones harboring the correct expression construct for zalpha11-Fc4 were identified by restriction digest to verify the presence of the zalpha11-Fc4 insert and to confirm that the various DNA sequences have been joined correctly to one another. The insert of positive clones were subjected to sequence analysis. Larger scale plasmid DNA is isolated using the Qiagen Maxi kit (Qiagen) according to manufacturer's instructions.

Example 5

Transfection And Expression of Zalpha11 Soluble Receptor Polypeptides

BHK 570 cells (ATCC No. CRL-10314), passage 27, were plated at $1.2×10^6$ cells/well (6-well plate) in 800 µl of serum free (SF) DMEM media (DMEM, Gibco/BRL High Glucose) (Gibco BRL, Gaithersburg, Md.). The cells were transfected with expression plasmids containing zalpha11CEE, zalpha11CFLG or zalpha11CHIS described above (see, Example 4), using Lipofectin™ (Gibco BRL), in serum free (SF) DMEM. Three micrograms of zalpha11CEE, zalpha11CFLG or zalpha11CHIS each were separately diluted into 1.5 ml tubes to a total final volume of 100 µl SF DMEM. In separate tubes, 15 µl of Lipofectin™ (Gibco BRL) was mixed with 100 µl of SF DMEM. The Lipofectin™ mix was incubated at room temperature for 30-45 minutes then the DNA mix was added and allowed to incubate approximately 10-15 minutes at room temperature.

The entire DNA: Lipofectin™ mixture was added to the plated cells and distributed evenly over them. The cells were incubated at 37° C. for approximately five hours, then transferred to separate 150 mm MAXI plates in a final volume of 30 ml DMEM/5% fetal bovine serum (FBS) (Hyclone, Logan, Utah). The plates were incubated at 37° C., 5% $CO_2$, overnight and the DNA: Lipofectin™ mixture was replaced with selection media (5% FBS/DMEM with 1 µM methotrexate (MTX) the next day.

Approximately 10-12 days post-transfection, the plates were washed with 10 ml SF DMEM. The wash media was aspirated and replaced with 7.25 ml serum-free DMEM. Sterile Teflon meshes (Spectrum Medical Industries, Los Angeles, Calif.) pre-soaked in SF DMEM were then placed over the clonal cell colonies. A sterile nitrocellulose filter pre-soaked in SF DMEM was then placed over the mesh. Orientation marks on the nitrocellulose were transferred to the culture dish. The plates were then incubated for 5-6 hours in a 37° C., 5% $CO_2$ incubator.

Following incubation, the filters/meshes were removed, and the media aspirated and replaced with 5% FBS/DMEM with 1 µM MTX. The filters were then blocked in 10% nonfat dry milk/Western A buffer (Western A: 50 mM Tris pH 7.4, 5 mM EDTA, 0.05% NP-40, 150 mM NaCl and 0.25% gelatin) for 15 minutes at room temperature on a rotating shaker. The filters were then incubated with an anti-Glu-Glu, anti-FLAG®, or anti-HIS antibody-HRP conjugates, respectively, in 2.5% nonfat dry milk/Western A buffer for one hour at room temperature on a rotating shaker. The filters were then washed three times at room temperature with Western A for 5-10 minutes per wash. The filters were developed with ultra ECL reagent (Amersham Corp., Arlington Heights, Ill.) according the manufacturer's directions and visualized on the Lumi-Imager (Roche Corp.)

Positive expressing clonal colonies were mechanically picked to 12-well plates in one ml of 5% FCS/DMEM with 5 µM MTX, then grown to confluence. Conditioned media samples were then tested for expression levels via SDS-PAGE and Western analysis. The three highest expressing clones for each construct were picked; two out of three were frozen down as back up and one was expanded for mycoplasma testing and large-scale factory seeding.

B. Mammalian Expression of Soluble Zalpha11 Receptor Zalpha11-Fc4

BHK 570 cells (ATCC NO: CRL-10314) were plated in 10 cm tissue culture dishes and allowed to grow to approximately 50 to 70% confluency overnight at 37°C, 5% $CO_2$, in DMEM/FBS media (DMEM, Gibco/BRL High Glucose, (Gibco BRL, Gaithersburg, Md.), 5% fetal bovine serum (Hyclone, Logan, Utah), 1 mM L-glutamine (JRH Biosciences, Lenexa, Kans.), 1 mM sodium pyruvate (Gibco BRL)). The cells were then transfected with the plasmid containing zalpha11-Fc4 (see, Example 9), using Lipofectamine™ (Gibco BRL), in serum free (SF) media formulation (DMEM, 10 mg/ml transferrin, 5 mg/ml insulin, 2 mg/ml fetuin, 1% L-glutamine and 1% sodium pyruvate). The plasmid containing zalpha11-Fc4 was diluted into 15 ml tubes to a total final volume of 640 ml with SF media. 35 ml of Lipofectamine™(Gibco BRL) was mixed with 605 ml of SF medium. The Lipofectamine™ mix was added to the DNA mix and allowed to incubate approximately 30 minutes at room temperature. Five milliliters of SF media was added to the DNA:Lipofectamine™ mixture. The cells were rinsed once with 5 ml of SF media, aspirated, and the DNA:Lipofectamine™ mixture is added. The cells were incubated at 37° C. for five hours, then 6.4 ml of DMEM/10% FBS, 1% PSN media was added to each plate. The plates were incubated at 37° C. overnight and the DNA:Lipofectamine™ mixture was replaced with fresh 5% FBS/DMEM media the next day. On day 2 post-transfection, the cells were split into the selection media (DMEM/FBS media from above with the addition of 1 mM methotrexate (Sigma Chemical Co., St. Louis, Mo.)) in 150 mm plates at 1:10, 1:20 and 1:50. The media on the cells was replaced with fresh selection media at day 5 post-transfection. Approximately 10 days post-transfection, two 150 mm culture dishes of methotrexate resistant colonies from each transfection were trypsinized and the cells are pooled and plated into a T-162 flask and transferred to large scale culture.

Example 6

Purification of Zalpha11 Soluble Receptors from BHK 570 Cells

A. Purification of Zalpha11CEE Polypeptide from BHK 570

Unless otherwise noted, all operations were carried out at 4° C. The following procedure was used for purifying zalpha11polypeptide containing C-terminal GluGlu (EE) tags. Thirty liters of cell factory conditioned media was concentrated to 1.6 liters with an Amicon S10Y3 spiral cartridge on a ProFlux A30. A Protease inhibitor solution was added to the concentrated 1.6 liters of cell factory conditioned media from transfected BHK 570 cells (Example 5) to final concentrations of 2.5 mM ethylenediaminetetraacetic acid (EDTA, Sigma Chemical Co. St. Louis, Mo.), 0.003 mM leupeptin (Boehringer-Mannheim, Indianapolis, Ind.), 0.001 mM pepstatin (Boehringer-Mannheim) and 0.4 mM Pefabloc (Boehringer-Mannheim). Samples were removed for analysis and the bulk volume was frozen at −80° C. until the purification was started. Total target protein concentrations of the concentrated cell factory conditioned media was determined via SDS-PAGE and Western blot analysis with the anti-EE HRP conjugated antibody.

A 100 ml column of anti-EE G-Sepharose (prepared as described below) was poured in a Waters AP-5, 5 cm×10 cm glass column. The column was flow packed and equilibrated on a BioCad Sprint (PerSeptive BioSystems, Framingham, Mass.) with phosphate buffered saline (PBS) pH 7.4. The concentrated cell factory conditioned media was thawed, 0.2 micron sterile filtered, pH adjusted to 7.4, then loaded on the column overnight with 1 ml/minute flow rate. The column was washed with 10 column volumes (CVs) of phosphate buffered saline (PBS, pH 7.4), then plug eluted with 200 ml of PBS (pH 6.0) containing 0.5 mg/ml EE peptide (Anaspec, San Jose, Calif.) at 5 ml minute. The EE peptide used has the sequence EYMPME (SEQ ID NO:14). The column was washed for 10 CVs with PBS, then eluted with 5 CVs of 0.2M glycine, pH 3.0. The pH of the glycine-eluted column was adjusted to 7.0 with 2 CVs of 5×PBS, then equilibrated in PBS (pH 7.4). Five ml fractions were collected over the entire elution chromatography and absorbance at 280 and 215 nM were monitored; the pass through and wash pools were also saved and analyzed. The EE-polypeptide elution peak fractions were analyzed for the target protein via SDS-PAGE Silver staining and Western Blotting with the anti-EE HRP conjugated antibody. The polypeptide elution fractions of interest were pooled and concentrated from 60 ml to 5.0 ml using a 10,000 Dalton molecular weight cutoff membrane spin concentrator (Millipore, Bedford, Mass.) according to the manufacturer's instructions.

To separate zalpha11CEE from other co-purifying proteins, the concentrated polypeptide elution pooled fractions were subjected to a POROS HQ-50 (strong anion exchange resin from PerSeptive BioSystems, Framingham, Mass.) at pH 8.0. A 1.0×6.0 cm column was poured and flow packed on a BioCad Sprint. The column was counter ion charged then equibrated in 20 mM TRIS pH 8.0 (Tris (Hydroxymethyl Aminomethane)). The sample was diluted 1:13 (to reduce the ionic strength of PBS) then loaded on the Poros HQ column at 5 ml/minute. The column was washed for 10 CVs with 20 mM Tris pH 8.0 then eluted with a 40 CV gradient of 20 mM Tris/1 M sodium chloride (NaCl) at 10 ml/minute. 1.5 ml fractions were collected over the entire chromatography and absorbance at 280 and 215 nM were monitored. The elution peak fractions were analyzed via SDS-PAGE Silver staining. Fractions of interest were pooled and concentrated to 1.5-2 ml using a 10,000 Dalton molecular weight cutoff membrane spin concentrator (Millipore, Bedford, Mass.) according to the manufacturer's instructions.

To separate zalpha11CEE polypeptide from free EE peptide and any contaminating co-purifying proteins, the pooled concentrated fractions were subjected to chromatography on a 1.5×90 cm Sephadex S200 (Pharmacia, Piscataway, N.J.) column equilibrated and loaded in PBS at a flow rate of 1.0 ml/min using a BioCad Sprint. 1.5 ml fractions were collected across the entire chromatography and the absorbance at 280 and 215 nM were monitored. The peak fractions were characterized via SDS-PAGE Silver staining, and only the most pure fractions were pooled. This material represented purified zalpha11CEE polypeptide.

This purified material was finally subjected to a 4 ml Acti-Clean Etox (Sterogene) column to remove any remaining endotoxins. The sample was passed over the PBS equilibrated gravity column four times then the column was washed with a single 3 ml volume of PBS, which was pooled with the "cleaned" sample. The material was then 0.2 micron sterile filtered and stored at −80° C. until it was aliquoted.

On Western blotted, Coomassie Blue and Silver stained SDS-PAGE gels, the zalpha11CEE polypeptide was one major band of an apparent molecular weight of 50,000 Daltons. The mobility of this band was the same on reducing and non-reducing gels.

The protein concentration of the purified material was performed by BCA analysis (Pierce, Rockford, Ill.) and the protein was aliquoted, and stored at −80° C. according to our standard procedures. On IEF (isoelectric focusing) gels the protein runs with a PI of less than 4.5. The concentration of zalpha11CEE polypeptide was 1.0 mg/ml.

Purified zalpha11CEE polypeptide was prepared for injection into rabbits and sent to R & R Research and Development (Stanwood, Wash.) for antibody production. Rabbits were injected to produce anti-huzalpha11-CEE-BHK serum (Example 10, below).

To prepare anti-EE Sepharose, a 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.) dissolved in TEA, was added to a final concentration of 36 mg/ml of protein G-Sepharose gel. The gel was rocked at room temperature for 45 min and the liquid was removed using the filter unit as described above. Nonspecific sites on the gel were then blocked by incubating for 10 min. at room temperature with 5 volumes of 20 mM ethanolamine in 200 mM TEA. The gel was then washed with 5 volumes of PBS containing 0.02% sodium azide and stored in this solution at 4° C.

B. Purification of Zalpha11CFLAG Polypeptide from BHK 570

Unless otherwise noted, all operations were carried out at 4° C. The following procedure was used for purifying zalpha11 polypeptide containing C-terminal FLAG® (FLG) (Sigma-Aldrich Co.) tags. Thirty liters of cell factory conditioned media was concentrated to 1.7 liters with an Amicon S10Y3 spiral cartridge on a ProFlux A30. A Protease inhibitor solution was added to the 1.7 liters of concentrated cell factory conditioned media from transfected BHK 570 cells (see, Example 5) to final concentrations of 2.5 mM ethylenediaminetetraacetic acid (EDTA, Sigma Chemical Co. St. Louis, Mo.), 0.003 mM leupeptin (Boehringer-Mannheim, Indianapolis, Ind.), 0.001 mM pepstatin (Boehringer-Mannheim) and 0.4 mM Pefabloc (Boehringer-Mannheim). Samples were removed for analysis and the bulk volume was frozen at −80° C. until the purification was started. Total target protein concentrations of the cell factory conditioned media was determined via SDS-PAGE and Western blot analysis with the anti-FLAG® (Kodak) HRP conjugated antibody. A 125 ml column of anti-FLAG® M2-Agarose affinity gel (Sigma-Aldrich Co.) was poured in a Waters AP-5, 5 cm×10 cm glass column. The column was flow packed and equilibrated on a BioCad Sprint (PerSeptive BioSystems, Framingham, Mass.) with phosphate buffered saline (PBS) pH 7.4. The concentrated cell factory conditioned media was thawed, 0.2 micron sterile filtered, pH adjusted to 7.4, then loaded on the column overnight with 1 ml/minute flow rate. The column was washed with 10 column volumes (CVs) of phosphate buffered saline (PBS, pH 7.4), then plug eluted with 250 ml of PBS (pH 6.0) containing 0.5 mg/ml FLAG® (Sigma-Aldrich Co.) peptide at 5 ml/minute. The FLAG® peptide used has the sequence DYKDDDDK (SEQ ID NO:23). The column was washed for 10 CVs with PBS, then eluted with 5 CVs of 0.2M glycine, pH 3.0. The pH of the glycine-eluted column was adjusted to 7.0 with 2 CVs of 5×PBS, then equilibrated in PBS (pH 7.4). Five ml fractions were collected over the entire elution chromatography and absorbence at 280 and 215 nM were monitored; the pass through and wash pools were also saved and analyzed. The FLAG®-polypeptide elution peak fractions were analyzed for the target protein via SDS-PAGE Silver staining and Western Blotting with the anti-FLAG HRP conjugated antibody. The polypeptide elution fractions of interest were pooled and concentrated from 80 ml to 12 ml using a 10,000 Dalton molecular weight cutoff membrane spin concentrator (Millipore, Bedford, Mass.) according to the manufacturer's instructions.

To separate zalpha11 CFLG from other co-purifying proteins, the polypeptide elution pooled fractions were subjected to a POROS HQ-50 (strong anion exchange resin from PerSeptive BioSystems, Framingham, Mass.) at pH 8.0. A 1.0× 6.0 cm column was poured and flow packed on a BioCad Sprint. The column was counter ion charged then equilibrated in 20 mM TRIS pH 8.0 (Tris (Hydroxymethyl Aminomethane)). The sample was diluted 1:13 (to reduce the ionic strength of PBS) then loaded on the Poros HQ-50 column at 5 ml/minute. The column was washed for 10 column volumes (CVs) with 20 mM Tris pH 8.0 then eluted with a 40 CV gradient of 20 mM Tris/1 M sodium chloride (NaCl) at 10 ml/minute. 1.5 ml fractions were collected over the entire chromatography and absorbance at 280 and 215 nM were monitored. The elution peak fractions were analyzed via SDS-PAGE Silver staining. Fractions of interest were pooled and concentrated to 1.5-2 ml using a 10,000 Dalton molecular weight cutoff membrane spin concentrator (Millipore, Bedford, Mass.) according to the manufacturer's instructions.

To separate zalpha11CFLG polypeptide from free FLAG® peptide and any contaminating co-purifying proteins, the pooled concentrated fractions were subjected to chromatography on a 1.5×90 cm Sephacryl S200 (Pharmacia, Piscataway, N.J.) column equilibrated and loaded in PBS at a flow rate of 1.0 ml/min using a BioCad Sprint. 1.5 ml fractions were collected across the entire chromatograohy and the absorbance at 280 and 215 nM were monitored. The peak fractions were characterized via SDS-PAGE Silver staining, and only the most pure fractions were pooled. This material represented purified zalpha11CFLG polypeptide.

This purified material was finally subjected to a 4 ml Acti-Clean Etox (Sterogene) column to remove any remaining endotoxins. The sample was passed over the PBS equilibrated gravity column four times then the column was washed with a single 3 ml volume of PBS, which was pooled with the "cleaned" sample. The material was then 0.2 micron sterile filtered and stored at –80° C. until it was aliquoted.

On Western blotted, Coomassie Blue and Silver stained SDS-PAGE gels, the zalpha11CFLG polypeptide was one major band of an apparent molecular weight of 50,000 Daltons. The mobility of this band was the same on reducing and non-reducing gels.

The protein concentration of the purified material was performed by BCA analysis (Pierce, Rockford, Ill.) and the protein was aliquoted, and stored at –80° C. according to our standard procedures. On IEF (isoelectric focusing) gels the protein runs with a PI of less than 4.5. The concentration of zalpha11 CFLG polypeptide was 1.2 mg/ml.

C. Purification of Zalpha11-Fc4 Polypeptide from Transfected BHK 570 cells

Unless otherwise noted, all operations were carried out at 4° C. The following procedure was used for purifying zalpha11 polypeptide containing C-terminal fusion to human IgG/Fc (zalpha11-Fc4; Examples 4 and 5). 12,000 ml of conditioned media from BHK 570 cells transfected with zalpha11-Fc4 (Example 5) was filtered through a 0.2 mm sterilizing filter and then supplemented with a solution of protease inhibitors, to final concentrations of 0.001 mM leupeptin (Boerhinger-Mannheim, Indianapolis, Ind.), 0.001 mM pepstatin (Boerhinger-Mannheim) and 0.4 mM Pefabloc (Boerhinger-Mannheim). A protein G sepharose (6 ml bed volume, Pharmacia Biotech) was packed and washed with 500 ml PBS (Gibco/BRL) The supplemented conditioned media was passed over the column with a flow rate of 10 ml/minute, followed by washing with 1000 ml PBS (BRL/Gibco). zalpha11-Fc4 was eluted from the column with 0.1 M Glycine pH 3.5 and 2 ml fractions were collected directly into 0.2 ml 2M Tris pH 8.0, to adjust the final pH to 7.0 in the fractions.

The eluted fractions were characterized by SDS-PAGE and western blotting with anti-human Fc (Amersham) antibodies. Western blot analysis of reducing SDS-PAGE gels reveal an immunoreactive protein of 80,000 KDa in fractions 2-10. Silver stained SDS-PAGE gels also revealed an 80,000 KDa zalpha11:Fc polypeptide in fractions 2-10. Fractions 2-10 were pooled.

The protein concentration of the pooled fractions was performed by BCA analysis (Pierce, Rockford, Ill.) and the material was aliquoted, and stored at –80° C. according to our standard procedures. The concentration of the pooled fractions was 0.26 mg/ml.

Example 7

Assay Using Zalpha11 Soluble Receptor Zalpha11CEE, Zalpha11CFLG and Zalpha11-Fc4 Soluble Receptors in Competitive Inhibition Assay BaF3/Zalpha11 cells were spun down and washed in mIL-3 free media. The cells were spun and washed 3 times to ensure the removal of the mIL-3. Cells were then counted in a hemacytometer. Cells were plated in a 96-well format at 5000 cells per well in a volume of 100 µl per well using the mIL-3 free media.

Both media from the monkey spleen cell activation and the CD3+ selected cells, described in Example 3, were added in separate experiments at 50%, 25%, 12.5%, 6.25%, 3.125%, 1.5%, 0.75% and 0.375% concentrations, with or without zalpha11 soluble receptors (CEE, C-flag, and Fc4 constructs; See, Example 6) at 10 µg/ml. The total assay volume was 200 µl.

The assay plates were incubated 37° C., 5% $CO_2$ for 3 days at which time Alamar Blue (Accumed) was added at 20 µl/well. Plates were again incubated at 37° C., 5% $CO_2$ for 24 hours. Plates were read on the Fmax™ plate reader (Molecular Devices) as described above (Example 2). Results demonstrated complete inhibition of cell growth from each of the different zalpha11 soluble receptor constructs at 10 g/ml, confirming that the factor in each sample was specific for the zalpha11 receptor.

Titration curves, diluting out the soluble receptors, were also run using the above stated assay. Both the zalpha11CEE and zalpha11CFLG soluble zalpha11 receptors were able to completely inhibit growth as low as 20 ng/ml. The zalpha11-Fc4 soluble zalpha11 receptor was only as effective at 1.5 µg/ml.

Example 8

Expression of Human Zalpha11 Soluble Receptor in *E. coli*

A. Construction of Expression Vector pCZR225 that Expresses Huzalpha11/MBP-6H fusion Polypeptide An expression plasmid containing a polynucleotide encoding a human zalpha11 soluble receptor fused C-terminally to maltose binding protein (MBP) was constructed via homologous recombination. The polynucleotide sequence for the MBP-zalpha11 soluble receptor fusion polypeptide is shown in SEQ ID NO:29, with the corresponding protein sequence shown in SEQ ID NO:30. The fusion polypeptide, designated huzalpha11/MBP-6H, in Example 9, contains an MBP portion (amino acid 1 (Met) to amino acid 388 (Ser) of SEQ ID NO:30) fused to the human zalpha11 soluble receptor (amino acid 389 (Cys) to amino acid 606 (His) of SEQ ID NO:30). A fragment of human zalpha11 cDNA (SEQ ID NO:31) was isolated using PCR. Two primers were used in the production of the human zalpha11 fragment in a PCR reaction: (1) Primer ZC20,187 (SEQ ID NO:32), containing 40 bp of the vector flanking sequence and 25 bp corresponding to the amino terminus of the human zalpha11, and (2) primer ZC20,185 (SEQ ID NO:33), containing 40 bp of the 3' end corresponding to the flanking vector sequence and 25 bp corresponding to the carboxyl terminus of the human zalpha11. The PCR Reaction conditions were as follows: 25 cycles of 94° C. for 30 seconds, 50° C. for 30 seconds, and 72° C. for 1 minute; followed by 4° C. soak, run in duplicate. Two μl of the 100 μl PCR reaction was run on a 1.0% agarose gel with 1×TBE buffer for analysis, and the expected approximately 660 bp fragment was seen. The remaining 90 μl of PCR reaction was combined with the second PCR tube precipitated with 400 μl of absolute ethanol. The precipitated DNA used for recombining into the Sma1 cut recipient vector pTAP98 to produce the construct encoding the MBP-zalpha11 fusion, as described below.

Plasmid pTAP98 was derived from the plasmids pRS316 and pMAL-c2. The plasmid pRS316 is a *Saccharomyces cerevisiae* shuttle vector (Hieter P. and Sikorski, R., *Genetics* 122:19-27, 1989). pMAL-C2 (NEB) is an *E. coli* expression plasmid. It carries the tac promoter driving MalE (gene encoding MBP) followed by a His tag, a thrombin cleavage site, a cloning site, and the rrnB terminator. The vector pTAP98 was constructed using yeast homologous recombination. 100 ng of EcoR1 cut pMAL-c2 was recombined with 1 μg Pvu1 cut pRS316, 1 μg linker, and 1 μg Sca1/EcoR1 cut pRS316. The linker consisted of oligos ZC19,372 (SEQ ID NO:34) (100 pmol): ZC19,351 (SEQ ID NO:35) (1 pmol): ZC19,352 (SEQ ID NO:36) (1 pmol), and ZC19,371 (SEQ ID NO:37) (100 pmol) combined in a PCR reaction. PCR reaction conditions were as follows: 10 cycles of 94° C. for 30 seconds, 50° C. for 30 seconds, and 72° C. for 30 seconds; followed by 4° C. soak. PCR products were concentrated via 100% ethanol precipitation.

One hundred microliters of competent yeast cells (*S. cerevisiae*) were combined with 10 μl of a mixture containing approximately 1 μg of the human zalpha11 receptor PCR product above, and 100 ng of SmaI digested pTAP98 vector, and transferred to a 0.2 cm electroporation cuvette. The yeast/DNA mixture was electropulsed at 0.75 kV (5 kV/cm), infinite ohms, 25 μF. To each cuvette was added 600 μl of 1.2 M sorbitol and the yeast was then plated in two 300 μl aliquots onto two -URA D plates and incubated at 30° C.

After about 48 hours, the Ura+ yeast transformants from a single plate were resuspended in 1 ml H$_2$O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 200 μl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 μl ethanol (EtOH), followed by centrifugation for 10 minutes at 4° C. The DNA pellet was resuspended in 100 μl H$_2$O.

Transformation of electrocompetent *E. coli* cells (MC1061, Casadaban et. al. *J. Mol. Biol.* 138, 179-207) was done with 1 μl yeast DNA prep and 40 μl of MC1061 cells. The cells were electropulsed at 2.0 kV, 25 μF and 400 ohms. Following electroporation, 0.6 ml SOC (2% Bacto™ Tryptone (Difco, Detroit, Mich.), 0.5% yeast extract (Difco), 10 mM NaCl, 2.5 mM KCl, 10 mM MgCl2, 10 mM MgSO4, 20 mM glucose) was plated in one aliquot on MM/CA+AMP 100 mg/L plates (Pryor and Leiting, *Protein Expression and Purification* 10:309-319, 1997).

Cells harboring the correct expression construct for human zalpha11 receptor were identified by expression. Cells were grown in MM/CA with 100 μg/ml Ampicillin for two hours, shaking, at 37° C. 1 ml of the culture was induced with 1 mM IPTG. 2-4 hours later the 250 μl of each culture was mixed with 250 μl acid washed glass beads and 250 μl Thorner buffer with 5% βME and dye (8M urea, 100 mM Tris pH7.0, 10% glycerol, 2 mM EDTA, 5% SDS). Samples were vortexed for one minute and heated to 65° C. for 10 minutes. 20 μl were loaded per lane on a 4%-12% PAGE gel (NOVEX). Gels were run in 1×MES buffer. The positive clones were designated pCZR225 and subjected to sequence analysis. The polynucleotide sequence of MBP-zalpha11 fusion is shown in SEQ ID NO:50.

B. Bacterial Expression of Human Huzalpha11/MBP-6H Fusion Polypeptide

One microliter of sequencing DNA was used to transform strain BL21. The cells were electropulsed at 2.0 kV, 25° F. and 400 ohms. Following electroporation, 0.6 ml MM/CA with 100 mg/L Ampicillin.

Cells were grown in MM/CA with 100 μg/ml Ampicillin for two hours, shaking, at 37° C. 1 ml of the culture was induced with 1 mM IPTG. 2-4 hours later the 250 μl of each culture was mixed with 250 μl acid washed glass beads and 250 μl Thorner buffer with 5% βME and dye (8M urea, 100 mM Tris pH7.0, 10% glycerol, 2 mM EDTA, 5% SDS). Samples were vortexed for one minute and heated to 65° C. for 10 minutes. 20 μl were loaded per lane on a 4%-12% PAGE gel (NOVEX). Gels were run in 1×MES buffer. The positive clones were used to grow up for protein purification of the huzalpha11/MBP-6H fusion protein (Example 9, below).

Example 9

Purification of Huzalpha11/MBP-6H Soluble Receptor from *E. coli* Fermentation

Unless otherwise noted, all operations were carried out at 4° C. The following procedure was used for purifying huzalpha11/MBP-6H soluble receptor polypeptide. *E. Coli* cells containing the pCZR225 construct and expressing huzalpha11/MBP-6H soluble receptor (Example 8) were grown up in SuperBroth II (12 g/L Casien, 24 g/L Yeast Extract, 11.4 g/L di-potassium phosphate, 1.7 g/L Mono-potassium phosphate; Becton Dickenson, Cockeysville, Md.), and frozen in 0.5% glycerol. Twenty grams of the frozen cells in SuperBroth II+Glycerol were used to purify the protein. The frozen cells were thawed and diluted 1:10 in a protease inhibitor solution (Extraction buffer) prior to lysing the cells and releasing the huzalpha11/MBP-6H soluble receptor protein. The diluted cells contained final concentrations of 20 mM Tris (JT Baker, Philipsburg, N.J.) 100 mM Sodium Chloride (NaCl, Mallinkrodt, Paris, Ky.), 0.5 mM phenylmethylsulfonyl fluoride (PMSF, Sigma Chemical Co., St. Louis, Mo.), 2 μg/ml Leupeptin (Fluka, Switzerland), and 2 μg/ml Aprotinin (Sigma). A French Press cell breaking system (Constant Systems Ltd., Warwick, UK) with temperature of –7 to –10° C. and 30K PSI was used to lyse the cells. The diluted cells were checked for breakage by A$_{600}$ readings before and after the French Press. The lysed cells were centrifuged @ 18,000 G for 45 minutes to remove the broken cell debris, and the supernatant used to purify the protein. Total target protein concentrations of the supernatant was determined via BCA Protein Assay (Pierce, Rockford, Ill.), according to manufacturer's instructions.

A 25 ml column of Talon Metal Affinity resin (Clontech, Palo Alto, Calif.) (prepared as described below) was poured in a Bio-Rad, 2.5 cm D×10 cm H glass column. The column was packed and equilibrated by gravity with 10 column volumes (CVs) of Talon Equilibration buffer (20 mM Tris, 100 mM NaCl, pH 8.0). The supernatant was batch loaded to Talon metal affinity resin and was rocked overnight. The resin was poured back into the column and was washed with 10 CV's of Talon Equilibration buffer by gravity, then gravity eluted with 140 ml of Elution buffer (Talon Equilibration buffer+200 mM Imidazole-Fluka Chemical). The talon column was cleaned with 5 CVs of 20 mM 2-(N-Morpholino) ethanesulfonic acid pH 5.0 (MES, Sigma), 5 CVs of distilled $H_2O$, then stored in 20% Ethanol/0.1% Sodium Azide. Fourteen ml fractions were collected over the entire elution chromatography and the fractions were read with absorbance at 280 and 320 nM and BCA protein assay; the pass through and wash pools were also saved and analyzed. The protein elution fractions of interest were pooled and loaded straight to Amylose resin (New England Biolabs, Beverly, Mass.).

To obtain more pure huzalpha11/MBP-6H polypeptide, the talon affinity elution pooled fractions were subjected to Amylose resin (22 mls) at pH 7.4. A 2.5 cm D×10 cm H Bio-Rad column was poured, packed and equilibrated in 10 CVs of Amylose equilibration buffer-20 mM Tris (JT Baker), 100 mM NaCl (Mallinkrodt), 1 mM PMSF (Sigma), 10 mM beta-Mercaptoethanol (BME, ICN Biomedicals Inc., Aurora, Ohio) pH 7.4. The sample was loaded by gravity flow rate of 0.5 ml/min. The column was washed for 10 CVs with Amylose equilibration buffer, then eluted with ~2 CV of Amylose equilibration buffer+10 mM Maltose (Fluka Biochemical, Switzerland) by gravity. 5 ml fractions were collected over the entire chromatography and absorbance at 280 and 320 nM were read. The Amylose column was regenerated with 1 CV of distilled $H_2O$, 5 CVs of 0.1% (w/v) SDS (Sigma), 5 CVs of distilled $H_2O$, and then 5 CVs of Amylose equilibration buffer.

Fractions of interest were pooled and dialyzed in a Slide-A-Lyzer (Pierce) with 4×4 L PBS pH 7.4 (Sigma) to remove low molecular weight contaminants, buffer exchange and desalt. After the changes of PBS, the material harvested represented the purified huzalpha11/MBP-6H polypeptide. The purified huzalpha11/MBP-6H polypeptide was analyzed via SDS-PAGE Coomassie staining and Western blot analysis with the anti-rabbit HRP conjugated antibody (Rockland, Gilbertsville, Pa.). The concentration of the huzalpha11/MBP-6H polypeptide was 1.92 mg/ml as determined by BCA analysis.

Purified huzalpha11/MBP-6H polypeptide was prepared for injection into rabbits and sent to R & R Research and Development (Stanwood, Wash.) for antibody production. Rabbits were injected to produce anti anti-huzalpha11/MBP-6H serum (Example 10, below).

Example 10

Zalpha11 Soluble Receptor Polyclonal Antibodies

Polyclonal antibodies were prepared by immunizing two female New Zealand white rabbits with the purified huzalpha11/MBP-6H polypeptide (Example 9), or the purified recombinant zalpha11CEE soluble receptor (Example 6A). Corresponding polyclonal antibodies were designated rabbit anti-huzalpha11/MBP-6H and rabbit anti-huzalpha11-CEE-BHK respectively. The rabbits were each given an initial intraperitoneal (IP) injection of 200 mg of purified protein in Complete Freund's Adjuvant (Pierce, Rockford, Ill.) followed by booster IP injections of 100 mg purified protein in Incomplete Freund's Adjuvant every three weeks. Seven to ten days after the administration of the third booster injection, the animals were bled and the serum was collected. The rabbits were then boosted and bled every three weeks.

The zalpha11-specific polyclonal antibodies were affinity purified from the rabbit serum using an CNBr-SEPHAROSE 4B protein column (Pharmacia LKB) that was prepared using 10 mg of the purified huzalpha11/MBP-6H polypeptide (Example 9) per gram CNBr-SEPHAROSE, followed by 20× dialysis in PBS overnight. Zalpha11-specific antibodies were characterized by an ELISA titer check using 1 mg/ml of the appropriate protein antigen as an antibody target. The lower limit of detection (LLD) of the rabbit anti-huzalpha11/MBP-6H affinity purified antibody is a dilution of 500 pg/ml. The LLD of the rabbit anti-huzalpha11-CEE-BHK affinity purified antibody is a dilution of 50 pg/ml.

Example 11

Identification of Cells Expressing Zalpha11 Receptor Using RT-PCR

Specific human cell types were isolated and screened for zalpha11 expression by RT-PCR. B-cells were isolated from fresh human tonsils by mechanical disruption through 100 μm nylon cell strainers (Falcon™; Bectin Dickenson, Franklin Lakes, N.J.). The B-cell suspensions were enriched for CD19+ B-cells by positive selection with VarioMACS VS+ magnetic column and CD19 microbeads (Miltenyi Biotec, Auburn, Calif.) as per manufacturer's instructions. T-cells and monocytes were isolated from human apheresed blood samples. CD3+ T-cells were purified by CD3 microbead VarioMACS positive selection and monocytes were purified by VarioMACS negative selection columns (Miltenyi) as per manufacturer's instructions. Samples from each population were stained and analyzed by fluorescent antibody cell sorting (FACS) (Bectin Dickinson, San Jose, Calif.) analysis to determine the percent enrichment and resulting yields. CD19+ B-cells were approximately 96%, purified CD3+ T-cells were approximately 95% purified, and monocytes were approximately 96% purified.

RNA was prepared, using a standard method in the art, from all three cell types that were either resting or activated. RNA was isolated from resting cells directly from the column preparations above. The CD19+ and CD3+ cells were activated by culturing at 500,000 cells/ml in RPMI+10% FBS containing PMA 5 ng/ml (Calbiochem, La Jolla, Calif.) and Ionomycin 0.5 ug/ml (Calbiochem) for 4 and 24 hours. The monocytes were activated by culturing in RPMI+10% FBS containing LPS 10 ng/ml (Sigma St. Louis Mo.) and rhIFN-γ 10 ng/ml (R&D, Minneapolis, Minn.) for 24 hours. Cells were harvested and washed in PBS. RNA was prepared from the cell pellets using RNeasy Midiprep™ Kit (Qiagen, Valencia, Calif.) as per manufacturer's instructions and first strand cDNA synthesis was generated with Superscript II™ Kit (GIBCO BRL, Grand Island, N.Y.) as per manufacturer's protocol.

Oligos ZC19907 (SEQ ID NO:38) and ZC19908 (SEQ ID NO:39) were used in a PCR reaction to screen the above described samples for a 1.2 kb fragment corresponding to zalpha11 message. PCR amplification was performed with Taq Polymerase (BRL Grand Island N.Y.), and conditions as follows: 35 cycles of 95° C. for 1 min., 60° C. for 1 min., 72° C. for 30 sec.; 1 cycle at 72° C. for 10 min.; and 4° C. soak. 10 ul of each 50 μl reaction volume was run on a 2% agarose 1×TAE gel to identify resultant products. PCR products were scored as (−) for no product, (+) for band visible, (++) increased presence of band and (+++) being the most predominant band, with results shown in Table 5 below.

TABLE 5

| cDNA Source | Activation | PCR Product |
|---|---|---|
| CD19+ cells | 0 hr resting | + |
| | 4 hr activated | ++ |
| | 24 hr activated | +++ |
| CD3+ cells | 0 hr resting | − |
| | 4 hr activated | ++ |
| | 24 hr activated | − |
| monocytes | 0 hr resting | − |
| | 24 hr activated | − |

These results indicated that zalpha11 message is present in resting human CD19+ B-cells and increases with mitogenic activation. It also appears to be expressed by human CD3+ T-cells only after 4 hour activation. There was no apparent message in either resting or activated human monocytes.

Example 12

Zalpha11 Immunohistochemistry

A. Cell and Tissue Preparations

Positive controls consisted of BaF3 cells transfected with zalpha11 receptor (Example 2) and lymphoid tissues known to express zalpha11 receptor including mouse lymph node, spleen and thymus received from HSD (Harlan Sprague Dawley, Indianapolis, Ind.), monkey lymph node and spleen received from Regional Primate Research Center (University of Washington, Seattle, Wash.), human lymph node and spleen received from CHTN (Cleveland, Ohio). Negative controls performed on each sample included: (1) untransfected BaF3 cells, (2) liver and brain tissue from mouse and human known not to express zalpha11 receptor, (3) staining with antibody dilution buffer (Ventann Bioteck Systems, Tucson Ariz.) in the absence of primary antibody, and (4) using zalpha11 soluble receptor protein in competition experiments.

Other cell samples were examined. Both non-stimulated and stimulated HL60 cells were assayed. HL60 cells are a promyelocytic cell line, which can be differentiated into myeloid or granulocyte lineages with different reagents. Stimulated HL60 samples were prepared as follows: (1) HL60 cells were treated with 10 ng/ml of phorbol-myristate-acetate (PMA) (Sigma, St. Louis, Mo.) for 48 hours to differentiate into monocyte lineage cells; and (2) HL60 cells treated with 1.25% DMSO (Sigma) for 4 days to differentiate into neutrophil-like cells. In addition, human polymorphonuclear (PMN) cells, human granulocytes, human peripheral blood lymphocytes (PBL) and human monocytes from fresh human blood were examined (prepared in house using routine methods in the art). The cells and tissues described above were fixed overnight in 10% NBF (Surgipath, Richmond, Ill.), and embedded in paraplast X-tra (Oxford Scientific, St. Louis, Mo.), and sectioned at 5 µm with a Reichart-Jung 2050 microme (Leica Instruments GmbH, Nussloch, Germany).

B. Immunohistochemistry

Tissue slides were deparaffinized, hydrated to buffer (water), and subjected to steam HIER treatment in Antigen Retrieval Citra buffer (BioGenex, San Roman, Calif.) for 20 minutes. 5% normal goat serum (Vector, Burlingame, Calif.) was used to block non-specific binding for 10 minutes. Immunocytochemical screening analyses were performed using polyclonal antibodies to zalpha11 soluble receptor protein (rabbit anti-huzalpha11-MBP-6H and rabbit anti-huzalpha11-CEE-BHK; Example 10) as the primary antibodies, at dilutions of 1:200 and 1:400 respectively. Biotin conjugated goat anti-rabbit IgG (Vector; Cat. No. BA-1000, 1.5 mg/ml) was used as the secondary antibody at dilution of 1:200. In separate samples, protein competition was performed by using additional zalpha11 CEE soluble receptor protein (in 10× fold excess) (Example 6A) to the primary antibody to pre-block primary antibody immunoreaction. This competition was used as a control for the rabbit polyclonal antibody specificity to zalpha11. Detection was performed on the Ventana ChemMate 500 instrument using a ChemMate DAB Kit (labeled Streptavidin-Biotin Kit with application of a streptavidin-horseradish peroxidase conjugate, and DAB substrate) according to manufacturer's instruction and using the manufacturer's hematoxylin counterstain for 30 seconds (Ventana Biotek Systems, Tucson, Ariz.).

High expression of zalpha11 was observed in the PMA-activated HL60 cells. Low level expression was observed in PBL and HL60 cells without stimulation. A subset of cells in the spleen, thymus and lymph node of mouse showed positive staining. Lymph node and spleen of both human and monkey, and HL60 cells with DMSO stimulation showed minimal or no staining. The signal seen in the cells and tissues was mostly competed out by using the excess zalpha11 soluble receptor protein. The negative control tissues of brain and liver showed no staining.

Example 13

Identifying Peripheral Blood Mononuclear Cells (PBMNC's) that Express Zalpha11 Receptor Using Polyclonal Rabbit Anti-Sera to Zalpha11 Soluble Receptor 200 ml fresh heparinized blood was obtained from a normal donor. Blood was diluted 1:1 in PBS, and separated using a Ficoll-Paque PLUS gradient (Pharmacia Biotech, Uppsala, Sweden), and the lymphocyte interface collected. Cells were washed 2× in PBS and resuspended in RPMI+5% FBS media at a concentration of $2 \times 10^6$ cells/ml.

In order to determine whether expression of zalpha11 receptor is affected by the activation state of the lymphocyte cells, i.e., between resting and activated cells several stimulation conditions were used: 1) unstimulated, i.e., media alone (RPMI+5% FBS media); 2) stimulated with PMA 10 ng/ml+Ionomycin 0.5 µg/ml (both from Calbiochem); and 3) PHA activation (phytohemagglutinin-P, Difco/VWR). The cells were incubated at 37° C. for 17 hours then collected for staining to detect expression of zalpha11 receptor.

An indirect staining protocol was used. Briefly, the human lymphocyte cells were suspended in staining buffer (PBS+ 0.02% NaN3+BSA 1% normal human serum 2%) and plated at $2 \times 10^5$ cells in 50 µl/well in a 96 well plate. Antibodies to the zalpha11CEE soluble receptor (Example 15) were used to determine whether they co-stained with a B-cell (CD19), T-cell (CD3) or monocyte marker (CD14) on the isolated human lymphocytes. A rabbit polyclonal sera to zalpha11 soluble receptor (Rb anti-huzalpha11-CEE-BHK) (Example 10) at 10 µg/ml was used as the antibody to identify zalpha11 on the lymphocytes. A secondary antibody, goat anti-rabbit Ig-FITC (Biosource, Camarillo, Calif.), was used to visualize the Rb anti-huzalpha11-CEE-BHK antibody binding to the zalpha11 receptors. Other antibodies were simultaneously used to stain T cells (CD3-PE; PharMingen, San Diego, Calif.), B cells (CD19-PE) (PharMingen), and monocytes (CD14-PE) (PharMingen) in order to identify co-staining of the anti-zalpha11 receptor antibody on these cell types. Various controls were used to determine non-specific binding and background levels of staining: (1) an irrelevant rabbit polyclonal sera was used as a non-specific control; and (2) secondary antibody alone was used to determine background binding of that reagent. Purified, zalpha11CEE soluble receptor (Example 6) was used in about a 10-fold excess as a competitive inhibitor to verify the specificity of the rabbit anti-huzalpha11-CEE-BHK antibody to zalpha11 soluble receptor.

After plating the cells and adding the primary and co-staining antibodies, the cells were incubated on ice for 30 minutes, washed 2× with staining buffer, and stained with the secondary antibody, goat anti-rabbit Ig-FITC (Biosource), for 30 minutes on ice. Cells were washed 2× staining buffer, and resuspended at 200 µl per well in staining buffer containing the viability stain 7AAD at about 1 µg/ml final concentration (Sigma, St. Louis, Mo.). Samples were read on the FACS-Caliber (Becton-Dickinson, San Jose, Calif.) and viable cells analyzed.

The rabbit polyclonal to zalpha11 receptor stained resting B cells. The signal on resting B cells was brighter than the signal achieved using the irrelevant rabbit sera, and the signal was diminished to a greater extent on B cells than on T cells with the addition of excess zalpha11-CEE soluble receptor. This experiment was repeated using separated B and T cells, and the results were very similar. Again the staining with the polyclonal rabbit anti-huzalpha11-CEE-BHK antibody to zalpha11 receptor was highest on resting B cells.

Example 14

Zalpha11 Receptor Expression in Various Tissues Using Real-Time Quantitative RT/PCR A. Primers and Probes for Quantitative RT-PCR- Real-time quantitative RT-PCR using the ABI PRISM 7700 Sequence Detection System (PE Applied Biosystems, Inc., Foster City, Calif.) has been previously described (See, Heid, C. A. et al., *Genome Research* 6:986-994, 1996; Gibson, U.E.M. et al., *Genome Research* 6:995-1001, 1996; Sundaresan, S. et al., *Endocrinology* 139:4756-4764, 1998. This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by 5' nuclease activity of Taq polymerase which releases the reporter dye from the probe resulting in an increase in fluorescent emission.

The primers and probes used for real-time quantitative RT-PCR analyses of zalpha11 receptor expression were designed using the primer design software Primer Express™ (PE Applied Biosystems, Foster City, Calif.). Primers for human zalpha11 receptor were designed spanning an intron-exon junction to eliminate amplification of genomic DNA. The forward primer, ZC22,277 (SEQ ID NO:40) and the reverse primer, ZC22,276 (SEQ ID NO:41) were used in a PCR reaction (below) at about 300 nM concentration to synthesize a 143 bp product. The corresponding zalpha11 Taq-Man™ probe, designated ZG31 (SEQ ID NO:42) was synthesized and labeled by PE Applied Biosystems. The ZG31 probe was labeled at the 5' end with a reporter fluorescent dye (6-carboxy-fluorescein) (FAM) (PE Applied Biosystems) and at the 3' end with a quencher fluorescent dye (6-carboxy-tetramethyl-rhodamine) (TAMRA) (PE Applied Biosystems).

As a control to test the integrity and quality of RNA samples tested, all RNA samples (below) were screened for rRNA using a primer and probe set ordered from PE Applied Biosystems (cat No. 430-4483). The kit contains an rRNA forward primer (SEQ ID NO:43) and the rRNA reverse primer (SEQ ID NO:44), rRNA TaqMan® probe (SEQ ID NO:45) The rRNA probe was labeled at the 5' end with a reporter fluorescent dye VIC (PE Applied Biosystems) and at the 3' end with the quencher fluorescent dye TAMRA (PE Applied Biosystems). The rRNA results also serve as an internal control and allow for the normalization of the zalpha11 mRNA expression results seen in the test samples.

RNA samples from human CD3, CD19 and monocyte cell types were prepared and described as per Example 11 above. Control RNA was prepared, using RNeasy Miniprep™ Kit (Qiagen, Valencia, Calif.) as per manufacturer's instructions, from approximately 10 million BaF3 cells expressing human zalpha11 receptor (Example 2A).

B. Real-time Quantitative RT-PCR

Relative levels of zalpha11 mRNA were determined by analyzing total RNA samples using the one-step RT-PCR method (PE Applied Biosystems). Total RNA from BaF3 cells expressing human zalpha11 receptor was isolated by standard methods and used to generate a standard curve used for quantitation. The curve consisted of 10-fold serial dilutions ranging from $2.5-2.5\times10^{-4}$ ng/µl for the rRNA screen and 250-0.025 ng/µl for the zalpha11 screen with each standard curve point analyzed in triplicate. The total RNA samples from the cells were also analyzed in triplicate for human zalpha11 receptor transcript levels and for levels of rRNA as an endogenous control. In a total volume of 25 µl, each RNA sample was subjected to a One-Step RT-PCR reaction containing: approximately 25 ng of total RNA in buffer A (50 mM KCL, 10 mM Tris-HCL); the internal standard dye, carboxy-x-rhodamine (ROX); appropriate primers (approximately 50 nM rRNA primers (SEQ ID NO:43 and SEQ ID NO:44) for the rRNA samples; and approximately 300 nM ZC22,277 (SEQ ID NO:40) and ZC22,276 (SEQ ID NO:41) primers for zalpha11 samples); the appropriate probe (approximately 50 nM rRNA TaqMan® probe (SEQ ID NO:45) for rRNA samples, approximately 100 nM ZG31 (SEQ ID NO:42) probe for zalpha11 samples); 5.5 mM $MgCl_2$; 300 µM each d-CTP, d-ATP, and d-GTP and 600 µM of d-UTP; MuLV reverse transcriptase (0.25 U/µl); Ampli-Taq™ Gold DNA polymerase (0.025 U/µl) (PE Applied Biosystems); and RNase Inhibitor (0.4 U/µl) (PE Applied Biosystems). PCR thermal cycling conditions were as follows: an initial reverse transcription (RT) step of one cycle at 48° C. for 30 minutes; followed by an AmpliTaq Gold™ (PE Applied Biosystems) activation step of one cycle at 95° C. for 10 minutes; followed by 40 cycles of amplification at 95° C. for 15 seconds and 60° C. for 1 minute.

Relative zalpha11 RNA levels were determined by using the Standard Curve Method as described by the manufacturer, PE Biosystems (User Bulletin No. 2: ABI Prism 7700 Sequence Detection System, Relative Quantitation of Gene Expression, Dec. 11, 1997). The rRNA measurements were used to normalize the zalpha11 levels and the resting CD3+ RNA sample was used as a calibrator. Resting CD3 was arbitrarily chosen as the calibrator and given a value of 1.00. The rest of the samples were compared relative to the calibrator. Data are shown in Table 6 below.

TABLE 6

| Sample | Resting | 4 hr Stimulation | 24 hr Stimulation |
|---|---|---|---|
| CD3 | 1.00 | 15.27 | 16.70 |
| CD19 | 20.14 | 65.08 | 25.42 |
| Monocytes | 0.05 | no data | 0.26 |

There was a 15-fold increase in zalpha11 receptor expression in CD3+ at 4 and 24 hrs. Resting CD19 had 20 fold increase in receptor expression relative to resting CD3+. There was a 3 fold increase with 4 hr stimulation that fell back to resting levels by 24 hrs. Monocytes showed no detectable zalpha11 receptor expression in this assay.

C. Purified Human T, NK, and B Cells as a Primary Source Used to Assess Human Zalpha11 Receptor Expression Whole blood (150 ml) was collected from a healthy human donor and mixed 1:1 with PBS in 50 ml conical tubes. Thirty ml of diluted blood was then underlayed with 15 ml of Ficoll Paque Plus (Amersham Pharmacia Biotech, Uppsala, Sweden). These gradients were centrifuged 30 min at 500 g and allowed to stop without braking. The RBC-depleted cells at the interface (PBMC) were collected and washed 3 times with PBS. The isolated human PBMC yield was 200×10e6 prior to selection described below.

The PBMCs were suspended in 1.5 ml MACS buffer (PBS, 0.5% EDTA, 2 mM EDTA) and 3×10e6 cells were set aside for control RNA and for flow cytometric analysis. The 0.25 ml anti-human CD8 microbeads (Miltenyi Biotec) were added and the mixture was incubated for 15 min at 4 degrees C. These cells labeled with CD8 beads were washed with 30 ml MACS buffer, and then resuspended in 2 ml MACS buffer.

A VS+ column (Miltenyi) was prepared according to the manufacturer's instructions. The VS+ column was then placed in a VarioMACS magnetic field (Miltenyi). The column was equilibrated with 5 ml MACS buffer. The isolated primary mouse cells were then applied to the column. The CD8 negative cells were allowed to pass through. The column was rinsed with 9 ml (3×3 ml) MACS buffer. The column was then removed from the magnet and placed over a 15 ml falcon tube. CD8+ cells were eluted by adding 5 ml MACS buffer to the column and bound cells flushed out using the plunger provided by the manufacturer. The yield of CD8+ selected human peripheral T cells was 51×10e6 total cells. The CD8-negative flow through cells were collected, counted, stained with anti-human CD4 coated beads, then incubated and passed over a new VS+ column at the same concentrations as described above. The yield of CD4+ selected human peripheral T cells was 42×10e6 total cells.

A sample of each of the CD8+ and CD4+ selected human T cells was removed for staining and sorting on a fluorescence activated cell sorter (FACS) to assess their purity. A PE-conjugated anti-human CD4 antibody, an anti-human CD8-FITC Ab, and an anti-human CD19-CyChrome Ab (all from PharMingen) were used for staining the CD8+ and CD4+ selected cells. The CD8-selected cells in this first experiment were 80% CD8+, and the CD4+ selected cells were 85% CD4+. In 2 subsequent experiments (Example 14B), the CD8+ purified cells were 84% and 81% pure, and the CD4+ cells were 85% and 97% pure, respectively. In one experiment, we stained the non-binding (flow-through) cells with anti-human CD19-coated beads (Miltenyi) and ran them over a third magnetic bead column to isolate CD19+ B cells (these were 92% pure).

The human CD8+, CD4+ and CD19+ selected cells were activated by incubating 0.5×10$^6$ cells/ml in RPMI+5% human ultraserum (Gemini Bioproducts, Calabasas, Calif.)+PMA 10 ng/ml and Ionomycin 0.5 µg/ml (Calbiochem) for 4, 16, or 24 hours at 37° C. The T-cells (2.5×10e6/well) were alternately stimulated in 24-well plates pre-coated overnight with 0.5 µg/ml plate-bound anti-CD3 mAb UCHT1 (PharMingen) with or without soluble anti-CD28 mAb (PharMingen) at 5 µg/ml. At each timepoint, the cells were harvested, pelleted, washed once with PBS, and pelleted again. The supernatant was removed and the pellets were snap-frozen in a dry ice/ethanol bath, then stored at −80° C. for RNA preparation at a later date.

In a separate experiment, human NK cells were enriched from Ficolled PBMC by negative selection using the human NK enrichment system (consisting of antibodies to CD3, CD4, CD14, CD19, CD66b, and glycophorin A) from Stem Cell Technologies (Vancouver, B.C., Canada). Cell pellets were prepared from freshly isolated NK cells from 2 different donors, or from NK cells cultured 24 hours in media only or in media supplemented with 20 ng/ml IL-15. RNA from a human NK cell line derived from a malignant non-Hodgkin's lymphoma and designated NK-92 (ATCC No. CRL-2407) was also tested. As positive controls, RNA was isolated from the human B cell lines CESS (ATCC No. TIB-190), IM-9 (ATCC No. CCL-159), and HS-Sultan (CRL-1484).

Real Time-PCR was performed on these human NK, CD8+, CD4+ and CD19+ selected cells as described above for assessing human zalpha11 receptor expression. Relative levels of zalpha11 receptor RNA were determined by analysis of total RNA samples using the One-Step RT-PCR method (PE Applied Biosystems). RNA from BaF3 cells expressing human zalpha11 receptor was used to generate appropriate control for standard curves for the real-time PCR described in Example 14C above. Results of the experiments analyzing the expression of the zalpha11 Ligand and zalpha receptor in stimulated and unstimulated cells are as described in Example 14D-E below.

D. Expression of Human Zalpha11 Receptor and Ligand in CD4+, CD8+ and CD19+ Cells The first experiment used RT-PCR, described above, to assess zalpha11 receptor expression in unstimulated and anti-CD3 stimulated CD4+ and CD8+ samples at timepoints of 0 h (unstimulated ("resting") cells), and at 4 h, 15.5 h and 24 h, after stimulation. The resting CD4+ sample was arbitrarily chosen as the calibrator and given a value of 1.00. There was approximately a 4-fold increase in receptor expression in unstimulated CD4+ cells from 4 h to 24 h of culture and about an 8-fold increase over the same time period in anti-CD3 stimulated CD4+ cells. The CD8+ cells showed a 7-fold increase in zalpha11 receptor expression that peaked at 4 hrs and decreased over time. With anti-CD3 stimulation, the CD8+ cells had a constant 8-fold increase in receptor expression.

The second experiment used RT-PCR to assess zalpha11 receptor expression in anti-CD3-stimulated, PMA+Ionomycin-stimulated and unstimulated CD4+ and CD8+ samples at timepoints of 0 h, and at 3.5 h, 16 h and 24 h after activation. The resting CD8+ sample was arbitrarily chosen as the calibrator and given a value of 1.00. The resting CD4+ and CD8+ cells did not have significant amounts of receptor expression. The expression was about 3 fold higher in the PMA+Ionomycin-stimulated CD4+ samples at 3.5 h, 16 h and 24 h after stimulation. The expression in anti-CD3 activated CD4+ cells peaked at 10-fold above background levels at 3.5 h after stimulation, then fell back to levels 4-fold above background at 16 h after stimulation. The CD8+ cells showed a 4-fold expression increase at 3.5 h after PMA+Ionomycin stimulation, with expression decreasing at subsequent timepoints. As in the first experiment, the anti-CD3 stimulated CD8+ cells again exhibited an 8-fold above background induction of receptor expression.

The final experiment used RT-PCR to assess zalpha11 receptor expression in anti-CD3- and anti-CD3/anti-CD28-stimulated and unstimulated CD4+ and CD8+ samples at timepoints of 0 h, and at 2 h, 4 h, and 16 h after stimulation. CD19+ cells activated with PMA+Ionomycin were also screened for receptor expression at the same time intervals. The resting CD4+ sample was arbitrarily chosen as the calibrator and given a value of 1.00. The 2 h anti-CD3 stimulated CD4+ cells only had a 4-fold induction of receptor, compared to the 10-fold induction seen at 3.5 h in the previous experiment. The combination of anti-CD3 and anti-CD28 increased expression to 8-fold above background. The 16 h anti-CD3/anti-CD28 stimulated CD8+ cells had very low receptor expression levels, as seen in the CD8+ cells in previous experiments (above). The CD19+ cells stimulated with PMA+Ionomycin had the most significant receptor expression with a 19-fold increase at 2 h, but the expression levels decreased back to those of resting cells by 16 h.

A certain amount of variation was expected between blood draws (i.e. multiple samples at different times from the same patient and between multiple patients). Therefore, data trends were analyzed within each study or from a single blood sample and the three experiments above were compared for an overall conclusion. The trend from the Real Time PCR experiments described above is that of all the cell types tested, CD19+B cells activated with PMA+ ionomycin expressed the highest levels of zalpha11 receptor RNA. CD4+ and CD8+ cells can also be stimulated to express receptor, but at lower levels than in B cells.

E. Expression of Human zalpha11 Receptor in Human NK Cells

Real Time PCR was also performed on human NK cells, purified as described in Example 14C, above. The NK-92 sample was arbitrarily chosen as the calibrator and given a value of 1.00. There was approximately a 4.5-fold increase in receptor expression in the positive control CESS cells, a 1.5-fold increase in IM-9 cells, and no increase in the HS-Sultan cells (0.9-fold relative to NK-92). The NK cells, either fresh or cultured overnight with or without IL-15, expressed very similar levels of zalpha11 Receptor as NK-92 (with values ranging from 0.9-1.2-fold different relative to NK-92).

Example 15

Identification of Cells Expressing Zalpha11 Receptor Using in Situ Hybridization Specific human tissues were isolated and screened for zalpha11 expression by in situ hybridization. Various human tissues prepared, sectioned and subjected to in situ hybridization included thymus, spleen, tonsil, lymph node and lung. The tissues were fixed in 10% buffered formalin and blocked in paraffin using standard techniques. Tissues were sectioned at 4 to 8 microns. Tissues were prepared using a standard protocol ("Development of non-isotopic in situ hybridization" at http://dir.niehs.nih.gov/dirlep/ish.html). Briefly, tissue sections were deparaffinized with HistoClear (National Diagnostics, Atlanta, Ga.) and then dehydrated with ethanol. Next they were digested with Proteinase K (50 µg/ml) (Boehringer Diagnostics, Indianapolis, Ind.) at 37° C. for 2 to 20 minutes. This step was followed by acetylation and re-hydration of the tissues.

Two in situ probes generated by PCR were designed against the human zalpha11 sequence. Two sets of oligos were designed to generate probes for separate regions of the zalpha11 cDNA: (1) Oligos ZC23,684 (SEQ ID NO:60) and ZC23,656 (SEQ ID NO:61) were used to generate a 413 bp probe for zalpha11; and (2) Oligos ZC23,685 (SEQ ID NO:62) and ZC23,657 (SEQ ID NO:63) were used to generate a 430 bp probe for zalpha11. The second probe is 1500 bp 3' of the first zalpha11 probe. The antisense oligo from each set also contained the working sequence for the T7 RNA polymerase promoter to allow for easy transcription of antisense RNA probes from these PCR products. The PCR reaction conditions were as follows: 30 cycles at 94° C. for 30 sec, 60° C. for 1 min., 72° C. for 1.5 min. The PCR products were purified by Qiagen spin columns followed by phenol/chloroform extraction and ethanol precipitation. Probes were subsequently labeled with digoxigenin (Boehringer) or biotin (Boehringer) using an In Vitro transcription System (Promega, Madison, Wis.) as per manufacturer's instruction.

In situ hybridization was performed with a digoxigenin- or biotin-labeled zalpha11 probe (above). The probe was added to the slides at a concentration of 1 to 5 pmol/ml for 12 to 16 hours at 55-60° C. Slides were subsequently washed in 2×SSC and 0.1×SSC at 50° C. The signals were amplified using tyramide signal amplification (TSA) (TSA, in situ indirect kit; NEN) and visualized with Vector Red substrate kit (Vector Lab) as per manufacturer's instructions. The slides were then counter-stained with hematoxylin (Vector Laboratories, Burlingame, Calif.).

A signal was seen in the thymus, tonsil, lung, and lymph node. The positive-staining cells appeared to be lymphocytes.

Example 16

Secretion Trap Assay

A secretion trap assay was used to identify the cDNA for the zalpha11 Ligand. The positive DNA pools obtained from the expression cloning effort were described in commonly owned U.S. patent application Ser. No. 09/522,217.

Conditioned medium from DNA clones transfected into BHK cells in 96-well format, were put into the proliferation assay using BaF3/zalpha11 cells described in Example 2. Several DNA pools gave positive activities that were repeated and neutralized with zalpha11 soluble receptors (Example 6). One positive DNA pool was transfected into COS cells in 12-well format, using the Lipofectamine™ method described below.

A secretion trap assay was then performed using zalpha11 soluble receptors (C-terminal Glu-Glu tagged either with or without biotinylation; C-terminal Flag tagged; or Fc4 zalpha11 soluble receptor fusions) (Example 6) to test the direct binding between the zalpha11 Ligand in the positive pool and zalpha11 soluble receptors (see below). The result was positive, enabling the detection and isolation of clones expressing the zalpha11 Ligand. Plates were shaken at 37° C. for 24 hours, and then DNA minipreps (QiaPrep™ 96 Turbo Miniprep Kit; Qiagen) were prepared in 96-well format using a TomTech Quadra 9600. The plasmid DNA was then pooled in the format of rows and columns, transfected into COS cells, and then the positive pools were determined by secretion trap as described below.

COS Cell Transfections

The COS cell transfection was performed as follows: Mix 3 ul pooled DNA and 5 ul Lipofectamine™ in 92 ul serum free DMEM media (55 mg sodium pyruvate, 146 mg L-glutamine, 5 mg transferrin, 2.5 mg insulin, 1 μg selenium and 5 mg fetuin in 500 ml DMEM), incubate at room temperature for 30 minutes and then add 400 ul serum free DMEM media.

Add this 500 ul mixture onto $1.5 \times 10^5$ COS cells/well plated on 12-well tissue culture plate and incubate for 5 hours at 37° C. Add 500 ul 20% FBS DMEM media (100 ml FBS, 55 mg sodium pyruvate and 146 mg L-glutamine in 500 ml DMEM) and incubate overnight.

Secretion Trap Assay

The secretion trap was performed as follows: Media was rinsed off cells with PBS and then fixed for 15 minutes with 1.8% Formaldehyde in PBS. Cells were then washed with TNT (0.1M Tris-HCL, 0.15M NaCl, and 0.05% Tween-20 in $H_2O$), and permeated with 0.1% Triton-X in PBS for 15 minutes, and again washed with TNT. Cells were blocked for 1 hour with TNB (0.1M Tris-HCL, 0.15M NaCl and 0.5% Blocking Reagent (NEN Renaissance TSA-Direct Kit) in $H_2O$), and washed again with TNT. If using the biotinylated protein, the cells were blocked for 15 minute incubations with Avidin and then Biotin (Vector Labs), washing in-between with TNT. Depending on which soluble receptor was used, the cells were incubated for 1 hour with: (A) 1-3 μg/ml zalpha11 soluble receptor zalpha11-Fc4 fusion protein (Example 6); (B) 3 μg/ml zalpha11 soluble receptor C-terminal FLAG tagged, zalpha11CFLG (Example 6); (C) 3 μg/ml zalpha11 soluble receptor C-terminal GluGlu tagged, zalpha11 CEE (Example 6); or (D) 3 μg/ml biotinylated zalpha11 soluble receptor zalpha11CEE (Example 6) in TNB. Cells were then washed with TNT. Depending on which soluble receptor was used, cells were incubated for another hour with: (A) 1:200 diluted goat-anti-human Ig-HRP (Fc specific); (B) 1:1000 diluted M2-HRP; (C) 1:1000 diluted anti-GluGlu antibody-HRP; or (D) 1:300 diluted streptavidin-HRP (NEN kit) in TNB. Again cells were washed with TNT.

Positive binding was detected with fluorescein tyramide reagent diluted 1:50 in dilution buffer (NEN kit) and incubated for 4-6 minutes, and washed with TNT. Cells were preserved with Vectashield Mounting Media (Vector Labs Burlingame, Calif.) diluted 1:5 in TNT. Cells were visualized using a FITC filter on fluorescent microscope.

Example 17

Mouse Zalpha11 Ligand Binds to Human Zalpha11 Soluble Receptor in Secretion Trap Assay A plasmid containing DNA encoding the mouse zalpha11 Ligand (SEQ ID NO:47) was transfected into COS cells, and the binding of human zalpha11 soluble receptor Zalpha11-Fc4 (Example 6C) to the transfected COS cells was tested by a secretion trap assay (Example 16). The assay confirmed that the mouse zalpha11 Ligand binds to human zalpha11 soluble receptor.

The COS cell transfection was performed as per Example 16 using 0.7 μg of the plasmid in 3 μl. The secretion trap was performed as per Example 16 using 1 μg/ml zalpha11 soluble receptor Fc4 fusion protein (Example 6C) in TNB, and 1:200 diluted goat-anti-human Ig-HRP (Fc specific) in TNB for the detectable antibody. Positive binding of the soluble human zalpha11 receptor to the prepared fixed cells was detected with fluorescein tyramide reagent, preserved and visualized according to Example 16. The positive result indicated the mouse zalpha11 Ligand binds to human zalpha11 soluble receptor.

Example 18

Mouse Zalpha11 Ligand Activates Human Zalpha11 Receptor in BaF3 Assay Using Alamar Blue BaF3/Zalpha11 cells were spun down, washed and plated in mIL-3 free media as described in Example 2. Proliferation of the BaF3/Zalpha11 cells was assessed using serum-free conditioned media from BHK cells expressing mouse zalpha11 Ligand (SEQ ID NO:47). Conditioned media was diluted with mIL-3 free media to: 50%, 25%, 12.5%, 6.25%, 3.125%, 1.5%, 0.75% and 0.375% concentrations. The proliferation assay was performed as per Example 2. Results confirmed the proliferative response of the BaF3/Zalpha11 cells to mouse zalpha11 Ligand. The response, as measured, was approximately 5-fold over background at the 50% concentration.

Example 19

Zalpha11 Ligand Activates Human Zalpha11 Receptor in Luciferase Assay

A. Construction of BaF3/KZ134/Zalpha11 Cell Line

The KZ134 plasmid was constructed with complementary oligonucleotides ZC12,749 (SEQ ID NO:48) and ZC12,748 (SEQ ID NO:49) that contain STAT transcription factor binding elements from 4 genes. A modified c-fos Sis inducible element (m67SIE, or hSIE) (Sadowski, H. et al., *Science* 261:1739-1744, 1993), the p21 SIE1 from the p21 WAF1 gene (Chin, Y. et al., *Science* 272:719-722, 1996), the mammary gland response element of the β-casein gene (Schmitt-Ney, M. et al., *Mol. Cell. Biol.* 11:3745-3755, 1991), and a STAT inducible element of the Fcg RI gene, (Seidel, H. et al., *Proc. Natl. Acad. Sci.* 92:3041-3045, 1995). These oligonucleotides contain Asp718-XhoI compatible ends and were ligated, using standard methods, into a recipient firefly luciferase reporter vector with a c-fos promoter (Poulsen, L. K. et al., *J. Biol. Chem.* 273:6229-6232, 1998) digested with the same enzymes and containing a neomycin selectable marker. The KZ134 plasmid was used to stably transfect BaF3 cells, using standard transfection and selection methods, to make the BaF3/KZ134 cell line.

A stable BaF3/KZ134 indicator cell line, expressing the full-length zalpha11 receptor was constructed as per Example 1, using about 30 μg of the zalpha11 expression vector. Clones were diluted, plated and selected using standard techniques. Clones were screened by luciferase assay (see Example 19B, below) using the human zalpha11 Ligand conditioned media as an inducer. Clones with the highest luciferase response (via STAT luciferase) and the lowest background were selected. A stable transfectant cell line was selected. The cell line was called BaF3/KZ134/zalpha11.

B. Human and Mouse Zalpha11 Ligand Activates Human Zalpha11 Receptor in BaF3/KZ134/Zalpha 11 Luciferase Assay BaF3/KZ134/Zalpha11 cells were spun down and washed in mIL-3 free media. The cells were spun and washed 3 times to ensure removal of mIL-3. Cells were then counted in a hemacytometer. Cells were plated in a 96-well format at about 30,000 cells per well in a volume of 100 μl per well using the mIL-3 free media. The same procedure was used for untransfected BaF3/KZ134 cells for use as a control in the subsequent assay.

STAT activation of the BaF3/KZ134/Zalpha11 cells was assessed using conditioned media from (1) BHK570 cells transfected with an expression vector encoding the human zalpha11 Ligand (SEQ ID NO:10) or (2) BHK570 cells transfected with an expression vector encoding the mouse zalpha11 Ligand (SEQ ID NO:47), or (3) mIL-3 free media to measure media-only control response. Conditioned media was diluted with RPMI mIL-3 free media to 50%, 25%, 12.5%, 6.25%, 3.125%, 1.5%, 0.75% and 0.375% concentrations. 100 µl of the diluted conditioned media was added to the BaF3/KZ134/Zalpha11 cells. The assay using the conditioned media was done in parallel on untransfected BaF3/KZ134 cells as a control. The total assay volume was 200 µl. The assay plates were incubated at 37° C., 5% $CO_2$ for 24 hours at which time the cells were pelleted by centrifugation at 2000 rpm for 10 min., and the media was aspirated and 25 µl of lysis buffer (Promega) was added. After 10 minutes at room temperature, the plates were measured for activation of the STAT reporter construct by reading them on a luminometer (Labsystems Luminoskan, model RS) which added 40 µl of luciferase assay substrate (Promega) at a five second integration.

Results confirmed the STAT reporter response of the BaF3/KZ134/Zalpha11 cells to the human zalpha11 Ligand. The response, as measured, was approximately 50 fold over media-only control at the 50% concentration. STAT activation in response to human zalpha11 Ligand was absent in the untransfected BaF3/KZ134 control cells, showing that the response is mediated through the Zalpha11 receptor.

Results also confirmed the STAT reporter response of the BaF3/KZ134/Zalpha11 cells to the mouse zalpha11 Ligand. The response, as measured, was approximately 40 fold over media-only control at the 50% concentration. Moreover, STAT activation in response to mouse zalpha11 Ligand was evident (about 5-fold) on the untransfected BaF/KZ134 control cells, suggesting that the murine BaF3 cells may have endogenous mouse receptor.

Example 20

Mouse Zalpha11 Ligand is Active in Mouse Bone Marrow Assay

A. Isolation of Non-Adherent Low Density Marrow Cells:

Fresh mouse femur aspirate (marrow) was obtained from 6-10 week old male Balb/C or C57BL/6 mice. The marrow was then washed with RPMI+10% FBS (JRH, Lenexa Kans.; Hyclone, Logan Utah) and suspended in RPMI+10% FBS as a whole marrow cell suspension. The whole marrow cell suspension was then subjected to a density gradient (Nycoprep, 1.077, Animal; Gibco BRL) to enrich for low density, mostly mononuclear, cells as follows: The whole marrow cell suspension (About 8 ml) was carefully pipeted on top of about 5 ml Nycoprep gradient solution in a 15 ml conical tube, and then centrifuged at 600×g for 20 minutes. The interface layer, containing the low density mononuclear cells, was then removed, washed with excess RPMI+10% FBS, and pelleted by centrifugation at 400×g for 5-10 minutes. This pellet was resuspended in RPMI+10% FBS and plated in a T-75 flask at approximately $10^6$ cells/ml, and incubated at 37° C. 5% $CO_2$ for approximately 2 hours. The resulting cells in suspension were Non-Adherent Low Density (NA LD) Marrow Cells.

B. 96-Well Assay

NA LD Mouse Marrow Cells were plated at 25,000 to 45,000 cells/well in 96 well tissue culture plates in RPMI+ 10% FBS+1 ng/mL mouse Stem Cell Factor (mSCF) (R&D Systems, Minneapolis, Minn.), plus 5% conditioned medium from one of the following: (1) BHK 570 cells expressing mouse zalpha11 Ligand (SEQ ID NO:47), (2) BHK 570 cells expressing human zalpha11 Ligand (SEQ ID NO:10), or (3) control BHK 570 cells containing vector and not expressing either Ligand. These cells were then subjected to a variety of cytokine treatments to test for expansion or differentiation of hematopoietic cells from the marrow. To test, the plated NA LD mouse marrow cells were subjected to human Interleukin-15 (hIL-15) (R&D Systems), or one of a panel of other cytokines (R&D Systems). Serial dilution of hIl-15, or the other cytokines, were tested, with 2-fold serial dilution from about 50 ng/ml down to about 6025 ng/ml concentration. After 8 to 12 days the 96-well assays were scored for cell proliferation by Alamar blue assay as described in Example 2.

C. Results from the 96-Well NA LD Mouse Marrow assay

Conditioned media from the BHK cells expressing both mouse and human zalpha11 Ligand acted in synergy with hIL-15 to promote the expansion of a population of hematopoietic cells in the NA LD mouse marrow. This expansion of hematopoietic cells was not shown with control BHK conditioned medium plus IL-15. The population hematopoietic cells expanded by the mouse zalpha11 Ligand with hIL-15, and those hematopoietic cells expanded by the human zalpha11 Ligand with hIL-15, were further propagated in cell culture. These hematopoietic cells were stained with a Phycoerythrin labeled anti-Pan NK cell antibody (Pharmingen) and subjected to flow cytometry analysis, which demonstrated that the expanded cells stained positively for this natural killer (NK) cell marker.

The same 96-well assay was run, using fresh human marrow cells bought from Poietic Technologies, Gaithersburg, Md. Again, in conjunction with IL-15, the mouse and human zalpha11 Ligand expanded a hematopoietic cell population that stained positively for the NK cell marker using the antibody disclosed above.

The soluble zalpha11 receptor or soluble zalpha11 heterodimeric polypeptide, such as soluble zalpha11/IL-2Rγ can be used in this assay to measure binding, antagonist or inhibitory effects of the soluble zalpha11 receptor or soluble zalpha11 heterodimeric polypeptide, such as soluble zalpha11/IL-2Rγ on the zalpha11 Ligand.

Example 21

Purification of Zalpha11-MBP Receptor

Unless otherwise stated, all operations were carried out at 4° C. The following procedure was used for purifying human (or mouse) zalpha11-MBP soluble receptor fusions from E. Coli (Example 8). Pre-spun frozen E. Coli paste was thawed and diluted into 2 liters of Buffer B (0.02 M TRIS (EM Science); 0.2 M NaCl (Mallincrodt); 0.01 M 2-mercaptoethanol (EM Science); pH 8.0; with 5 mg/l Pepstatin A (Boehringer Mannheim); 5 mg/l Aprotinin (Boerhinger Mannheim); and 1 mg/l PMSF (Fluka)) plus 1-2 ml of an antifoaming reagent AF289 antifoam (Sigma). The mixture was processed in a pre-chilled French Press cell disrupter (Constant Systems LTD) with 20-30 kPSI.

The lysate was then centrifuged at 18,000×g for 45 minutes at 4° C. and the supernatant retained. A 200 ml slurry of Amylose resin (New England BioLabs), pre-equilibrated in Buffer A (0.02 M TRIS (EM Science); 0.2 M NaCl (Mallincrodt); 0.01 M 2-mercapto-ethanol (EM Science); pH 8.0), was added to the lysate supernatant and incubated overnight in 21 roller bottles to allow for maximum batch absorption of the MBP fusion protein. The resin was washed in batch column format for ≥5 column volumes with Buffer A, then batch eluted with Buffer C (Buffer A with 0.02 M Maltose (Sigma). Crude fractions were collected and monitored by absorbance 280 nm.

The eluted protein was analyzed by SDS NuPAGE (NOVEX) Coomassie (Sigma) staining. Sample and bulk protein were stored at −80° C.

Example 22

Activity of Human and Mouse Zalpha11 Ligand Expanded Cells and Mature Murine NK Cells in NK Cell Cytotoxicity Assays A. NK Cell Assay NK cell-mediated target cytolysis was examined by a standard $^{51}$Cr-release assay. Target cells ($K_{562}$ cells (ATCC No. CCL-243) in human assays, and YAC-1 cells (ATCC No. TIB-160) in mouse assays) lack expression of major histocompatibility complex (MHC) molecules, rendering them susceptible to NK cell-mediated lysis. A negative control target cell line in mouse assays is the $MHC^+$ thymoma EL4 (ATCC No. TIB-39). We grew K562, EL4, and YAC-1 cells in RP10 medium (standard RPMI 1640 (Gibco/BRL), Grand Island, N.Y.) supplemented with 10% FBS (Hyclone, Logan, Utah), as well as 4 mM glutamine (Gibco/BRL), 100 I.U./ml penicillin+100 MCG/ml streptomycin (Gibco/BRL), 50 μM β-mercaptoethanol (Gibco/BRL) and 10 mM HEPES buffer (Gibco/BRL). On the day of assay, $1-2\times10^6$ target cells were harvested and resuspended at $2.5-5\times10^6$ cells/ml in RP10 medium. We added 50-100 μl of 5 mCi/ml $^{51}$Cr-sodium chromate (NEN, Boston, Mass.) directly to the cells and incubated them for 1 hour at 37° C., then washed them twice with 12 ml of PBS and resuspended them in 2 ml of RP10 medium. After counting the cells on a hemacytometer, the target cells were diluted to $0.5-\times10^5$ cells/ml and 100 μl ($0.5-1\times10^4$ cells) were mixed with effector cells as described below.

In human assays, effector cells were prepared from selected and expanded human $CD34^+$ BM cells which were harvested, washed, counted, mixed at various concentrations with $^{51}$Cr-labeled target cells in 96-well round bottomed plates, and incubated for 4 hours at 37° C. After co-incubation of effector cells and the labeled target cells, half of the supernatant from each well was collected and counted in a gamma counter for 1 min/sample. The percentage of specific $^{51}$Cr release was calculated from the formula $100\times(X-Y)/(Z-Y)$, where X is $^{51}$Cr release in the presence of effector cells, Y is the spontaneous release in the absence of effectors, and Z is the total $^{51}$Cr release from target cells incubated with 0.5% Triton X-100. Data were plotted as the % specific lysis versus the effector-to-target ratio in each well.

B. Activity of Human Zalpha11 Ligand Expanded Cells

Isolated $CD34^+$ human HPCs cultured with flt3+/−zalpha11 Ligand and flt3+IL-15+/−zalpha11 Ligand, were harvested the cells on day 15 to assess their capacity to lyse $MHC^-$K562 cells in a standard $^{51}$Cr-release assay as described above, and to analyze their surface phenotype by flow cytometry. As expected from previous reports (Mrozek, E et al., Blood 87:2632-2640, 1996; and Yu, H et al., Blood 92:3647-3657, 1998), simultaneous addition of IL-15 and flt3L did induce the outgrowth of a small population of $CD56^+$ cells. Interestingly, although BM cells cultured simultaneously with zalpha11 Ligand and flt3L did not expand significantly, there was a significant increase in total cell numbers in cultures containing a combination of flt3L, zalpha11 Ligand and IL-15.

For an assessment of the surface phenotype of these human BM cultures, we stained small aliquots of the cells for 3-color flow cytometric analysis with anti-CD3-FITC, anti-CD56-PE and anti-CD16-CyChrome mAbs (all from PharMingen, San Diego, Calif.) and analyzed them on a FACSCalibur using CellQuest software (Becton Dickinson, Mountain View, Calif.). This flow cytometric analysis confirmed that the cells growing out of these cultures were differentiated NK cells, as they were large and granular and expressed both CD56 and CD16, and were $CD3^-$ (Lanier, L L Annu. Rev. Immunol. 16:359-393, 1998). Furthermore, these cells exhibited significantly higher effector function than those cells grown with IL-15 and flt3. More specifically, cells grown in all three cytokines lysed more than 40% of the K562 targets at an effector-to-target ratio (E:T) of 1.5, whereas cells grown in IL-15+flt3L lysed fewer than 5% of the targets at an E:T of 2. These data demonstrate that, in combination with IL-15, zalpha11 Ligand (commonly owned U.S. patent application Ser. No. 09/522,217) stimulates the differentiation of NK cells from $CD34^+$ BM cells.

C. Activity of Mouse Zalpha11 Ligand Expanded Cells

To test the effects of mouse zalpha11 Ligand (commonly owned U.S. patent application Ser. No. 09/522,217) on murine hematopoietic progenitor cells, purified Lineage-negative (Lin−) bone marrow cells from C57Bl/6 mice were expanded in flt3+IL-15+/−zalpha11 Ligand. On day 6 of culture, the cells ("effectors") were harvested and counted, then resuspended in 0.4 ml of RP10 medium (Example 22A). Two aliquots (0.15 ml each) of each sample expanded with or without zalpha11 Ligand (Example 22A) were diluted serially 3-fold in duplicate in 96-well round bottomed plates, for a total of 6 wells of 100 μl each. The remaining 100 μl of cells were stained for NK cell surface markers with FITC-anti-2B4 and PE-anti-DX5 mAbs (PharMingen) and analyzed by flow cytometry. Each group of cells exposed to flt3+IL-15 with or without the presence of mouse zalpha11 Ligand had similar fractions of 2B4+DX5+ cells, ranging from 65-75% positive for both NK markers.

For the NK lysis assay, target cells (YAC-1 and EL4) were labeled with $^{51}$Cr as described above. After counting the target cells on a hemacytometer, the target cells were diluted to $0.5-1\times10^5$ cells/ml and 100 μl of YAC-1 or EL4 ($0.5-1\times10^4$ cells) were mixed with 100 μl effector cells and incubated for 4 hours at 37° C. Specific lysis was determined for each well as described above.

We found that cells grown in the presence of flt3+IL-15+zalpha11 Ligand exhibited enhanced lytic activity (roughly 2-fold) against the YAC-1 targets (but did not kill the $MHC^+$ control cell line EL4). At an effector-to-target ratio (E:T) of 5, NK cells generated in the presence of all 3 cytokines (zalpha11 Ligand+flt3+IL-15) lysed 12% of the YAC-1 cells, whereas those NK cells expanded with flt3+IL-15 lysed 6% of the YAC-1 targets. Subsequent experiments confirmed this trend.

In a second approach to determine the biological activity of zalpha11 Ligand on murine NK cells, we isolated immature $CD4^-CD8^-$ ("double negative", DN) mouse thymocytes using routine methods and cultured them with IL-15+flt3+IL-7 or IL-15+flt3+IL-2, with or without zalpha11 Ligand. On day 6 of culture, the cells were harvested and assayed for NK lytic activity on YAC-1 and EL4 cells as described above.

We found that cells cultured in the presence of zalpha11 Ligand had the greatest lytic activity in this assay, with enhanced lytic activity over those cells cultured in the presence of the other cytokines. Specifically, DN thymocytes grown with IL-15+flt3+IL-7 killed 18% of the YAC-1 cells at E:T of 24 while cells grown in the presence of IL-15+flt3+IL-7 plus zalpha11 Ligand killed 48% of the targets at the same E:T. DN thymocytes grown in IL-15+flt3+IL-2 killed 15% of the YAC-1 targets at an E:T of 6, whereas cells grown with these 3 cytokines and zalpha11 Ligand killed 35% of the YAC-1 cells at an E:T of 9. Flow cytometry was performed on the cultured cells one day before the NK lysis assay. As was true for the bone marrow cultures, despite the proliferative effect of zalpha11 Ligand (cell numbers increase approximately 2-fold when zalpha11 Ligand is added), it did not significantly enhance the fraction of DX5$^+$ cells (17-20% of total cells in the cultures with IL-7, and 35-46% of total in cultures with IL-2). These data imply that zalpha11 Ligand, in combination with IL-15 and flt3, enhances the lytic activity of NK cells generated from murine bone marrow or thymus.

D. Activity of Mouse Zalpha11 Ligand on Mature Murine NK Cells

In order to test the effects of mouse zalpha11 Ligand on mature NK cells, we isolated spleens from four 5-week old C57B1/6 mice (Jackson Laboratories, Bar Harbor, Me.) and mashed them with frosted-end glass slides to create a cell suspension. Red blood cells were removed by hypotonic lysis as follows: cells were pelleted and the supernatant removed by aspiration. We disrupted the pellet with gentle vortexing, then added 900 μl of sterile water while shaking, followed quickly (less than 5 sec later) by 100 μl of 10×HBSS (Gibco/BRL). The cells were then resuspended in 10 ml of 1×HBSS and debris was removed by passing the cells over a nylon mesh-lined cell strainer (Falcon). These RBC-depleted spleen cells were then pelleted and resuspended in MACS buffer (PBS+1% BSA+2 mM EDTA) and counted. We stained 300×10$^6$ of the cells with anti-DX5-coated magnetic beads (Miltenyi Biotec) and positively selected DX5$^+$ NK cells over a MACS VS+ separation column, according to the manufacturer's instructions, leading to the recovery of 8.4×10$^6$ DX5$^+$ cells and 251×10$^6$ DX5$^-$ cells. Each of these groups of cells were cultured in 24-well plates (0.67×10$^6$ cells/well, 2 wells per treatment condition) in RP10 medium (Example 22A) alone or with 1) 30 ng/ml mouse zalpha11 Ligand (commonly owned U.S. patent application Ser. No. 09/522,217), 2) 30 ng/ml recombinant mouse IL-2 (R&D Systems, Inc., Minneapolis, Minn.), 3) 30 ng/ml recombinant human IL-15 (R&D), 4) 30 ng/ml each of mouse zalpha11 Ligand and hIL-15, or 5) 30 ng/ml each of mIL-2 and hIL-15. The cells were harvested after 21 hours, washed, and resuspended in RP10 medium and counted. The cells were then assayed for their ability to lyse $^{51}$Cr-labeled YAC-1 or EL4 targets cells, as described in Example 22A.

In general, there was little NK activity from the DX5$^-$ (non-NK cells) groups, but the DX5$^-$ cells cultured with zalpha11 Ligand and hIL-15 did lyse 25% of the YAC-1 target cells at an E:T of 82. By comparison, DX5$^-$ cells cultured with hIL-15 alone lysed 14% of the YAC-1 targets at an E:T of 110. This suggests that zalpha11 Ligand and IL-15 are acting together on the residual NK1.1$^+$ NK cells in this cell preparation. As for the DX5$^+$ cell preparation, treatment with mouse zalpha11 Ligand alone did not significantly increase their effector function (their lysis of YAC-1 cells was similar to the untreated group). As expected, both IL-2 and IL-15 significantly improved NK activity. The highest level of lysis, however, was detected in the group treated with zalpha11 Ligand and hIL-15 (65% lysis of YAC-1 cells at an E:T of 3.3, vs. 45% lysis at an E:T of 4 for the hIL-15 treatment group). Taken together, these results suggest that although zalpha11 Ligand alone may not increase NK cell lysis activity, it does enhance NK lysis activity of mature NK cells, when administered with IL-15.

The soluble zalpha11 receptor or soluble zalpha11 heterodimeric polypeptide, such as soluble zalpha11/IL-2Rγ can be used in this assay to measure binding, antagonist or inhibitory effects of the soluble zalpha11 receptor or soluble zalpha11 heterodimeric polypeptide, such as soluble zalpha11/IL-2Rγ on the zalpha11 Ligand.

Example 23

Zalpha11 Ligand Proliferation of Human and Mouse T-Cells in a T-Cell Proliferation Assay A. Murine Zalpha11 Ligand Proliferation of Mouse T-Cells T cells from C57B1/6 mice (Jackson Laboratories, Bar Harbor, Me.) were isolated from pooled splenocytes and lymphocytes from axillary, brachial, inguinal, cervical, and mesenteric lymph nodes (LNs). Spleens were mashed with frosted-end glass slides to create a cell suspension. LNs were teased apart with forceps and passed through a cell strainer to remove debris. Pooled splenocytes and LN cells were separated into CD8$^+$ and CD4$^+$ subsets using two successive MACS magnetic separation columns, according to the manufacturer's instructions (Miltenyi Biotec, Auburn, Calif.). Whole thymocytes were collected from the same mice.

Cells were cultured at 3×10$^5$ cells/well (thymocytes) or 10$^5$ cells/well (mature T cells) with increasing concentrations of purified murine zalpha11 Ligand (0-30 ng/ml) (commonly owned U.S. patent application Ser. No. 09/522,217) in 96-well flat bottomed plates pre-coated overnight at 4° C. with various concentrations of anti-CD3 mAb 2C11 (PharMingen) for 3 days at 37° C. The anti-CD3 antibody served to activate the murine T-cells through the T-cell receptor. Each well was pulsed with 1 μCi $^3$H-thymidine on day 2 and plates were harvested and counted 16 hours later to assess proliferation.

When we tested zalpha11 Ligand in T cell proliferation assays, we found that it co-stimulated anti-CD3-activated murine thymocytes, leading to an accelerated outgrowth of CD8$^+$CD4$^-$ cells (the majority of the thymocytes cultured with anti-CD3+ zalpha11 Ligand were CD8$^+$CD4$^-$ by day 3 of culture, while cells cultured with anti-CD3 alone did not significantly skew to this phenotype until day 5). We did not observe significant levels of proliferation of thymocytes to zalpha11 Ligand in the absence of anti-CD3.

Interestingly, when we assayed mature peripheral murine T cells for their ability to respond to zalpha11 Ligand+anti-CD3, we found that only the CD8$^+$, but not the CD4$^+$ subset, responded in a dose-dependent manner to zalpha11 Ligand. We also observed weak but reproducible proliferation of CD8$^+$ cells (but not CD4$^+$ cells) in response to zalpha11 Ligand alone. Interestingly, this was not observed for human T cells (see Example 22B, below).

B. Human Zalpha11 Ligand Proliferation of Human T-Cells

Human CD4+ and CD8+ T cells were isolated from PBMC as described in Example 14. Cells were cultured at about 10$^5$ cells/well with increasing concentrations of purified human zalpha11 Ligand (0-50 ng/ml) (commonly owned U.S. patent application Ser. No. 09/522,217) in 96-well flat bottomed plates pre-coated overnight at 4° C. with various concentrations of anti-human CD3 mAb UCHT1 (PharMingen) for 3 days at 37° C. Each well was pulsed with 1 uCi $^3$H-thymidine on day 2 and plates were harvested and counted 16 hours later. Unlike our results with mouse T cells, our preliminary data suggests that human zalpha11 Ligand co-stimulates CD4+, but not CD8+, human T cells in a dose-dependent fashion. The soluble zalpha11 receptor or soluble zalpha11 heterodimeric polypeptide, such as soluble zalpha11/IL-2Rγ can be used in this assay to measure binding, antagonist or inhibitory effects of the soluble zalpha11 receptor or soluble zalpha11 heterodimeric polypeptide, such as soluble zalpha11/IL-2Rγ on the zalpha11 Ligand Example 24

Human zalpha11 Receptor Monoclonal Antibodies

Zalpha11 receptor Monoclonal antibodies were prepared by immunizing 5 male BalbC mice (Harlan Sprague Dawley, Indianapolis, Ind.) with the purified recombinant protein, huzalpha11-CEE-BHK (Example 6). The mice were each given an initial intraperitoneal (IP) injection of 20 mg of purified protein in Complete Freund's Adjuvant (Pierce, Rockford, Ill.) followed by booster IP injections of 10 mg purified protein in Incomplete Freund's Adjuvant every two weeks. Seven to ten days after the administration of the third booster injection, the animals were bled and the serum was collected.

The mouse sera samples raised to the huzalpha11-CEE-BHK were characterized by an ELISA titer check using purified recombinant CHO huzalpha11-Fc protein (Example 10C) as an antibody target. One mouse serum sample had titer to the specific antibody target at a dilution of 1:1,000,000 (1:1 E6). Four mouse serum samples had titer to the specific antibody target at a dilution of 1:100,000 (1:1 E5).

Splenocytes were harvested from the 4 high-titer mice and fused to murine SP2/0 myeloma cells using PEG 1500 (Boerhinger Mannheim, UK) in two separate fusion procedures using a 4:1 fusion ratio of splenocytes to myeloma cells (*Antibodies: A Laboratory Manual*, E. Harlow and D. Lane, Cold Spring Harbor Press). Following 10 days growth post-fusion, specific antibody-producing hybridomas were identified by ELISA using purified recombinant BHK human zalpha11-Fc4 protein (Example 6C) as an antibody target and by FACS using Baf3 cells expressing the huzalpha11 sequence (Example 2) as an antibody target. The resulting 4 hybridomas positive by both methods were cloned three times by limiting dilution. The antibodies were designated: 249.28.2.1.2.2; 247.10.2.15.4.6; 249.19.2.2.3.5; and 249.15.2.4.2.7.

Example 25

Zalpha11 Receptor Purified Recombinant Human Protein Dose-Response Study in Normal Mice A. Summary Normal nine week old female C57B1/6 (Harlan Sprague Dawley, Indianapolis, Ind.) mice were treated by intraperitoneal injection once daily for seven days with one of three dose levels of purified recombinant human zalpha11-Fc4 soluble receptor (Example 6C) (5, 50 or 250 μg/mouse/day) or PBS vehicle plus 250 μg per dose of BSA. Body weights were monitored every other day. On day seven the five mice from the highest dose group and five of the vehicle control group were sacrificed. Blood, bone marrow and tissues were harvested and analyzed. The remaining mice were sacrificed and harvests done the following day. Potential perturbations in lymphoid tissues were examined, as well as general physiologic and toxicologic parameters.

There was no clinical evidence of toxicity. Liver, kidney, spleen, thymus and brain were weighed, and there were no differences between the treatment groups in organ weights. No histologic changes were found in the examined tissues.

B. Dosing Solution Preparation

Purified recombinant human zalpha11 receptor-FC4 fusion protein (zalpha11-FC4) (Example 6C) was diluted into sterile phosphate buffered saline (PBS) (GibcoBRL, Grand Island, N.Y.) at concentrations to deliver 5, 50 or 250 micrograms of protein in 0.1 ml of PBS vehicle. Bovine serum albumin (BSA) (Sigma, St. Louis, Mo.) was dissolved in PBS to make a 250 μg dose per 0.1 ml then filtered through an 0.2 μm syringe-tip filter for the vehicle control treatment. The solutions for daily dosing were made on Day 0, aliquoted and frozen in a frosty −20°☐ C freezer for use. On the day of administration the appropriate aliquots were thawed and 0.1 ml of solution was injected intraperitoneally at approximately mid-morning each day for seven days.

C. Study Design

The mice were nine weeks old at the start of the study. Each zalpha11-FC4 treatment group consisted of five mice; the control group had 10 mice. The mice in the highest dose and half of the control mice were sacrificed the day after the last of seven treatments (Day 7). The two lower dose and remaining control groups were sacrificed the following day (Day 8).

The body weights of the mice were recorded every other day during treatment. There was no difference in weight gain between the treatment groups over the week of treatment.

At sacrifice, tissues harvested to assess lymphocyte populations by FACS analysis included bone marrow, thymus and spleen. Flow Cytometry analysis of the lymphoid organs and bone marrow was performed with the FACSCalibur, (Becton Dickinson, Mansfield, Mass.). The tissues harvested for histologic examination for signs of toxicity of the protein included: spleen, thymus, liver, kidney, adrenal gland, mesenteric lymph node, duodenum, pancreas, jejunum, sternum, uterus, ovaries, urinary and gall bladders, salivary gland, heart and lungs. All tissues fixed for histology were kept at 4°C overnight in 10% Normal Buffered Saline (Surgipath, Richmond, Ill.). The following day the NBF was replaced with 70% ethanol and the tissues returned to 4° C. until processing for histology.

The tissues were processed and stained for H&E analysis in house, then sent to the contract pathologist, David Fairchild. Blood was collected for complete blood cell counts and serum chemistry profiles. The CBC's were done in-house with the Cell Dyn 3500 Hematology Analyzer (Abbott Diagnostics Division, Abbott Park, Ill.). The serum was kept frozen in a frosty −20° C. freezer until submission to *Phoenix* Central Laboratory (Everett, Wash.) for complete serum chemistry panels. To compare myeloid:erythroid ratios between the 250 μg dose groups of zalpha11R and BSA, an aliquot of the bone marrow from one femur was applied to CytoSpin slides (CYTOSPIN 3 CYTOCENTRIFUGE and CYTO SLIDES, Shandon, Pittsburgh, Pa.). The bone marrow slides were analyzed at *Phoenix* Central Laboratories.

D. Study Results

There were no apparent clinical indications of physiologic effects or of toxicity of rh-zalpha11R-FC4 fusion protein at doses tested (250 μg/day or lower). Body weights remained normal for the duration of the treatments. Red blood cell and platelet counts were normal. There were two mice in the 250

μg dose zalpha11-FC4 group whose differential WBC count revealed a possible elevation in the percentage of monocytes, however the other three mice in the group had monocyte percentages equivalent to the average of the control mice. The differential white blood cell monocyte count difference is not considered a significant finding. There were no other differences in complete blood counts. The bone marrow cytology did not reveal a shift in the myeloid and erythroid progenitor populations, and all cell types present appeared normal. All the standard serum chemistry parameters were in normal ranges. There were no differences between the treatment groups in the weights of the thymus, spleen, kidney, liver or brain. Histologic evaluation of the following tissues showed no evidence of abnormalities: thymus, spleen, liver, kidney, adrenal gland, duodenum, pancreas, jejunum, caecum, colon, mesenteric lymph nodes, uterus, ovaries, salivary gland, heart, trachea, lung and brain. The absence of physiologic effects in normal mice indicates that the zalpha11 soluble receptor has low toxicity in vivo, which is desirable for a therapeutic agent.

Example 26

Zalpha11 Ligand-Dependent Proliferation of B-Cell Cells Stimulated Anti-CD40 or Anti-IgM A. Purification of Human B Cells A vial containing 1×10$^8$ frozen, apheresed human peripheral blood mononuclear cells (PBMCs) was quickly thawed in a 37° C. water bath and resuspended in 25 ml B cell medium (RPMI Medium 1640 (JRH Biosciences. Lenexa, Kans.), 10% Heat inactivated fetal bovine serum, 5% L-glutamine, 5% Pen/Strep) (Gibco BRL)) in a 50 ml tube (Falcon VWR, Seattle, Wash.). Cells were tested for viability using Trypan Blue (Gibco BRL). Ten milliliters of Ficoll/Hypaque Plus (Pharmacia LKB Biotechnology Inc., Piscataway, N.J.) was layered under the cell suspension and spun for 30 minutes at 1800 rpm and allowed to stop with the brake off. The interface was then removed and transferred to a fresh 50 ml Falcon tube, brought up to a final volume of 40 ml with PBS and spun for 10 minutes at 1200 rpm with the brake on. The viability of the isolated cells was tested using Trypan Blue. Alternately fresh drawn human blood was diluted 1:1 with PBS (Gibco BRL) and layered over Ficoll/Hypaque Plus (Pharmacia), spun and washed as above. Cells isolated from either fresh or frozen sources gave equivalent results.

B cells were purified from the Ficoll floated peripheral blood cells of normal human donors (above) with anti-CD19 magnetic beads (Miltenyi Biotec, Auburn, Calif.) following the manufacturer's instructions. The purity of the resulting preparations was monitored by flow cytometric analysis with anti-CD22 FITC Ab (Pharmingen, SanDiego, Calif.). B cell preparations were typically >90% pure.

B. Purification of Murine B Cells

A suspension of murine splenocytes was prepared by teasing adult C57B1/6 mouse (Charles River Laboratories, Wilmington, Mass.) spleens apart with bent needles in B cell medium. RBCs were removed by hypotonic lysis. CD43 positive cells were removed with CD43 magnetic beads (Miltenyi Biotec) following the manufacturer's instructions. The purity of the resulting preparations was monitored by flow cytometric analysis with anti-CD45R FITC Ab (Pharmingen). B cell preparations were typically >90% pure.

C. Proliferation of Anti-CD40-Stimulated B-Cells in the Presence of Human or Murine Zalpha11 Ligand The B cells from either the human or mouse source were resuspended at a final concentration of 1×10$^6$ cells/ml in B cell medium and plated at 100 μl/well in a 96 well U bottom plate (Falcon, VWR) containing various stimulation conditions to bring the final volume to 200 μl/well. For anti-CD40 stimulation human cultures were supplemented with 1 ug/ml anti-human CD40 (Genzyme, Cambridge, Mass.) and mouse cultures were supplemented with 1 μg/ml anti-murine CD40 (Serotec, UK). Human or murine zalpha11 Ligand (commonly owned U.S. patent application Ser. No. 09/522,217) was added at dilutions ranging from 1 pg/ml-100 ng/ml as appropriate. The specificity of the effect of zalpha11 Ligand was confirmed by inhibition of zalpha11 Ligand with 25 mg/ml soluble human zalpha11CEE (Example 6A). All treatments were performed in triplicate. The cells were then incubated at 37° C. in a humidified incubator for 120 hours (human) or 72 hours (mouse). Sixteen hours prior to harvesting, 1 μCi $^3$H-thymidine (Amersham, Piscataway, N.J.) was added to all wells to assess whether the B-cells had proliferated. The cells were harvested into a 96 well filter plate (UniFilter GF/C, Packard, Meriden, Conn.) using a cell harvester (Packard) and collected according to manufacturer's instructions. The plates were dried at 55° C. for 20-30 minutes and the bottom of the wells were sealed with an opaque plate sealer. To each well was added 0.25 ml of scintillation fluid (Microscint-O, Packard) and the plate was read using a TopCount Microplate Scintillation Counter (Packard).

Incubation with Zalpha11 Ligand at concentrations of 3 ng/ml or more enhanced the proliferation induced by soluble anti-CD40 in a dose dependent manner in both murine and human B cells by as much as 30 fold. The murine and human B cells responded equally as well to their respective zalpha11 Ligand. In both species, the stimulation was specific to zalpha11 Ligand, as it was reversed by the presence of soluble zalpha11 receptor in the culture.

D. Proliferation of Anti-IgM-Stimulated B-Cells in the Presence of Human or Murine Zalpha11 Ligand The B cells from either human or mouse source as described above (parts A and B) were plated as described above (part C). For anti-IgM stimulation of human cells the plates were pre-coated overnight with 10 mg/ml F(ab')$_2$ anti-human IgM Abs (Southern Biotech Associates, Birmingham, Ala.) and washed with sterile media just prior to use. The cultures were supplemented with 0-10 ng/ml hu rIL-4 (R&D Systems, Minneapolis, Minn.). For anti-IgM stimulation of murine cells soluble anti-IgM (Biosource, Camarillo, Calif.) was added to the cultures at 10 mg/ml. To each of the preceding anti-IgM/IL-4 conditions, human or murine Zalpha11 ligand was added at dilutions ranging from 1 pg/ml-100 ng/ml as described above. The specificity of the effect of zalpha11 Ligand was confirmed by inhibition with soluble human zalpha11 receptor as described above (Part C). All treatments were performed in triplicate. The cells were incubated, labeled with $^3$H-thymidine, harvested, and analyzed as described in part C above.

Incubation with Zalpha11 ligand at concentrations of 0.3 ng/ml or more inhibited the proliferation induced by insoluble anti-IgM (mouse) or anti-IgM and IL-4 (human) in a dose-dependent manner. This inhibition was specific to zalpha11 Ligand, as it was reversed by the presence of soluble zalpha11 receptor in the culture.

E. Anti-CD40 B Cell Proliferation Requires IL-2 Receptor Gamma

Murine B-cells were purified and stimulated with anti-CD40 monoclonal antibody as described in Example 26B and C above. The co-stimulation induced by murine zalpha11 Ligand was completely blocked by the addition of anti-IL-2 receptor gamma (IL-2Rγ) monoclonal antibodies that block IL-2γ utilization. The antibodies 3E12 and TUG/m2 (PharMingen, San Diego, Calif.) were included in the proliferation assay at 50 μg/ml. These results demonstrate that the IL-2Rγ in B cells is physiologically involved with the zalpha11 Ligand stimulation of B cells. Moreover, these results provide indirect functional support in vivo for the finding that the IL-2Rγ heterodimerizes with the zalpha11 receptor in vitro (Example 27, below).

F. The Effects of Zalpha11 Ligand on B Cells are Inhibited by Soluble Zalpha11 Receptor Constructs Murine B-cells were purified and stimulated with anti-CD40 monoclonal antibody or anti-IgM antibodies as described in Example 26C and D above. The effect induced by murine zalpha11 Ligand was completely blocked by the addition of either purified hu-zalpha11R: IL-2Rγ a heterodimeric soluble receptor (Example 28), or a mu-zalpha11-Fc, a homodimeric soluble receptor (Example 6C). Again, these results provide further functional support for the finding that the IL-2Rγ heterodimerizes with the zalpha11 receptor (Example 27, below), and acts as an antagonist to the zalpha11 Ligand's effect on B-cells.

Example 27

Human Zalpha11 Receptor Heterodimerizes with IL-2 Receptor Gamma

A. Assay Using Conditioned Media from Transfected BHK-570 Cells Expressing Human Zalpha11 Ligand Soluble human zalpha11 receptor zalpha11 CFLAG (Example 6B), or gp130 (Hibi, M. et al., Cell 63:1149-1157, 1990) were biotinylated by reaction with a five-fold molar excess of sulfo-NHS-LC-Biotin (Pierce, Inc., Rockford, Ill.) according to the manufacturer's protocol. Soluble zalpha11 receptor and soluble IL-2 receptor-γ (sIL-2Rγ) (R&D Systems, Minneapolis, Minn.) were labeled with a five fold molar excess of Ru-BPY-NHS (Igen, Inc., Gaithersburg, Md.) according to manufacturer's protocol. The biotinylated and Ru-BPY-NHS-labeled forms of the soluble zalpha11 receptor were respectively designated Bio-zalpha11 receptor and Ru-zalpha11; the biotinylated and Ru-BPY-NHS-labeled forms of the soluble IL-2Rγ were respectively designated Bio-IL2Rγ and Ru-IL2Rγ.

For initial receptor binding characterization of human zalpha11 Ligand, conditioned media from transfected BHK-570 cells expressing human zalpha11 Ligand or control media from untransfected BHK-570 cells was used to determine if zalpha11 Ligand could mediate homodimerization of zalpha11 receptor and if it could mediate the heterodimerization of zalpha11 receptor with IL-2Rγ or gp130. To do this, 50 □l of conditioned media, from control cells or conditioned media from cells expressing zalpha11 Ligand, was combined with 50 □l of TBS-B (20 mM Tris, 150 mM NaCl, 1 mg/ml BSA, pH 7.2) containing 400 ng/ml of Ru-zalpha11 receptor and Bio-zalpha11, or 400 ng/ml of Ru-zalpha11 receptor and Bio-gp130, or 400 ng/ml of Ru-IL2Rγ and Bio-zAlpha11. Following incubation for one hour at room temperature, 30 □g of streptavidin coated, 2.8 mm magnetic beads (Dynal, Inc., Oslo, Norway) were added and the reaction incubated an additional hour at room temperature. 200 □l ORIGEN assay buffer (Igen, Inc., Gaithersburg, Md.) was then added and the extent of receptor association measured using an M8 ORIGEN analyzer (Igen, Inc.).

Conditioned media containing zalpha11 Ligand caused the heterodimerization of Bio-zalpha11 receptor with Ru-IL2Rγ. No receptor dimerization was observed in the presence of control media. Conditioned media containing zalpha11 Ligand did not cause the homodimerization of RU-zalpha11 receptor with Bio-zalpha11 receptor, nor the heterodimerization of Ru-zalpha11 receptor with Bio-gp130.

B. Assay Using Purified Human Zalpha11 Ligand

To assess the ligand specificity of the heterodimerization of zalpha11 receptor and IL2Rγ, 50 □l of TBS-B containing 400 ng/ml of Ru-zalpha11 receptor and Bio-zAlpha11, or 400 ng/ml Ru-IL2Rγ and Bio-zAlpha11 was combined 50 □l of TBS-B containing IL-2, IL-4, IL-15 or purified human zalpha11 Ligand (commonly owned U.S. patent application Ser. No. 09/522,217) at concentrations from 133 pg/ml to 300 ng/ml. Following incubation for one hour a room temperature, 3 □g of streptavidin coated, 2.8 mm magnetic beads (Dynal, Inc.) were added and the reaction incubated an additional hour at room temperature. 200 □l Origlo assay buffer (Igen, Inc.) was then added and the extent of receptor association measured using an M8 Origen analyzer (Igen, Inc.). The human zalpha11 Ligand caused the heterodimerization of Bio-zalpha11 receptor with Ru-IL-2Rγ in a dose dependent manner with a half maximal concentration of 10 ng/ml. No homodimerization of Ru-zalpha11 receptor with Bio-zalpha11 receptor was observed at any concentration of zalpha11 Ligand tested. No homodimerization of Ru-zalpha11 receptor with Bio-zalpha11 receptor or heterodimerization of Bio-zalpha11 receptor with Ru-IL2Rγ was observed with IL-2, IL-4 or IL-15, at any of the concentrations tested. Thus, the results show that the human zalpha11 receptor heterodimerizes specifically with the IL-2 receptor-γ in the presence of human zalpha11 Ligand, and that the zalpha11 receptor does not homodimerize or heterodimerize in the presence of other cytokines tested.

Example 28

Construct for Generating Human Zalpha11 Receptor/IL-2Rγ Heterodimer

A vector expressing a secreted human hzalpha11/hIL2Rgamma heterodimer was constructed. In this construct, the extracellular domain of hzalpha11 was fused to the heavy chain of IgG gamma 1 (IgGβ1) (SEQ ID NO:16), while the extracellular portion of hIL-2Rγ was fused to a human kappa light chain (human κ light chain) (SEQ ID NO:18).

A. Construction of IgG Gamma 1 and Human K Light Chain Fusion Vectors

The heavy chain of IgGγ1 was cloned into the Zem229R mammalian expression vector (ATCC deposit No. 69447) such that any extracellular portion of a receptor having a 5' EcoRI and 3' NheI site can be cloned in resulting in an N-terminal extracellular domain-C-terminal IgGγ1 fusion. The IgGγ1 fragment used in this construct was made by using PCR to isolate the IgGγ1 sequence from a Clontech hFetal Liver cDNA library as a template. A PCR reaction using oligos ZC11,450 (SEQ ID NO:50) and ZC11,443 (SEQ ID NO:51) was run as follows: 40 cycles of 94° C. for 60 sec., 53° C. for 60 sec., and 72° C. for 120 sec.; and 72° C. for 7 min. PCR products were separated by agarose gel electrophoresis and purified using a QiaQuick™ (Qiagen) gel extraction kit.

The isolated, 990 bp, DNA fragment was digested with Mlu I and EcoRI (Boerhinger-Mannheim), ethanol precipitated and ligated with oligos ZC11,440 (SEQ ID NO:52) and ZC11,441 (SEQ ID NO:53), which comprise an MluI/EcoRI linker, into Zem229R previously digested with and EcoRI using standard molecular biology techniques disclosed herein. This generic cloning vector was called Vector#76 hIgGgamma1 w/ Ch1 #786 Zem229R (Vector #76). The polynucleotide sequence of the extracellular domain of hzalpha11 fused to the heavy chain of IgG gamma 1 is shown in SEQ ID NO:15 and the corresponding polypeptide sequence shown in SEQ ID NO:16.

The human κ light chain was cloned in the Zem228R mammalian expression vector (ATCC deposit No. 69446) such that any extracellular portion of a receptor having a 5' EcoRI site and a 3' KpnI site can be cloned in resulting in a N-terminal extracellular domain-C-terminal human κ light chain fusion. The human κ light chain fragment used in this construct was made by using PCR to isolate the human κ light chain sequence from the same Clontech hFetal Liver cDNA library used above. A PCR reaction using oligos ZC11,501 (SEQ ID NO:54) and ZC11,451 (SEQ ID NO:55) was run under conditions described above. PCR products were separated by agarose gel electrophoresis and purified using a QiaQuick™ (Qiagen) gel extraction kit. The isolated, 315 bp, DNA fragment was digested with MluI and EcoRI (Boerhinger-Mannheim), ethanol precipitated and ligated with the MluI/EcoRI linker described above, into Zem228R previously digested with and EcoRI using standard molecular biology techniques disclosed herein. This generic cloning vector was called Vector #77 hKlight #774 Zem228R (Vector #77). The polynucleotide sequence of the extracellular portion of hIL-2Rγ was fused to a human kappa light chain is shown in SEQ ID NO:17 and the corresponding polypeptide sequence shown in SEQ ID NO:18.

B. Insertion of Zalpha11 Receptor or IL-2Rγ Extracellular Domains into Fusion Vector Constructs Using the construction vectors above, a construct having human zalpha11 fused to IgGγ1 was made. This construction was done by PCRing human zalpha11 receptor from a CD4+ bone marrow library (selected, and made in house) with oligos ZC24,052 (SEQ ID NO:56) and ZC24,053 (SEQ ID NO:57), under conditions described as follows: 30 cycles of 94° C. for 60 sec., 57° C. for 60 sec., and 72° C. for 120 sec.; and 72° C. for 7 min. The resulting PCR product was digested with EcoRI and NheI, gel purified, as described herein, and ligated into a previously EcoRI and NheI digested and band-purified Vector #76 (above). The resulting vector was sequenced to confirm that the human zalpha11/IgG gamma 1 fusion (hzalpha11/Ch1 IgG) was correct. The hzalpha11/Ch1 IgG gamma1 vector was called Vector #190.

A separate construct having IL-2Rγ fused to κ light was also constructed. The IL-2Rγ/human κ light chain construction was performed as above by PCRing from the same CD4+ library mentioned above with oligos ZC12,834 (SEQ ID NO:58) and ZC12,831 (SEQ ID NO:59), digesting the resulting band with EcoRI and KpnI and then ligating this product into a previously EcoRI and KpnI digested and band-purified Vec#77 (above). The resulting vector was sequenced to confirm that the human IL-2Rγ/human κ light chain fusion (hIL-2Rγ/Klight) was correct. This hIL-2gamma/Klight #1052 Zem228R vector was called Vector #101.

D. Co-Expression of the Human Zalpha11 and Human IL-2Rγ Receptors

Approximately 16 µg of each of Vectors #190 and #101, above, were co-transfected into BHK-570 cells (ATCC No. CRL-10314) using LipofectaminePlus™ reagent (Gibco/BRL), as per manufacturer's instructions. The transfected cells were selected for 10 days in DMEM+5% FBS (Gibco/BRL) containing 1 µM of methotrexate (MTX) (Sigma, St. Louis, Mo.) and 0.5 mg/ml G418 (Gibco/BRL) for 10 days. The resulting pool of transfectants was selected again in 10 µm of MTX and 0.5 mg/ml G418 for 10 days.

The resulting pool of doubly-selected cells was used to generate protein. Three Factories (Nunc, Denmark) of this pool were used to generate 10 L of serum free conditioned medium. This conditioned media was passed over a 1 ml protein-A column and eluted in (10) 750 microliter fractions. 4 of these fractions found to have the highest concentration were pooled and dialyzed (10 kD MW cutoff) against PBS. Finally the dialyzed material was submitted for amino acid analysis (AAA) and found to have a concentration of 227.17 µg/ml AAA. A total of 681.5 µg was obtained from this 10 L purification. The purified soluble human zalpha11 receptor/IL-2Rγ receptor was used to assess its ability to compete with the human zalpha11 Ligand a BaF3 proliferation assay (Example 29, below).

Example 29

Soluble Human Zalpha11 Receptor/Human IL2 Gamma Receptor-Fc as a Zalpha11 Ligand Antagonist BaF3 cells stably expressing the human zalpha11 receptor (Example 2) were plated at 5500 cells per well in standard 96-well tissue culture plates in base medium plus 3 ng/ml human zalpha11 Ligand. Base medium is 500 ml RPMI 1640 (JRH Biosciences), 5 ml 100× Sodium Pyruvate (Gibco BRL), 5 ml 100×L-glutamine (Gibco BRL), and 50 ml heat-inactivated Fetal Bovine Serum (FBS) (Hyclone Laboratories). To the cells, a decreasing dose of either purified soluble human zalpha11 receptor-Fc homodimer (Example 6C) or purified soluble human zalpha11 receptor/human IL2 gamma receptor-Fc heterodimer (Example 27) were added. An Alamar Blue proliferation assay was run and fluorimetry performed as per Example 2B.

The zalpha11 receptor/IL2 gamma receptor-Fc heterodimer inhibited human zalpha11 Ligand activity in a dose dependent manner, with 0.312 µg/ml able to completely inhibit the activity of 3 ng/ml human zalpha11 Ligand. The soluble zalpha11 receptor-Fc homodimer also was able to inhibit zalpha11 Ligand activity in a dose dependent manner, however it required about 10 µg/ml of soluble homodimer to completely inhibit the activity of 3 ng/ml zalpha11 Ligand. These data suggested the zalpha11 receptor/IL2 gamma receptor-Fc heterodimer soluble receptor is approximately 30 to 100 fold more potent than the homodimeric soluble zalpha11 receptor in inhibiting human zalpha11 Ligand.

Example 30

Zalpha11 Receptor Distribution

To assess zalpha11 receptor distribution on various cells types, we generated both rabbit polyclonal and mouse monoclonal antibodies (mAbs) directed against the human receptor (Example 24 and Example 10) and conjugated these antibodies to biotin for use in flow cytometry. We initially used the polyclonal antibodies, which were of relatively low affinity, to stain a panel of cell lines: IL-3 dependent murine pre-B cell line wild-type BaF3 cells (Palacios and Steinmetz, ibid.; Mathey-Prevot et al., ibid.); BaF3 cells transfected with human zalpha11 (Example 2); human Burkitt's lymphoma cell lines Raji (ATCC No. CCL-86), Ramos (ATCC No. CRL-1596), RPMI 8226 (ATCC No. CCL-155), and Daudi (ATCC No. CCL-213); human T cell leukemia cell line Jurkat (ATCC No. TIB-152); human myelomonocytic leukemia cell lines Thp-1 (ATCC No. TIB-202) and U937 (ATCC No. CRL-1593.2); human pro-myelomonocytic cells HL-60 (ATCC No. CCL-240); murine B cell lymphoma cell line A20 (ATCC No TIB-208); and murine thymoma cell line EL4 (ATCC No. TIB-39).

The cells were harvested, washed once with FACS wash buffer with serum (WBS). WBS consisted of Hank's balanced salt solution (Gibco/BRL)+10 mM HEPES (Gibco/BRL)+1% BSA (Sigma)+10% normal goat serum (Gemini Bioproducts, Woodland, Calif.)+10% normal rabbit serum (Sigma); wash buffer (WB) was identical to WBS except that it is serum free. After washing, the cells were resuspended in 100 µl WB containing 10 µg/ml rabbit anti-zalpha11 polyclonal antibodies (Example 10). The cells were kept on ice with Ab for 20 min, then washed with WB and resuspended in WB containing goat anti-rabbit-FITC (BioSource, International), incubated another 20 min on ice, then washed and resuspended in 400 µl WB for analysis on a FACSCalibur flow cytometer (Becton Dickinson). Control samples were stained with the secondary goat anti-rabbit-FITC Ab only. Positive staining was defined as a shift above the staining with secondary alone. Although the polyclonal antibodies were of low affinity, we were reasonably confident that we detected zalpha11 expression on the BaF3/zalpha11 transfectant, on all four human Burkitt's lymphomas (Raji, Ramos, Daudi, and RPMI 8226), and on Jurkat T cells. Our data with the monocytic cell lines were more ambiguous. Resting (undifferentiated) HL-60 cells did not bind the anti-zalpha11 antibodies, but we did detect a positive signal on HL-60 cells activated for 24 hours with PMA (Calbiochem, La Jolla, Calif.) which induces HL-60 cell differentiation into a monocyte-like cell. We also saw a positive signal on U937 and Thp-1 cells, although this signal may have been due to non-specific binding. The polyclonal antibodies weakly cross-reacted on the mouse B cell line A20, but we saw no staining of the EL4 murine thymoma.

The four anti-zalpha11 monoclonal antibodies (Example 24) were conjugated to biotin, and a subset of the cells described above were screened for zalpha11 receptor expression (BaF3, BaF3/zalpha11, Raji, Jurkat, and resting HL-60). Cells were harvested, washed, then resuspended in 100 µl WB containing 15 µg/ml of one of each of the 4 biotinylated mAbs. The cells were incubated with mAb for 20 min on ice, then washed with 1.5 ml WB and pelleted in a centrifuge. The supernatant was removed by aspiration and the pellets were resuspended in 100 µl of CyChrome-conjugated streptavidin (CyC-SA; PharMingen), then incubated on ice for another 20 min and washed and pelleted as before. Control tubes contained cells stained only with CyC-SA. Pellets were resuspended in 400 µl WB and flow cytometry performed as above. Positive staining was defined as a signal exceeding the background level of staining with CyC-SA alone. Using the BaF3/zalpha11 transfectant as a control, we were able to rank the 4 mAbs in terms of their respective mean fluorescence intensities (MFI), which can reflect antibody affinity and/or the extent of biotinylation of the mAbs. The mAbs were ranked as follows, from highest to lowest MFI: 249.28.2.1.2.2, 247.10.2.15.4.6, 249.19.2.2.3.5, and 249.15.2.4.2.7. This pattern was essentially the same on both Raji and Jurkat cells, indicating that zalpha11 is expressed on these B and T cell lines. The staining patterns on non-activated HL60 cells were identical for all the mAbs, and the signal was very weak. We speculate that this does not reflect actual expression of zalpha11 by this cell line, but rather is a function of non-specific binding of the mouse mAbs to the human cells, probably via Fc-receptors.

Example 31

Reconstitution of Human Zalpha11 Receptor In Vitro

To identify components involved in the zalpha11-signaling complex, receptor reconstitution studies were performed as follows. BHK 570 cells (ATCC No. CRL-10314) transfected, using standard methods described herein, with the KZ134 luciferase reporter plasmid (Example 19) served as a bioassay cell line to measure signal transduction response from a transfected zalpha11 receptor complex to the luciferase reporter in the presence of zalpha11 Ligand. BHK cells do not endogenously express the zalpha11 receptor. The bioassay cell line was transfected with zalpha11 receptor alone, or co-transfected with zalpha11 receptor along with one of a variety of other known receptor subunits. Each receptor subunit was cloned using PCR followed by ligation into appropriate expression vectors; correct sequence of each construct was confirmed before transfection. Cell lines were tested for receptor expression by RT/PCR prior to assays. Receptor complexes tested included: zalpha11 receptor alone; zalpha11 receptor with IL-2Rγ; zalpha11 receptor with IL-2Rγ and IL-2Rβ; zalpha11 receptor with IL-2Rγ and IL-13Rα; zalpha11 receptor with IL-2Rγ and IL-2Rα; and zalpha11 receptor with IL-2Rγ and IL-4Rα. Each independent receptor complex cell line was assayed in the presence of human zalpha11 Ligand and luciferase activity measured as described in Example 19. The untransfected bioassay cell line served as a control for the background luciferase activity, and was used as a baseline to compare signaling by the various receptor complex combinations. In each cell line containing both zalpha11 receptor and IL-2Rγ, maximal luciferase activity was about two-fold over background in the presence of zalpha11 Ligand. No increase in signal was observed in the presence of any other receptor subunit tested (IL-2Rβ, IL-2Rα, IL-4Rα, or IL-13Rα).

Other zalpha11 receptor complexes that can be assessed by this method include combinations of zalpha11 receptor with one or more of the IL-4/IL-13 receptor family receptor components (IL-13Rα'), as well as other Interleukin receptors (e.g., IL-15 Rα, IL-7Rα, IL-9Rα).

Example 32

$^{125}$I-Labeled Human Zalpha11 Ligand Binding Study in Cell Lines 25 micrograms of purified human zalpha11 Ligand (commonly owned U.S. patent application Ser. No. 09/522,217) was labeled with 2 mCI $^{125}$I using iodobeads (Pierce, Rockford Ill.), according to manufacturer's instructions. This labeled protein was used to assess human zalpha11 Ligand binding to human Raji cells (ATCC No. CCL-86), using binding to wild-type murine BaF3 cells, and BaF3 cells transfected with zalpha11 receptor (BaF3/hzalpha11 cells) as controls. Zalpha11 Ligand binding to BaF3/hzalpha11 cells was expected (positive control), while no binding to wild-type BaF3 cells was expected (negative control), based on proliferation assay results (Example 2). About 5×10$^5$ Raji cells/well, 1×10$^6$ BaF3/hzalpha11 and 1×10$^6$ BaF3 cells cells/well, were each plated in 96-well plates. Ten ng/ml of labeled human zalpha11 Ligand was added in duplicate to wells, with a dilution series of unlabeled human zalpha11 Ligand competitor added from 250 fold molar excess in 1:4 dilutions down to 0.061 fold molar excess. Each point was run in duplicate. After the labeled human zalpha11 Ligand was added to wells, it was allowed to incubate at 4° C. for 2 h to allow for binding of Ligand to the cells. The cells were then washed 3× in binding buffer (RPMI-1710 (JRH Biosciences) with 1% BSA (Sigma)), and counted on the COBRA II AUTO-GAMMA gamma counter (Packard Instrument Company, Meriden, Conn.).

Binding of the labeled zalpha11 Ligand to cells was evident in the Raji and the BaF3/hzalpha11 cells. In addition, for Raji cells, an average 250 fold molar excess of unlabeled zalpha11 Ligand decreased binding 3 fold in the presence of a non-specific unlabeled competitor (Interferon Gamma from R&D Systems, Minneapolis, Minn.), and 3.7 fold relative to no competitor. Competition was observed in a dose dependent fashion for the specific unlabeled competitor, human zalpha11 Ligand. Thus, the zalpha11 Ligand binding to Raji cells was specific. Similarly, for positive control BaF3/zalpha11 cells, the 250 fold molar excess of unlabeled zalpha11 Ligand decreased binding 2 fold relative to the non-specific competitor and 3.06 fold relative to no competitor. Thus, the zalpha11 Ligand binding to BaF3/zalpha11 cells also was specific. No competable binding was observed with the wild-type BaF3 cells. Thus, the zalpha11 Ligand was shown to bind specifically to Raji cells, and to Baf3/hzalpha11 cells, but not to the negative control Baf3 cells.

The bound radiolabeled zalpha11 Ligand is then cross-linked to the molecule to which it binds on the cell surface of Raji cells using standard cross-linking methods, to identify the receptor complex to which it binds on these cells. Moreover, anti-zalpha11 receptor antibodies (Example 24 and Example 10), and other anti-cytokine receptor subunit antibodies are employed to assess which subunit components comprise a functional hzalpha11 receptor complex, for example, on the Raji cells and other cell lines to which zalpha11 Ligand binds. Such antibodies can be used to compete for zalpha11 Ligand in a binding assay as described above, and hence show which receptor subunits are present of the Raji cell surface, and on other cell lines to which zalpha11 Ligand binds. Moreover, such antibodies can be used to immunoprecipitate radiolabeled zalpha11 Ligand cross-linked material using methods known in the art and described herein. In addition anti-zalpha11 Ligand antibodies (commonly owned U.S. patent application Ser. No. 09/522,217) can be used to immunoprecipitate radiolabeled zalpha11 Ligand cross-linked material.

Example 33

Zalpha11 Receptor Expression on Human Blood Cells

A. Preparation and Culture of Human Peripheral Blood Cells

Fresh drawn human blood was diluted 1:1 with PBS (GIBCO BRL) and layered over Ficoll/Hypaque Plus (Pharmacia LKB Biotechnology Inc., Piscataway, N.J.) and spun for 30 minutes at 1800 rpm and allowed to stop with the brake off. The interface layer was removed and transferred to a fresh 50 ml Falcon tube (Falcon, VWR, Seattle, Wash.), brought up to a final volume of 40 ml with PBS and spun for 10 minutes at 1200 rpm with the brake on. The viability of the isolated cells was tested using Trypan Blue (GIBCO BRL) and the cells were resuspended at a final concentration of $1 \times 10^6$ cells/ml cell medium (RPMI Medium 1640, 10% Heat inactivated fetal bovine serum, 5% L-glutamine, 5% Pen/Strep) (GIBCO BRL).

Cells were cultured in 6 well plates (Falcon, VWR) for 0, 4 or 24 hours with a variety of different stimuli described below. Anti-IgM, anti-CD40 and anti-CD3 stimulation were done as in Example 26. Phorbol myristate acetate (PMA) and ionomycin (Sigma, St. Louis, Mo.) were added to appropriate wells at 10 ng/ml and 0.5 mg/ml respectively. The cells were incubated at 37° C. in a humidified incubator for various times.

B. Antibody Staining and Analysis

Cells were collected out of the plates, washed and resuspended in ice cold staining media (HBSS, 1% fetal bovine serum, 0.1% sodium azide) at a concentration of about ten million cells per milliliter. Blocking of Fc receptor and non-specific binding of antibodies to the cells was achieved by adding 10% normal goat serum (Gemini Bioproducts, Woodland, Calif.) and 10% normal human serum (Ultraserum, Gemini) to the cell suspension. Aliquots of the cell suspensions were mixed with a FITC labeled monoclonal antibody against one of the lineage markers CD3, CD19 or CD14 (PharMingen, La Jolla, Calif.) and a biotinylated monoclonal antibody against the human zalpha11 receptor (hu-zalpha11) (Example 24). After incubation on ice for 60 minutes the cells were washed twice with ice cold staining media and resuspended in 50 ml staining media containing streptavidin-PE (Caltag, Burlingame, Calif.). After a 30 minute incubation on ice, the cells were washed twice with ice cold wash buffer (PBS, 1% fetal bovine serum, 0.1% sodium azide) and resuspended in wash buffer containing 1 mg/ml 7-AAD (Molecular Probes, Eugene, Oreg.) as a viability marker. Flow data was acquired on living cells using a FACSCalibur flow cytometer (BD Immunocytometry Systems, San Jose, Calif.). Both acquisition and analysis were performed using CellQuest software (BD Immunocytometry Systems).

Results showed that the human zalpha11 receptor is expressed on human peripheral blood cells expressing either CD3, CD19 or CD14. Activation of either T cells with anti-CD3 or B cells with anti-CD40 resulted in an increased level of cell surface zalpha11 at 24 hours. No increase in the level of expression of zalpha11 was seen at 4 hours with any stimulus on either cell population. Treatment of the cells with zalpha11 ligand resulted in a decrease of zalpha11 staining on CD3 positive and CD19 positive cells but not CD14 positive cells at both 4 and 24 hours.

Example 34

Human Zalpha11 Ligand Activity is Blocked with Anti-IL-2γ Antibodies in a BaF3/Zalpha11 Proliferation Assay The role of the IL-2□ receptor was investigated using anti-IL-2□ receptor monoclonal antibodies to assess whether they would block zalpha11 Ligand activity in a BaF3/zalpha11 proliferation assay (Example 2). Conditioned-media from BHK570 cells transfected with the human zalpha11 Ligand was added to the assay at 5%, 2.5%, 1.25% and 0.625% concentrations, with or without IL-2 receptor antibodies.

The following mouse anti-IL-2 receptor monoclonal antibodies from PharMingen International, San Diego, Calif. were added at 50 µg/ml each: (a) 4G3+TUGm2 or (b)TM-□1. 4G3 and TUGm2 are purified rat anti-mouse $\gamma_C$ chain antibodies, TM-□1 is a purified rat anti-mouse CD122 (IL-2 receptor □ chain) antibody. Assay results demonstrated almost complete inhibition of the zalpha11 Ligand response with the 4G3+TUGm2 antibody combination in comparison to the no-antibody control. The TM-□1 antibody had no effect. These results suggest a role for the IL-2□ receptor in the zalpha11 Ligand proliferative response, and further supports that the IL-2Rγ heterodimerizes with the zalpha11 receptor to elicit that response.

Example 35

Post-translational Mannosylation of Zalpha11 Receptor Polypeptide on a Highly Conserved Trp Residue Mannosylation of the human zalpha11 receptor was assessed using the method for C-2 mannosylation of Tryptophan as described in Hofsteenge, J et al., *Biochemistry* 33:13524-13530, 1994, and Loeffler, A et al., *Biochemistry* 35:12005-14, 1996. Moreover, these investigators showed that in a motif of amino acids, WXXW (SEQ ID NO:67), that Trp can be mannosylated.

A soluble zalpha11 receptor bearing a C-terminal Glu-Glu (CEE) (SEQ ID NO:14) or FLAG (SEQ ID NO:23) tag was expressed in BHK cells and purified by anti-Flag or anti-EE affinity chromatography (Example 4A). A soluble zalpha11 receptor C-terminally tagged with an Fc4 tag (SEQ ID NO:25) and expressed in CHO cells was affinity purified by anti-Fc4 affinity chromatography (Example 4B). These polypeptides were enzymatically cleaved to generate peptide fragments for the study.

All enzymatic digestions were performed overnight at a protein concentration of 1.0 mg/ml. PNGaseF (Oxford GlycoSciences, Abingdon, Oxford UK) digestion was performed by diluting each soluble zalpha11 receptor polypeptide into a 50 mM EDTA, 20 mM Na-Phosphate pH 7.5 buffer and incubating it with 0.4 U of enzyme per μg of protein. Glu-C (Roche Molecular Biochemicals, Indianapolis, Ind.) digestion was performed at a 1:50 ratio of enzyme to protein by buffer exchanging the sample into 25 mM $NH_4HCO_3$ pH 7.8 and incubating it at 25° C., except for the Fc4 tagged material, which was digested in 50 mM Na-Phosphate pH 7.8+5% Acetonitrile (EM Science, Darmstadt, Germany) at 37° C. The Glu-C digestion generated a zalpha11 WSXWS-containing peptide as shown from amino acid 178 (Leu) to amino acid 199 (Ser) of SEQ ID NO:6 (197 (Leu) to amino acid 218 (Ser) of SEQ ID NO:2). Asp-N (Roche Molecular Biochemicals, Indianapolis, Ind.) digestion was performed by buffer exchanging the protein into 50 mM Na-Phosphate pH 7.7 and incubating it at 37° C. with enzyme at a 1:50 ratio to zalpha11 receptor polypeptide. The Asp-N digestion generated a zalpha11 WSXWS-containing peptide as shown from amino acid 179 (Glu) to amino acid 210 (Ser) of SEQ ID NO:6 (198 (Leu) to amino acid 229 (Glu) of SEQ ID NO:2).

LCMS and LCMS-MS analyses were performed on a Magic HPLC (Michrom Bioresources, Auburn, Calif.) connected in-line to a Finnigan LCQ mass spectrometer (Finnigan MAT, San Jose, Calif.). LC separation was done on a Vydac C4 5μ 300 Å column (Michrom Bioresources) with an elution gradient of 20%-80% solvent B over 80 minutes where solvent A was 2% Acetonitrile+0.1% TFA and solvent B was 90% Acetonitrile+0.095% TFA (EM Science; Sigma, St. Louis, Mo.). The LCQ mass spectrometer was set to collect MS spectra for the duration of the run. LCMS-MS analysis of polypeptide digests was performed on the same instrument system using a Vydac C18 5μ 300 Å column (Michrom Bioresources) with an elution gradient of 5-65% solvent B over 80 minutes with the same solvent system described for LCMS analysis above. The LCQ mass spectrometer was configured to collect MS, zoom-scan and MS-MS spectra for each ion over a minimum threshold.

The extent of tryptophan mannosylation was estimated by comparing ion intensities for the 2+ and 3+ ions of the peptides containing the WSXWS motif (SEQ ID NO:13) from both Glu-C and Asp-N digestion described above. Peak composition was first determined utilizing the MS data and a peptide map was generated. Next, an average spectrum was created starting approximately 1 minute before the early eluting mannosylated WSXWS (SEQ ID NO:13) containing peptide and ending approximately 1 minute after its later eluting non-mannosylated companion peptide. The normalized intensities of the ions corresponding to mannosylated and non-mannosylated peptide were compared and used to generate a percentage occupancy number. Values generated for both 2+ and 3+ charge states were averaged to generate a percent occupancy value for each digest. This value was then averaged with the value from the companion digest for each lot of protein to generate a final value.

Table 7 below summarizes the data that were calculated for each Peptide-tag and host cell used for zalpha11 soluble receptor expression.

TABLE 7

| C-terminal-Tag | Expression Host | % WSXWS Mannosylated |
| --- | --- | --- |
| Glu-Glu | BHK | ~46% |
| FLAG | BHK | ~35% |
| Fc4 | CHO | ~11% |

One of skill in the art would appreciate that mannosylation or non-mannosylation of the zalpha11 receptor WSXWS motif (SEQ ID NO:13) can affect the ability of the zalpha11 receptor or zalpha11 soluble receptor to homodimerize, heterodimerize, and/or it's ability to bind the zalpha11 Ligand. As the mannosylation on zalpha11 receptor appears to differ depending on the cell type in which the receptor so expressed, optimization of the expression and production of zalpha11 receptor and soluble receptor polypeptides may take into consideration whether the zalpha11 receptor produced by the cell is mannosylated or non-mannosylated. As such, one of skill in the art would appreciate that the polypeptides of the present invention can be either mannosylated or non-mannosylated.

As the mannosylation event is within the WSXWS motif (SEQ ID NO:13) of the zalpha11 class I cytokine receptor, the mannosylation of the Trp or the lack thereof can affect the polypeptide functionally. For example, insertions or deletions in the WSXWS motif (SEQ ID NO:13) of the EPOR can abrogate cell surface expression, destroy or reduce proliferative response, decrease receptor internalization, and affect EPO binding (Yoshimura, A et al., *J. Biol. Chem.* 267:11619-11625, 1992; Quelle, D E et al., *Mol. Cell. Biol.* 12:4553-4561, 1992; Hilton, D J et al., *Proc. Natl. Acad. Sci. USA* 92:190-194, 1995). However, mutation in the WSXWS motif (SEQ ID NO:13) can also result in more efficient export from the ER and greater expression of the receptor on the cell surface (Hilton, D J et al., supra.). Effects on cell surface expression, ligand binding and stimulatory response have also been seen with studies on WSXWS motif (SEQ ID NO:13) and related motifs in mutational analysis on IL-2Rβ, GM-CSFR, and GHR (Miyazaki, et al., *EMBO J.* 10:3191-3197, 1991; Ronco, L. V. et al., *J. Biol. Chem.* 269:277-283, 1994; Baumgartner, J W et al., *J. Biol. Chem.* 269:29094-29101, 1994).

Similarly, mannosylation of the first Trp residue in the WSXWS motif (SEQ ID NO:13) of zalpha11 receptor polypeptides, including full-length and soluble receptors described herein, can have important structural and functional implications such as having affects on the overall stability of the receptor, rate of proteolysis, intracellular processing, antigenicity, cell surface expression, dimerization or multimerization, co-receptor binding, signaling or internalization, affects on zalpha11 Ligand binding and stability of receptor-ligand interaction. Comparison of mannosylated and non-mannosylated zalpha11 receptors can be made using X-ray crystallography or NMR on purified zalpha11 polypeptides (e.g., soluble receptors), or functional studies comparing zalpha11 expressed in cell lines that either mannosylated (e.g., BHK or other cell line) or are defective or reduced in mannosylation (e.g., CHO or other cell line) and comparing the receptors in the various assays described herein.

Example 36

BHK Tranfectant Binding Studies

Purified human zalpha11 Ligand (25 μg) protein (commonly owned U.S. patent application Ser. No. 09/522,217) was iodinated with $^{125}I$ (Amersham) using iodo-beads (Pierce) and purified on a Sephadex G25 PD-10 column (Pharmacia). BHK transfectants (Example 31) expressing either human zalpha11 alone or human zalpha11+human IL-2R□ receptor were plated at 30K/well in a 24-well dish 24 hours prior to the binding study. BHK transfectants were incubated for 2 hours at 4° C. with 2.5 ng (0.147 pMoles) $^{125}I$ zalpha11 Ligand (specific activity $6.4\times10^7$ cpm/ug) in the presence of various concentrations of cold zalpha11 Ligand (in a range from about a 10,884 fold excess to no competition in 15, 4-fold dilutions). Cells were washed three times with binding buffer before lysis in 0.8M NaOH, followed by gamma emission counting. Analysis of these data yielded an affinity of approximately 1 nM for the zalpha11 transfectants and approximately 0.1 nM for the human zalpha11+human IL-2R□ receptor transfectants. This result suggested that zalpha11 Ligand has high affinity on both the homodimeric human zalpha11 or heterodimeric human zalpha11+human IL-2R□ receptor, and that the affinity is higher for the heterodimer.

Example 37

Murine Homodimeric Zalpha11Receptor-mG2a Fusion Protein

The expression vector pEZE2 was used to express the murine zalpha11receptor-murine IgGamma2a Fc fusion protein (zalpha11m-mG2a). The mouse zalpha11 extracellular domain murine immunoglobulin gamma 2a heavy chain Fc region fusion protein (zalpha11m-mG2a) DNA sequence is shown in SEQ ID NO:72, and the corresponding polypeptide sequence is shown in SEQ ID NO:73.

The pEZE2 vector is a plasmid derived from pDC312 (Immunex Corp., Seattle, Wash.), and contains an EASE segment as described in WIPO Publication WO 97/25420. The presence of the EASE segment in an expression vector can improve expression of recombinant proteins about two to eight fold in stable cell pools. The pEZE2 plasmid is a dicistronic expression vector that can be used to express two different proteins in mammalian cells, such as Chinese Hamster Ovary (CHO) cells. The pEZE2 expression unit contains a CMV enhancer/promoter; an adenovirus tripartite leader sequence; a multiple cloning site (MCS) for insertion of the coding region for the recombinant protein of interest; an encephalomyocarditis virus internal ribosome entry site; a coding segment for mouse dihydrofolate reductase; and the SV40 transcription terminator. In addition, pEZE2 contains an *E. coli* origin of replication and the bacterial beta lactamase gene.

The zalpha11m-mG2a fusion protein is a disulfide-linked homodimer consisting of two chains of the mouse zalpha11 extracellular domain fused to a wild type murine immunoglobulin gamma 2a Fc region. The murine immunoglobulin gamma 2a Fc confers effector functions, FcγRI binding and C1q complement fixation.

The mouse zalpha11 extracellular domain murine immunoglobulin gamma 2a Fc constant region fusion construct was generated by overlap PCR of three separate DNA fragments, each generated by separate PCR amplification reactions. The first fragment contained an optimized tPA (tissue plasminogen activator) signal sequence (SEQ ID NO:80). The optimized tPA (otPA) signal sequence was amplified using oligonucleotide primers ZC26,644 (SEQ ID NO:74) and ZC26,641 (SEQ ID NO:75) using an in-house previously generated expression vector as the template. PCR reaction mix contained 20 pmoles of each primer, 10 ng template cDNA, 20 μM each dNTP, 1×Taq buffer (Life Technologies, Gaithersburg, Md.), 0.5 μl Taq polymerase in a 100 μl reaction. PCR conditions: 1 cycle, 94° C., 2 minutes, 25 cycles, 94° C., 30 seconds, 60° C., 30 seconds, 72° C., 30 seconds, 1 cycle, 72° C., 5 minutes. The second fragment contained the mouse zalpha11 extracellular domain coding region of amino acids 20 to 257 of SEQ ID NO:12. Oligonucleotide primers ZC26,642 (SEQ ID NO:76) and ZC26,662 (SEQ ID NO:77) were used to amplify this mouse zalpha11 segment using a previously generated clone of mouse zalpha11 (SEQ ID NO:11) as the template. This PCR fragment was made using the same PCR reaction mix specified above. PCR reaction conditions were as follows: 1 cycle, 94° C., 2 minutes, 25 cycles, 94° C., 30 seconds, 50° C., 30 seconds, 72° C., 45 seconds, 1 cycle, 72° C., 5 minutes.

The murine gamma 2a heavy chain Fc region was generated from a previously generated clone of murine Ig gamma 2a heavy chain cDNA. The segment containing the hinge, $C_H2$, and $C_H3$ domains of the murine immunoglobulin gamma 2a heavy chain constant region was generated by PCR amplification using oligonucleotide primers ZC26,643 (SEQ ID NO:78) and ZC26,645 (SEQ ID NO:79). This PCR fragment was made using the same reaction mix specified above. PCR conditions were as follows: 1 cycle, 94° C., 2 minutes, 25 cycles, 94° C., 30 seconds, 60° C., 30 seconds, 72° C., 30 seconds, 1 cycle, 72° C., 5 minutes.

To prepare the fusion protein-coding segment, three protein coding domains were linked by overlap PCR using oligonucleotides ZC26,644 (SEQ ID NO:74) and ZC26,662 (SEQ ID NO:77) to link the first two PCR products and ZC26,644 (SEQ ID NO:74) and ZC26,645 (SEQ ID NO:79) to link in the Fc region. Two reactions were set up: The first ran 25 cycles of 94° C. for 2 min., 55° C. for 30 sec. and 72° C. for 1 min. 30 sec. The other reaction ran 25 cycles of 94 degrees C. for 2 min., 60° C. for 30 sec and 72° C. for 1 min. and 30 sec. The PCR products in the two reactions were pooled and purified by using the QIAquick PCR purification kit (Qiagen) as per manufacturer's protocol. The product was eluted in 60 μl of buffer. 30 μl of this eluate was digested with Fse1 and Asc1 restriction enzymes in diluted NEB 10× buffer No. 4 (New England Biolabs, Beverly, Mass.) as per manufacturer's directions. The material was then run on a 1% TAE agarose gel and the approximately 1500 bp band was excised and the DNA purified using a Qiagen Agarose gel extraction kit (Qiagen) as per manufacturers instructions. The fragment was eluted in 30 μl $H_2O$.

To prepare the recipient vector for the insert, about 3 μg of pEZE2 vector was digested w/ Asc1 and Fse1 in the same manner as above, with the exception of 1 μl of Calf Intestinal Phosphatase (CIP) (New England Biolabs) added after restriction enzyme digest (the reaction was allowed to proceed an additional 2 hrs). The vector was then run on an agarose gel and purified as per above. The material was eluted in 30 μl of H2O.

The fusion protein-coding segment was cloned into the MCS of pEZE2 from the FseI site to the AscI site in the polylinker, and ligated in 20 µl using standard molecular biological reagents and procedures. The ligation reaction was incubated O/N at 16° C. About 4 µl of this ligation mix was electroporated into 50 µl of DH12s *E. Coli* electrocompetent cells (Life Technologies, Rockvelle, Md.) and the cells rescued in 1 ml of LB media and allowed to shake/incubate for 1 hr. and 100 µl spread on Amp 100 agar plates. The plates were allowed to incubate o/n at 37° C. A single colony was sequence analyzed. A mutation was found that would result in a change from Glu to Lys at position 25 in SEQ ID NO:73. This amino acid substitution is within the otPA leader, and may have resulted in improper processing of the signal peptide, as N-terminal showed that the leader sequence was incompletely cleaved and started at a pyroglutamine residue upstream of the predicted start. However, this homodimeric construct was still active in inhibiting the zalpha11 Ligand (Example 40).

A large prep was created using the Qiagen Maxi prep kit (Qiagen) as per manufacturers instructions. The plasmid was used to transfect CHO cells. The cells were selected in medium without hypoxanthine or thymidine and the transgene was amplified using methotrexate (Example 38). The presence of protein was assayed by Western blotting using anti human gamma 1 heavy chain constant region and anti human kappa light chain antibodies (Rockland Immunochemicals, Gilbertsville Pa.).

Example 38

Production of zAlpha11m-mG2A in DG-44 CHO Cells

20 µg of a zAlpha11m-mG2A/pEZE2 construct (Example 37) was digested with 40 units of Pvu I at 37° C. for three hours and was then precipitated with isopropanol and pelleted in a 1.5 mL microfuge tube. The supernatant was aspirated away from the pellet and the pellet was resuspended in 100 µl of water. About 200 µg (20 µl) of sheared salmon sperm DNA was added to the digested zAlpha11m-mG2A/pEZE2 construct. The DNA mixture was co-precipitated using 0.1 volumes of sodium acetate (pH 5.2) and 2.2 volumes of ethanol. The tube was placed on dry ice for 15 minutes then was spun down in a microfuge at 14,000 RPM for 15 minutes forming a DNA pellet. The supernatant was aspirated off the pellet, and the pellet was washed with 1 mL of 70% ethanol and allowed to incubate for 5 minutes at room temperature. The tube was spun in a microfuge for 10 minutes at 14,000 RPM and the supernatant was aspirated off the pellet. The pellet was allowed to air dry for 30 minutes. The pellet was then resuspended in 100 µl of water and allowed to incubate at room temperature for 10 minutes. 500 µl containing about $5 \times 10^6$ DG-44 CHO cells was added to the DNA in the microfuge tube, then the DNA/cell mixture was placed in a 0.4 cm gap cuvette and electroporated using the following parameters: 1,070 µF, high capacitance and 376 V. The contents of the cuvette were then removed and diluted to 25 mLs with EX-CELL™ 325 PF-CHO Protein Free Media (JRH Biosciences, Lenexa, Kans.) with 3 mM L-Glutamine and placed in a 125 mL shake flask. The flask was placed in an incubator on a shaker at 37° C., 6% $CO_2$ and shaking at 120 RPM.

The DG-44 CHO zAlpha11m-mG2A culture was amplified with methotrexate (MTX) using standard methods to a final MTX level of 50 nM MTX. The culture was dilution-cloned and screened using a series of western blots. A final clone was chosen and further selected in MTX to a level of 200 nM MTX and was then scaled up for production. Production of each lot of the clone was accomplished by seeding 8×4 L spinner flasks with 2 L of culture at approximately $5 \times 10^5$ cells/mL. Cultures were spun at 70 RPM, maintained at 37° C., 6% $CO_2$ and allowed to incubate for either 72 or 96 hours. The cells were spun down and the supernatants were 0.2 µm filtered. A sufficient number of cells were recovered to seed the next series of flasks. Four total lots were produced in this manner for protein purification (Example 39).

Example 39

Purification of the Homodimeric Zalpha11m-mG2a Soluble Receptor Protein

All procedures performed at 4° C., unless otherwise noted. Conditioned media (Example 38) was directly captured on an appropriately sized POROS 50 A (coupled protein A; PerSeptive BioSystems, Framingham, Mass.) column at an optimal capture flow rate. The column was washed with 20 column volumes (CV) of loading buffer, then rapidly eluted with 3 CV of 0.1 M Glycine pH 2.5. The collected fractions had a predetermined volume of 2M TRIS pH 8.0 added prior to the elution to neutralize the pH to about 7.2.

Brilliant Blue (Sigma) stained NuPAGE gels were ran to analyze the elution. Fractions of interested were pooled and concentrated against a 30 kD MWCO centrifugal concentrator to a nominal volume. The concentrated Protein A pool was injected onto an appropriately sized Phamicia Sephacryl 200 column (Pharmacia) to remove aggregates and to buffer exchange the protein into PBS pH 7.2.

Brilliant Blue (Sigma) stained NuPAGE gels (NOVEX) were again used to analyze the elution. Fractions were pooled and concentrated as before to ~1-2 mgs/ml. Western and Brilliant Blue (Sigma) stained NuPAGE gels (NOVEX) were ran to confirm purity and content. In addition, the protein was submitted for amino acid analysis (AAA), and N-terminal sequencing for further analysis.

Example 40

Soluble Homodimeric Zalpha11m-mg2a Fusion Protein as a Zalpha11 Ligand Antagonist BaF3 cells stably expressing the mouse zalpha11 receptor (constructed as per Example 2 using primers to SEQ ID NO:11) were plated at 5500 cells per well in standard 96-well tissue culture plates in base medium plus 3 ng/ml human zalpha11 Ligand. Base medium is 500 ml RPMI 1640 (JRH Biosciences), 5 ml 100× Sodium Pyruvate (Gibco BRL), 5 ml 100×L-glutamine (Gibco BRL), and 50 ml heat-inactivated Fetal Bovine Serum (FBS) (Hyclone Laboratories). To the cells, a decreasing dose of either purified homodimeric zalpha11m-mg2a (Example 39) was added. An Alamar Blue proliferation assay was run and fluorimetry performed as per Example 2B.

The homodimeric zalpha11m-mG2a fusion protein inhibited human zalpha11 Ligand activity in a dose dependent manner, with 1-5 µg/ml able to inhibit the activity of 1.25 ng/ml human zalpha11 Ligand.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

SEQUENCE LISTING

<160> NUMBER OF SEQ ID NOS: 86

<210> SEQ ID NO 1
<211> LENGTH: 1614
<212> TYPE: DNA
<213> ORGANISM: Homo sapiens
<220> FEATURE:
<221> NAME/KEY: CDS
<222> LOCATION: (1)...(1614)

<400> SEQUENCE: 1

| | | | | | | | | | | | | | | | | |
|---|---|---|---|---|---|---|---|---|---|---|---|---|---|---|---|---|
| atg | ccg | cgt | ggc | tgg | gcc | gcc | ccc | ttg | ctc | ctg | ctg | ctg | ctc | cag | gga | 48 |
| Met | Pro | Arg | Gly | Trp | Ala | Ala | Pro | Leu | Leu | Leu | Leu | Leu | Leu | Gln | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggc | tgg | ggc | tgc | ccc | gac | ctc | gtc | tgc | tac | acc | gat | tac | ctc | cag | acg | 96 |
| Gly | Trp | Gly | Cys | Pro | Asp | Leu | Val | Cys | Tyr | Thr | Asp | Tyr | Leu | Gln | Thr | |
| | | | 20 | | | | 25 | | | | | 30 | | | | |

| | | | | | | | | | | | | | | | | |
|---|---|---|---|---|---|---|---|---|---|---|---|---|---|---|---|---|
| gtc | atc | tgc | atc | ctg | gaa | atg | tgg | aac | ctc | cac | ccc | agc | acg | ctc | acc | 144 |
| Val | Ile | Cys | Ile | Leu | Glu | Met | Trp | Asn | Leu | His | Pro | Ser | Thr | Leu | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| ctt | acc | tgg | caa | gac | cag | tat | gaa | gag | ctg | aag | gac | gag | gcc | acc | tcc | 192 |
| Leu | Thr | Trp | Gln | Asp | Gln | Tyr | Glu | Glu | Leu | Lys | Asp | Glu | Ala | Thr | Ser | |
| 50 | | | | | 55 | | | | | 60 | | | | | | |

| | | | | | | | | | | | | | | | | |
|---|---|---|---|---|---|---|---|---|---|---|---|---|---|---|---|---|
| tgc | agc | ctc | cac | agg | tcg | gcc | cac | aat | gcc | acg | cat | gcc | acc | tac | acc | 240 |
| Cys | Ser | Leu | His | Arg | Ser | Ala | His | Asn | Ala | Thr | His | Ala | Thr | Tyr | Thr | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| tgc | cac | atg | gat | gta | ttc | cac | ttc | atg | gcc | gac | gac | att | ttc | agt | gtc | 288 |
| Cys | His | Met | Asp | Val | Phe | His | Phe | Met | Ala | Asp | Asp | Ile | Phe | Ser | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| aac | atc | aca | gac | cag | tct | ggc | aac | tac | tcc | cag | gag | tgt | ggc | agc | ttt | 336 |
| Asn | Ile | Thr | Asp | Gln | Ser | Gly | Asn | Tyr | Ser | Gln | Glu | Cys | Gly | Ser | Phe | |
| | | | | 100 | | | | | 105 | | | | | 110 | | |

| | | | | | | | | | | | | | | | | |
|---|---|---|---|---|---|---|---|---|---|---|---|---|---|---|---|---|
| ctc | ctg | gct | gag | agc | atc | aag | ccg | gct | ccc | cct | ttc | aac | gtg | act | gtg | 384 |
| Leu | Leu | Ala | Glu | Ser | Ile | Lys | Pro | Ala | Pro | Pro | Phe | Asn | Val | Thr | Val | |
| | | | 115 | | | | | 120 | | | | | 125 | | | |

| | | | | | | | | | | | | | | | | |
|---|---|---|---|---|---|---|---|---|---|---|---|---|---|---|---|---|
| acc | ttc | tca | gga | cag | tat | aat | atc | tcc | tgg | cgc | tca | gat | tac | gaa | gac | 432 |
| Thr | Phe | Ser | Gly | Gln | Tyr | Asn | Ile | Ser | Trp | Arg | Ser | Asp | Tyr | Glu | Asp | |
| | | 130 | | | | | 135 | | | | | 140 | | | | |

| | | | | | | | | | | | | | | | | |
|---|---|---|---|---|---|---|---|---|---|---|---|---|---|---|---|---|
| cct | gcc | ttc | tac | atg | ctg | aag | ggc | aag | ctt | cag | tat | gag | ctg | cag | tac | 480 |
| Pro | Ala | Phe | Tyr | Met | Leu | Lys | Gly | Lys | Leu | Gln | Tyr | Glu | Leu | Gln | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agg | aac | cgg | gga | gac | ccc | tgg | gct | gtg | agt | ccg | agg | aga | aag | ctg | atc | 528 |
| Arg | Asn | Arg | Gly | Asp | Pro | Trp | Ala | Val | Ser | Pro | Arg | Arg | Lys | Leu | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| tca | gtg | gac | tca | aga | agt | gtc | tcc | ctc | ctc | ccc | ctg | gag | ttc | cgc | aaa | 576 |
| Ser | Val | Asp | Ser | Arg | Ser | Val | Ser | Leu | Leu | Pro | Leu | Glu | Phe | Arg | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| gac | tcg | agc | tat | gag | ctg | cag | gtg | cgg | gca | ggg | ccc | atg | cct | ggc | tcc | 624 |
| Asp | Ser | Ser | Tyr | Glu | Leu | Gln | Val | Arg | Ala | Gly | Pro | Met | Pro | Gly | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| tcc | tac | cag | ggg | acc | tgg | agt | gaa | tgg | agt | gac | ccg | gtc | atc | ttt | cag | 672 |
| Ser | Tyr | Gln | Gly | Thr | Trp | Ser | Glu | Trp | Ser | Asp | Pro | Val | Ile | Phe | Gln | |
| | | 210 | | | | | 215 | | | | | 220 | | | | |

| | | | | | | | | | | | | | | | | |
|---|---|---|---|---|---|---|---|---|---|---|---|---|---|---|---|---|
| acc | cag | tca | gag | gag | tta | aag | gaa | ggc | tgg | aac | cct | cac | ctg | ctg | ctt | 720 |
| Thr | Gln | Ser | Glu | Glu | Leu | Lys | Glu | Gly | Trp | Asn | Pro | His | Leu | Leu | Leu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ctc | ctc | ctg | ctt | gtc | ata | gtc | ttc | att | cct | gcc | ttc | tgg | agc | ctg | aag | 768 |
| Leu | Leu | Leu | Leu | Val | Ile | Val | Phe | Ile | Pro | Ala | Phe | Trp | Ser | Leu | Lys | |
| | | | | 245 | | | | | 250 | | | | | 255 | | |

```
acc cat cca ttg tgg agg cta tgg aag aag ata tgg gcc gtc ccc agc      816
Thr His Pro Leu Trp Arg Leu Trp Lys Lys Ile Trp Ala Val Pro Ser
        260                 265                 270 cct gag cgg ttc ttc atg ccc ctg tac aag ggc tgc agc gga gac ttc      864
Pro Glu Arg Phe Phe Met Pro Leu Tyr Lys Gly Cys Ser Gly Asp Phe
            275                 280                 285 aag aaa tgg gtg ggt gca ccc ttc act ggc tcc agc ctg gag ctg gga      912
Lys Lys Trp Val Gly Ala Pro Phe Thr Gly Ser Ser Leu Glu Leu Gly
290                 295                 300 ccc tgg agc cca gag gtg ccc tcc acc ctg gag gtg tac agc tgc cac      960
Pro Trp Ser Pro Glu Val Pro Ser Thr Leu Glu Val Tyr Ser Cys His
305                 310                 315                 320 cca cca cgg agc ccg gcc aag agg ctg cag ctc acg gag cta caa gaa     1008
Pro Pro Arg Ser Pro Ala Lys Arg Leu Gln Leu Thr Glu Leu Gln Glu
            325                 330                 335 cca gca gag ctg gtg gag tct gac ggt gtg ccc aag ccc agc ttc tgg     1056
Pro Ala Glu Leu Val Glu Ser Asp Gly Val Pro Lys Pro Ser Phe Trp
            340                 345                 350 ccg aca gcc cag aac tcg ggg ggc tca gct tac agt gag gag agg gat     1104
Pro Thr Ala Gln Asn Ser Gly Gly Ser Ala Tyr Ser Glu Glu Arg Asp
        355                 360                 365 cgg cca tac ggc ctg gtg tcc att gac aca gtg act gtg cta gat gca     1152
Arg Pro Tyr Gly Leu Val Ser Ile Asp Thr Val Thr Val Leu Asp Ala
        370                 375                 380 gag ggg cca tgc acc tgg ccc tgc agc tgt gag gat gac ggc tac cca     1200
Glu Gly Pro Cys Thr Trp Pro Cys Ser Cys Glu Asp Asp Gly Tyr Pro
385                 390                 395                 400 gcc ctg gac ctg gat gct ggc ctg gag ccc agc cca ggc cta gag gac     1248
Ala Leu Asp Leu Asp Ala Gly Leu Glu Pro Ser Pro Gly Leu Glu Asp
            405                 410                 415 cca ctc ttg gat gca ggg acc aca gtc ctg tcc tgt ggc tgt gtc tca     1296
Pro Leu Leu Asp Ala Gly Thr Thr Val Leu Ser Cys Gly Cys Val Ser
            420                 425                 430 gct ggc agc cct ggg cta gga ggg ccc ctg gga agc ctc ctg gac aga     1344
Ala Gly Ser Pro Gly Leu Gly Gly Pro Leu Gly Ser Leu Leu Asp Arg
        435                 440                 445 cta aag cca ccc ctt gca gat ggg gag gac tgg gct ggg gga ctg ccc     1392
Leu Lys Pro Pro Leu Ala Asp Gly Glu Asp Trp Ala Gly Gly Leu Pro
    450                 455                 460 tgg ggt ggc cgg tca cct gga ggg gtc tca gag agt gag gcg ggc tca     1440
Trp Gly Gly Arg Ser Pro Gly Gly Val Ser Glu Ser Glu Ala Gly Ser
465                 470                 475                 480 ccc ctg gcc ggc ctg gat atg gac acg ttt gac agt ggc ttt gtg ggc     1488
Pro Leu Ala Gly Leu Asp Met Asp Thr Phe Asp Ser Gly Phe Val Gly
                485                 490                 495 tct gac tgc agc agc cct gtg gag tgt gac ttc acc agc ccc ggg gac     1536
Ser Asp Cys Ser Ser Pro Val Glu Cys Asp Phe Thr Ser Pro Gly Asp
            500                 505                 510 gaa gga ccc ccc cgg agc tac ctc cgc cag tgg gtg gtc att cct ccg     1584
Glu Gly Pro Pro Arg Ser Tyr Leu Arg Gln Trp Val Val Ile Pro Pro
        515                 520                 525 cca ctt tcg agc cct gga ccc cag gcc agc                            1614
Pro Leu Ser Ser Pro Gly Pro Gln Ala Ser
        530                 535

<210> SEQ ID NO 2
<211> LENGTH: 538
<212> TYPE: PRT
<213> ORGANISM: Homo sapiens

<400> SEQUENCE: 2
```

-continued

```
Met Pro Arg Gly Trp Ala Ala Pro Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Ile Phe Ser Val
                85                  90                  95

Asn Ile Thr Asp Gln Ser Gly Asn Tyr Ser Gln Glu Cys Gly Ser Phe
                100                 105                 110

Leu Leu Ala Glu Ser Ile Lys Pro Ala Pro Pro Phe Asn Val Thr Val
            115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
            195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
        275                 280                 285

Lys Lys Trp Val Gly Ala Pro Phe Thr Gly Ser Ser Leu Glu Leu Gly
    290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
            355                 360                 365

Arg Pro Tyr Gly Leu Val Ser Ile Asp Thr Val Thr Val Leu Asp Ala
    370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415
```

```
Pro Leu Leu Asp Ala Gly Thr Thr Val Leu Ser Cys Gly Cys Val Ser
            420                 425                 430

Ala Gly Ser Pro Gly Leu Gly Pro Leu Gly Ser Leu Leu Asp Arg
        435                 440                 445

Leu Lys Pro Pro Leu Ala Asp Gly Glu Asp Trp Ala Gly Gly Leu Pro
    450                 455                 460

Trp Gly Arg Ser Pro Gly Gly Val Ser Glu Ser Glu Ala Gly Ser
465             470                 475                 480

Pro Leu Ala Gly Leu Asp Met Asp Thr Phe Asp Ser Gly Phe Val Gly
            485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
            515                 520                 525

Pro Leu Ser Ser Pro Gly Pro Gln Ala Ser
            530                 535
```

<210> SEQ ID NO 3
<211> LENGTH: 696
<212> TYPE: DNA
<213> ORGANISM: Homo sapiens
<220> FEATURE:
<221> NAME/KEY: CDS
<222> LOCATION: (1)...(696)

<400> SEQUENCE: 3

```
ctg aac acg aca att ctg acg ccc aat ggg aat gaa gac acc aca gct      48
Leu Asn Thr Thr Ile Leu Thr Pro Asn Gly Asn Glu Asp Thr Thr Ala
1               5                   10                  15 gat ttc ttc ctg acc act atg ccc act gac tcc ctc agt gtt tcc act      96
Asp Phe Phe Leu Thr Thr Met Pro Thr Asp Ser Leu Ser Val Ser Thr
                20                  25                  30 ctg ccc ctc cca gag gtt cag tgt ttt gtg ttc aat gtc gag tac atg     144
Leu Pro Leu Pro Glu Val Gln Cys Phe Val Phe Asn Val Glu Tyr Met
            35                  40                  45 aat tgc act tgg aac agc agc tct gag ccc cag cct acc aac ctc act     192
Asn Cys Thr Trp Asn Ser Ser Ser Glu Pro Gln Pro Thr Asn Leu Thr
    50                  55                  60 ctg cat tat tgg tac aag aac tcg gat aat gat aaa gtc cag aag tgc     240
Leu His Tyr Trp Tyr Lys Asn Ser Asp Asn Asp Lys Val Gln Lys Cys
65                  70                  75                  80 agc cac tat cta ttc tct gaa gaa atc act tct ggc tgt cag ttg caa     288
Ser His Tyr Leu Phe Ser Glu Glu Ile Thr Ser Gly Cys Gln Leu Gln
                85                  90                  95 aaa aag gag atc cac ctc tac caa aca ttt gtt gtt cag ctc cag gac     336
Lys Lys Glu Ile His Leu Tyr Gln Thr Phe Val Val Gln Leu Gln Asp
            100                 105                 110 cca cgg gaa ccc agg aga cag gcc aca cag atg cta aaa ctg cag aat     384
Pro Arg Glu Pro Arg Arg Gln Ala Thr Gln Met Leu Lys Leu Gln Asn
        115                 120                 125 ctg gtg atc ccc tgg gct cca gag aac cta aca ctt cac aaa ctg agt     432
Leu Val Ile Pro Trp Ala Pro Glu Asn Leu Thr Leu His Lys Leu Ser
    130                 135                 140 gaa tcc cag cta gaa ctg aac tgg aac aac aga ttc ttg aac cac tgt     480
Glu Ser Gln Leu Glu Leu Asn Trp Asn Asn Arg Phe Leu Asn His Cys
145                 150                 155                 160 ttg gag cac ttg gtg cag tac cgg act gac tgg gac cac agc tgg act     528
Leu Glu His Leu Val Gln Tyr Arg Thr Asp Trp Asp His Ser Trp Thr
                165                 170                 175
```

```
gaa caa tca gtg gat tat aga cat aag ttc tcc ttg cct agt gtg gat     576
Glu Gln Ser Val Asp Tyr Arg His Lys Phe Ser Leu Pro Ser Val Asp
        180                 185                 190 ggg cag aaa cgc tac acg ttt cgt gtt cgg agc cgc ttt aac cca ctc     624
Gly Gln Lys Arg Tyr Thr Phe Arg Val Arg Ser Arg Phe Asn Pro Leu
    195                 200                 205 tgt gga agt gct cag cat tgg agt gaa tgg agc cac cca atc cac tgg     672
Cys Gly Ser Ala Gln His Trp Ser Glu Trp Ser His Pro Ile His Trp
210                 215                 220 ggg agc aat act tca aaa gag aat                                     696
Gly Ser Asn Thr Ser Lys Glu Asn
225                 230

<210> SEQ ID NO 4
<211> LENGTH: 232
<212> TYPE: PRT
<213> ORGANISM: Homo sapiens

<400> SEQUENCE: 4

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn
225                 230

<210> SEQ ID NO 5
<211> LENGTH: 654
<212> TYPE: DNA
<213> ORGANISM: Homo sapiens
<220> FEATURE:
<221> NAME/KEY: CDS
<222> LOCATION: (1)...(654)

<400> SEQUENCE: 5
```

```
tgc ccc gac ctc gtc tgc tac acc gat tac ctc cag acg gtc atc tgc         48
Cys Pro Asp Leu Val Cys Tyr Thr Asp Tyr Leu Gln Thr Val Ile Cys
1               5                   10                  15 atc ctg gaa atg tgg aac ctc cac ccc agc acg ctc acc ctt acc tgg         96
Ile Leu Glu Met Trp Asn Leu His Pro Ser Thr Leu Thr Leu Thr Trp
            20                  25                  30 caa gac cag tat gaa gag ctg aag gac gag gcc acc tcc tgc agc ctc        144
Gln Asp Gln Tyr Glu Glu Leu Lys Asp Glu Ala Thr Ser Cys Ser Leu
        35                  40                  45 cac agg tcg gcc cac aat gcc acg cat gcc acc tac acc tgc cac atg        192
His Arg Ser Ala His Asn Ala Thr His Ala Thr Tyr Thr Cys His Met
50                  55                  60 gat gta ttc cac ttc atg gcc gac gac att ttc agt gtc aac atc aca        240
Asp Val Phe His Phe Met Ala Asp Asp Ile Phe Ser Val Asn Ile Thr
65                  70                  75                  80 gac cag tct ggc aac tac tcc cag gag tgt ggc agc ttt ctc ctg gct        288
Asp Gln Ser Gly Asn Tyr Ser Gln Glu Cys Gly Ser Phe Leu Leu Ala
                85                  90                  95 gag agc atc aag ccg gct ccc cct ttc aac gtg act gtg acc ttc tca        336
Glu Ser Ile Lys Pro Ala Pro Pro Phe Asn Val Thr Val Thr Phe Ser
            100                 105                 110 gga cag tat aat atc tcc tgg cgc tca gat tac gaa gac cct gcc ttc        384
Gly Gln Tyr Asn Ile Ser Trp Arg Ser Asp Tyr Glu Asp Pro Ala Phe
        115                 120                 125 tac atg ctg aag ggc aag ctt cag tat gag ctg cag tac agg aac cgg        432
Tyr Met Leu Lys Gly Lys Leu Gln Tyr Glu Leu Gln Tyr Arg Asn Arg
130                 135                 140 gga gac ccc tgg gct gtg agt ccg agg aga aag ctg atc tca gtg gac        480
Gly Asp Pro Trp Ala Val Ser Pro Arg Arg Lys Leu Ile Ser Val Asp
145                 150                 155                 160 tca aga agt gtc tcc ctc ctc ccc ctg gag ttc cgc aaa gac tcg agc        528
Ser Arg Ser Val Ser Leu Leu Pro Leu Glu Phe Arg Lys Asp Ser Ser
                165                 170                 175 tat gag ctg cag gtg cgg gca ggg ccc atg cct ggc tcc tcc tac cag        576
Tyr Glu Leu Gln Val Arg Ala Gly Pro Met Pro Gly Ser Ser Tyr Gln
            180                 185                 190 ggg acc tgg agt gaa tgg agt gac ccg gtc atc ttt cag acc cag tca        624
Gly Thr Trp Ser Glu Trp Ser Asp Pro Val Ile Phe Gln Thr Gln Ser
        195                 200                 205 gag gag tta aag gaa ggc tgg aac cct cac                                654
Glu Glu Leu Lys Glu Gly Trp Asn Pro His
    210                 215
```

<210> SEQ ID NO 6
<211> LENGTH: 218
<212> TYPE: PRT
<213> ORGANISM: Homo sapiens

<400> SEQUENCE: 6

```
Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
            20                  25                  30

Gln Asp Gln Tyr Glu Glu Leu Lys Asp Glu Ala Thr Ser Cys Ser Leu
        35                  40                  45

His Arg Ser Ala His Asn Ala Thr His Ala Thr Tyr Thr Cys His Met
50                  55                  60

Asp Val Phe His Phe Met Ala Asp Asp Ile Phe Ser Val Asn Ile Thr
65                  70                  75                  80
```

```
Asp Gln Ser Gly Asn Tyr Ser Gln Glu Cys Gly Ser Phe Leu Leu Ala
                85                  90                  95
Glu Ser Ile Lys Pro Ala Pro Pro Phe Asn Val Thr Val Thr Phe Ser
            100                 105                 110
Gly Gln Tyr Asn Ile Ser Trp Arg Ser Asp Tyr Glu Asp Pro Ala Phe
        115                 120                 125
Tyr Met Leu Lys Gly Lys Leu Gln Tyr Glu Leu Gln Tyr Arg Asn Arg
    130                 135                 140
Gly Asp Pro Trp Ala Val Ser Pro Arg Arg Lys Leu Ile Ser Val Asp
145                 150                 155                 160
Ser Arg Ser Val Ser Leu Leu Pro Leu Glu Phe Arg Lys Asp Ser Ser
                165                 170                 175
Tyr Glu Leu Gln Val Arg Ala Gly Pro Met Pro Gly Ser Ser Tyr Gln
            180                 185                 190
Gly Thr Trp Ser Glu Trp Ser Asp Pro Val Ile Phe Gln Thr Gln Ser
        195                 200                 205
Glu Glu Leu Lys Glu Gly Trp Asn Pro His
    210                 215
```

<210> SEQ ID NO 7
<211> LENGTH: 654
<212> TYPE: DNA
<213> ORGANISM: Artificial Sequence
<220> FEATURE:
<223> OTHER INFORMATION: Degenerate polynucleotide sequence of soluble
      zalpha11 Receptor polypeptide as shown in SEQ ID
      NO:6
<220> FEATURE:
<221> NAME/KEY: misc_feature
<222> LOCATION: (1)...(654)
<223> OTHER INFORMATION: n = A,T,C or G

<400> SEQUENCE: 7

```
tgyccngayy tngtntgyta yacngaytay ytncaracng tnathtgyat hytngaratg      60
tggaayytnc ayccnwsnac nytnacnytn acntggcarg aycartayga rgarytnaar    120
gaygargcna cnwsntgyws nytncaymgn wsngcncaya aygcnacnca ygcnacntay    180
acntgycaya tggaygtntt ycayttyatg gcngaygaya thttywsngt naayathacn    240
gaycarwsng gnaaytayws ncargartgy ggnwsnttyy tnytngcnga rwsnathaar    300
ccngcnccnc cnttyaaygt nacngtnacn ttywsnggnc artayaayat hwsntggmgn    360
wsngaytayg argayccngc nttytayatg ytnaarggna arytncarta ygarytncar    420
taymgnaaym gnggngaycc ntgggcngtn wsnccnmgnm gnaarytnat hwsngtngay    480
wsnmgnwsng tnwsnytnyt nccnytngar ttymgnaarg aywsnwsnta ygarytncar    540
gtnmgngcng gnccnatgcc nggnwsnwsn taycarggna cntggwsnga rtggwsngay    600
ccngtnatht tycaracnca rwsngargar ytnaargarg gntggaaycc ncay          654
```

<210> SEQ ID NO 8
<211> LENGTH: 696
<212> TYPE: DNA
<213> ORGANISM: Artificial Sequence
<220> FEATURE:
<223> OTHER INFORMATION: Degenerate polynucleotide sequence of
      IL-2Rgamma polypeptide as shown in SEQ ID NO:4
<220> FEATURE:
<221> NAME/KEY: misc_feature
<222> LOCATION: (1)...(696)
<223> OTHER INFORMATION: n = A,T,C or G

<400> SEQUENCE: 8

```
ytnaayacna cnathytnac nccnaayggn aaygargaya cnacngcnga yttyttyytn    60
acnacnatgc cnacngayws nytnwsngtn wsnacnytnc cnytnccnga rgtncartgy   120
ttygtnttya aygtngarta yatgaaytgy acntggaayw snwsnwsnga rccncarccn   180
acnaayytna cnytncayta ytggtayaar aaywsngaya aygayaargt ncaraartgy   240
wsncaytayy tnttywsnga r <210> SEQ ID NO 10
<211> LENGTH: 162
<212> TYPE: PRT
<213> ORGANISM: Homo sapiens

<400> SEQUENCE: 10

```
Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
            35                  40                  45

Leu Lys Asn Tyr Val Asn Asp Leu Val Pro Glu Phe Leu Pro Ala Pro
50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
                100                 105                 110

Gly Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser
```

<210> SEQ ID NO 11
<211> LENGTH: 1735
<212> TYPE: DNA
<213> ORGANISM: mus musculus
<220> FEATURE:
<221> NAME/KEY: CDS
<222> LOCATION: (143)...(1729)

<400> SEQUENCE: 11

```
ctgcccacct caaaccttca cctcccacca ccaccactcc gagtcccgct gtgactccca      60
cgcccaggag accacccaag tgccccagcc taaagaatgg ctttctgaga aagaccctga     120
aggagtaggt ctgggacaca gc atg ccc cgg ggc cca gtg gct gcc tta ctc     172
                         Met Pro Arg Gly Pro Val Ala Ala Leu Leu
                         1               5                   10 ctg ctg att ctc cat gga gct tgg agc tgc ctg gac ctc act tgc tac      220
Leu Leu Ile Leu His Gly Ala Trp Ser Cys Leu Asp Leu Thr Cys Tyr
                15                  20                  25 act gac tac ctc tgg acc atc acc tgt gtc ctg gag aca cgg agc ccc      268
Thr Asp Tyr Leu Trp Thr Ile Thr Cys Val Leu Glu Thr Arg Ser Pro
            30                  35                  40 aac ccc agc ata ctc agt ctc acc tgg caa gat gaa tat gag gaa ctt      316
Asn Pro Ser Ile Leu Ser Leu Thr Trp Gln Asp Glu Tyr Glu Glu Leu
        45                  50                  55 cag gac caa gag acc ttc tgc agc cta cac agg tct ggc cac aac acc      364
Gln Asp Gln Glu Thr Phe Cys Ser Leu His Arg Ser Gly His Asn Thr
    60                  65                  70 aca cat ata tgg tac acg tgc cat atg cgc ttg tct caa ttc ctg tcc      412
Thr His Ile Trp Tyr Thr Cys His Met Arg Leu Ser Gln Phe Leu Ser
75                  80                  85                  90
```

```
gat gaa gtt ttc att gtc aat gtg acg gac cag tct ggc aac aac tcc    460
Asp Glu Val Phe Ile Val Asn Val Thr Asp Gln Ser Gly Asn Asn Ser
             95                 100                 105 caa gag tgt ggc agc ttt gtc ctg gct gag agc atc aaa cca gct ccc    508
Gln Glu Cys Gly Ser Phe Val Leu Ala Glu Ser Ile Lys Pro Ala Pro
        110                 115                 120 ccc ttg aac gtg act gtg gcc ttc tca gga cgc tat gat atc tcc tgg    556
Pro Leu Asn Val Thr Val Ala Phe Ser Gly Arg Tyr Asp Ile Ser Trp
             125                 130                 135 gac tca gct tat gac gaa ccc tcc aac tac gtg ctg agg ggc aag cta    604
Asp Ser Ala Tyr Asp Glu Pro Ser Asn Tyr Val Leu Arg Gly Lys Leu
        140                 145                 150 caa tat gag ctg cag tat cgg aac ctc aga gac ccc tat gct gtg agg    652
Gln Tyr Glu Leu Gln Tyr Arg Asn Leu Arg Asp Pro Tyr Ala Val Arg
155                 160                 165                 170 ccg gtg acc aag ctg atc tca gtg gac tca aga aac gtc tct ctt ctc    700
Pro Val Thr Lys Leu Ile Ser Val Asp Ser Arg Asn Val Ser Leu Leu
             175                 180                 185 cct gaa gag ttc cac aaa gat tct agc tac cag ctg cag gtg cgg gca    748
Pro Glu Glu Phe His Lys Asp Ser Ser Tyr Gln Leu Gln Val Arg Ala
             190                 195                 200 gcg cct cag cca ggc act tca ttc agg ggg acc tgg agt gag tgg agt    796
Ala Pro Gln Pro Gly Thr Ser Phe Arg Gly Thr Trp Ser Glu Trp Ser
        205                 210                 215 gac ccc gtc atc ttt cag acc cag gct ggg gag ccc gag gca ggc tgg    844
Asp Pro Val Ile Phe Gln Thr Gln Ala Gly Glu Pro Glu Ala Gly Trp
        220                 225                 230 gac cct cac atg ctg ctc ctg gct gtc ttg atc att gtc ctg gtt        892
Asp Pro His Met Leu Leu Leu Ala Val Leu Ile Ile Val Leu Val
235                 240                 245                 250 ttc atg ggt ctg aag atc cac ctg cct tgg agg cta tgg aaa aag ata    940
Phe Met Gly Leu Lys Ile His Leu Pro Trp Arg Leu Trp Lys Lys Ile
             255                 260                 265 tgg gca cca gtg ccc acc cct gag agt ttc ttc cag ccc ctg tac agg    988
Trp Ala Pro Val Pro Thr Pro Glu Ser Phe Phe Gln Pro Leu Tyr Arg
        270                 275                 280 gag cac agc ggg aac ttc aag aaa tgg gtt aat acc cct ttc acg gcc   1036
Glu His Ser Gly Asn Phe Lys Lys Trp Val Asn Thr Pro Phe Thr Ala
        285                 290                 295 tcc agc ata gag ttg gtg cca cag agt tcc aca aca aca tca gcc tta   1084
Ser Ser Ile Glu Leu Val Pro Gln Ser Ser Thr Thr Thr Ser Ala Leu
        300                 305                 310 cat ctg tca ttg tat cca gcc aag gag aag aag ttc ccg ggg ctg ccg   1132
His Leu Ser Leu Tyr Pro Ala Lys Glu Lys Lys Phe Pro Gly Leu Pro
315                 320                 325                 330 ggt ctg gaa gag caa ctg gag tgt gat gga atg tct gag cct ggt cac   1180
Gly Leu Glu Glu Gln Leu Glu Cys Asp Gly Met Ser Glu Pro Gly His
                 335                 340                 345 tgg tgc ata atc ccc ttg gca gct ggc caa gcg gtc tca gcc tac agt   1228
Trp Cys Ile Ile Pro Leu Ala Ala Gly Gln Ala Val Ser Ala Tyr Ser
             350                 355                 360 gag gag aga gac cgg cca tat ggt ctg gtg tcc att gac aca gtg act   1276
Glu Glu Arg Asp Arg Pro Tyr Gly Leu Val Ser Ile Asp Thr Val Thr
        365                 370                 375 gtg gga gat gca gag ggc ctg tgt gtc tgg ccc tgt agc tgt gag gat   1324
Val Gly Asp Ala Glu Gly Leu Cys Val Trp Pro Cys Ser Cys Glu Asp
380                 385                 390 gat ggc tat cca gcc atg aac ctg gat gct ggc cga gag tct ggc cct   1372
Asp Gly Tyr Pro Ala Met Asn Leu Asp Ala Gly Arg Glu Ser Gly Pro
```

```
                395                 400                 405                 410
aat tca gag gat ctg ctc ttg gtc aca gac cct gct ttt ctg tct tgc        1420
Asn Ser Glu Asp Leu Leu Val Thr Asp Pro Ala Phe Leu Ser Cys
                    415                 420                 425 ggc tgt gtc tca ggt agt ggt ctc agg ctt gga ggc tcc cca ggc agc        1468
Gly Cys Val Ser Gly Ser Gly Leu Arg Leu Gly Gly Ser Pro Gly Ser
            430                 435                 440 cta ctg gac agg ttg agg ctg tca ttt gca aag gaa ggg gac tgg aca        1516
Leu Leu Asp Arg Leu Arg Leu Ser Phe Ala Lys Glu Gly Asp Trp Thr
        445                 450                 455 gca gac cca acc tgg aga act ggg tcc cca gga ggg ggc tct gag agt        1564
Ala Asp Pro Thr Trp Arg Thr Gly Ser Pro Gly Gly Gly Ser Glu Ser
    460                 465                 470 gaa gca ggt tcc ccc cct ggt ctg gac atg gac aca ttt gac agt ggc        1612
Glu Ala Gly Ser Pro Pro Gly Leu Asp Met Asp Thr Phe Asp Ser Gly
475                 480                 485                 490 ttt gca ggt tca gac tgt ggc agc ccc gtg gag act gat gaa gga ccc        1660
Phe Ala Gly Ser Asp Cys Gly Ser Pro Val Glu Thr Asp Glu Gly Pro
                495                 500                 505 cct cga agc tat ctc cgc cag tgg gtg gtc agg acc cct cca cct gtg        1708
Pro Arg Ser Tyr Leu Arg Gln Trp Val Val Arg Thr Pro Pro Pro Val
            510                 515                 520 gac agt gga gcc cag agc agc tagcat                                     1735
Asp Ser Gly Ala Gln Ser Ser
        525

<210> SEQ ID NO 12
<211> LENGTH: 529
<212> TYPE: PRT
<213> ORGANISM: mus musculus

<400> SEQUENCE: 12

Met Pro Arg Gly Pro Val Ala Ala Leu Leu Leu Ile Leu His Gly
1               5                   10                  15

Ala Trp Ser Cys Leu Asp Leu Thr Cys Tyr Thr Asp Tyr Leu Trp Thr
                20                  25                  30

Ile Thr Cys Val Leu Glu Thr Arg Ser Pro Asn Pro Ser Ile Leu Ser
            35                  40                  45

Leu Thr Trp Gln Asp Glu Tyr Glu Glu Leu Gln Asp Gln Glu Thr Phe
        50                  55                  60

Cys Ser Leu His Arg Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Val Arg Ala Ala Pro Gln Pro Gly Thr
```

-continued

```
            195                 200                 205
Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Pro His Met Leu Leu
225                 230                 235                 240

Leu Leu Ala Val Leu Ile Ile Val Leu Val Phe Met Gly Leu Lys Ile
                245                 250                 255

His Leu Pro Trp Arg Leu Trp Lys Lys Ile Trp Ala Pro Val Pro Thr
            260                 265                 270

Pro Glu Ser Phe Phe Gln Pro Leu Tyr Arg Glu His Ser Gly Asn Phe
        275                 280                 285

Lys Lys Trp Val Asn Thr Pro Phe Thr Ala Ser Ser Ile Glu Leu Val
    290                 295                 300

Pro Gln Ser Ser Thr Thr Thr Ser Ala Leu His Leu Ser Leu Tyr Pro
305                 310                 315                 320

Ala Lys Glu Lys Lys Phe Pro Gly Leu Pro Gly Leu Glu Glu Gln Leu
                325                 330                 335

Glu Cys Asp Gly Met Ser Glu Pro Gly His Trp Cys Ile Ile Pro Leu
            340                 345                 350

Ala Ala Gly Gln Ala Val Ser Ala Tyr Ser Glu Glu Arg Asp Arg Pro
        355                 360                 365

Tyr Gly Leu Val Ser Ile Asp Thr Val Thr Val Gly Asp Ala Glu Gly
    370                 375                 380

Leu Cys Val Trp Pro Cys Ser Cys Glu Asp Gly Tyr Pro Ala Met
385                 390                 395                 400

Asn Leu Asp Ala Gly Arg Glu Ser Gly Pro Asn Ser Glu Asp Leu Leu
                405                 410                 415

Leu Val Thr Asp Pro Ala Phe Leu Ser Cys Gly Cys Val Ser Gly Ser
            420                 425                 430

Gly Leu Arg Leu Gly Gly Ser Pro Gly Ser Leu Leu Asp Arg Leu Arg
        435                 440                 445

Leu Ser Phe Ala Lys Glu Gly Asp Trp Thr Ala Asp Pro Thr Trp Arg
    450                 455                 460

Thr Gly Ser Pro Gly Gly Gly Ser Glu Ser Glu Ala Gly Ser Pro Pro
465                 470                 475                 480

Gly Leu Asp Met Asp Thr Phe Asp Ser Gly Phe Ala Gly Ser Asp Cys
                485                 490                 495

Gly Ser Pro Val Glu Thr Asp Glu Gly Pro Pro Arg Ser Tyr Leu Arg
            500                 505                 510

Gln Trp Val Val Arg Thr Pro Pro Pro Val Asp Ser Gly Ala Gln Ser
        515                 520                 525

Ser
```

```
<210> SEQ ID NO 13
<211> LENGTH: 5
<212> TYPE: PRT
<213> ORGANISM: Artificial Sequence
<220> FEATURE:
<223> OTHER INFORMATION: WSXWS polypeptide consensus motif
<220> FEATURE:
<221> NAME/KEY: VARIANT
<222> LOCATION: (1)...(5)
<223> OTHER INFORMATION: Xaa = Any Amino Acid

<400> SEQUENCE: 13

Trp Ser Xaa Trp Ser
```

<210> SEQ ID NO 14
<211> LENGTH: 6
<212> TYPE: PRT
<213> ORGANISM: Artificial Sequence
<220> FEATURE:
<223> OTHER INFORMATION: Glu-Glu (CEE) Tag amino acid sequence

<400> SEQUENCE: 14

Glu Tyr Met Pro Met Glu
1               5

<210> SEQ ID NO 15
<211> LENGTH: 1701
<212> TYPE: DNA
<213> ORGANISM: Artificial Sequence
<220> FEATURE:
<223> OTHER INFORMATION: soluble zalpha11R/IgGgamma1 construct
<220> FEATURE:
<221> NAME/KEY: CDS
<222> LOCATION: (1)...(1701)

<400> SEQUENCE: 15

| atg | ccg | cgt | ggc | tgg | gcc | gcc | ccc | ttg | ctc | ctg | ctg | ctg | ctc | cag | gga | 48 |
| Met | Pro | Arg | Gly | Trp | Ala | Ala | Pro | Leu | Leu | Leu | Leu | Leu | Leu | Gln | Gly | |
| 1   |     |     |     | 5   |     |     |     |     | 10  |     |     |     |     | 15  |     | |

| ggc | tgg | ggc | tgc | ccc | gac | ctc | gtc | tgc | tac | acc | gat | tac | ctc | cag | acg | 96 |
| Gly | Trp | Gly | Cys | Pro | Asp | Leu | Val | Cys | Tyr | Thr | Asp | Tyr | Leu | Gln | Thr | |
|     |     |     | 20  |     |     |     |     | 25  |     |     |     |     | 30  |     |     | |

| gtc | atc | tgc | atc | ctg | gaa | atg | tgg | aac | ctc | cac | ccc | agc | acg | ctc | acc | 144 |
| Val | Ile | Cys | Ile | Leu | Glu | Met | Trp | Asn | Leu | His | Pro | Ser | Thr | Leu | Thr | |
|     |     | 35  |     |     |     |     | 40  |     |     |     |     | 45  |     |     |     | |

| ctt | acc | tgg | caa | gac | cag | tat | gaa | gag | ctg | aag | gac | gag | gcc | acc | tcc | 192 |
| Leu | Thr | Trp | Gln | Asp | Gln | Tyr | Glu | Glu | Leu | Lys | Asp | Glu | Ala | Thr | Ser | |
| 50  |     |     |     |     | 55  |     |     |     |     | 60  |     |     |     |     |     | |

| tgc | agc | ctc | cac | agg | tcg | gcc | cac | aat | gcc | acg | cat | gcc | acc | tac | acc | 240 |
| Cys | Ser | Leu | His | Arg | Ser | Ala | His | Asn | Ala | Thr | His | Ala | Thr | Tyr | Thr | |
| 65  |     |     |     |     | 70  |     |     |     |     | 75  |     |     |     |     | 80  | |

| tgc | cac | atg | gat | gta | ttc | cac | ttc | atg | gcc | gac | gac | att | ttc | agt | gtc | 288 |
| Cys | His | Met | Asp | Val | Phe | His | Phe | Met | Ala | Asp | Asp | Ile | Phe | Ser | Val | |
|     |     |     |     | 85  |     |     |     |     | 90  |     |     |     |     | 95  |     | |

| aac | atc | aca | gac | cag | tct | ggc | aac | tac | tcc | cag | gag | tgt | ggc | agc | ttt | 336 |
| Asn | Ile | Thr | Asp | Gln | Ser | Gly | Asn | Tyr | Ser | Gln | Glu | Cys | Gly | Ser | Phe | |
|     |     |     | 100 |     |     |     |     | 105 |     |     |     |     | 110 |     |     | |

| ctc | ctg | gct | gag | agc | atc | aag | ccg | gct | ccc | cct | ttc | aac | gtg | act | gtg | 384 |
| Leu | Leu | Ala | Glu | Ser | Ile | Lys | Pro | Ala | Pro | Pro | Phe | Asn | Val | Thr | Val | |
|     |     | 115 |     |     |     |     | 120 |     |     |     |     | 125 |     |     |     | |

| acc | ttc | tca | gga | cag | tat | aat | atc | tcc | tgg | cgc | tca | gat | tac | gaa | gac | 432 |
| Thr | Phe | Ser | Gly | Gln | Tyr | Asn | Ile | Ser | Trp | Arg | Ser | Asp | Tyr | Glu | Asp | |
| 130 |     |     |     |     | 135 |     |     |     |     | 140 |     |     |     |     |     | |

| cct | gcc | ttc | tac | atg | ctg | aag | ggc | aag | ctt | cag | tat | gag | ctg | cag | tac | 480 |
| Pro | Ala | Phe | Tyr | Met | Leu | Lys | Gly | Lys | Leu | Gln | Tyr | Glu | Leu | Gln | Tyr | |
| 145 |     |     |     |     | 150 |     |     |     |     | 155 |     |     |     |     | 160 | |

| agg | aac | cgg | gga | gac | ccc | tgg | gct | gtg | agt | ccg | agg | aga | aag | ctg | atc | 528 |
| Arg | Asn | Arg | Gly | Asp | Pro | Trp | Ala | Val | Ser | Pro | Arg | Arg | Lys | Leu | Ile | |
|     |     |     |     | 165 |     |     |     |     | 170 |     |     |     |     | 175 |     | |

| tca | gtg | gac | tca | aga | agt | gtc | tcc | ctc | ctc | ccc | ctg | gag | ttc | cgc | aaa | 576 |
| Ser | Val | Asp | Ser | Arg | Ser | Val | Ser | Leu | Leu | Pro | Leu | Glu | Phe | Arg | Lys | |
|     |     |     | 180 |     |     |     |     | 185 |     |     |     |     | 190 |     |     | |

| gac | tcg | agc | tat | gag | ctg | cag | gtg | cgg | gca | ggg | ccc | atg | cct | ggc | tcc | 624 |
| Asp | Ser | Ser | Tyr | Glu | Leu | Gln | Val | Arg | Ala | Gly | Pro | Met | Pro | Gly | Ser | |
|     |     | 195 |     |     |     |     | 200 |     |     |     |     | 205 |     |     |     | |

-continued

| | | |
|---|---|---|
| tcc tac cag ggg acc tgg agt gaa tgg agt gac ccg gtc atc ttt cag<br>Ser Tyr Gln Gly Thr Trp Ser Glu Trp Ser Asp Pro Val Ile Phe Gln<br>210                      215                    220 | 672 |
| acc cag tca gag gag tta aag gaa ggc tgg aac cct cac gct agc acc<br>Thr Gln Ser Glu Glu Leu Lys Glu Gly Trp Asn Pro His Ala Ser Thr<br>225                      230                    235                    240 | 720 |
| aag ggc cca tcg gtc ttc ccc ctg gca ccc tcc tcc aag agc acc tct<br>Lys Gly Pro Ser Val Phe Pro Leu Ala Pro Ser Ser Lys Ser Thr Ser<br>                  245                    250                    255 | 768 |
| ggg ggc aca gcg gcc ctg ggc tgc ctg gtc aag gac tac ttc ccc gaa<br>Gly Gly Thr Ala Ala Leu Gly Cys Leu Val Lys Asp Tyr Phe Pro Glu<br>                260                    265                    270 | 816 |
| ccg gtg acg gtg tcg tgg aac tca ggc gcc ctg acc agc ggc gtg cac<br>Pro Val Thr Val Ser Trp Asn Ser Gly Ala Leu Thr Ser Gly Val His<br>275                      280                    285 | 864 |
| acc ttc ccg gct gtc cta cag tcc tca gga ctc tac tcc ctc agc agc<br>Thr Phe Pro Ala Val Leu Gln Ser Ser Gly Leu Tyr Ser Leu Ser Ser<br>            290                    295                    300 | 912 |
| gtg gtg acc gtg ccc tcc agc agc ttg ggc acc cag acc tac atc tgc<br>Val Val Thr Val Pro Ser Ser Ser Leu Gly Thr Gln Thr Tyr Ile Cys<br>305                      310                    315                    320 | 960 |
| aac gtg aat cac aag ccc agc aac acc aag gtg gac aag aaa gtt gag<br>Asn Val Asn His Lys Pro Ser Asn Thr Lys Val Asp Lys Lys Val Glu<br>                  325                    330                    335 | 1008 |
| ccc aaa tct tgt gac aaa act cac aca tgc cca ccg tgc cca gca cct<br>Pro Lys Ser Cys Asp Lys Thr His Thr Cys Pro Pro Cys Pro Ala Pro<br>                    340                    345                    350 | 1056 |
| gaa ctc ctg ggg gga ccg tca gtc ttc ctc ttc ccc cca aaa ccc aag<br>Glu Leu Leu Gly Gly Pro Ser Val Phe Leu Phe Pro Pro Lys Pro Lys<br>                355                    360                    365 | 1104 |
| gac acc ctc atg atc tcc cgg acc cct gag gtc aca tgc gtg gtg gtg<br>Asp Thr Leu Met Ile Ser Arg Thr Pro Glu Val Thr Cys Val Val Val<br>370                      375                    380 | 1152 |
| gac gtg agc cac gaa gac cct gag gtc aag ttc aac tgg tac gtg gac<br>Asp Val Ser His Glu Asp Pro Glu Val Lys Phe Asn Trp Tyr Val Asp<br>385                      390                    395                    400 | 1200 |
| ggc gtg gag gtg cat aat gcc aag aca aag ccg cgg gag gag cag tac<br>Gly Val Glu Val His Asn Ala Lys Thr Lys Pro Arg Glu Glu Gln Tyr<br>                  405                    410                    415 | 1248 |
| aac agc acg tac cgt gtg gtc agc gtc ctc acc gtc ctg cac cag gac<br>Asn Ser Thr Tyr Arg Val Val Ser Val Leu Thr Val Leu His Gln Asp<br>                    420                    425                    430 | 1296 |
| tgg ctg aat ggc aag gag tac aag tgc aag gtc tcc aac aaa gcc ctc<br>Trp Leu Asn Gly Lys Glu Tyr Lys Cys Lys Val Ser Asn Lys Ala Leu<br>                435                    440                    445 | 1344 |
| cca gcc ccc atc gag aaa acc atc tcc aaa gcc aaa ggg cag ccc cga<br>Pro Ala Pro Ile Glu Lys Thr Ile Ser Lys Ala Lys Gly Gln Pro Arg<br>450                      455                    460 | 1392 |
| gaa cca cag gtg tac acc ctg ccc cca tcc cgg gat gag ctg acc aag<br>Glu Pro Gln Val Tyr Thr Leu Pro Pro Ser Arg Asp Glu Leu Thr Lys<br>465                      470                    475                    480 | 1440 |
| aac cag gtc agc ctg acc tgc ctg gtc aaa ggc ttc tat ccc agc gac<br>Asn Gln Val Ser Leu Thr Cys Leu Val Lys Gly Phe Tyr Pro Ser Asp<br>                  485                    490                    495 | 1488 |
| atc gcc gtg gag tgg gag agc aat ggg cag ccg gag aac aac tac aag<br>Ile Ala Val Glu Trp Glu Ser Asn Gly Gln Pro Glu Asn Asn Tyr Lys<br>500                      505                    510 | 1536 |
| acc acg cct ccc gtg ctg gac tcc gac ggc tcc ttc ttc ctc tac agc<br>Thr Thr Pro Pro Val Leu Asp Ser Asp Gly Ser Phe Phe Leu Tyr Ser | 1584 |

```
                      515                 520                 525
aag ctc acc gtg gac aag agc agg tgg cag cag ggg aac gtc ttc tca    1632
Lys Leu Thr Val Asp Lys Ser Arg Trp Gln Gln Gly Asn Val Phe Ser
        530                 535                 540 tgc tcc gtg atg cat gag gct ctg cac aac cac tac acg cag aag agc    1680
Cys Ser Val Met His Glu Ala Leu His Asn His Tyr Thr Gln Lys Ser
545                 550                 555                 560 ctc tcc ctg tct ccg ggt aaa                                        1701
Leu Ser Leu Ser Pro Gly Lys
                565

<210> SEQ ID NO 16
<211> LENGTH: 567
<212> TYPE: PRT
<213> ORGANISM: Artificial Sequence
<220> FEATURE:
<223> OTHER INFORMATION: soluble zalpha11R/IgGgamma1 construct

<400> SEQUENCE: 16

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Ala Ser Thr
225                 230                 235                 240

Lys Gly Pro Ser Val Phe Pro Leu Ala Pro Ser Ser Lys Ser Thr Ser
                245                 250                 255

Gly Gly Thr Ala Ala Leu Gly Cys Leu Val Lys Asp Tyr Phe Pro Glu
            260                 265                 270

Pro Val Thr Val Ser Trp Asn Ser Gly Ala Leu Thr Ser Gly Val His
        275                 280                 285

Thr Phe Pro Ala Val Leu Gln Ser Ser Gly Leu Tyr Ser Leu Ser Ser
```

-continued

```
                    290                 295                 300
Val Val Thr Val Pro Ser Ser Leu Gly Thr Gln Thr Tyr Ile Cys
305                 310                 315                 320

Asn Val Asn His Lys Pro Ser Asn Thr Lys Val Asp Lys Val Glu
                325                 330                 335

Pro Lys Ser Cys Asp Lys Thr His Thr Cys Pro Pro Cys Pro Ala Pro
            340                 345                 350

Glu Leu Leu Gly Gly Pro Ser Val Phe Leu Phe Pro Pro Lys Pro Lys
        355                 360                 365

Asp Thr Leu Met Ile Ser Arg Thr Pro Glu Val Thr Cys Val Val Val
370                 375                 380

Asp Val Ser His Glu Asp Pro Glu Val Lys Phe Asn Trp Tyr Val Asp
385                 390                 395                 400

Gly Val Glu Val His Asn Ala Lys Thr Lys Pro Arg Glu Glu Gln Tyr
                405                 410                 415

Asn Ser Thr Tyr Arg Val Val Ser Val Leu Thr Val Leu His Gln Asp
            420                 425                 430

Trp Leu Asn Gly Lys Glu Tyr Lys Cys Lys Val Ser Asn Lys Ala Leu
        435                 440                 445

Pro Ala Pro Ile Glu Lys Thr Ile Ser Lys Ala Lys Gly Gln Pro Arg
    450                 455                 460

Glu Pro Gln Val Tyr Thr Leu Pro Pro Ser Arg Asp Glu Leu Thr Lys
465                 470                 475                 480

Asn Gln Val Ser Leu Thr Cys Leu Val Lys Gly Phe Tyr Pro Ser Asp
                485                 490                 495

Ile Ala Val Glu Trp Glu Ser Asn Gly Gln Pro Glu Asn Asn Tyr Lys
            500                 505                 510

Thr Thr Pro Pro Val Leu Asp Ser Asp Gly Ser Phe Phe Leu Tyr Ser
        515                 520                 525

Lys Leu Thr Val Asp Lys Ser Arg Trp Gln Gln Gly Asn Val Phe Ser
    530                 535                 540

Cys Ser Val Met His Glu Ala Leu His Asn His Tyr Thr Gln Lys Ser
545                 550                 555                 560

Leu Ser Leu Ser Pro Gly Lys
                565
```

```
<210> SEQ ID NO 17
<211> LENGTH: 1083
<212> TYPE: DNA
<213> ORGANISM: Artificial Sequence
<220> FEATURE:
<223> OTHER INFORMATION: soluble human IL-2Rgamma/human kappa light
      chain construct
<220> FEATURE:
<221> NAME/KEY: CDS
<222> LOCATION: (1)...(1083)

<400> SEQUENCE: 17 atg ttg aag cca tca tta cca ttc aca tcc ctc tta ttc ctg cag ctg      48
Met Leu Lys Pro Ser Leu Pro Phe Thr Ser Leu Leu Phe Leu Gln Leu
1               5                   10                  15 ccc ctg ctg gga gtg ggg ctg aac acg aca att ctg acg ccc aat ggg      96
Pro Leu Leu Gly Val Gly Leu Asn Thr Thr Ile Leu Thr Pro Asn Gly
            20                  25                  30 aat gaa gac acc aca gct gat ttc ttc ctg acc act atg ccc act gac     144
Asn Glu Asp Thr Thr Ala Asp Phe Phe Leu Thr Thr Met Pro Thr Asp
        35                  40                  45
```

| | |
|---|---:|
| tcc ctc agt gtt tcc act ctg ccc ctc cca gag gtt cag tgt ttt gtg<br>Ser Leu Ser Val Ser Thr Leu Pro Leu Pro Glu Val Gln Cys Phe Val<br>50                       55                      60 | 192 |
| ttc aat gtc gag tac atg aat tgc act tgg aac agc agc tct gag ccc<br>Phe Asn Val Glu Tyr Met Asn Cys Thr Trp Asn Ser Ser Ser Glu Pro<br>65                       70                     75                     80 | 240 |
| cag cct acc aac ctc act ctg cat tat tgg tac aag aac tcg gat aat<br>Gln Pro Thr Asn Leu Thr Leu His Tyr Trp Tyr Lys Asn Ser Asp Asn<br>                 85                     90                     95 | 288 |
| gat aaa gtc cag aag tgc agc cac tat cta ttc tct gaa gaa atc act<br>Asp Lys Val Gln Lys Cys Ser His Tyr Leu Phe Ser Glu Glu Ile Thr<br>                100                   105                  110 | 336 |
| tct ggc tgt cag ttg caa aaa aag gag atc cac ctc tac caa aca ttt<br>Ser Gly Cys Gln Leu Gln Lys Lys Glu Ile His Leu Tyr Gln Thr Phe<br>               115                    120                   125 | 384 |
| gtt gtt cag ctc cag gac cca cgg gaa ccc agg aga cag gcc aca cag<br>Val Val Gln Leu Gln Asp Pro Arg Glu Pro Arg Arg Gln Ala Thr Gln<br>130                      135                   140 | 432 |
| atg cta aaa ctg cag aat ctg gtg atc ccc tgg gct cca gag aac cta<br>Met Leu Lys Leu Gln Asn Leu Val Ile Pro Trp Ala Pro Glu Asn Leu<br>145                    150                   155                   160 | 480 |
| aca ctt cac aaa ctg agt gaa tcc cag cta gaa ctg aac tgg aac aac<br>Thr Leu His Lys Leu Ser Glu Ser Gln Leu Glu Leu Asn Trp Asn Asn<br>                165                   170                  175 | 528 |
| aga ttc ttg aac cac tgt ttg gag cac ttg gtg cag tac cgg act gac<br>Arg Phe Leu Asn His Cys Leu Glu His Leu Val Gln Tyr Arg Thr Asp<br>                   180                   185                  190 | 576 |
| tgg gac cac agc tgg act gaa caa tca gtg gat tat aga cat aag ttc<br>Trp Asp His Ser Trp Thr Glu Gln Ser Val Asp Tyr Arg His Lys Phe<br>               195                   200                  205 | 624 |
| tcc ttg cct agt gtg gat ggg cag aaa cgc tac acg ttt cgt gtt cgg<br>Ser Leu Pro Ser Val Asp Gly Gln Lys Arg Tyr Thr Phe Arg Val Arg<br>210                      215                   220 | 672 |
| agc cgc ttt aac cca ctc tgt gga agt gct cag cat tgg agt gaa tgg<br>Ser Arg Phe Asn Pro Leu Cys Gly Ser Ala Gln His Trp Ser Glu Trp<br>225                    230                   235                   240 | 720 |
| agc cac cca atc cac tgg ggg agc aat act tca aaa gag aat act gtg<br>Ser His Pro Ile His Trp Gly Ser Asn Thr Ser Lys Glu Asn Thr Val<br>               245                   250                  255 | 768 |
| gct gca cca tct gtc ttc atc ttc ccg cca tct gat gag cag ttg aaa<br>Ala Ala Pro Ser Val Phe Ile Phe Pro Pro Ser Asp Glu Gln Leu Lys<br>               260                   265                  270 | 816 |
| tct ggt acc gcc tct gtt gtg tgc ctg ctg aat aac ttc tat ccc aga<br>Ser Gly Thr Ala Ser Val Val Cys Leu Leu Asn Asn Phe Tyr Pro Arg<br>               275                   280                  285 | 864 |
| gag gcc aaa gta cag tgg aag gtg gat aac gcc ctc caa tcg ggt aac<br>Glu Ala Lys Val Gln Trp Lys Val Asp Asn Ala Leu Gln Ser Gly Asn<br>290                      295                   300 | 912 |
| tcc cag gag agt gtc aca gag cag gac agc aag gac agc acc tac agc<br>Ser Gln Glu Ser Val Thr Glu Gln Asp Ser Lys Asp Ser Thr Tyr Ser<br>305                    310                   315                   320 | 960 |
| ctc agc agc acc ctg acg ctg agc aaa gca gac tac gag aaa cac aaa<br>Leu Ser Ser Thr Leu Thr Leu Ser Lys Ala Asp Tyr Glu Lys His Lys<br>               325                   330                  335 | 1008 |
| gtc tac gcc tgc gaa gtc acc cat cag ggc ctg agc tcg ccc gtc aca<br>Val Tyr Ala Cys Glu Val Thr His Gln Gly Leu Ser Ser Pro Val Thr<br>               340                   345                  350 | 1056 |
| aag agc ttc aac agg gga gag tgt tag<br>Lys Ser Phe Asn Arg Gly Glu Cys *<br>               355                   360 | 1083 |

<210> SEQ ID NO 18
<211> LENGTH: 360
<212> TYPE: PRT
<213> ORGANISM: Artificial Sequence
<220> FEATURE:
<223> OTHER INFORMATION: soluble human IL-2Rgamma/human kappa light

<400> SEQUENCE: 18

```
Met Leu Lys Pro Ser Leu Pro Phe Thr Ser Leu Leu Phe Leu Gln Leu
 1               5                  10                  15

Pro Leu Leu Gly Val Gly Leu Asn Thr Thr Ile Leu Thr Pro Asn Gly
                20                  25                  30

Asn Glu Asp Thr Thr Ala Asp Phe Phe Leu Thr Thr Met Pro Thr Asp
            35                  40                  45

Ser Leu Ser Val Ser Thr Leu Pro Leu Pro Glu Val Gln Cys Phe Val
        50                  55                  60

Phe Asn Val Glu Tyr Met Asn Cys Thr Trp Asn Ser Ser Ser Glu Pro
 65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Thr Val
                245                 250                 255

Ala Ala Pro Ser Val Phe Ile Phe Pro Pro Ser Asp Glu Gln Leu Lys
            260                 265                 270

Ser Gly Thr Ala Ser Val Val Cys Leu Leu Asn Asn Phe Tyr Pro Arg
        275                 280                 285

Glu Ala Lys Val Gln Trp Lys Val Asp Asn Ala Leu Gln Ser Gly Asn
    290                 295                 300

Ser Gln Glu Ser Val Thr Glu Gln Asp Ser Lys Asp Ser Thr Tyr Ser
305                 310                 315                 320

Leu Ser Ser Thr Leu Thr Leu Ser Lys Ala Asp Tyr Glu Lys His Lys
                325                 330                 335

Val Tyr Ala Cys Glu Val Thr His Gln Gly Leu Ser Ser Pro Val Thr
            340                 345                 350

Lys Ser Phe Asn Arg Gly Glu Cys
        355                 360
```

```
<210> SEQ ID NO 19
<211> LENGTH: 36
<212> TYPE: DNA
<213> ORGANISM: Artificial Sequence
<220> FEATURE:
<223> OTHER INFORMATION: Oligonucleotide primer ZC19905

<400> SEQUENCE: 19
acaggatccg tcagcatgcc gcgtggctgg gccgcc                              36

<210> SEQ ID NO 20
<211> LENGTH: 33
<212> TYPE: DNA
<213> ORGANISM: Artificial Sequence
<220> FEATURE:
<223> OTHER INFORMATION: Oligonucleotide primer ZC19906

<400> SEQUENCE: 20
acagaattct tagctggcct ggggtccagg cgt                                 33

<210> SEQ ID NO 21
<211> LENGTH: 36
<212> TYPE: DNA
<213> ORGANISM: Artificial Sequence
<220> FEATURE:
<223> OTHER INFORMATION: Oligonucleotide primer ZC19931

<400> SEQUENCE: 21
ggttggtacc gcaagatgcc gcgtggctgg gccgcc                              36

<210> SEQ ID NO 22
<211> LENGTH: 29
<212> TYPE: DNA
<213> ORGANISM: Artificial Sequence
<220> FEATURE:
<223> OTHER INFORMATION: Oligonucleotide primer ZC19932

<400> SEQUENCE: 22
cggaggatcc gtgagggttc cagccttcc                                      29

<210> SEQ ID NO 23
<211> LENGTH: 8
<212> TYPE: PRT
<213> ORGANISM: Artificial Sequence
<220> FEATURE:
<223> OTHER INFORMATION: FLAG tag amino acid sequence

<400> SEQUENCE: 23

Asp Tyr Lys Asp Asp Asp Asp Lys
1               5

<210> SEQ ID NO 24
<211> LENGTH: 66
<212> TYPE: DNA
<213> ORGANISM: Artificial Sequence
<220> FEATURE:
<223> OTHER INFORMATION: Oligonucleotide primer spanning vector flanking
      region and the 5' end of the zalpha11

<400> SEQUENCE: 24
tccactttgc ctttctctcc acaggtgtcc agggaattca tcgataatgc cgcgtggctg    60
ggccgc                                                               66

<210> SEQ ID NO 25
```

<211> LENGTH: 699
<212> TYPE: DNA
<213> ORGANISM: Homo sapiens

<400> SEQUENCE: 25

```
gagcccagat cttcagacaa aactcacaca tgcccaccgt gcccagcacc tgaagccgag      60
ggggcaccgt cagtcttcct cttcccccca aaacccaagg acaccctcat gatctcccgg     120
accccctgagg tcacatgcgt ggtggtggac gtgagccacg aagaccctga ggtcaagttc    180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagcccctcc catcctccat cgagaaaacc   360
atctccaaag ccaagggca gccccgagaa ccacaggtgt acaccctgcc cccatcccgg      420
gatgagctga ccaagaacca ggtcagcctg acctgcctgg tcaaaggctt ctatcccagc     480
gacatcgccg tggagtggga gagcaatggg cagccggaga acaactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac   660
tacacgcaga agagcctctc cctgtctccg ggtaaataa                            699
```

<210> SEQ ID NO 26
<211> LENGTH: 62
<212> TYPE: DNA
<213> ORGANISM: Artificial Sequence
<220> FEATURE:
<223> OTHER INFORMATION: First Oligonucleotide primer spanning 3' end of
      the zalpha11 extracellular domain and the 5' end of Fc4

<400> SEQUENCE: 26

```
gcacggtggg catgtgtgag ttttgtctga agatctgggc tcgtgagggt tccagccttc      60
ct                                                                      62
```

<210> SEQ ID NO 27
<211> LENGTH: 61
<212> TYPE: DNA
<213> ORGANISM: Artificial Sequence
<220> FEATURE:
<223> OTHER INFORMATION: Second Oligonucleotide primer spanning 3' end
      of the zalpha11 extracellular domain and the 5' end of Fc4

<400> SEQUENCE: 27

```
agacccagtc agaggagtta aaggaaggct ggaaccctca cgagcccaga tcttcagaca      60
a                                                                       61
```

<210> SEQ ID NO 28
<211> LENGTH: 67
<212> TYPE: DNA
<213> ORGANISM: Artificial Sequence
<220> FEATURE:
<223> OTHER INFORMATION: Oligonucleotide primer spanning the 3' end of
      Fc4 and the vector flanking region

<400> SEQUENCE: 28

```
gtgggcctct ggggtgggta caaccccaga gctgttttaa tctagattat ttacccggag      60
acaggga                                                                 67
```

<210> SEQ ID NO 29
<211> LENGTH: 1821
<212> TYPE: DNA

<213> ORGANISM: Artificial Sequence
<220> FEATURE:
<223> OTHER INFORMATION: Polynucleotide encoding MBP-human zalpha11
      soluble receptor fusion
<220> FEATURE:
<221> NAME/KEY: CDS
<222> LOCATION: (1)...(1821)

<400> SEQUENCE: 29

```
atg aaa atc gaa gaa ggt aaa ctg gta atc tgg att aac ggc gat aaa        48
Met Lys Ile Glu Glu Gly Lys Leu Val Ile Trp Ile Asn Gly Asp Lys
1               5                   10                  15 ggc tat aac ggt ctc gct gaa gtc ggt aag aaa ttc gag aaa gat acc        96
Gly Tyr Asn Gly Leu Ala Glu Val Gly Lys Lys Phe Glu Lys Asp Thr
                20                  25                  30 gga att aaa gtc acc gtt gag cat ccg gat aaa ctg gaa gag aaa ttc       144
Gly Ile Lys Val Thr Val Glu His Pro Asp Lys Leu Glu Glu Lys Phe
            35                  40                  45 cca cag gtt gcg gca act ggc gat ggc cct gac att atc ttc tgg gca       192
Pro Gln Val Ala Ala Thr Gly Asp Gly Pro Asp Ile Ile Phe Trp Ala
        50                  55                  60 cac gac cgc ttt ggt ggc tac gct caa tct ggc ctg ttg gct gaa atc       240
His Asp Arg Phe Gly Gly Tyr Ala Gln Ser Gly Leu Leu Ala Glu Ile
65                  70                  75                  80 acc ccg gac aaa gcg ttc cag gac aag ctg tat ccg ttt acc tgg gat       288
Thr Pro Asp Lys Ala Phe Gln Asp Lys Leu Tyr Pro Phe Thr Trp Asp
                85                  90                  95 gcc gta cgt tac aac ggc aag ctg att gct tac ccg atc gct gtt gaa       336
Ala Val Arg Tyr Asn Gly Lys Leu Ile Ala Tyr Pro Ile Ala Val Glu
                100                 105                 110 gcg tta tcg ctg att tat aac aaa gat ctg ctg ccg aac ccg cca aaa       384
Ala Leu Ser Leu Ile Tyr Asn Lys Asp Leu Leu Pro Asn Pro Pro Lys
            115                 120                 125 acc tgg gaa gag atc ccg gcg ctg gat aaa gaa ctg aaa gcg aaa ggt       432
Thr Trp Glu Glu Ile Pro Ala Leu Asp Lys Glu Leu Lys Ala Lys Gly
        130                 135                 140 aag agc gcg ctg atg ttc aac ctg caa gaa ccg tac ttc acc tgg ccg       480
Lys Ser Ala Leu Met Phe Asn Leu Gln Glu Pro Tyr Phe Thr Trp Pro
145                 150                 155                 160 ctg att gct gct gac ggg ggt tat gcg ttc aag tat gaa aac ggc aag       528
Leu Ile Ala Ala Asp Gly Gly Tyr Ala Phe Lys Tyr Glu Asn Gly Lys
                165                 170                 175 tac gac att aaa gac gtg ggc gtg gat aac gct ggc gcg aaa gcg ggt       576
Tyr Asp Ile Lys Asp Val Gly Val Asp Asn Ala Gly Ala Lys Ala Gly
                180                 185                 190 ctg acc ttc ctg gtt gac ctg att aaa aac aaa cac atg aat gca gac       624
Leu Thr Phe Leu Val Asp Leu Ile Lys Asn Lys His Met Asn Ala Asp
            195                 200                 205 acc gat tac tcc atc gca gaa gct gcc ttt aat aaa ggc gaa aca gcg       672
Thr Asp Tyr Ser Ile Ala Glu Ala Ala Phe Asn Lys Gly Glu Thr Ala
        210                 215                 220 atg acc atc aac ggc ccg tgg gca tgg tcc aac atc gac acc agc aaa       720
Met Thr Ile Asn Gly Pro Trp Ala Trp Ser Asn Ile Asp Thr Ser Lys
225                 230                 235                 240 gtg aat tat ggt gta acg gta ctg ccg acc ttc aag ggt caa cca tcc       768
Val Asn Tyr Gly Val Thr Val Leu Pro Thr Phe Lys Gly Gln Pro Ser
                245                 250                 255 aaa ccg ttc gtt ggc gtg ctg agc gca ggt att aac gcc gcc agt ccg       816
Lys Pro Phe Val Gly Val Leu Ser Ala Gly Ile Asn Ala Ala Ser Pro
                260                 265                 270 aac aaa gag ctg gca aaa gag ttc ctc gaa aac tat ctg ctg act gat       864
```

```
                Asn Lys Glu Leu Ala Lys Glu Phe Leu Glu Asn Tyr Leu Leu Thr Asp
                    275                 280                 285 gaa ggt ctg gaa gcg gtt aat aaa gac aaa ccg ctg ggt gcc gta gcg        912
Glu Gly Leu Glu Ala Val Asn Lys Asp Lys Pro Leu Gly Ala Val Ala
    290                 295                 300 ctg aag tct tac gag gaa gag ttg gcg aaa gat cca cgt att gcc gcc        960
Leu Lys Ser Tyr Glu Glu Glu Leu Ala Lys Asp Pro Arg Ile Ala Ala
305                 310                 315                 320 acc atg gaa aac gcc cag aaa ggt gaa atc atg ccg aac atc ccg cag        1008
Thr Met Glu Asn Ala Gln Lys Gly Glu Ile Met Pro Asn Ile Pro Gln
                325                 330                 335 atg tcc gct ttc tgg tat gcc gtg cgt act gcg gtg atc aac gcc gcc        1056
Met Ser Ala Phe Trp Tyr Ala Val Arg Thr Ala Val Ile Asn Ala Ala
                340                 345                 350 agc ggt cgt cag act gtc gat gaa gcc ctg aaa gac gcg cag act aat        1104
Ser Gly Arg Gln Thr Val Asp Glu Ala Leu Lys Asp Ala Gln Thr Asn
            355                 360                 365 tcg agc tcc cac cat cac cat cac cac gcg aat tcg gta ccg ctg gtt        1152
Ser Ser Ser His His His His His His Ala Asn Ser Val Pro Leu Val
        370                 375                 380 ccg cgt gga tcc tgc ccc gac ctc gtc tgc tac acc gat tac ctc cag        1200
Pro Arg Gly Ser Cys Pro Asp Leu Val Cys Tyr Thr Asp Tyr Leu Gln
385                 390                 395                 400 acg gtc atc tgc atc ctg gaa atg tgg aac ctc cac ccc agc acg ctc        1248
Thr Val Ile Cys Ile Leu Glu Met Trp Asn Leu His Pro Ser Thr Leu
                    405                 410                 415 acc ctt acc tgg caa gac cag tat gaa gag ctg aag gac gag gcc acc        1296
Thr Leu Thr Trp Gln Asp Gln Tyr Glu Glu Leu Lys Asp Glu Ala Thr
                420                 425                 430 tcc tgc agc ctc cac agg tcg gcc cac aat gcc acg cat gcc acc tac        1344
Ser Cys Ser Leu His Arg Ser Ala His Asn Ala Thr His Ala Thr Tyr
            435                 440                 445 acc tgc cac atg gat gta ttc cac ttc atg gcc gac gac att ttc agt        1392
Thr Cys His Met Asp Val Phe His Phe Met Ala Asp Asp Ile Phe Ser
        450                 455                 460 gtc aac atc aca gac cag tct ggc aac tac tcc cag gag tgt ggc agc        1440
Val Asn Ile Thr Asp Gln Ser Gly Asn Tyr Ser Gln Glu Cys Gly Ser
465                 470                 475                 480 ttt ctc ctg gct gag agc atc aag ccg gct ccc cct ttc aac gtg act        1488
Phe Leu Leu Ala Glu Ser Ile Lys Pro Ala Pro Pro Phe Asn Val Thr
                    485                 490                 495 gtg acc ttc tca gga cag tat aat atc tcc tgg cgc tca gat tac gaa        1536
Val Thr Phe Ser Gly Gln Tyr Asn Ile Ser Trp Arg Ser Asp Tyr Glu
                500                 505                 510 gac cct gcc ttc tac atg ctg aag ggc aag ctt cag tat gag ctg cag        1584
Asp Pro Ala Phe Tyr Met Leu Lys Gly Lys Leu Gln Tyr Glu Leu Gln
            515                 520                 525 tac agg aac cgg gga gac ccc tgg gct gtg agt ccg agg aga aag ctg        1632
Tyr Arg Asn Arg Gly Asp Pro Trp Ala Val Ser Pro Arg Arg Lys Leu
        530                 535                 540 atc tca gtg gac tca aga agt gtc tcc ctc ctc ccc ctg gag ttc cgc        1680
Ile Ser Val Asp Ser Arg Ser Val Ser Leu Leu Pro Leu Glu Phe Arg
545                 550                 555                 560 aaa gac tcg agc tat gag ctg cag gtg cgg gca ggg ccc atg cct ggc        1728
Lys Asp Ser Ser Tyr Glu Leu Gln Val Arg Ala Gly Pro Met Pro Gly
                    565                 570                 575 tcc tcc tac cag ggg acc tgg agt gaa tgg agt gac ccg gtc atc ttt        1776
Ser Ser Tyr Gln Gly Thr Trp Ser Glu Trp Ser Asp Pro Val Ile Phe
                580                 585                 590
```

```
cag acc cag tca gag gag tta aag gaa ggc tgg aac cct cac tag       1821
Gln Thr Gln Ser Glu Glu Leu Lys Glu Gly Trp Asn Pro His *
        595                 600                 605
```

<210> SEQ ID NO 30
<211> LENGTH: 606
<212> TYPE: PRT
<213> ORGANISM: Artificial Sequence
<220> FEATURE:
<223> OTHER INFORMATION: Polynucleotide encoding MBP-human zalpha11
      soluble receptor fusion

<400> SEQUENCE: 30

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335
```

```
Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
            355                 360                 365

Ser Ser Ser His His His His His His Ala Asn Ser Val Pro Leu Val
            370                 375                 380

Pro Arg Gly Ser Cys Pro Asp Leu Val Cys Tyr Thr Asp Tyr Leu Gln
385                 390                 395                 400

Thr Val Ile Cys Ile Leu Glu Met Trp Asn Leu His Pro Ser Thr Leu
            405                 410                 415

Thr Leu Thr Trp Gln Asp Gln Tyr Glu Glu Leu Lys Asp Glu Ala Thr
            420                 425                 430

Ser Cys Ser Leu His Arg Ser Ala His Asn Ala Thr His Ala Thr Tyr
            435                 440                 445

Thr Cys His Met Asp Val Phe His Phe Met Ala Asp Asp Ile Phe Ser
            450                 455                 460

Val Asn Ile Thr Asp Gln Ser Gly Asn Tyr Ser Gln Glu Cys Gly Ser
465                 470                 475                 480

Phe Leu Leu Ala Glu Ser Ile Lys Pro Ala Pro Pro Phe Asn Val Thr
            485                 490                 495

Val Thr Phe Ser Gly Gln Tyr Asn Ile Ser Trp Arg Ser Asp Tyr Glu
            500                 505                 510

Asp Pro Ala Phe Tyr Met Leu Lys Gly Lys Leu Gln Tyr Glu Leu Gln
            515                 520                 525

Tyr Arg Asn Arg Gly Asp Pro Trp Ala Val Ser Pro Arg Arg Lys Leu
            530                 535                 540

Ile Ser Val Asp Ser Arg Ser Val Ser Leu Leu Pro Leu Glu Phe Arg
545                 550                 555                 560

Lys Asp Ser Ser Tyr Glu Leu Gln Val Arg Ala Gly Pro Met Pro Gly
            565                 570                 575

Ser Ser Tyr Gln Gly Thr Trp Ser Glu Trp Ser Asp Pro Val Ile Phe
            580                 585                 590

Gln Thr Gln Ser Glu Glu Leu Lys Glu Gly Trp Asn Pro His
            595                 600                 605

<210> SEQ ID NO 31
<211> LENGTH: 657
<212> TYPE: DNA
<213> ORGANISM: Artificial Sequence
<220> FEATURE:
<223> OTHER INFORMATION: A fragment of human zalpha11 cDNA

<400> SEQUENCE: 31
tgccccgacc tcgtctgcta caccgattac ctccagacgg tcatctgcat cctggaaatg      60
tggaacctcc accccagcac gctcaccctt acctggcaag accagtatga agagctgaag     120
gacgaggcca cctcctgcag cctccacagg tcggcccaca atgccacgca tgccacctac     180
acctgccaca tggatgtatt ccacttcatg gccgacgaca ttttcagtgt caacatcaca     240
gaccagtctg gcaactactc ccaggagtgt ggcagctttc tcctggctga gagcatcaag     300
ccggctcccc ctttcaacgt gactgtgacc ttctcaggac agtataatat ctcctggcgc     360
tcagattacg aagaccctgc cttctacatg ctgaagggca agcttcagta tgagctgcag     420
tacaggaacc ggggagaccc ctgggctgtg agtccgagga aaagctgat ctcagtggac     480
tcaagaagtg tctccctcct ccccctggag ttccgcaaag actcgagcta tgagctgcag     540
```

```
gtgcgggcag ggcccatgcc tggctcctcc taccagggga cctggagtga atggagtgac    600
ccggtcatct ttcagaccca gtcagaggag ttaaaggaag gctggaaccc tcactag      657

<210> SEQ ID NO 32
<211> LENGTH: 65
<212> TYPE: DNA
<213> ORGANISM: Artificial Sequence
<220> FEATURE:
<223> OTHER INFORMATION: Oligonucleotide primerZC20187

<400> SEQUENCE: 32
tcaccacgcg aattcggtac cgctggttcc gcgtggatcc tgccccgacc tcgtctgcta    60
caccg                                                                65

<210> SEQ ID NO 33
<211> LENGTH: 68
<212> TYPE: DNA
<213> ORGANISM: Artificial Sequence
<220> FEATURE:
<223> OTHER INFORMATION: Oligonucleotide primerZC20185

<400> SEQUENCE: 33
tctgtatcag gctgaaaatc ttatctcatc cgccaaaaca ctagtgaggg ttccagcctt    60
cctttaac                                                             68

<210> SEQ ID NO 34
<211> LENGTH: 40
<212> TYPE: DNA
<213> ORGANISM: Artificial Sequence
<220> FEATURE:
<223> OTHER INFORMATION: Oligonucleotide primerZC19372

<400> SEQUENCE: 34
tgtcgatgaa gccctgaaag acgcgcagac taattcgagc                          40

<210> SEQ ID NO 35
<211> LENGTH: 60
<212> TYPE: DNA
<213> ORGANISM: Artificial Sequence
<220> FEATURE:
<223> OTHER INFORMATION: Oligonucleotide primerZC19351

<400> SEQUENCE: 35
acgcgcagac taattcgagc tcccaccatc accatcacca cgcgaattcg gtaccgctgg    60

<210> SEQ ID NO 36
<211> LENGTH: 60
<212> TYPE: DNA
<213> ORGANISM: Artificial Sequence
<220> FEATURE:
<223> OTHER INFORMATION: Oligonucleotide primerZC19352

<400> SEQUENCE: 36
actcactata gggcgaattg cccgggggat ccacgcggaa ccagcggtac cgaattcgcg    60

<210> SEQ ID NO 37
<211> LENGTH: 42
<212> TYPE: DNA
<213> ORGANISM: Artificial Sequence
<220> FEATURE:
<223> OTHER INFORMATION: Oligonucleotide primerZC19371

<400> SEQUENCE: 37
```

-continued acggccagtg aattgtaata cgactcacta tagggcgaat tg                               42

<210> SEQ ID NO 38
<211> LENGTH: 24
<212> TYPE: DNA
<213> ORGANISM: Artificial Sequence
<220> FEATURE:
<223> OTHER INFORMATION: Oligonucleotide primerZC19907

<400> SEQUENCE: 38
atggatgtat tccacttcat ggcc                                                  24

<210> SEQ ID NO 39
<211> LENGTH: 24
<212> TYPE: DNA
<213> ORGANISM: Artificial Sequence
<220> FEATURE:
<223> OTHER INFORMATION: Oligonucleotide primerZC19908

<400> SEQUENCE: 39
actgtcaaac gtgtccatat ccag                                                  24

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide primerZC22277

<400> SEQUENCE: 40
ccaggagtgt ggcagctttc                                                       20

<210> SEQ ID NO 41
<211> LENGTH: 21
<212> TYPE: DNA
<213> ORGANISM: Artificial Sequence
<220> FEATURE:
<223> OTHER INFORMATION: Oligonucleotide primerZC22276

<400> SEQUENCE: 41
gcttgccctt cagcatgtag a                                                     21

<210> SEQ ID NO 42
<211> LENGTH: 23
<212> TYPE: DNA
<213> ORGANISM: Artificial Sequence
<220> FEATURE:
<223> OTHER INFORMATION: Zalpha11 TaqMan Probe, ZG31

<400> SEQUENCE: 42
cggctccccc tttcaacgtg act                                                   23

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide primer, rRNA forward primer

<400> SEQUENCE: 43
cggctaccac atccaaggaa                                                       20

<210> SEQ ID NO 44
<211> LENGTH: 18
<212> TYPE: DNA
<213> ORGANISM: Artificial Sequence

```
<220> FEATURE:
<223> OTHER INFORMATION: Oligonucleotide primer, rRNA reverse primer

<400> SEQUENCE: 44
gctggaatta ccgcggct                                                      18

<210> SEQ ID NO 45
<211> LENGTH: 22
<212> TYPE: DNA
<213> ORGANISM: Artificial Sequence
<220> FEATURE:
<223> OTHER INFORMATION: rRNA TaqMan probe

<400> SEQUENCE: 45
tgctggcacc agacttgccc tc                                                 22

<210> SEQ ID NO 46
<211> LENGTH: 3072
<212> TYPE: DNA
<213> ORGANISM: Mus musculus
<220> FEATURE:
<221> NAME/KEY: CDS
<222> LOCATION: (54)...(491)

<400> SEQUENCE: 46
gagaaccaga ccaaggccct gtcatcagct cctggagact cagttctggt ggc atg          56
                                                            Met
                                                            1 gag agg acc ctt gtc tgt ctg gta gtc atc ttc ttg ggg aca gtg gcc         104
Glu Arg Thr Leu Val Cys Leu Val Val Ile Phe Leu Gly Thr Val Ala
        5                   10                  15 cat aaa tca agc ccc caa ggg cca gat cgc ctc ctg att aga ctt cgt         152
His Lys Ser Ser Pro Gln Gly Pro Asp Arg Leu Leu Ile Arg Leu Arg
            20                  25                  30 cac ctt att gac att gtt gaa cag ctg aaa atc tat gaa aat gac ttg         200
His Leu Ile Asp Ile Val Glu Gln Leu Lys Ile Tyr Glu Asn Asp Leu
        35                  40                  45 gat cct gaa ctt cta tca gct cca caa gat gta aag ggg cac tgt gag         248
Asp Pro Glu Leu Leu Ser Ala Pro Gln Asp Val Lys Gly His Cys Glu
50                  55                  60                  65 cat gca gct ttt gcc tgt ttt cag aag gcc aaa ctc aag cca tca aac         296
His Ala Ala Phe Ala Cys Phe Gln Lys Ala Lys Leu Lys Pro Ser Asn
                70                  75                  80 cct gga aac aat aag aca ttc atc att gac ctc gtg gcc cag ctc agg         344
Pro Gly Asn Asn Lys Thr Phe Ile Ile Asp Leu Val Ala Gln Leu Arg
            85                  90                  95 agg agg ctg cct gcc agg agg gga gga aag aaa cag aag cac ata gct         392
Arg Arg Leu Pro Ala Arg Arg Gly Gly Lys Lys Gln Lys His Ile Ala
        100                 105                 110 aaa tgc cct tcc tgt gat tcg tat gag aaa agg aca ccc aaa gaa ttc         440
Lys Cys Pro Ser Cys Asp Ser Tyr Glu Lys Arg Thr Pro Lys Glu Phe
    115                 120                 125 cta gaa aga cta aaa tgg ctc ctt caa aag atg att cat cag cat ctc         488
Leu Glu Arg Leu Lys Trp Leu Leu Gln Lys Met Ile His Gln His Leu
130                 135                 140                 145 tcc tagaacacat aggacccgaa gattcctgag gatccgagaa gattcccgag              541
Ser gactgaggag acgccggaca ctatagacgc tcacgaatgc aggagtacat cttgcctctt       601
gggattgcaa gtggagaagt acgatacgtt atgataagaa caactcagaa aagctatagg       661
ttaagatcct ttcgcccatt aactaagcag acattgtggt tccctgcaca gactccatgc       721
```

```
tgtcaacatg gaaaatctca actcaacaag agcccagctt cccgtgtcag ggatttctgg      781
tgcttctcaa gctgtggctt catcttattg cccaactgtg acattctttg attggaaggg      841
gaaaactaaa gcttttagca aaaatacagc tagggaattt gtcgatctgc gagagtaaga      901
cctcttatga tcctaacgga atgatgtaag ctggaaataa taagcataag atgaaattga      961
aaattgaagt cttattctt taagaaaaac tttgtacttg aaagcatgtc tgaagagttt      1021
actcattacc acaaacatct agcatattga taactaacat ctttatactc tacaagagag     1081
gctttccaga taggtacagt ttttcttctc tattaggtct atcaaaattt aacctattat     1141
gagggtcacc cctggctttc actgtttttc taaagaggca agggtgtagt aagaagcagg     1201
cttaagttgc cttcctccca atgtcaagtt cctttataag ctaatagttt aatcttgtga     1261
agatggcaat gaaagcctgt ggaagtgcaa acctcactat cttctggagc caagtagaat     1321
tttcaagttt gtagctctca cctcaagtgg ttatgggtgt cctgtgatga atctgctagc     1381
tccagcctca gtctcctctc ccacatcctt tcctttcttt cctctttgaa acttctaaga     1441
aaaagcaatc caaacaagtt cagcacttaa gacacattgc atgcacactt ttgataagtt     1501
aaatccaacc atctatttaa aatcaaaatc aggagatgag ccaagagacc agaggttctg     1561
ttccagtttt aaacagactt ttactgaaca tcccaatctt ttaaccacag aggctaaatt     1621
gagcaaatag ttttgccatt tgatataatt ccaacagta tgtttcaatg tcaagttaaa      1681
aagtctacaa agctattttc cctggagtgg tatcatcgct ttgagaattt cttatggtta     1741
aaatggatct gagatccaag catggcctgg gggatggttt tgatctaagg aaaaaggtgt     1801
ctgtacctca cagtgccttt aaaacaagca gagatcccgt gtaccgccct aagatagcac     1861
agactagtgt taactgattc ccagaaaagt gtcacaatca gaaccaacgc attctcttaa     1921
actttaaaaa tatgtattgc aaagaacttg tgtaactgta aatgtgtgac tgttgatgac     1981
attatacaca catagcccac gtaagtgtcc aatggtgcta gcattggttg ctgagtttgc     2041
tgctcgaaag ctgaagcaga gatgcagtcc ttcacaaagc aatgatggac agagagggga     2101
gtctccatgt tttattcttt tgttgtttct ggctgtgtaa ctgttgactt cttgacattg     2161
tgatttttat atttaagaca atgtatttat tttggtgtgt ttattgttct agccttttaa     2221
atcactgaca atttctaatc aagaagtaca aataattcaa tgcagcacag gctaagagct     2281
tgtatcgttt ggaaaagcca gtgaaggctt ctccactagc catgggaaag ctacgcttta     2341
gagtaaacta gacaaaattg cacagcagtc ttgaacctct ctgtgctcaa gactcagcca     2401
gtcctttgac attattgttc actgtgggtg ggaacacatt ggacctgaca cactgttgtg     2461
tgtccatgaa ggttgccact ggtgtaagct tttttggtt ttcattctct tatctgtaga      2521
acaagaatgt ggggctttcc taagtctatt ctgtattta ttctgaactt cgtatgtctg      2581
agttttaatg ttttgagtac tcttacagga acacctgacc acactttga gttaaatttt       2641 atcccaagtg tgatatttag ttgttcaaaa agggaaggga tatacataca tacatacata     2701
catacataca tatatatata tatataca tatatatata tatatatatg tatatatata       2761
tatatataga gagagagaga gagagagaga gagaaagaga gagaggttgt tgtaggtcat     2821
aggagttcag aggaaatcag ttatggccgt taatactgta gctgaaagtg ttttctttgt     2881
gaataaattc atagcattat tgatctatgt tattgctctg ttttatttac agtcacacct     2941
gagaatttag ttttaatatg aatgatgtac tttataactt aatgattatt tattatgtat     3001
ttggttttga atgtttgtgt tcatggcttc ttatttaaga cctgatcata ttaaatgcta     3061
cccagtccgg a                                                          3072
```

<210> SEQ ID NO 47
<211> LENGTH: 146
<212> TYPE: PRT
<213> ORGANISM: Mus musculus

<400> SEQUENCE: 47

Met Glu Arg Thr Leu Val Cys Leu Val Val Ile Phe Leu Gly Thr Val
1               5                   10                  15

Ala His Lys Ser Ser Pro Gln Gly Pro Asp Arg Leu Leu Ile Arg Leu
            20                  25                  30

Arg His Leu Ile Asp Ile Val Glu Gln Leu Lys Ile Tyr Glu Asn Asp
        35                  40                  45

Leu Asp Pro Glu Leu Leu Ser Ala Pro Gln Asp Val Lys Gly His Cys
    50                  55                  60

Glu His Ala Ala Phe Ala Cys Phe Gln Lys Ala Lys Leu Lys Pro Ser
65                  70                  75                  80

Asn Pro Gly Asn Asn Lys Thr Phe Ile Ile Asp Leu Val Ala Gln Leu
                85                  90                  95

Arg Arg Arg Leu Pro Ala Arg Arg Gly Gly Lys Lys Gln Lys His Ile
            100                 105                 110

Ala Lys Cys Pro Ser Cys Asp Ser Tyr Glu Lys Arg Thr Pro Lys Glu
        115                 120                 125

Phe Leu Glu Arg Leu Lys Trp Leu Leu Gln Lys Met Ile His Gln His
    130                 135                 140

Leu Ser
145

<210> SEQ ID NO 48
<211> LENGTH: 100
<212> TYPE: DNA
<213> ORGANISM: Artificial Sequence
<220> FEATURE:
<223> OTHER INFORMATION: Oligonucleotide primer ZC12749

<400> SEQUENCE: 48
gtaccttccc gtaaatccct ccccttcccg aattacacc cgcgtatttc cagaaaagg      60 aactgtagat ttctaggaat tcaatccttg gccacgcgtc                          100

<210> SEQ ID NO 49
<211> LENGTH: 100
<212> TYPE: DNA
<213> ORGANISM: Artificial Sequence
<220> FEATURE:
<223> OTHER INFORMATION: Oligonucleotide primer ZC12748

<400> SEQUENCE: 49
tcgagacgcg tggccaagga ttgaattcct agaaatctac agttcctttt ctgggaaata    60
cgcgggtgta attccggaa ggggagggat ttacgggaag                           100

<210> SEQ ID NO 50
<211> LENGTH: 36
<212> TYPE: DNA
<213> ORGANISM: Artificial Sequence
<220> FEATURE:
<223> OTHER INFORMATION: Oligonucleotide primer ZC11450

<400> SEQUENCE: 50
acttgtggaa ttcgctagca ccaagggccc atcggt                              36

```
<210> SEQ ID NO 51
<211> LENGTH: 32
<212> TYPE: DNA
<213> ORGANISM: Artificial Sequence
<220> FEATURE:
<223> OTHER INFORMATION: Oligonucleotide primer ZC11443

<400> SEQUENCE: 51
gcctagaacg cgttcattta cccggagaca gg                              32

<210> SEQ ID NO 52
<211> LENGTH: 8
<212> TYPE: DNA
<213> ORGANISM: Artificial Sequence
<220> FEATURE:
<223> OTHER INFORMATION: Oligonucleotide primer ZC11440

<400> SEQUENCE: 52 aattgaga                                                          8

<210> SEQ ID NO 53
<211> LENGTH: 8
<212> TYPE: DNA
<213> ORGANISM: Artificial Sequence
<220> FEATURE:
<223> OTHER INFORMATION: Oligonucleotide primer ZC11441

<400> SEQUENCE: 53 cgcgtctc                                                          8

<210> SEQ ID NO 54
<211> LENGTH: 37
<212> TYPE: DNA
<213> ORGANISM: Artificial Sequence
<220> FEATURE:
<223> OTHER INFORMATION: Oligonucleotide primer ZC11501

<400> SEQUENCE: 54
gtcacttgaa ttcggtaccg cctctgttgt gtgcctg                         37

<210> SEQ ID NO 55
<211> LENGTH: 32
<212> TYPE: DNA
<213> ORGANISM: Artificial Sequence
<220> FEATURE:
<223> OTHER INFORMATION: Oligonucleotide primer ZC11451

<400> SEQUENCE: 55
gacctgaacg cgtctaacac tctcccctgt tg                              32

<210> SEQ ID NO 56
<211> LENGTH: 41
<212> TYPE: DNA
<213> ORGANISM: Artificial Sequence
<220> FEATURE:
<223> OTHER INFORMATION: Oligonucleotide primer ZC24052

<400> SEQUENCE: 56
tcagtcggaa ttcgcagaag ccatgccgcg tggctgggcc g                    41

<210> SEQ ID NO 57
<211> LENGTH: 34
<212> TYPE: DNA
<213> ORGANISM: Artificial Sequence
<220> FEATURE:
<223> OTHER INFORMATION: Oligonucleotide primer ZC24053
```

```
<400> SEQUENCE: 57
ctgtgacgct agcgtgaggg ttccagcctt cctt                                   34

<210> SEQ ID NO 58
<211> LENGTH: 41
<212> TYPE: DNA
<213> ORGANISM: Artificial Sequence
<220> FEATURE:
<223> OTHER INFORMATION: Oligonucleotide primer ZC12834

<400> SEQUENCE: 58
tcagtcggaa ttcgcagaag ccatgttgaa gccatcatta c                           41

<210> SEQ ID NO 59
<211> LENGTH: 90
<212> TYPE: DNA
<213> ORGANISM: Artificial Sequence
<220> FEATURE:
<223> OTHER INFORMATION: Oligonucleotide primer ZC12831

<400> SEQUENCE: 59
aagacggtac cagatttcaa ctgctcatca gatggcggga agatgaagac agatggtgca       60
gccacagtag gattctcttt tgaagtattg                                        90

<210> SEQ ID NO 60
<211> LENGTH: 20
<212> TYPE: DNA
<213> ORGANISM: Artificial Sequence
<220> FEATURE:
<223> OTHER INFORMATION: Oligonucleotide primer ZC23684

<400> SEQUENCE: 60
tcacccttac ctggcaagac                                                   20

<210> SEQ ID NO 61
<211> LENGTH: 43
<212> TYPE: DNA
<213> ORGANISM: Artificial Sequence
<220> FEATURE:
<223> OTHER INFORMATION: Oligonucleotide primer ZC23656

<400> SEQUENCE: 61
taatacgact cactataggg aggggagac acttcttgag tcc                          43

<210> SEQ ID NO 62
<211> LENGTH: 20
<212> TYPE: DNA
<213> ORGANISM: Artificial Sequence
<220> FEATURE:
<223> OTHER INFORMATION: Oligonucleotide primer ZC23685

<400> SEQUENCE: 62
aggtctgaat cccgactctg                                                   20

<210> SEQ ID NO 63
<211> LENGTH: 43
<212> TYPE: DNA
<213> ORGANISM: Artificial Sequence
<220> FEATURE:
<223> OTHER INFORMATION: Oligonucleotide primer ZC23657

<400> SEQUENCE: 63
taatacgact cactataggg aggacgtaat tggtgtttaa taa                         43
```

-continued

```
<210> SEQ ID NO 64
<211> LENGTH: 1707
<212> TYPE: DNA
<213> ORGANISM: homo sapiens
<220> FEATURE:
<221> NAME/KEY: CDS
<222> LOCATION: (1)...(1707)

<400> SEQUENCE: 64 atg ccg cgt ggc tgg gcc gcc ccc ttg ctc ctg ctg ctg ctc cag gga       48
Met Pro Arg Gly Trp Ala Ala Pro Leu Leu Leu Leu Leu Leu Gln Gly
1               5                   10                  15 gcc ctc gag ggg atg gag agg aag ctc tgc agt ccc aag cca ccc ccc       96
Ala Leu Glu Gly Met Glu Arg Lys Leu Cys Ser Pro Lys Pro Pro Pro
                20                  25                  30 acc aag gcc tct ctc ccc act gac cct cca ggc tgg ggc tgc ccc gac      144
Thr Lys Ala Ser Leu Pro Thr Asp Pro Pro Gly Trp Gly Cys Pro Asp
            35                  40                  45 ctc gtc tgc tac acc gat tac ctc cag acg gtc atc tgc atc ctg gaa      192
Leu Val Cys Tyr Thr Asp Tyr Leu Gln Thr Val Ile Cys Ile Leu Glu
        50                  55                  60 atg tgg aac ctc cac ccc agc acg ctc acc ctt acc tgg ata ctt tct      240
Met Trp Asn Leu His Pro Ser Thr Leu Thr Leu Thr Trp Ile Leu Ser
65                  70                  75                  80 aat aat act ggg tgc tat atc aag gac aga aca ctg gac ctc agg caa      288
Asn Asn Thr Gly Cys Tyr Ile Lys Asp Arg Thr Leu Asp Leu Arg Gln
                85                  90                  95 gac cag tat gaa gag ctg aag gac gag gcc acc tcc tgc agc ctc cac      336
Asp Gln Tyr Glu Glu Leu Lys Asp Glu Ala Thr Ser Cys Ser Leu His
                100                 105                 110 agg tcg gcc cac aat gcc acg cat gcc acc tac acc tgc cac atg gat      384
Arg Ser Ala His Asn Ala Thr His Ala Thr Tyr Thr Cys His Met Asp
            115                 120                 125 gta ttc cac ttc atg gcc gac gac att ttc agt gtc aac atc aca gac      432
Val Phe His Phe Met Ala Asp Asp Ile Phe Ser Val Asn Ile Thr Asp
        130                 135                 140 cag tct ggc aac tac tcc cag gag tgt ggc agc ttt ctc ctg gct gag      480
Gln Ser Gly Asn Tyr Ser Gln Glu Cys Gly Ser Phe Leu Leu Ala Glu
145                 150                 155                 160 agc aga cag tat aat atc tcc tgg cgc tca gat tac gaa gac cct gcc      528
Ser Arg Gln Tyr Asn Ile Ser Trp Arg Ser Asp Tyr Glu Asp Pro Ala
                165                 170                 175 ttc tac atg ctg aag ggc aag ctt cag tat gag ctg cag tac agg aac      576
Phe Tyr Met Leu Lys Gly Lys Leu Gln Tyr Glu Leu Gln Tyr Arg Asn
                180                 185                 190 cgg gga gac ccc tgg gct gtg agt ccg agg aga aag ctg atc tca gtg      624
Arg Gly Asp Pro Trp Ala Val Ser Pro Arg Arg Lys Leu Ile Ser Val
            195                 200                 205 gac tca aga agt gtc tcc ctc ctc ccc ctg gag ttc cgc aaa gac tcg      672
Asp Ser Arg Ser Val Ser Leu Leu Pro Leu Glu Phe Arg Lys Asp Ser
        210                 215                 220 agc tat gag ctg cag gtg cgg gca ggg ccc atg cct ggc tcc tcc tac      720
Ser Tyr Glu Leu Gln Val Arg Ala Gly Pro Met Pro Gly Ser Ser Tyr
225                 230                 235                 240 cag ggg acc tgg agt gaa tgg agt gac ccg gtc atc ttt cag acc cag      768
Gln Gly Thr Trp Ser Glu Trp Ser Asp Pro Val Ile Phe Gln Thr Gln
                245                 250                 255 tca gag gag tta aag gaa ggc tgg aac cct cac ctg ctg ctt ctc ctc      816
Ser Glu Glu Leu Lys Glu Gly Trp Asn Pro His Leu Leu Leu Leu Leu
                260                 265                 270
```

```
ctg ctt gtc ata gtc ttc att cct gcc ttc tgg agc ctg aag acc cat    864
Leu Leu Val Ile Val Phe Ile Pro Ala Phe Trp Ser Leu Lys Thr His
        275                 280                 285 cca ttg tgg agg cta tgg aag aag ata tgg gcc gtc ccc agc cct gag    912
Pro Leu Trp Arg Leu Trp Lys Lys Ile Trp Ala Val Pro Ser Pro Glu
    290                 295                 300 cgg ttc ttc atg ccc ctg tac aag ggc tgc agc gga gac ttc aag aaa    960
Arg Phe Phe Met Pro Leu Tyr Lys Gly Cys Ser Gly Asp Phe Lys Lys
305                 310                 315                 320 tgg gtg ggt gca ccc ttc act ggc tcc agc ctg gag ctg gga ccc tgg   1008
Trp Val Gly Ala Pro Phe Thr Gly Ser Ser Leu Glu Leu Gly Pro Trp
                325                 330                 335 agc cca gag gtg ccc tcc acc ctg gag gtg tac agc tgc cac cca cca   1056
Ser Pro Glu Val Pro Ser Thr Leu Glu Val Tyr Ser Cys His Pro Pro
            340                 345                 350 cgg agc ccg gcc aag agg ctg cag ctc acg gag cta caa gaa cca gca   1104
Arg Ser Pro Ala Lys Arg Leu Gln Leu Thr Glu Leu Gln Glu Pro Ala
        355                 360                 365 gag ctg gtg gag tct gac ggt gtg ccc aag ccc agc ttc tgg ccg aca   1152
Glu Leu Val Glu Ser Asp Gly Val Pro Lys Pro Ser Phe Trp Pro Thr
370                 375                 380 gcc cag aac tcg ggg ggc tca gct tac agt gag gag agg gat cgg cca   1200
Ala Gln Asn Ser Gly Gly Ser Ala Tyr Ser Glu Glu Arg Asp Arg Pro
385                 390                 395                 400 tac ggc ctg gtg tcc att gac aca gtg act gtg cta gat gca gag ggg   1248
Tyr Gly Leu Val Ser Ile Asp Thr Val Thr Val Leu Asp Ala Glu Gly
                405                 410                 415 cca tgc acc tgg ccc tgc agc tgt gag gat gac ggc tac cca gcc ctg   1296
Pro Cys Thr Trp Pro Cys Ser Cys Glu Asp Asp Gly Tyr Pro Ala Leu
            420                 425                 430 gac ctg gat gct ggc ctg gag ccc agc cca ggc cta gag gac cca ctc   1344
Asp Leu Asp Ala Gly Leu Glu Pro Ser Pro Gly Leu Glu Asp Pro Leu
        435                 440                 445 ttg gat gca ggg acc aca gtc ctg tcc tgt ggc tgt gtc tca gct ggc   1392
Leu Asp Ala Gly Thr Thr Val Leu Ser Cys Gly Cys Val Ser Ala Gly
450                 455                 460 agc cct ggg cta gga ggg ccc ctg gga agc ctc ctg gac aga cta aag   1440
Ser Pro Gly Leu Gly Gly Pro Leu Gly Ser Leu Leu Asp Arg Leu Lys
465                 470                 475                 480 cca ccc ctt gca gat ggg gag gac tgg gct ggg gga ctg ccc tgg ggt   1488
Pro Pro Leu Ala Asp Gly Glu Asp Trp Ala Gly Gly Leu Pro Trp Gly
                485                 490                 495 ggc cgg tca cct gga ggg gtc tca gag agt gag gcg ggc tca ccc ctg   1536
Gly Arg Ser Pro Gly Gly Val Ser Glu Ser Glu Ala Gly Ser Pro Leu
            500                 505                 510 gcc ggc ctg gat atg gac acg ttt gac agt ggc ttt gtg ggc tct gac   1584
Ala Gly Leu Asp Met Asp Thr Phe Asp Ser Gly Phe Val Gly Ser Asp
        515                 520                 525 tgc agc agc cct gtg gag tgt gac ttc acc agc ccc ggg gac gaa gga   1632
Cys Ser Ser Pro Val Glu Cys Asp Phe Thr Ser Pro Gly Asp Glu Gly
530                 535                 540 ccc ccc cgg agc tac ctc cgc cag tgg gtg gtc att cct ccg cca ctt   1680
Pro Pro Arg Ser Tyr Leu Arg Gln Trp Val Val Ile Pro Pro Pro Leu
545                 550                 555                 560 tcg agc cct gga ccc cag gcc agc taa                               1707
Ser Ser Pro Gly Pro Gln Ala Ser  *
                565

<210> SEQ ID NO 65
<211> LENGTH: 568
```

```
<212> TYPE: PRT
<213> ORGANISM: homo sapiens

<400> SEQUENCE: 65

Met Pro Arg Gly Trp Ala Ala Pro Leu Leu Leu Leu Leu Gln Gly
1               5                   10                  15

Ala Leu Glu Gly Met Glu Arg Lys Leu Cys Ser Pro Lys Pro Pro
                20                  25                  30

Thr Lys Ala Ser Leu Pro Thr Asp Pro Pro Gly Trp Gly Cys Pro Asp
            35                  40                  45

Leu Val Cys Tyr Thr Asp Tyr Leu Gln Thr Val Ile Cys Ile Leu Glu
    50                  55                  60

Met Trp Asn Leu His Pro Ser Thr Leu Thr Leu Thr Trp Ile Leu Ser
65                  70                  75                  80

Asn Asn Thr Gly Cys Tyr Ile Lys Asp Arg Thr Leu Asp Leu Arg Gln
                85                  90                  95

Asp Gln Tyr Glu Glu Leu Lys Asp Glu Ala Thr Ser Cys Ser Leu His
                100                 105                 110

Arg Ser Ala His Asn Ala Thr His Ala Thr Tyr Thr Cys His Met Asp
            115                 120                 125

Val Phe His Phe Met Ala Asp Asp Ile Phe Ser Val Asn Ile Thr Asp
130                 135                 140

Gln Ser Gly Asn Tyr Ser Gln Glu Cys Gly Ser Phe Leu Leu Ala Glu
145                 150                 155                 160

Ser Arg Gln Tyr Asn Ile Ser Trp Arg Ser Asp Tyr Glu Asp Pro Ala
                165                 170                 175

Phe Tyr Met Leu Lys Gly Lys Leu Gln Tyr Glu Leu Gln Tyr Arg Asn
            180                 185                 190

Arg Gly Asp Pro Trp Ala Val Ser Pro Arg Arg Lys Leu Ile Ser Val
        195                 200                 205

Asp Ser Arg Ser Val Ser Leu Leu Pro Leu Glu Phe Arg Lys Asp Ser
    210                 215                 220

Ser Tyr Glu Leu Gln Val Arg Ala Gly Pro Met Pro Gly Ser Ser Tyr
225                 230                 235                 240

Gln Gly Thr Trp Ser Glu Trp Ser Asp Pro Val Ile Phe Gln Thr Gln
                245                 250                 255

Ser Glu Glu Leu Lys Glu Gly Trp Asn Pro His Leu Leu Leu Leu Leu
            260                 265                 270

Leu Leu Val Ile Val Phe Ile Pro Ala Phe Trp Ser Leu Lys Thr His
        275                 280                 285

Pro Leu Trp Arg Leu Trp Lys Lys Ile Trp Ala Val Pro Ser Pro Glu
    290                 295                 300

Arg Phe Phe Met Pro Leu Tyr Lys Gly Cys Ser Gly Asp Phe Lys Lys
305                 310                 315                 320

Trp Val Gly Ala Pro Phe Thr Gly Ser Ser Leu Glu Leu Gly Pro Trp
                325                 330                 335

Ser Pro Glu Val Pro Ser Thr Leu Glu Val Tyr Ser Cys His Pro Pro
            340                 345                 350

Arg Ser Pro Ala Lys Arg Leu Gln Leu Thr Glu Leu Gln Glu Pro Ala
        355                 360                 365

Glu Leu Val Glu Ser Asp Gly Val Pro Lys Pro Ser Phe Trp Pro Thr
    370                 375                 380

Ala Gln Asn Ser Gly Gly Ser Ala Tyr Ser Glu Glu Arg Asp Arg Pro
385                 390                 395                 400
```

```
Tyr Gly Leu Val Ser Ile Asp Thr Val Thr Val Leu Asp Ala Glu Gly
            405                 410                 415
Pro Cys Thr Trp Pro Cys Ser Cys Glu Asp Gly Tyr Pro Ala Leu
        420                 425                 430
Asp Leu Asp Ala Gly Leu Glu Pro Ser Pro Gly Leu Glu Asp Pro Leu
        435                 440                 445
Leu Asp Ala Gly Thr Thr Val Leu Ser Cys Gly Cys Val Ser Ala Gly
    450                 455                 460
Ser Pro Gly Leu Gly Pro Leu Gly Ser Leu Leu Asp Arg Leu Lys
465                 470                 475                 480
Pro Pro Leu Ala Asp Gly Glu Asp Trp Ala Gly Leu Pro Trp Gly
            485                 490                 495
Gly Arg Ser Pro Gly Gly Val Ser Ser Glu Ala Gly Ser Pro Leu
            500                 505                 510
Ala Gly Leu Asp Met Asp Thr Phe Asp Ser Gly Phe Val Gly Ser Asp
            515                 520                 525
Cys Ser Ser Pro Val Glu Cys Asp Phe Thr Ser Pro Gly Asp Glu Gly
            530                 535                 540
Pro Pro Arg Ser Tyr Leu Arg Gln Trp Val Val Ile Pro Pro Pro Leu
545                 550                 555                 560
Ser Ser Pro Gly Pro Gln Ala Ser
            565

<210> SEQ ID NO 66
<211> LENGTH: 741
<212> TYPE: DNA
<213> ORGANISM: Artificial Sequence
<220> FEATURE:
<223> OTHER INFORMATION: Degenerate polynucleotide sequence of SEQ ID
      NO:69
<220> FEATURE:
<221> NAME/KEY: misc_feature
<222> LOCATION: (1)...(741)
<223> OTHER INFORMATION: n = A,T,C or G

<400> SEQUENCE: 66
atggarmgna arytntgyws nccnaarccn ccnccnacna argcnwsnyt nccnacngay        60
ccnccnggnt ggggntgycc ngayytngtn tgytayacng aytayytnca racngtnath       120
tgyathytng aratgtggaa yytncayccn wsnacnytna cnytnacntg gathytnwsn       180
aayaayacng gntgytayat haargaymgn acnytngayy tnmgncarga ycartaygar       240
garytnaarg aygargcnac nwsntgywsn ytncaymgnw sngcncayaa ycnacncay        300 gcnacntaya cntgycayat ggaygtntty cayttyatgg cngaygayat httywsngtn       360
aayathacng aycarwsngg naaytaywsn cargartgyg gnwsnttyyt nytngcngar       420
wsnmgncart ayaayathws ntggmgnwsn gaytaygarg ayccngcntt ytayatgytn       480
aarggnaary tncartayga rytncartay mgnaaymgng gngayccntg ggcngtnwsn       540
ccnmgnmgna arytnathws ngtngaywsn mgnwsngtnw snytnytncc nytngartty       600
mgnaargayw snwsntayga rytncargtn mgngcnggnc cnatgccngg nwsnwsntay       660
carggnacnt ggwsngartg gwsngayccn gtnathttyc aracncarws ngargarytn       720
aargarggnt ggaayccnca y                                                 741

<210> SEQ ID NO 67
<211> LENGTH: 4
<212> TYPE: PRT
```

-continued

```
<213> ORGANISM: Artificial Sequence
<220> FEATURE:
<223> OTHER INFORMATION: WXXW motif
<220> FEATURE:
<221> NAME/KEY: VARIANT
<222> LOCATION: (1)...(4)
<223> OTHER INFORMATION: Xaa = Any Amino Acid

<400> SEQUENCE: 67

Trp Xaa Xaa Trp
1

<210> SEQ ID NO 68
<211> LENGTH: 741
<212> TYPE: DNA
<213> ORGANISM: Homo sapiens
<220> FEATURE:
<221> NAME/KEY: CDS
<222> LOCATION: (1)...(741)

<400> SEQUENCE: 68 atg gag agg aag ctc tgc agt ccc aag cca ccc ccc acc aag gcc tct      48
Met Glu Arg Lys Leu Cys Ser Pro Lys Pro Pro Pro Thr Lys Ala Ser
1               5                   10                  15 ctc ccc act gac cct cca ggc tgg ggc tgc ccc gac ctc gtc tgc tac      96
Leu Pro Thr Asp Pro Pro Gly Trp Gly Cys Pro Asp Leu Val Cys Tyr
            20                  25                  30 acc gat tac ctc cag acg gtc atc tgc atc ctg gaa atg tgg aac ctc     144
Thr Asp Tyr Leu Gln Thr Val Ile Cys Ile Leu Glu Met Trp Asn Leu
        35                  40                  45 cac ccc agc acg ctc acc ctt acc tgg ata ctt tct aat aat act ggg     192
His Pro Ser Thr Leu Thr Leu Thr Trp Ile Leu Ser Asn Asn Thr Gly
50                  55                  60 tgc tat atc aag gac aga aca ctg gac ctc agg caa gac cag tat gaa     240
Cys Tyr Ile Lys Asp Arg Thr Leu Asp Leu Arg Gln Asp Gln Tyr Glu
65                  70                  75                  80 gag ctg aag gac gag gcc acc tcc tgc agc ctc cac agg tcg gcc cac     288
Glu Leu Lys Asp Glu Ala Thr Ser Cys Ser Leu His Arg Ser Ala His
                85                  90                  95 aat gcc acg cat gcc acc tac acc tgc cac atg gat gta ttc cac ttc     336
Asn Ala Thr His Ala Thr Tyr Thr Cys His Met Asp Val Phe His Phe
            100                 105                 110 atg gcc gac gac att ttc agt gtc aac atc aca gac cag tct ggc aac     384
Met Ala Asp Asp Ile Phe Ser Val Asn Ile Thr Asp Gln Ser Gly Asn
        115                 120                 125 tac tcc cag gag tgt ggc agc ttt ctc ctg gct gag agc aga cag tat     432
Tyr Ser Gln Glu Cys Gly Ser Phe Leu Leu Ala Glu Ser Arg Gln Tyr
    130                 135                 140 aat atc tcc tgg cgc tca gat tac gaa gac cct gcc ttc tac atg ctg     480
Asn Ile Ser Trp Arg Ser Asp Tyr Glu Asp Pro Ala Phe Tyr Met Leu
145                 150                 155                 160 aag ggc aag ctt cag tat gag ctg cag tac agg aac cgg gga gac ccc     528
Lys Gly Lys Leu Gln Tyr Glu Leu Gln Tyr Arg Asn Arg Gly Asp Pro
                165                 170                 175 tgg gct gtg agt ccg agg aga aag ctg atc tca gtg gac tca aga agt     576
Trp Ala Val Ser Pro Arg Arg Lys Leu Ile Ser Val Asp Ser Arg Ser
            180                 185                 190 gtc tcc ctc ctc ccc ctg gag ttc cgc aaa gac tcg agc tat gag ctg     624
Val Ser Leu Leu Pro Leu Glu Phe Arg Lys Asp Ser Ser Tyr Glu Leu
        195                 200                 205 cag gtg cgg gca ggg ccc atg cct ggc tcc tcc tac cag ggg acc tgg     672
Gln Val Arg Ala Gly Pro Met Pro Gly Ser Ser Tyr Gln Gly Thr Trp
    210                 215                 220
```

```
agt gaa tgg agt gac ccg gtc atc ttt cag acc cag tca gag gag tta   720
Ser Glu Trp Ser Asp Pro Val Ile Phe Gln Thr Gln Ser Glu Glu Leu
225             230                 235                 240 aag gaa ggc tgg aac cct cac                                       741
Lys Glu Gly Trp Asn Pro His
            245
```

<210> SEQ ID NO 69
<211> LENGTH: 247
<212> TYPE: PRT
<213> ORGANISM: Homo sapiens

<400> SEQUENCE: 69

```
Met Glu Arg Lys Leu Cys Ser Pro Lys Pro Pro Thr Lys Ala Ser
1               5                   10                  15

Leu Pro Thr Asp Pro Pro Gly Trp Gly Cys Pro Asp Leu Val Cys Tyr
                20              25                  30

Thr Asp Tyr Leu Gln Thr Val Ile Cys Ile Leu Glu Met Trp Asn Leu
            35                  40                  45

His Pro Ser Thr Leu Thr Leu Thr Trp Ile Leu Ser Asn Asn Thr Gly
    50                  55                  60

Cys Tyr Ile Lys Asp Arg Thr Leu Asp Leu Arg Gln Asp Gln Tyr Glu
65                  70                  75                  80

Glu Leu Lys Asp Glu Ala Thr Ser Cys Ser Leu His Arg Ser Ala His
                85                  90                  95

Asn Ala Thr His Ala Thr Tyr Thr Cys His Met Asp Val Phe His Phe
            100                 105                 110

Met Ala Asp Asp Ile Phe Ser Val Asn Ile Thr Asp Gln Ser Gly Asn
        115                 120                 125

Tyr Ser Gln Glu Cys Gly Ser Phe Leu Leu Ala Glu Ser Arg Gln Tyr
    130                 135                 140

Asn Ile Ser Trp Arg Ser Asp Tyr Glu Asp Pro Ala Phe Tyr Met Leu
145                 150                 155                 160

Lys Gly Lys Leu Gln Tyr Glu Leu Gln Tyr Arg Asn Arg Gly Asp Pro
                165                 170                 175

Trp Ala Val Ser Pro Arg Arg Lys Leu Ile Ser Val Asp Ser Arg Ser
            180                 185                 190

Val Ser Leu Leu Pro Leu Glu Phe Arg Lys Asp Ser Ser Tyr Glu Leu
    195                 200                 205

Gln Val Arg Ala Gly Pro Met Pro Gly Ser Ser Tyr Gln Gly Thr Trp
210                 215                 220

Ser Glu Trp Ser Asp Pro Val Ile Phe Gln Thr Gln Ser Glu Glu Leu
225             230                 235                 240

Lys Glu Gly Trp Asn Pro His
            245
```

<210> SEQ ID NO 70
<211> LENGTH: 4
<212> TYPE: PRT
<213> ORGANISM: Artificial Sequence
<220> FEATURE:
<223> OTHER INFORMATION: Domain linker motif; PAPP motif

<400> SEQUENCE: 70

```
Pro Ala Pro Pro
1
```

<210> SEQ ID NO 71
<211> LENGTH: 261
<212> TYPE: PRT
<213> ORGANISM: Artificial Sequence
<220> FEATURE:
<223> OTHER INFORMATION: Representative variant soluble receptor with
      domain linker
<220> FEATURE:
<221> NAME/KEY: VARIANT
<222> LOCATION: (1)...(261)
<223> OTHER INFORMATION: Xaa = Any Amino Acid

<400> SEQUENCE: 71

Met Glu Arg Lys Leu Cys Ser Pro Lys Pro Pro Thr Lys Ala Ser
1               5                   10                  15

Leu Pro Thr Asp Pro Pro Gly Trp Gly Cys Pro Asp Leu Val Cys Tyr
            20                  25                  30

Thr Asp Tyr Leu Gln Thr Val Ile Cys Ile Leu Glu Met Trp Asn Leu
        35                  40                  45

His Pro Ser Thr Leu Thr Leu Thr Trp Ile Leu Ser Asn Asn Thr Gly
    50                  55                  60

Cys Tyr Ile Lys Asp Arg Thr Leu Asp Leu Arg Gln Asp Gln Tyr Glu
65                  70                  75                  80

Glu Leu Lys Asp Glu Ala Thr Ser Cys Ser Leu His Arg Ser Ala His
                85                  90                  95

Asn Ala Thr His Ala Thr Tyr Thr Cys His Met Asp Val Phe His Phe
            100                 105                 110

Met Ala Asp Asp Ile Phe Ser Val Asn Ile Thr Asp Gln Ser Gly Asn
        115                 120                 125

Tyr Ser Gln Glu Cys Gly Ser Phe Leu Leu Ala Glu Ser Xaa Xaa Pro
    130                 135                 140

Ala Pro Pro Xaa Xaa Xaa Xaa Xaa Xaa Xaa Arg Gln Tyr Asn Ile
145                 150                 155                 160

Ser Trp Arg Ser Asp Tyr Glu Asp Pro Ala Phe Tyr Met Leu Lys Gly
                165                 170                 175

Lys Leu Gln Tyr Glu Leu Gln Tyr Arg Asn Arg Gly Asp Pro Trp Ala
            180                 185                 190

Val Ser Pro Arg Arg Lys Leu Ile Ser Val Asp Ser Arg Ser Val Ser
        195                 200                 205

Leu Leu Pro Leu Glu Phe Arg Lys Asp Ser Ser Tyr Glu Leu Gln Val
    210                 215                 220

Arg Ala Gly Pro Met Pro Gly Ser Ser Tyr Gln Gly Thr Trp Ser Glu
225                 230                 235                 240

Trp Ser Asp Pro Val Ile Phe Gln Thr Gln Ser Glu Glu Leu Lys Glu
                245                 250                 255

Gly Trp Asn Pro His
            260

<210> SEQ ID NO 72
<211> LENGTH: 1461
<212> TYPE: DNA
<213> ORGANISM: Artificial Sequence
<220> FEATURE:
<223> OTHER INFORMATION: Mouse zalpha11 extracellular domain murine
      immunoglobulin gamma 2a heavy chain Fc region
      fusion protein (zalpha11m-mG2a) Polynucleotide
<220> FEATURE:
<221> NAME/KEY: CDS
<222> LOCATION: (1)...(1461)

<400> SEQUENCE: 72

-continued

```
atg gat gca atg aag aga ggg ctc tgc tgt gtg ctg ctg tgt ggc        48
Met Asp Ala Met Lys Arg Gly Leu Cys Cys Val Leu Leu Cys Gly
1               5                   10                  15 gcc gtc ttc gtt tcg ctc agc cag aaa atc cat gcc gag ttg aga cgc    96
Ala Val Phe Val Ser Leu Ser Gln Lys Ile His Ala Glu Leu Arg Arg
            20                  25                  30 ttc cgg aga tgc ctg gac ctc act tgc tac act gac tac ctc tgg acc   144
Phe Arg Arg Cys Leu Asp Leu Thr Cys Tyr Thr Asp Tyr Leu Trp Thr
        35                  40                  45 atc acc tgt gtc ctg gag aca cgg agc ccc aac ccc agc ata ctc agt   192
Ile Thr Cys Val Leu Glu Thr Arg Ser Pro Asn Pro Ser Ile Leu Ser
    50                  55                  60 ctc acc tgg caa gat gaa tat gag gaa ctt cag gac caa gag acc ttc   240
Leu Thr Trp Gln Asp Glu Tyr Glu Glu Leu Gln Asp Gln Glu Thr Phe
65                  70                  75                  80 tgc agc cta cac agg tct ggc cac aac acc aca cat ata tgg tac acg   288
Cys Ser Leu His Arg Ser Gly His Asn Thr Thr His Ile Trp Tyr Thr
                85                  90                  95 tgc cat atg cgc ttg tct caa ttc ctg tcc gat gaa gtt ttc att gtc   336
Cys His Met Arg Leu Ser Gln Phe Leu Ser Asp Glu Val Phe Ile Val
            100                 105                 110 aat gtg acg gac cag tct ggc aac aac tcc caa gag tgt ggc agc ttt   384
Asn Val Thr Asp Gln Ser Gly Asn Asn Ser Gln Glu Cys Gly Ser Phe
        115                 120                 125 gtc ctg gct gag agc atc aaa cca gct ccc ccc ttg aac gtg act gtg   432
Val Leu Ala Glu Ser Ile Lys Pro Ala Pro Pro Leu Asn Val Thr Val
    130                 135                 140 gcc ttc tca gga cgc tat gat atc tcc tgg gac tca gct tat gac gaa   480
Ala Phe Ser Gly Arg Tyr Asp Ile Ser Trp Asp Ser Ala Tyr Asp Glu
145                 150                 155                 160 ccc tcc aac tac gtg ctg agg ggc aag cta caa tat gag ctg cag tat   528
Pro Ser Asn Tyr Val Leu Arg Gly Lys Leu Gln Tyr Glu Leu Gln Tyr
                165                 170                 175 cgg aac ctc aga gac ccc tat gct gtg agg ccg gtg acc aag ctg atc   576
Arg Asn Leu Arg Asp Pro Tyr Ala Val Arg Pro Val Thr Lys Leu Ile
            180                 185                 190 tca gtg gac tca aga aac gtc tct ctt ctc cct gaa gag ttc cac aaa   624
Ser Val Asp Ser Arg Asn Val Ser Leu Leu Pro Glu Glu Phe His Lys
        195                 200                 205 gat tct agc tac cag ctg cag gtg cgg gca gcg cct cag cca ggc act   672
Asp Ser Ser Tyr Gln Leu Gln Val Arg Ala Ala Pro Gln Pro Gly Thr
    210                 215                 220 tca ttc agg ggg acc tgg agt gag tgg agt gac ccc gtc atc ttt cag   720
Ser Phe Arg Gly Thr Trp Ser Glu Trp Ser Asp Pro Val Ile Phe Gln
225                 230                 235                 240 acc cag gct ggg gag ccc gag gca ggc tgg gac cct cac gag ccc aga   768
Thr Gln Ala Gly Glu Pro Glu Ala Gly Trp Asp Pro His Glu Pro Arg
                245                 250                 255 tct ccc aca atc aag ccc tgt cct cca tgc aaa tgc cca gca cct aac   816
Ser Pro Thr Ile Lys Pro Cys Pro Pro Cys Lys Cys Pro Ala Pro Asn
            260                 265                 270 ctc ttg ggt gga cca tcc gtc ttc atc ttc cct cca aag atc aag gat   864
Leu Leu Gly Gly Pro Ser Val Phe Ile Phe Pro Pro Lys Ile Lys Asp
        275                 280                 285 gta ctc atg atc tcc ctg agc ccc ata gtc aca tgt gtg gtg gtg gat   912
Val Leu Met Ile Ser Leu Ser Pro Ile Val Thr Cys Val Val Val Asp
    290                 295                 300 gtg agc gag gat gac cca gat gtc cag atc agc tgg ttt gtg aac aac   960
Val Ser Glu Asp Asp Pro Asp Val Gln Ile Ser Trp Phe Val Asn Asn
```

```
                305                 310                 315                 320
gtg gaa gta cac aca gct cag aca caa acc cat aga gag gat tac aac        1008
Val Glu Val His Thr Ala Gln Thr Gln Thr His Arg Glu Asp Tyr Asn
                325                 330                 335 agt act ctc cgg gtg gtc agt gcc ctc ccc atc cag cac cag gac tgg        1056
Ser Thr Leu Arg Val Val Ser Ala Leu Pro Ile Gln His Gln Asp Trp
            340                 345                 350 atg agt ggc aag gag ttc aaa tgc aag gtc aac aac aaa gac ctc cca        1104
Met Ser Gly Lys Glu Phe Lys Cys Lys Val Asn Asn Lys Asp Leu Pro
        355                 360                 365 gcg ccc atc gag aga acc atc tca aaa ccc aaa ggg tca gta aga gct        1152
Ala Pro Ile Glu Arg Thr Ile Ser Lys Pro Lys Gly Ser Val Arg Ala
    370                 375                 380 cca cag gta tat gtc ttg cct cca cca gaa gaa gag atg act aag aaa        1200
Pro Gln Val Tyr Val Leu Pro Pro Pro Glu Glu Glu Met Thr Lys Lys
385                 390                 395                 400 cag gtc act ctg acc tgc atg gtc aca gac ttc atg cct gaa gac att        1248
Gln Val Thr Leu Thr Cys Met Val Thr Asp Phe Met Pro Glu Asp Ile
                405                 410                 415 tac gtg gag tgg acc aac aac ggg aaa aca gag cta aac tac aag aac        1296
Tyr Val Glu Trp Thr Asn Asn Gly Lys Thr Glu Leu Asn Tyr Lys Asn
            420                 425                 430 act gaa cca gtc ctg gac tct gat ggt tct tac ttc atg tac agc aag        1344
Thr Glu Pro Val Leu Asp Ser Asp Gly Ser Tyr Phe Met Tyr Ser Lys
        435                 440                 445 ctg aga gtg gaa aag aag aac tgg gtg gaa aga aat agc tac tcc tgt        1392
Leu Arg Val Glu Lys Lys Asn Trp Val Glu Arg Asn Ser Tyr Ser Cys
    450                 455                 460 tca gtg gtc cac gag ggt ctg cac aat cac cac acg act aag agc ttc        1440
Ser Val Val His Glu Gly Leu His Asn His His Thr Thr Lys Ser Phe
465                 470                 475                 480 tcc cgg act ccg ggt aaa taa                                            1461
Ser Arg Thr Pro Gly Lys *
                485

<210> SEQ ID NO 73
<211> LENGTH: 486
<212> TYPE: PRT
<213> ORGANISM: Artificial Sequence
<220> FEATURE:
<223> OTHER INFORMATION: Mouse zalpha11 extracellular domain murine
      immunoglobulin gamma 2a heavy chain Fc region
      fusion protein (zalpha11m-mG2a) Polynucleotide

<400> SEQUENCE: 73

Met Asp Ala Met Lys Arg Gly Leu Cys Cys Val Leu Leu Leu Cys Gly
1               5                   10                  15

Ala Val Phe Val Ser Leu Ser Gln Lys Ile His Ala Glu Leu Arg Arg
            20                  25                  30

Phe Arg Arg Cys Leu Asp Leu Thr Cys Tyr Thr Asp Tyr Leu Trp Thr
        35                  40                  45

Ile Thr Cys Val Leu Glu Thr Arg Ser Pro Asn Pro Ser Ile Leu Ser
    50                  55                  60

Leu Thr Trp Gln Asp Glu Tyr Glu Glu Leu Gln Asp Gln Glu Thr Phe
65                  70                  75                  80

Cys Ser Leu His Arg Ser Gly His Asn Thr Thr His Ile Trp Tyr Thr
                85                  90                  95

Cys His Met Arg Leu Ser Gln Phe Leu Ser Asp Glu Val Phe Ile Val
            100                 105                 110
```

-continued

Asn Val Thr Asp Gln Ser Gly Asn Asn Ser Gln Glu Cys Gly Ser Phe
            115                 120                 125

Val Leu Ala Glu Ser Ile Lys Pro Ala Pro Pro Leu Asn Val Thr Val
    130                 135                 140

Ala Phe Ser Gly Arg Tyr Asp Ile Ser Trp Asp Ser Ala Tyr Asp Glu
145                 150                 155                 160

Pro Ser Asn Tyr Val Leu Arg Gly Lys Leu Gln Tyr Glu Leu Gln Tyr
                165                 170                 175

Arg Asn Leu Arg Asp Pro Tyr Ala Val Arg Pro Val Thr Lys Leu Ile
            180                 185                 190

Ser Val Asp Ser Arg Asn Val Ser Leu Leu Pro Glu Glu Phe His Lys
    195                 200                 205

Asp Ser Ser Tyr Gln Leu Gln Val Arg Ala Ala Pro Gln Pro Gly Thr
210                 215                 220

Ser Phe Arg Gly Thr Trp Ser Glu Trp Ser Asp Pro Val Ile Phe Gln
225                 230                 235                 240

Thr Gln Ala Gly Glu Pro Glu Ala Gly Trp Asp Pro His Glu Pro Arg
                245                 250                 255

Ser Pro Thr Ile Lys Pro Cys Pro Pro Cys Lys Cys Pro Ala Pro Asn
            260                 265                 270

Leu Leu Gly Gly Pro Ser Val Phe Ile Phe Pro Pro Lys Ile Lys Asp
    275                 280                 285

Val Leu Met Ile Ser Leu Ser Pro Ile Val Thr Cys Val Val Asp
290                 295                 300

Val Ser Glu Asp Asp Pro Asp Val Gln Ile Ser Trp Phe Val Asn Asn
305                 310                 315                 320

Val Glu Val His Thr Ala Gln Thr Gln Thr His Arg Glu Asp Tyr Asn
                325                 330                 335

Ser Thr Leu Arg Val Val Ser Ala Leu Pro Ile Gln His Gln Asp Trp
            340                 345                 350

Met Ser Gly Lys Glu Phe Lys Cys Lys Val Asn Asn Lys Asp Leu Pro
    355                 360                 365

Ala Pro Ile Glu Arg Thr Ile Ser Lys Pro Lys Gly Ser Val Arg Ala
370                 375                 380

Pro Gln Val Tyr Val Leu Pro Pro Glu Glu Glu Met Thr Lys Lys
385                 390                 395                 400

Gln Val Thr Leu Thr Cys Met Val Thr Asp Phe Met Pro Glu Asp Ile
                405                 410                 415

Tyr Val Glu Trp Thr Asn Asn Gly Lys Thr Glu Leu Asn Tyr Lys Asn
            420                 425                 430

Thr Glu Pro Val Leu Asp Ser Asp Gly Ser Tyr Phe Met Tyr Ser Lys
    435                 440                 445

Leu Arg Val Glu Lys Lys Asn Trp Val Glu Arg Asn Ser Tyr Ser Cys
450                 455                 460

Ser Val Val His Glu Gly Leu His Asn His His Thr Thr Lys Ser Phe
465                 470                 475                 480

Ser Arg Thr Pro Gly Lys
                485

<210> SEQ ID NO 74
<211> LENGTH: 23
<212> TYPE: DNA
<213> ORGANISM: Artificial Sequence
<220> FEATURE:
<223> OTHER INFORMATION: Oligonucleotide primer ZC26644

-continued

<400> SEQUENCE: 74
ggggtcgacg gccggccacc atg                                          23

<210> SEQ ID NO 75
<211> LENGTH: 35
<212> TYPE: DNA
<213> ORGANISM: Artificial Sequence
<220> FEATURE:
<223> OTHER INFORMATION: Oligonucleotide primer ZC26641

<400> SEQUENCE: 75
caagtgaggt ccaggcatct ccggaagcgt ctcaa                             35

<210> SEQ ID NO 76
<211> LENGTH: 35
<212> TYPE: DNA
<213> ORGANISM: Artificial Sequence
<220> FEATURE:
<223> OTHER INFORMATION: Oligonucleotide primer ZC26642

<400> SEQUENCE: 76
ttgagacgct tccggagatg cctggacctc acttg                             35

<210> SEQ ID NO 77
<211> LENGTH: 36
<212> TYPE: DNA
<213> ORGANISM: Artificial Sequence
<220> FEATURE:
<223> OTHER INFORMATION: Oligonucleotide primer ZC26662

<400> SEQUENCE: 77
tgtgggagat ctgggctcgt gagggtccca gcctgc                            36

<210> SEQ ID NO 78
<211> LENGTH: 30
<212> TYPE: DNA
<213> ORGANISM: Artificial Sequence
<220> FEATURE:
<223> OTHER INFORMATION: Oligonucleotide primer ZC26643

<400> SEQUENCE: 78
gagcccagat ctcccacaat caagccctgt                                   30

<210> SEQ ID NO 79
<211> LENGTH: 21
<212> TYPE: DNA
<213> ORGANISM: Artificial Sequence
<220> FEATURE:
<223> OTHER INFORMATION: Oligonucleotide primer ZC26645

<400> SEQUENCE: 79
aaacgcggcc gcggatccgg c                                            21

<210> SEQ ID NO 80
<211> LENGTH: 35
<212> TYPE: PRT
<213> ORGANISM: Homo sapiens

<400> SEQUENCE: 80

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg
        35

<210> SEQ ID NO 81
<211> LENGTH: 966
<212> TYPE: DNA
<213> ORGANISM: Homo sapiens
<220> FEATURE:
<221> NAME/KEY: CDS
<222> LOCATION: (1)...(966)

<400> SEQUENCE: 81

| | | | | | | | | | | | | | | | |
|---|---|---|---|---|---|---|---|---|---|---|---|---|---|---|---|
| ggg | ggc | ggg | ggc | gcc | gcg | cct | acg | gaa | act | cag | cca | cct | gtg | aca | aat | 48 |
| Gly | Gly | Gly | Gly | Ala | Ala | Pro | Thr | Glu | Thr | Gln | Pro | Pro | Val | Thr | Asn | |
| 1 | | | | 5 | | | | | 10 | | | | | 15 | | |
| ttg | agt | gtc | tct | gtt | gaa | aac | ctc | tgc | aca | gta | ata | tgg | aca | tgg | aat | 96 |
| Leu | Ser | Val | Ser | Val | Glu | Asn | Leu | Cys | Thr | Val | Ile | Trp | Thr | Trp | Asn | |
| | | | 20 | | | | | 25 | | | | | 30 | | | |
| cca | ccc | gag | gga | gcc | agc | tca | aat | tgt | agt | cta | tgg | tat | ttt | agt | cat | 144 |
| Pro | Pro | Glu | Gly | Ala | Ser | Ser | Asn | Cys | Ser | Leu | Trp | Tyr | Phe | Ser | His | |
| | | 35 | | | | | 40 | | | | | 45 | | | | |
| ttt | ggc | gac | aaa | caa | gat | aag | aaa | ata | gct | ccg | gaa | act | cgt | cgt | tca | 192 |
| Phe | Gly | Asp | Lys | Gln | Asp | Lys | Lys | Ile | Ala | Pro | Glu | Thr | Arg | Arg | Ser | |
| | 50 | | | | | 55 | | | | | 60 | | | | | |
| ata | gaa | gta | ccc | ctg | aat | gag | agg | att | tgt | ctg | caa | gtg | ggg | tcc | cag | 240 |
| Ile | Glu | Val | Pro | Leu | Asn | Glu | Arg | Ile | Cys | Leu | Gln | Val | Gly | Ser | Gln | |
| 65 | | | | | 70 | | | | | 75 | | | | | 80 | |
| tgt | agc | acc | aat | gag | agt | gag | aag | cct | agc | att | ttg | gtt | gaa | aaa | tgc | 288 |
| Cys | Ser | Thr | Asn | Glu | Ser | Glu | Lys | Pro | Ser | Ile | Leu | Val | Glu | Lys | Cys | |
| | | | | 85 | | | | | 90 | | | | | 95 | | |
| atc | tca | ccc | cca | gaa | ggt | gat | cct | gag | tct | gct | gtg | act | gag | ctt | caa | 336 |
| Ile | Ser | Pro | Pro | Glu | Gly | Asp | Pro | Glu | Ser | Ala | Val | Thr | Glu | Leu | Gln | |
| | | | 100 | | | | | 105 | | | | | 110 | | | |
| tgc | att | tgg | cac | aac | ctg | agc | tac | atg | aag | tgt | tct | tgg | ctc | cct | gga | 384 |
| Cys | Ile | Trp | His | Asn | Leu | Ser | Tyr | Met | Lys | Cys | Ser | Trp | Leu | Pro | Gly | |
| | | 115 | | | | | 120 | | | | | 125 | | | | |
| agg | aat | acc | agt | ccc | gac | act | aac | tat | act | ctc | tac | tat | tgg | cac | aga | 432 |
| Arg | Asn | Thr | Ser | Pro | Asp | Thr | Asn | Tyr | Thr | Leu | Tyr | Tyr | Trp | His | Arg | |
| | 130 | | | | | 135 | | | | | 140 | | | | | |
| agc | ctg | gaa | aaa | att | cat | caa | tgt | gaa | aac | atc | ttt | aga | gaa | ggc | caa | 480 |
| Ser | Leu | Glu | Lys | Ile | His | Gln | Cys | Glu | Asn | Ile | Phe | Arg | Glu | Gly | Gln | |
| 145 | | | | | 150 | | | | | 155 | | | | | 160 | |
| tac | ttt | ggt | tgt | tcc | ttt | gat | ctg | acc | aaa | gtg | aag | gat | tcc | agt | ttt | 528 |
| Tyr | Phe | Gly | Cys | Ser | Phe | Asp | Leu | Thr | Lys | Val | Lys | Asp | Ser | Ser | Phe | |
| | | | | 165 | | | | | 170 | | | | | 175 | | |
| gaa | caa | cac | agt | gtc | caa | ata | atg | gtc | aag | gat | aat | gca | gga | aaa | att | 576 |
| Glu | Gln | His | Ser | Val | Gln | Ile | Met | Val | Lys | Asp | Asn | Ala | Gly | Lys | Ile | |
| | | | 180 | | | | | 185 | | | | | 190 | | | |
| aaa | cca | tcc | ttc | aat | ata | gtg | cct | tta | act | tcc | cgt | gtg | aaa | cct | gat | 624 |
| Lys | Pro | Ser | Phe | Asn | Ile | Val | Pro | Leu | Thr | Ser | Arg | Val | Lys | Pro | Asp | |
| | | 195 | | | | | 200 | | | | | 205 | | | | |
| cct | cca | cat | att | aaa | aac | ctc | tcc | ttc | cac | aat | gat | gac | cta | tat | gtg | 672 |
| Pro | Pro | His | Ile | Lys | Asn | Leu | Ser | Phe | His | Asn | Asp | Asp | Leu | Tyr | Val | |
| | 210 | | | | | 215 | | | | | 220 | | | | | |
| caa | tgg | gag | aat | cca | cag | aat | ttt | att | agc | aga | tgc | cta | ttt | tat | gaa | 720 |
| Gln | Trp | Glu | Asn | Pro | Gln | Asn | Phe | Ile | Ser | Arg | Cys | Leu | Phe | Tyr | Glu | |
| 225 | | | | | 230 | | | | | 235 | | | | | 240 | |
| gta | gaa | gtc | aat | aac | agc | caa | act | gag | aca | cat | aat | gtt | ttc | tac | gtc | 768 |
| Val | Glu | Val | Asn | Asn | Ser | Gln | Thr | Glu | Thr | His | Asn | Val | Phe | Tyr | Val | |
| | | | | 245 | | | | | 250 | | | | | 255 | | |
| caa | gag | gct | aaa | tgt | gag | aat | cca | gaa | ttt | gag | aga | aat | gtg | gag | aat | 816 |

```
Gln Glu Ala Lys Cys Glu Asn Pro Glu Phe Glu Arg Asn Val Glu Asn
                260                 265                 270
aca tct tgt ttc atg gtc cct ggt gtt ctt cct gat act ttg aac aca    864
Thr Ser Cys Phe Met Val Pro Gly Val Leu Pro Asp Thr Leu Asn Thr
        275                 280                 285
gtc aga ata aga gtc aaa aca aat aag tta tgc tat gag gat gac aaa    912
Val Arg Ile Arg Val Lys Thr Asn Lys Leu Cys Tyr Glu Asp Asp Lys
    290                 295                 300
ctc tgg agt aat tgg agc caa gaa atg agt ata ggt aag aag cgc aat    960
Leu Trp Ser Asn Trp Ser Gln Glu Met Ser Ile Gly Lys Lys Arg Asn
305                 310                 315                 320
tcc aca                                                            966
Ser Thr <210> SEQ ID NO 82
<211> LENGTH: 322
<212> TYPE: PRT
<213> ORGANISM: Homo sapiens

<400> SEQUENCE: 82

Gly Gly Gly Gly Ala Ala Pro Thr Glu Thr Gln Pro Pro Val Thr Asn
1               5                   10                  15

Leu Ser Val Ser Val Glu Asn Leu Cys Thr Val Ile Trp Thr Trp Asn
                20                  25                  30

Pro Pro Glu Gly Ala Ser Ser Asn Cys Ser Leu Trp Tyr Phe Ser His
            35                  40                  45

Phe Gly Asp Lys Gln Asp Lys Lys Ile Ala Pro Glu Thr Arg Arg Ser
    50                  55                  60

Ile Glu Val Pro Leu Asn Glu Arg Ile Cys Leu Gln Val Gly Ser Gln
65                  70                  75                  80

Cys Ser Thr Asn Glu Ser Glu Lys Pro Ser Ile Leu Val Glu Lys Cys
                85                  90                  95

Ile Ser Pro Pro Glu Gly Asp Pro Glu Ser Ala Val Thr Glu Leu Gln
            100                 105                 110

Cys Ile Trp His Asn Leu Ser Tyr Met Lys Cys Ser Trp Leu Pro Gly
        115                 120                 125

Arg Asn Thr Ser Pro Asp Thr Asn Tyr Thr Leu Tyr Tyr Trp His Arg
    130                 135                 140

Ser Leu Glu Lys Ile His Gln Cys Glu Asn Ile Phe Arg Glu Gly Gln
145                 150                 155                 160

Tyr Phe Gly Cys Ser Phe Asp Leu Thr Lys Val Lys Asp Ser Ser Phe
                165                 170                 175

Glu Gln His Ser Val Gln Ile Met Val Lys Asp Asn Ala Gly Lys Ile
            180                 185                 190

Lys Pro Ser Phe Asn Ile Val Pro Leu Thr Ser Arg Val Lys Pro Asp
        195                 200                 205

Pro Pro His Ile Lys Asn Leu Ser Phe His Asn Asp Asp Leu Tyr Val
    210                 215                 220

Gln Trp Glu Asn Pro Gln Asn Phe Ile Ser Arg Cys Leu Phe Tyr Glu
225                 230                 235                 240

Val Glu Val Asn Asn Ser Gln Thr Glu Thr His Asn Val Phe Tyr Val
                245                 250                 255

Gln Glu Ala Lys Cys Glu Asn Pro Glu Phe Glu Arg Asn Val Glu Asn
            260                 265                 270

Thr Ser Cys Phe Met Val Pro Gly Val Leu Pro Asp Thr Leu Asn Thr
        275                 280                 285
```

```
Val Arg Ile Arg Val Lys Thr Asn Lys Leu Cys Tyr Glu Asp Asp Lys
    290                 295                 300

Leu Trp Ser Asn Trp Ser Gln Glu Met Ser Ile Gly Lys Lys Arg Asn
305                 310                 315                 320

Ser Thr

<210> SEQ ID NO 83
<211> LENGTH: 951
<212> TYPE: DNA
<213> ORGANISM: Homo sapiens
<220> FEATURE:
<221> NAME/KEY: CDS
<222> LOCATION: (1)...(951)

<400> SEQUENCE: 83 gac acc gag ata aaa gtt aac cct cct cag gat ttt gag ata gtg gat        48
Asp Thr Glu Ile Lys Val Asn Pro Pro Gln Asp Phe Glu Ile Val Asp
1               5                   10                  15 ccc gga tac tta ggt tat ctc tat ttg caa tgg caa ccc cca ctg tct        96
Pro Gly Tyr Leu Gly Tyr Leu Tyr Leu Gln Trp Gln Pro Pro Leu Ser
                20                  25                  30 ctg gat cat ttt aag gaa tgc aca gtg gaa tat gaa cta aaa tac cga       144
Leu Asp His Phe Lys Glu Cys Thr Val Glu Tyr Glu Leu Lys Tyr Arg
            35                  40                  45 aac att ggt agt gaa aca tgg aag acc atc att act aag aat cta cat       192
Asn Ile Gly Ser Glu Thr Trp Lys Thr Ile Ile Thr Lys Asn Leu His
        50                  55                  60 tac aaa gat ggg ttt gat ctt aac aag ggc att gaa gcg aag ata cac       240
Tyr Lys Asp Gly Phe Asp Leu Asn Lys Gly Ile Glu Ala Lys Ile His
65                  70                  75                  80 acg ctt tta cca tgg caa tgc aca aat gga tca gaa gtt caa agt tcc       288
Thr Leu Leu Pro Trp Gln Cys Thr Asn Gly Ser Glu Val Gln Ser Ser
                85                  90                  95 tgg gca gaa act act tat tgg ata tca cca caa gga att cca gaa act       336
Trp Ala Glu Thr Thr Tyr Trp Ile Ser Pro Gln Gly Ile Pro Glu Thr
            100                 105                 110 aaa gtt cag gat atg gat tgc gta tat tac aat tgg caa tat tta ctc       384
Lys Val Gln Asp Met Asp Cys Val Tyr Tyr Asn Trp Gln Tyr Leu Leu
        115                 120                 125 tgt tct tgg aaa cct ggc ata ggt gta ctt ctt gat acc aat tac aac       432
Cys Ser Trp Lys Pro Gly Ile Gly Val Leu Leu Asp Thr Asn Tyr Asn
130                 135                 140 ttg ttt tac tgg tat gag ggc ttg gat cat gca tta cag tgt gtt gat       480
Leu Phe Tyr Trp Tyr Glu Gly Leu Asp His Ala Leu Gln Cys Val Asp
145                 150                 155                 160 tac atc aag gct gat gga caa aat ata gga tgc aga ttt ccc tat ttg       528
Tyr Ile Lys Ala Asp Gly Gln Asn Ile Gly Cys Arg Phe Pro Tyr Leu
                165                 170                 175 gag gca tca gac tat aaa gat ttc tat att tgt gtt aat gga tca tca       576
Glu Ala Ser Asp Tyr Lys Asp Phe Tyr Ile Cys Val Asn Gly Ser Ser
            180                 185                 190 gag aac aag cct atc aga tcc agt tat ttc act ttt cag ctt caa aat       624
Glu Asn Lys Pro Ile Arg Ser Ser Tyr Phe Thr Phe Gln Leu Gln Asn
        195                 200                 205 ata gtt aaa cct ttg ccg cca gtc tat ctt act ttt act cgg gag agt       672
Ile Val Lys Pro Leu Pro Pro Val Tyr Leu Thr Phe Thr Arg Glu Ser
    210                 215                 220 tca tgt gaa att aag ctg aaa tgg agc ata cct ttg gga cct att cca       720
Ser Cys Glu Ile Lys Leu Lys Trp Ser Ile Pro Leu Gly Pro Ile Pro
225                 230                 235                 240
```

```
gca agg tgt ttt gat tat gaa att gag atc aga gaa gat gat act acc      768
Ala Arg Cys Phe Asp Tyr Glu Ile Glu Ile Arg Glu Asp Asp Thr Thr
            245                 250                 255 ttg gtg act gct aca gtt gaa aat gaa aca tac acc ttg aaa aca aca      816
Leu Val Thr Ala Thr Val Glu Asn Glu Thr Tyr Thr Leu Lys Thr Thr
            260                 265                 270 aat gaa acc cga caa tta tgc ttt gta gta aga agc aaa gtg aat att      864
Asn Glu Thr Arg Gln Leu Cys Phe Val Val Arg Ser Lys Val Asn Ile
            275                 280                 285 tat tgc tca gat gac gga att tgg agt gag tgg agt gat aaa caa tgc      912
Tyr Cys Ser Asp Asp Gly Ile Trp Ser Glu Trp Ser Asp Lys Gln Cys
        290                 295                 300 tgg gaa ggt gaa gac cta tcg aag aaa act ttg cta cgt                  951
Trp Glu Gly Glu Asp Leu Ser Lys Lys Thr Leu Leu Arg
305                 310                 315
```

<210> SEQ ID NO 84
<211> LENGTH: 317
<212> TYPE: PRT
<213> ORGANISM: Homo sapiens

<400> SEQUENCE: 84

```
Asp Thr Glu Ile Lys Val Asn Pro Pro Gln Asp Phe Glu Ile Val Asp
1               5                   10                  15

Pro Gly Tyr Leu Gly Tyr Leu Tyr Leu Gln Trp Gln Pro Pro Leu Ser
            20                  25                  30

Leu Asp His Phe Lys Glu Cys Thr Val Glu Tyr Glu Leu Lys Tyr Arg
        35                  40                  45

Asn Ile Gly Ser Glu Thr Trp Lys Thr Ile Ile Thr Lys Asn Leu His
    50                  55                  60

Tyr Lys Asp Gly Phe Asp Leu Asn Lys Gly Ile Glu Ala Lys Ile His
65                  70                  75                  80

Thr Leu Leu Pro Trp Gln Cys Thr Asn Gly Ser Glu Val Gln Ser Ser
                85                  90                  95

Trp Ala Glu Thr Thr Tyr Trp Ile Ser Pro Gln Gly Ile Pro Glu Thr
            100                 105                 110

Lys Val Gln Asp Met Asp Cys Val Tyr Tyr Asn Trp Gln Tyr Leu Leu
        115                 120                 125

Cys Ser Trp Lys Pro Gly Ile Gly Val Leu Leu Asp Thr Asn Tyr Asn
    130                 135                 140

Leu Phe Tyr Trp Tyr Glu Gly Leu Asp His Ala Leu Gln Cys Val Asp
145                 150                 155                 160

Tyr Ile Lys Ala Asp Gly Gln Asn Ile Gly Cys Arg Phe Pro Tyr Leu
                165                 170                 175

Glu Ala Ser Asp Tyr Lys Asp Phe Tyr Ile Cys Val Asn Gly Ser Ser
            180                 185                 190

Glu Asn Lys Pro Ile Arg Ser Ser Tyr Phe Thr Phe Gln Leu Gln Asn
        195                 200                 205

Ile Val Lys Pro Leu Pro Pro Val Tyr Leu Thr Phe Thr Arg Glu Ser
    210                 215                 220

Ser Cys Glu Ile Lys Leu Lys Trp Ser Ile Pro Leu Gly Pro Ile Pro
225                 230                 235                 240

Ala Arg Cys Phe Asp Tyr Glu Ile Glu Ile Arg Glu Asp Asp Thr Thr
                245                 250                 255

Leu Val Thr Ala Thr Val Glu Asn Glu Thr Tyr Thr Leu Lys Thr Thr
            260                 265                 270
```

```
Asn Glu Thr Arg Gln Leu Cys Phe Val Val Arg Ser Lys Val Asn Ile
            275                 280                 285

Tyr Cys Ser Asp Asp Gly Ile Trp Ser Glu Trp Ser Asp Lys Gln Cys
            290                 295                 300

Trp Glu Gly Glu Asp Leu Ser Lys Lys Thr Leu Leu Arg
305                 310                 315

<210> SEQ ID NO 85
<211> LENGTH: 519
<212> TYPE: DNA
<213> ORGANISM: Homo sapiens
<220> FEATURE:
<221> NAME/KEY: CDS
<222> LOCATION: (1)...(519)

<400> SEQUENCE: 85
```

| | | | | | | | | | | | | | | | | |
|---|---|---|---|---|---|---|---|---|---|---|---|---|---|---|---|---|
| atc | acg | tgc | cct | ccc | ccc | atg | tcc | gtg | gaa | cac | gca | gac | atc | tgg | gtc | 48 |
| Ile | Thr | Cys | Pro | Pro | Pro | Met | Ser | Val | Glu | His | Ala | Asp | Ile | Trp | Val | |
| 1 | | | | 5 | | | | | 10 | | | | | 15 | | |
| aag | agc | tac | agc | ttg | tac | tcc | agg | gag | cgg | tac | att | tgt | aac | tct | ggt | 96 |
| Lys | Ser | Tyr | Ser | Leu | Tyr | Ser | Arg | Glu | Arg | Tyr | Ile | Cys | Asn | Ser | Gly | |
| | | | 20 | | | | | 25 | | | | | 30 | | | |
| ttc | aag | cgt | aaa | gcc | ggc | acg | tcc | agc | ctg | acg | gag | tgc | gtg | ttg | aac | 144 |
| Phe | Lys | Arg | Lys | Ala | Gly | Thr | Ser | Ser | Leu | Thr | Glu | Cys | Val | Leu | Asn | |
| | | 35 | | | | | 40 | | | | | 45 | | | | |
| aag | gcc | acg | aat | gtc | gcc | cac | tgg | aca | acc | ccc | agt | ctc | aaa | tgc | att | 192 |
| Lys | Ala | Thr | Asn | Val | Ala | His | Trp | Thr | Thr | Pro | Ser | Leu | Lys | Cys | Ile | |
| | 50 | | | | | 55 | | | | | 60 | | | | | |
| aga | gac | cct | gcc | ctg | gtt | cac | caa | agg | cca | gcg | cca | ccc | tcc | aca | gta | 240 |
| Arg | Asp | Pro | Ala | Leu | Val | His | Gln | Arg | Pro | Ala | Pro | Pro | Ser | Thr | Val | |
| 65 | | | | | 70 | | | | | 75 | | | | | 80 | |
| acg | acg | gca | ggg | gtg | acc | cca | cag | cca | gag | agc | ctc | tcc | cct | tct | gga | 288 |
| Thr | Thr | Ala | Gly | Val | Thr | Pro | Gln | Pro | Glu | Ser | Leu | Ser | Pro | Ser | Gly | |
| | | | | 85 | | | | | 90 | | | | | 95 | | |
| aaa | gag | ccc | gca | gct | tca | tct | ccc | agc | tca | aac | aac | aca | gcg | gcc | aca | 336 |
| Lys | Glu | Pro | Ala | Ala | Ser | Ser | Pro | Ser | Ser | Asn | Asn | Thr | Ala | Ala | Thr | |
| | | | 100 | | | | | 105 | | | | | 110 | | | |
| aca | gca | gct | att | gtc | ccg | ggc | tcc | cag | ctg | atg | cct | tca | aaa | tca | cct | 384 |
| Thr | Ala | Ala | Ile | Val | Pro | Gly | Ser | Gln | Leu | Met | Pro | Ser | Lys | Ser | Pro | |
| | | 115 | | | | | 120 | | | | | 125 | | | | |
| tcc | aca | gga | acc | aca | gag | ata | agc | agt | cat | gag | tcc | tcc | cac | ggc | acc | 432 |
| Ser | Thr | Gly | Thr | Thr | Glu | Ile | Ser | Ser | His | Glu | Ser | Ser | His | Gly | Thr | |
| | 130 | | | | | 135 | | | | | 140 | | | | | |
| ccc | tct | cag | aca | aca | gcc | aag | aac | tgg | gaa | ctc | aca | gca | tcc | gcc | tcc | 480 |
| Pro | Ser | Gln | Thr | Thr | Ala | Lys | Asn | Trp | Glu | Leu | Thr | Ala | Ser | Ala | Ser | |
| 145 | | | | | 150 | | | | | 155 | | | | | 160 | |
| cac | cag | ccg | cca | ggt | gtg | tat | cca | cag | ggc | cac | agc | gac | | | | 519 |
| His | Gln | Pro | Pro | Gly | Val | Tyr | Pro | Gln | Gly | His | Ser | Asp | | | | |
| | | | | 165 | | | | | 170 | | | | | | | |

```
<210> SEQ ID NO 86
<211> LENGTH: 173
<212> TYPE: PRT
<213> ORGANISM: Homo sapiens

<400> SEQUENCE: 86

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30
```

-continued

```
Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
            85                  90                  95

Lys Glu Pro Ala Ala Ser Ser Pro Ser Ser Asn Asn Thr Ala Ala Thr
                100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp
                165                 170
```

What is claimed is:

1. An isolated heterodimeric receptor complex comprising receptor subunits, wherein the first receptor subunit comprises a receptor polypeptide comprising a sequence of amino acid residues as shown in SEQ ID NO:6, and wherein the second receptor subunit comprises a IL-2Rγ receptor polypeptide (SEQ ID NO:4).

2. The isolated heterodimeric receptor complex according to claim 1, wherein the heterodimeric receptor complex binds a ligand comprising a zalpha11 Ligand (IL-21) polypeptide (SEQ ID NO:10).

3. The isolated heterodimeric receptor complex according to claim 1, wherein the heterodimeric receptor complex antagonizes the activity of a ligand comprising a zalpha11 Ligand (IL-21) polypeptide (SEQ ID NO:10).

4. The isolated heterodimeric complex according to claim 1, wherein the receptor complex further comprises an affinity tag, label, chemical moiety, toxin, biotin/avidin label, radionuclide, enzyme, substrate, cofactor, inhibitor, fluorescent marker, chemiluminescent marker, toxin, cytotoxic molecule or an immunoglobulin Fc domain.

5. An isolated heterodimeric receptor complex comprising two receptor subunits, wherein the first receptor subunit comprises a receptor polypeptide comprising a sequence of amino acid residues as shown in SEQ ID NO:2 from amino acid number 20 (Cys), to amino acid number 538 (Ser), and wherein the second receptor subunit comprises an IL-2Rγ receptor polypeptide.

6. The isolated heterodimeric receptor complex according to claim 5, wherein the heterodimeric receptor complex binds a ligand comprising a zalpha11 Ligand (IL-21) polypeptide (SEQ ID NO:10).

7. An isolated multimeric receptor complex comprising receptor subunits, wherein at least one of receptor subunits comprises a receptor polypeptide comprising a sequence of amino acid residues as shown in SEQ ID NO:6, and wherein at least one other of the receptor subunits comprises a receptor polypeptide comprising IL-2Rγ receptor polypeptide (SEQ ID NO:4).

8. The isolated multimeric receptor complex according to claim 7, wherein the multimeric receptor complex binds a ligand comprising a zalpha11 Ligand (IL-21) polypeptide (SEQ ID NO:10).

9. The isolated heterodimeric receptor complex according to claim 7, wherein the heterodimeric receptor complex antagonizes the activity of a ligand comprising a zalpha11 Ligand (IL-21) polypeptide (SEQ ID NO:10).

10. An isolated multimeric receptor complex comprising receptor subunits, wherein at least one of receptor subunits comprises a receptor polypeptide comprising a sequence of amino acid residues as shown in SEQ ID NO:2 from amino acid number 20 (Cys), to amino acid number 538 (Ser), and wherein at least one other of the receptor subunits comprises a receptor polypeptide comprises an IL-2Rγ receptor polypeptide.

11. The isolated multimeric receptor complex according to claim 10, wherein the multimeric receptor complex binds a ligand comprising a zalpha11 Ligand (IL-21) polypeptide (SEQ ID NO:10).

* * * * *